(12) United States Patent
Dubensky, Jr. et al.

(10) Patent No.: US 7,977,091 B2
(45) Date of Patent: Jul. 12, 2011

(54) EUKARYOTIC LAYERED VECTOR INITIATION SYSTEMS

(75) Inventors: Thomas W. Dubensky, Jr., Rancho Santa Fe, CA (US); John M Polo, San Diego, CA (US); Carlos E Ibanez, San Diego, CA (US); Stephen M. W. Chang, San Diego, CA (US); Douglas J Jolly, Leucadia, CA (US); David A Driver, San Diego, CA (US); Barbara A Belli, San Diego, CA (US)

(73) Assignee: Novartis Vaccines & Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/538,494

(22) Filed: Aug. 10, 2009

(65) Prior Publication Data

US 2010/0173412 A1 Jul. 8, 2010

Related U.S. Application Data

(60) Continuation of application No. 10/346,880, filed on Jan. 16, 2003, now Pat. No. 7,572,628, which is a continuation of application No. 09/503,138, filed on Feb. 11, 2000, now abandoned, which is a continuation of application No. 09/191,747, filed on Nov. 12, 1998, now abandoned, which is a continuation of application No. 08/739,199, filed on Oct. 30, 1996, now abandoned, which is a division of application No. 08/404,796, filed on Mar. 15, 1995, now Pat. No. 6,015,686, which is a continuation-in-part of application No. 08/376,184, filed on Jan. 18, 1995, now abandoned, which is a continuation-in-part of application No. 08/348,472, filed on Nov. 30, 1994, now abandoned, which is a continuation-in-part of application No. 08/198,450, filed on Feb. 18, 1994, now abandoned, which is a continuation-in-part of application No. 08/122,791, filed on Sep. 15, 1993, now abandoned.

(51) Int. Cl.
C12N 15/63 (2006.01)
C12Q 1/68 (2006.01)

(52) U.S. Cl. .......................... 435/320.1; 435/6

(58) Field of Classification Search .................. None
See application file for complete search history.

(56) References Cited

U.S. PATENT DOCUMENTS

| | | | |
|---|---|---|---|
| 5,026,686 A | 6/1991 | Schlesinger et al. |
| 5,091,309 A | 2/1992 | Schlesinger et al. |
| 5,185,440 A | 2/1993 | Davis et al. |
| 5,217,879 A | 6/1993 | Huang et al. |
| 5,466,788 A | 11/1995 | Alquist et al. |
| 5,505,947 A | 4/1996 | Johnston et al. |
| 5,532,154 A | 7/1996 | Brown |
| 5,578,475 A | 11/1996 | Jessee |
| 5,591,579 A | 1/1997 | Olivo et al. |
| 5,643,576 A | 7/1997 | Johnston et al. |
| 5,691,177 A | 11/1997 | Guber et al. |
| 5,739,026 A | 4/1998 | Garoff et al. |
| 5,766,602 A | 6/1998 | Xiong et al. |
| 5,789,245 A | 8/1998 | Dubensky, Jr. et al. |
| 5,792,462 A | 8/1998 | Johnston et al. |
| 5,797,870 A | 8/1998 | March et al. |
| 5,811,407 A | 9/1998 | Johnston et al. |
| 5,814,482 A | 9/1998 | Dubensky, Jr. et al. |
| 5,843,712 A | 12/1998 | Levine |
| 5,843,723 A | 12/1998 | Dubensky, Jr. et al. |
| 5,851,757 A | 12/1998 | Olivo et al. |
| 6,342,372 B1 | 1/2002 | Dubensky, Jr. et al. |
| 6,376,236 B1 | 4/2002 | Dubensky, Jr. et al. |

FOREIGN PATENT DOCUMENTS

| | | |
|---|---|---|
| GB | 2200651 | 8/1988 |
| WO | 8800472 | 1/1988 |
| WO | 8910973 | 11/1988 |
| WO | 8910973 | 11/1989 |
| WO | 9102805 | 3/1991 |
| WO | 9206693 | 4/1992 |
| WO | 9210578 | 6/1992 |
| WO | 9417813 | 8/1994 |
| WO | 9426912 | 11/1994 |
| WO | 9507994 | 3/1995 |
| WO | 9517525 | 6/1995 |
| WO | 9519990 | 7/1995 |
| WO | 9525788 | 9/1995 |
| WO | 9527044 | 10/1995 |
| WO | 9531565 | 11/1995 |
| WO | 9527069 | 12/1995 |
| WO | 9532733 | 12/1995 |
| WO | 9617072 | 6/1996 |
| WO | 9537616 | 11/1996 |
| WO | 9639830 | 12/1996 |
| WO | 9716169 | 5/1997 |
| WO | 9724447 | 7/1997 |
| WO | 9730155 | 8/1997 |
| WO | 9738087 | 10/1997 |

(Continued)

OTHER PUBLICATIONS

Flexner et al., "Attenuation and Immunogenicity in Primates of Vaccinia Virus Recombinants Expressing Human Interleukin-2" Vaccine 8:17-21, 1990. Hampel et al., "Hairpin Catalytic RNA Model: Evidence for Helices and Sequences Requirement for Substrate RNA" Nucleic Acids Research 18(2):299-304, 1990.
Haseloff et al., "Simple RNA Enzymes with New and Highly Specific Endoribonuclease Activities" Nature 334:585-591, Aug. 1988.
Irvin et al., "Purification and Properties of a Second Antiviral Protein from Phytolacca americana which Inactivates Eukaryotic Ribosomes" Archives of Biochemistry and Biophysics 200(2):418-421, 1980.
Irvin et al., "Purification and Partial Characterization of the Antiviral Protein from Phytolacca americana which Inhibits Eukaryotic Protein Synthesis" Archives of Biochemistry and Biophysics 169:522-2538, 1975.
Jackson et al., "Nucleotide Sequence Analysis of the Structural Genes for Shiga-Like Toxin I encoded by Bacteriophage 900J from *Escherichia coli*" Microbial Pathogenesis 2:147-153, 1987.

(Continued)

*Primary Examiner* — Michele K Joike
(74) *Attorney, Agent, or Firm* — Regina Bautista; Helen Lee

(57) ABSTRACT

The present disclosure provides compositions and methods for utilizing recombinant alphavirus vectors. Also disclosed are compositions and methods for making and utilizing eukaryotic layered vector initiation systems.

4 Claims, 30 Drawing Sheets

FOREIGN PATENT DOCUMENTS

| WO | 974446 | 11/1997 |
|---|---|---|
| WO | 9813511 | 4/1998 |
| WO | 9815636 | 4/1998 |
| WO | 9853077 | 5/1998 |
| WO | 9826084 | 6/1998 |
| WO | 9836779 | 8/1998 |
| WO | 9909192 | 2/1999 |
| WO | 9911808 | 3/1999 |
| WO | 9915641 | 4/1999 |
| WO | 9918226 | 4/1999 |
| WO | 9925858 | 5/1999 |
| WO | 9925859 | 5/1999 |
| WO | 9930734 | 6/1999 |

OTHER PUBLICATIONS

Kekule et al., "The preS2/S Region of Integrated Hepatitis B Virus DNA Encodes a Transcriptional Transactivator" Nature 361:739-742, 1993.

Lamb et al., "Nucleotide Sequence of Cloned cDNA for Preproricin" Eur. J. Biochem. 148:265-270, 1985.

Levine et al., "Conversion of Lytic to Persistent Alphavirus Infection by the bcl-2 Cellular Oncogene" Nature 361:739-742, 1993.

Maher et al., "Specific Hybridization Arrest of Dihydrofolate Reductase mRNA in Vitro Using Anti-Sense RNA of Anti-Sense Oligonucleotides" Archives of Biochemistry and Biophysics 253(1):214-220, 1987.

Mansour et al., "An adenovirus Vector system Used to Express Polyoma Virus Tumor Antigens" Proc. Natl. Acad. Sci. 82:1359-1363, Mar. 1985.

McKnight, "The Nucleotide Sequence and Transcript map of the Herpes Simplex Virus Thymidine Kinase Gene" Nucleic Acids Research 8(24):5949-5964, 1980.

Mekalanos et al., "Cholera Toxin Genes: Nucleotide Sequence, Deletion Analysis and Vaccine Development" Nature 306:551-557, Dec. 1983.

Nolta et al., "Retroviral Vector-Mediated Gene Transfer into Primitive Human Hemotopoietic Progenitor Cells Effects of Mast Cell Growth Factor (MGF) Combined with Other Cytokines" Exp. Hematol. 20:1065-1071, 1992.

Reed et al., "Oncogenic Potential of bcl-2 Demonstrated by Gene Transfer" Nature 336:259-261, 1988.

Romano et al., Stem Cells, 18:19-39, 2000.

Rosenfeld et al., "Adenovirus-Mediated Transfer of a Recombinant alpha-1-Antitrypsin Gene to the Lung Eptihelium in Vivo" Science 252:431-434, 1991.

Sanchez et al., "Recombinant System for Overexpression of Cholera Toxin B Subunit in Vibrio cholerae as a s basis for Vaccine Development" Proc. Natl. Acad. Sci. 86:481-485, Jan. 1989.

Searle et al., "The Potential of Carboxypeptidase G2-Antibody Conjugates as Anti-Tumor Agents. I. Preparation of Antihuman Chorionic Gonadotrophin-Carboxypeptidase G2 and Cytotoxicity of the Conjugate Against JAP Choriocarcinoma Cells in vivo" Br. J. Cancer 53:377-384, 1986.

Stanton et al., "Nucleotide Sequence Comparison of Normal and Translocated Murine c-myc Genes" Nature 310:423-425, Aug. 1984.

Stripe et al., "Gelonin, a New Inhibitor of Protein Synthesis, Nontoxic to Intact Cells" J. Biological Chemistry 255 (14):6947-6953, 1980.

Wagner et al., "Nucleotide Sequence of the Thymidine Kinase Gene of Herpes Simplex Virus Type 1" Proc. Natl. Acad. Sci. 78(3):1441-1445, Mar. 1981.

Wang et al., "pH-Sensitive Immunoliposomes Mediate Target-cell-Specific Delivery and Controlled Expression of a Foreign Gene in Mouse" Proc. Natl. Acad. Sci. 84:7851-7855, 1987.

Wilson et al., "Prospects for Gene Therapy for Familial Hypercholesterolemia" Mol. Biol. Med. 7:223-232, 1990.

Wu et al., "Targeting Genes: Delivery and Persistent Expression of a Foreign Gene Driven by Mammalian Regulatory elements in Vivo" J. Biological Chemistry 264(29): 16985-16987, 1989.

Yamamoto et al., "The Human LDL Receptor: A Cysteine-Rich Protein with Multiple Alu Sequences in its mRNA" Cell 39:27-38, 1984.

Metsikko et al., "Oligomers of the Cytoplasmic Domain of the p62/E2 Membrane Protein of Semliki Forest Virus Bind to the Nucleocapsid in Vitro" Oct. 1990. J. Virology 64:4678-4683.

Reiss et al., "Newly systhesized class II MHC chains are required for VSV G presentation to CTL clones," Cellular Immunol. 139:229-238, 1992.

Salk et al., "A strategy for prophylactic vaccination against HIV," Science 260:1270-1272, 1993.

Dryga et al., "Identification of Mutations in the Sindbis Virus Variant Able to Establish Persistent Infection in BHK Cells: The Importance of a Mutation in the nsP2 Gene," Virology 228:74-83, 1997.

Tubulekas et al., "Alphavirus expression vectors and their use as recombinant vaccines: a minireview," Gene. vol. 190:191-195. 1995.

Williams et al., "Introduction of Foreign Genes into Tissue of Living Mice by DNA-Coated Microprojectiles," Proc. Natl. Acad. Sci. 88:2726-2730, 1991.

Liljestrom et al., "In vitro mutagenesis of a full-length cDNA clone of Semliki Forest Virus: the small 6,000-molecular weight membrane protein modulates virus release," J. Virology. 65:4107-4113, 1991.

Strauss et al., "Identification of the Active Site Residues in the nsP2 Proteinase of Sindbis Virus" Virology 192:932-940, 1992.

Strauss and Strauss, "The Alphaviruses: Gene Expression, Replication, and Evolution" Microbiological Reviews 58 (3):491-962, 1994.

Tysoe-Calnon et al., "Molecular Comparisons of the Beta 2 Microglobulin Binding Site in Class I Major Histocompatability Complex Alpha Chain and Proteins of Related Sequences" Biochemistry 277:359-369, 1991.

Watson et al., "A Mutant Cho-K1 Strain with Resistance to Pseudomonas Exotoxin A and Alphaviruses Faisl to Cleave Sindbis Virus Glycoprotein PE2" Journal Virology 65(5):2332-2339, 1991.

Weiss et al., "Establishment and Maintenance of Persistent Infection by Sindbis Virus in BHK Cells" J. Virology 33 (1):463-474,1980.

Weiss et al., "Evidence for Specificity in the Encapsidation of Sindbis Virus RNAs" J. Virology 63:5310-5318, 1989.

Weiss and Schlesinger, "Recombinant between Sindbis Virus RNAs" Journal Virology 65(8):4017-4023, 1991.

Weiss et al., "Interactions between Sindbis Virus RNAs and a 68 Amino Acid Derivative of the Viral Capsid Protein Further Defines the Capsid Binding Site" Nucleic Acids Research 22(5):780-786, 1994.

Wen and Schlesinger, "Regulated Expression of Sindbis and Vesicular Stomatitis Virus Glycoproteins in *Saccharomyces cerevisiae*" Proc. Natl. Acad. Sci. USA 83:3639-3643, 1986.

Xiong et al., "Sinbis Virus: an Efficient, Broad Host Range Vector for Gene Expression Animal Cells" Science 243:1188-1191, 1989.

Zhou et al., "Self-Replicating Semliki Forest Virus RNA as Recombinant Vaccine" Vaccine 12(16):1510-1514, 1994.

Zhou et al., "Generation of Cytoxic and Humoral Immune Responses by Nonreplicative Recombinant Semliki Forest Virus" Proc. Natl. Acad. Sci. USA 92:3009-3013, 1995.

Pushko et al., "Replicon-Helper Systems from Attenuated Venezuelan Equine Encephalitis Virus: Expression of Heterologus Genes in Vitro and Immunization Against Heterologous Pathogens in Vivo" Virology 239:389-401, 1997.

Frolov et al., "Sindbis Virus Replicons and Sindbis Virus: Assembly of Chimeras and of Particles Deficient in Virus RNA" J. Virology 71(4):2819-2829, Apr. 1997.

Frolov et al., "Alphavirus-Based Expression Vectors: Strategies and Applications" Proc. Natl. Acad. Sci. USA 93:11371-11377, Oct. 1996.

Palu et al., Journal of Biotechnology 68:1-13, 1999.

Polo et al., "Stable Alphavirus Packaging Cell Lines for Sindbis Virus-and Semiliki Forest Virus-Derived Vectors" Proc. Natl. Acad. Sci. USA 96:4598-4603, Apr. 1999.

Smerdou and Liljestrom, "Two-Helper RNA System for Production of Recombinant Semliki Forest Virus Particles" J. Virology 73(2):1092-1098, Feb. 1999.

Debensky et al., "Direct Transfection of Viral and Plasmid DNA into the Liver or Spleen of Mice" Proc. Natl. Acad. Sci. USA 81:7529-7533, Dec. 1984.

Jang et al., "Initiation of Protein Synthesis by Internal Entry of Ribosomes into the Nontranslated Region of Encephalomyocarditis Virus RNA in Vivo" J. Virology 63(4):161-1660, Apr. 1989.

Jolly, "Viral Vector Systems for Gene Therapy" Cancer Gene Therapy 1(1):51-64, 1994.
Luo et al., "Purification and Characterization of a Sindbis Virus-Induced Peptide which Simulates its Own Production and Blocks Virus RNA Synthesis" Virology 194:44-49, 1993.
Peters and Dalrymple, Chapter 26, entitled "Alphaviruses" —"Virology" second edition, edited by B.N. Fields, D.M. Knipe et al. Raven Press, Ltd., New York, 1990.
Schlesinger et al., "An In-Frame Insertion into the Sindbis Virus 6K Gene Leads to Defective Proteolytic Processing the Virus Glycoproteins, a Trans-Dominant Negative Inhibition of Normal Virus Formation, and Interference in Virus Shut Off of Host-Cell Protein Synthesis" Virology 193:424-432, 1993.
Taylor Schlesinger et al., "Sindbis Virus: A Newly Recognized Arthropod-Transmitted Virus" Ann. J. Trop. Med. Hyg. 4:844-862, 1955.
Wang et al., "Antiidiotypic Antibodies as Probes for the Sindbis Virus Receptor" Virology 181:694-702, 1991.
Wang et al., "pH-Sensitive Immunoliposomes Mediate Target-Cell-Specific Delivery and Controlled Expression of a Foreign Gene in Mouse" Proc. Natl. Acad. Sci. USA 84:7851-7855, Nov. 1987.
Acsadi et al., "Human Dystrophin Expression in mdx Mice After Intramuscular Injection of DNA Constructs" Nature 352:815-818, Aug. 1992.
Altmann et al., "Cotrasfection of ICAM-1 and HLA-DR Reconstitutes Human Antigen-Presenting Cell Function in Mouse L Cells" Nature 338:512-514, 1989.
Anderson et al., "Alternate Splicing of mRNAs Encoding Human Mast Cell Growth Factor and Localization of the Gene to Chromosome 12q22-q24" Cell Growth and Differentiation 2:373-378, 1991.
Autiero et al., "Binding to CD4 of synthetic Peptides Patterned on the Principal Neutralizing Domain of the HIV-1 Envelope Protein": Virology 185:820-828, 1991.
Bally et al., "In vitro and in vivo Synthesis of the Hepatitis B Virus Surface Antigen and of the Receptor for Polymerized Human Serum Albumin from Recombinant Human Adenovirus" EMBO Journal 4:3861-3865, 1985.
Barbeirei et al., "Purification and Partial Characterization of Another Form of the Antiviral Protein from the Seeds of Phyrolacca Americana L (pokeweed)" Biochem. J. 203:55-59, 1982.
Barneveld et al., "Monoclonal Antibodies Against Human Beta-Glucocerebrosidase" Eur. J. Biochem. 134:585-589, 1983.
Barranger et al., The Metabolic Basis of Inherited . . . , vol. 2, 6th Ed., Chapter 67, "Glucosylceramide Lipidoses: Gaucher Disease" pp. 1677-1698, 1990.
Beutler, Gaucher Disease: New Molecular Approaches to Diagnosis and Treatment Science 256:794-799, 1992.
Bzik et al., "Molecular Cloning and Sequence Analysis of the Plasmodium Falciparum Dihyrdofolate Reuctase-Thymidylate Synthase Gene" Proc. Natl. Acad. Sci. 84:8360-8364, Dec. 1987.
Calderwood et al., "Nucleotide Sequence of the Shiga-Like Toxin Genes of *Escherichia coli*" Proc. Natl. Acad. Sci. 84:4364-4368.
Caroll et al., "Active Site of Pseudomonas Aeruginosa Exotoxin A" J. Biological Chemistry 262(18):8707-8711, 1987.
Chen et al., "The Complete Primary Structure of Abrin-a B Chain" Fed. Eur. Biochemical Societies 309:115-118, 1992.
Chin et al., "Tissue-Specific Expression of Hepatic Functions" Ann. NY Acad. Sci. 478:120-130, 1986.
Choi et al., "Expression of Human Immunodeficiency Virus Type 1 (HIV-1) gag, pol, and env Proteins from Chimeric HIV-1-Poliovirus Minireplicons" J. Virology 65(6):2875-2883, 1991.
Collins et al., "Primary Amino Acid Sequence of alpha-Trichosanthin" and Molecular Models for Abrin A-chain and alpha-trichosanthin J. Biological Chemistry 265(15):8665-8669, 1990.
Correll et al., "High Levels of Human Glucocerebrosidase Activity in Macrophages of Long-Term Reconstituted Mice After Retroviral Infection of Hematopoietic Stem Cells" Blood 80(2): 331-336, 1992.
Coussens et al., "Tyrosine Kinase Receptor with Extensive Homology of EGF Receptor Shares Chromosomal Location with neu Oncogene" Science 230:1132-1139, 1986.
Evans et al., "An Engineered Poliovirus Chimaera Elicits Broadly Reactive HIV-1 Neutralizing Antibodies" Nature 339:385-388, 1989.

Evensen et al., "Direct Molecular Cloning and Expression of Two Distinct Abrin A-Chain" J. Biological Chemistry 266 (1):6848-6852, 1991.
Fainstein et al., "Nucleotide Sequence Analysis of Human abl and bcr-abl cDNAs" Oncogene 4:1477-1481, 1989.
Field et al., "Isolation and Characterization of Acyclovir-Resistant Mutants of Herpes Simplex Virus" J. Gen. Virol. 49:115-124, 1980.
Fisher-Hoc et al., "Protection of rhesus Monkeys from fatal Lassa Fever by Vaccination with a Recombinant Vaccinia Containing the Lassa Virus Glycoprotein Gene" Proc. Natl. Acad. Sci. 86:317-321, 1989.
Baumann and Schendel, "Interleukin-11 Regulates the Hepatic Expression of the Same Plasma Protein Genes as Interleukin-6" Journal Biological Chemistry 266:20424-20427, 1991.
Beier et al., "Association of Human Class I MHC Alleles with the Adenovirus E3/19K Protein" J. Immunology 152:3862-3872, 1994.
Berglund et al., "Semliki forest virus Expression System: Production of Conditionally Infectious Recombinant Particles" Bio/Technology 11:916-920, 1993.
Berglund et al., "Alphavirus as Vectors for Gene Delivery" Trends in Biotechnology 14:130-134, 1996.
Beuachemin et al., "Isolation and Characterization of Full-Length Functional cDNA Clones for Human Carcinoembryonic Antigen" Molecular and Cellular Biology 7 (9):3221-3230, Sep. 1987.
Boyer and Haenni, "Infectious Transcripts and cDNA Clones of RNA Viruses" Virology 198:415-426, 1994.
Bredenbeek and Rice, "Animal RNA Virus Expression Systems" Seminars Virology 3:297-310, 1992.
Bredenbeek et al., "Sindbis Virus Expression Vectors: Packaging of RNA Replicons by Using Defective Helper RNAs" Journal Virology 67(11):6439-6446, 1993.
Browne et al., "A Complex Between the MHC Class I Homologue Encoded by Human Cytomegalovirus and Beta 2 Microglobulin" Nature 347:770-772, 1990.
Davis et al., "In Vitro Synthesis of Infectious Venezuelan Equine Encephalitis Virus RNA from a cDNA Clone: Analysis of a Viable Deletion Mutant" Virology 171:189-204, 1989.
Davis et al., "Protection Against Influenza in mice by Vaccination with a Venezuelan Equine Encephalitis Virus Vector Expressing the HA Protein" J. Cell Biochem. Suppl. 19A 310, Abstract No. J2-308, 1995.
Dubensky et al., "Sindbis Virus DNA-Based Expression Vectors: Utility for in vitro and in vivo Gene Transfer" Journal Virology 70(1):508-519, 1996.
Dubuisson and Rice, "Sindbis Virus Attachment: Isolation and Characterization of Mutants with Impaired Binding to Vertebrate Cells" J. Virology 67(6):3363, 1993.
Frolov and Schlesinger, "Comparison of the Effects of Sindbis Virus and Sindbis Virus Replicons on Host Cell Protein Synthesis and Cytopathogenicity in BHK Cells" J. Virology 68(3):1721, 1994.
Gassman et al., "Analysis of the Borrelia burgdorferi geHo fla Gene and Antigenic Characterization of its Gene Product" J. Bacteriology 173(4):1452, 1991.
Geigenmuller-Gnirke et al., "Complementation between Sindbis Viral RNAs Produces Infectious Particles with a Bipartite Genome" Proc. Natl. Acad. Sci. USA 88:3253-3257, 1991.
Grakoui et al., "A cis-Acting Mutation in the Sindbis Virus Junction Region which Affects Subgenomic RNA Synthesis" Journal Virology 63 (12):5216-5227, 1989.
Hahn et al., "Infectious Sindbis Virus Transient Expression Vectors for Studying Antigen Processing and Presentation" Proc. Natl. Acad. Sci. USA 89:2679-2683, Apr. 1992.
Hertz and Huang "Utilization of Heterologus Alphavirus Junction Sequences as Promoters by Sindbis Virus" Journal Virology 66(2):857-864, 1992.
Herweijer et al., A Plasmid-Based Self-Amplifying Sindbis Virus Vector: Human Gene Therapy 6:1161-1167, 1995.
Huang et al., RNA Viruses as Gene Expression Vectors Virus Genes 3(1):85-91, 1989.
Huang et al., "Liposomal Gene Delivery: a Complex Package" Nature Biotechnology 15:620-621, 1997.

Johanning et al., "A Sindbis Virus mRNA Polynucleotide Vector Achieves Prolonged and High Level heterologous Gene Expression in vivo" Nucleic Acids Research 23(9):1495-1501, 1995.

Kuhn et al., "Infectious RNA Transcription from Ross River Virus cDNA Clones and, the Construction and Characterization of Defined Chimeas with Sindbis Virus" Virology 182:430-441, 1991.

Kuo et al., "An Assay for Circulating Antibodies to a Major Etiologic Virus of Human Non-A, Non-B Hepatitis" Science 244:362-364, 1989.

Lemm et al., "Mutations which Alter the Level or Structure of nsP4 can Affect the Efficiency of Sindbis Virus Replication in a Host-Dependent Manner" J. Virology 64(6):3001-3011, 1990.

Lemm et al., "Polypeptide Requirements for Assembly of Functional Sindbis Virus Replication Complexes: a Model for the Temporal Regulation of Minus-and Plus-Strand RNA Syntheses" EMBO J. 13(12):2925-2934, 1994.

Levis et al., "Deletion Mapping of Sindbis Virus DI RNAs Derived from cDNAs Defines the Sequences Essential for Replication and Packaging" Cell 44:137-145, 1986.

Levis et al., "Engineered Defective Interfering RNAs of Sindbis Virus Express Bacterial Chloramphenicol Acetyltransferase in Avian Cells" Proc. Natl. Acad. Sci. USA 84:4811-4815, 1987.

Levis et al., "Promoter for Sindbis Virus RNA-Dependent Subgenomic RNA Transcription" J. Virology 64(4):1726-1733, 1990.

Liljestrom and Garoff, "A New Generation of Animal Cell Expression Vectors Based on the Semliki Forest Virus Replicon" Bio/Technology 9:1356-1361, 1991.

Liljestrom, "Alphavirus Expression Systems" Current Opinion in Biotechnology 5:495-500, 1994.

London et al., "Infectious Enveloped RNA Virus Antigenic Chimeras" Proc. Natl. Acad. Sci. USA 89:207-211, Jan. 1992.

Oker-Blom and Summers, "Expression of Sindbis Virus 26S cDNA in Spodoptera frugiperda (Sf9) Cells, Using a Baculovirus Expression Vector" Journal Virology 63(3): 1256-1264, 1989.

Olivo et al., "A Cell Line that Expresses a Reporter Gene in Response to Infection by Sindbis Virus: a Prototype for Detection of Positive Strand RNA Viruses" Virology 198:381-384, 1994.

Orkin et al., Report and Recommendations of the Panel to Assess the NIH Investment in Research on Gene Therapy, pp. 1-40, 1995.

Owen and Kuhn, "Identification of a Region in the Sindbis Virus Nucleocapsid Protein that is involved in Specificity of RNA Encapsidation" J. Virology 70(5):2757-2763, 1996.

Polo et al., "Alphavirus Mediated Delivery of Ribozyme Therapeutics" J. Cell Biochem. Suppl. 19A:288, Abstract No. A6-413, 1995.

Recaniello and Baltimore, "Cloned Poliovirus Complementary DNA is Infectious in Mammalian Cells" Science 214:916-919, 1981.

Raju and Huang, "Analysis of Sindbis Virus Promoter Recognition in vivo, Using Novel Vectors with Two Subgenomic mRNA Promoters" J. Virology 65(5):2501-2510, 1991.

Rice et al., "Expression of Sindbis Virus Structural Proteins via Recombinant Vaccinia Virus: Synthesis, Processing, and Incorporation into Mature Sindbis Virions" J. Virology 56(1):227-239, 1985.

Rice et al., "Production of Infectious RNA Transcripts from Sindbis Virus cDNA Clones: Mapping of Lethal Mutations, Rescue of a Temperature-Sensitive Marker, and in vitro Mutagenesis to Generate Defined Mutants" J. Virology 61 (12):3809-3819, 1987.

Rolls et al., "Novel Infectious Particles Generated by Expression of the Vesicular Stomatitis Virus Glycoprotein from a Self-Replicating RNA" Cell 79:497-506, 1994.

Rolls et al., "Expression of Additional Genes in a Vector Derived from a Minimal RNA Virus" Virology 218:406-411, 1996.

Sarver and Stollar, "Sindbis Virus-Induced Cytophathic Effect in Clones of Aedes albopictdus (Singh) Cells" Virology 80:390-400, 1997.

Schlesinger, "Alphaviruses—Vectors for the Expression of Heterologous Genes" Trends Biotechnology 11:18-22, 1993.

Schowalter et al., "Heterologous Expression of Adenovirus E3-gp19K in an Ela-deleted Adenovirus Vector Inhibits MHC I Expression in vitro but does not Prolong Transgene Expression in vivo" Gene Therapy 4:351-360, 1997.

Semler et al., "Production of Infectious Poliovirus from Cloned cDNA is Dramatically Increased by SV40 Transcription and Replication Signals" Nucleic Acids Research 12(12):5123-5141, 1984.

Shirako and Strauss, "Regulation of Sindbis Virus RNA Replication: Uncleaved P12 and nsP4 Function in Minus-Strand RNA Synthesis, Whereas Cleaved Products from P123 are Required for Efficient Plus-Strand RNA Synthesis" J. Virology 68(3):1874-1885, 1994.

Strauss et al., "Complete Nucleotide Sequence of the Genomic RNA of Sindbis Virus" Virology 133:92-110, 1984.

| | | | | | |
|---|---|---|---|---|---|
|AACACTTCAA|GCAAGGCGAC|CCGGTACTGG|AGACGGATAT|CGCATCATTC|GACAAAAGCC|6900|
|AAGACGAGC|TATGGGGTTA|ACCGGTCTGA|TGATCTTGGA|GGACCTGGGT|GTGGATCAAC|6960|
|CACTACTCGA|CTTGATCGAG|TGCGCCTTTG|GAGAAATATC|ATCCACCAT|CTACCTACGG|7020|
|GTACTCGTTT|TAAATTCGGG|GCGATGATGA|AATCCGGAAT|GTTCCTCACA|CTTTTTGTCA|7080|
|ACACAGTTTT|GAATGTCGT|ATCGCCAC|GAGTACATAGA|AGAGAAGAA|GACAAAGAAA|7140|
|GATGTGCAGC|GTTCATTGGC|GACGACAACA|TCATACATGG|AGTAGTATCT|GCAGTCATCC|7200|
|TGGCTGAGAG|GTGCCTGAGA|GACCTTACTTC|TGGAGGTTAA|GATCATCGGT|ACTTCCACAG|7260|
|GTGAGAGAC|ACCTTACTTC|TGCAAAAGC|AGATTCGGT|AGATTCGGTT|CTCCCAGCCG|7320|
|CGTGCCGCGT|GGCGGATCCC|CTGAAAAGGC|CTGAAAGAAC|GGGGTAAACCG|GCGTGGTTTA|7380|
|ACGACGAGCA|AGACGAAGAC|AGAGACGAC|TTAGAGGGAC|TGAAACAAAG|GTAGACAATA|7440|
|GAGTAGGTAT|AACAGGACT|TTAGCAGTGG|CTCTACGTG|CCGGTATGAG|TTCCAAGCCA|7500|
|TTACACCTGT|CCCTGCTCCC|CTCTACCC|ACCACCACT|CAAAAGAAAG|TACATTTCAT|7560|
|CTGAACTAATA|AATAAGCAT|GCTTCTCAA|GCCATCTGGA|GTCAGCATAG|CTCGGCCGCC|7620|
|GCCCCTTTCC|CCTGCTGCTG|AGACCTCAA|TCCCAGAGG|CTTTAAATG|GCGTCAGTGA|7680|
|TGCTGCCG|ACAGGCAACT|ACACCGGAC|AAGGGATT|ATAAGGATT|GCGCAGCAG|7740|
|TAGTCATTGG|AATAAAGCAT|GCCCAAGAGC|AGACCTGAAT|GGCGGCAACT|CCGAGAAGA|7800|
|AGAAGCAGG|ACAGGCAACT|ACACCGGAA|CAACCCGGAA|CGAACACACCC|AAGTTGGAGG|7860|
|AGAAGCAGG|ACAGGCAGC|GCCCAAGAGC|AGAGAACCG|ACGGAGATGT|GCACTGGCCA|7920|
|CCGACAGATT|GTTTCAGTGG|GGTAATGAAA|GGTAATGAAA|CATGGGGAAC|CCTGTGCTAT|7980|
|TGGAAGGAAA|ATTTACCAA|TGACGAGAA|GTTCGCAGGA|CATGGGGAAC|TTGCCAGTCA|8040|
|CAAAGCTCAA|TGAGGGCTGA|GGGTGCAGTT|AGTTGGAGGGTA|CTCGGATCA|TATAACTGGC|8100|
|ACATGAGAAG|GCTCGGAAG|CGGTGAGCGC|AGATCGGATA|GTGAACCAT|GTAGGAGGCA|8160|
|ACCAGAGAG|GCTCAGAGC|TGAAGCTTC|CGGATCACGG|AAGAGCTTC|ATAGTCCTTCG|8220|
|GAGTGCACAG|CAGAGGACAG|CAGAGCAGC|GAACTTGCT|CATAGACAGG|AGCCTACGATA|8280|
|CAATGTGTT|GTCGGCTAA|CGGATCACCG|CCGATACGA|AAGAGTGGTC|AGTAACTGGC|8340|
|GCCGAACTTC|CAGAGCAGC|CAGGAACAG|GAAGATCACA|CGATACGA|GCCTACCC|8400|
|CCCTGCTCAA|CGGACTAGC|TGCCATATTG|CGGTACTTGG|TGCACTACGA|GCCTACGATA|8460|
|ACGACTTTAC|GTCGCTTAAG|TGCGATACAGC|CCCTGCTCAG|GAACCAAAGA|CATACCATAC|8520|
|CGTGCTTCAG|GTCAGGACAC|TTCCGCCCAG|GCCTCACCC|AGCGAGCGG|AGCGTTCGTTG|8580|
|GCATACAGAC|CTCAGGACAC|TTCCGCTAAG|GGGCTTAAG|GCCTCACCC|AGCGAGCGG|8640|
|ACCGCTGGC|AGGGGAACAT|CTCAGGAACG|GCCTCACCC|TCTCTTCAG|GCATACCATAC|8700|
|AGATAGCAC|CCGCAAGCG|GTAACGGTTA|GTAACGGTTA|AGGATACTTT|GATGACATCA|8760|
|AATGCCCTCC|AGGGACAGC|AACCAAATA|AAAACAAAAT|TAGCAACTCA|CTCCTCGCAA|8820|
|GTACACTGGC|CCGCCCAGATA|CCGGCACACG|AGAGGACG|GGAAAAATAT|GCAACGTACCTC|8880|
|CCGTTCACGG|TAAAAGAATT|CCTTGCACAG|TGTACGACCG|TCTGAAAACA|ACTGCAGGCT|9060|

```
TACTTTCACC AGCGTTTCTG GGTGAGCAAA AACAGGAAGG CAAAATGCCG CAAAAAAGGG 16020
AATAAGGGCG ACACGGAAAT GTTGAATACT CATACTCTTC CTTTTTCAAT ATTATTGAAG 16080
CATTTATCAG GGTTATTGTC TCATGAGCGG ATACATATTT GAATGTATTT AGAAAATAA  16140
ACAAATAGGG GTTCCGCGCA CATTTCCCCG AAAAGTGCCA CCTGACGTCG ACGGATCGGG 16200
AGATCTAATG AAAGACCCCA CCTGTAGGTT TGGCAAGCTA GCTTAAGTAA CGCCATTTTG 16260
CAAGGCATGG AAAATACACAT AACTGAGAAT AGAGAAGTTC AGATCAAGGT CAGGAACAGA 16320
TGGAACAGCT GAATATGGGC CAAAGCAGGA ATCTGTGGTA AGCAGTTCCT GCCCCGGCTC 16380
CAAGGCCAAGA ACAGATGGAA CAGCTGAATA TGGGCCAAAC AGGATATCTG TGGTAAGCAG 16440
AGGGCCAAGA ACAGATGGAA CAGCTGAATA TGGGCCAAAC AGGATATCTG TGGTAAGCAG 16440
TTCCTGCCCC GGCTCAGGGC CAAGAACAGA TGGTCCCCCA GTGCCCTCAG GCCCTGCC  16440
GTTTCTAGAG AACCATCAGA CAAGAACAGG GTGCCCAAG TCGCTTCTGT GACCCTGTGC 16560
CTTATTTGAA CTAACCAATC AGTTCGCTTC TCGCTTCTGT TCGCGCGGCTT CTGCTCCCG 16620
AGCTCAATAA AAGAGCCCAC AACCCCTCAC TCGGGG                             16656
```

1. ELVIS-luc
2. LTR-luc
3. dInsP ELVIS-luc
4. ELVIS-luc dIpro

KEY:
- ||||||||| — INVERTED REPEATS
- ⟶⟍ — 5'⟶3'
- N.S.P — NON STRUCTURAL PROTEINS
- JR — JUNCTION REGION
- G.O.I. — GENE OF INTEREST

SEQUENCE LISTING

```
<160> NUMBER OF SEQ ID NOS: 129

<210> SEQ ID NO 1
<211> LENGTH: 16656
<212> TYPE: DNA
<213> ORGANISM: Artificial Sequence
<220> FEATURE:
<223> OTHER INFORMATION: Representative ELVIS derived from Sindbis

<400> SEQUENCE: 1
attgacggcg tagtacacac tattgaatca aacagccgac caatcgcact accatcacaa      60
tggagaagcc agtagtaaac gtagacgtag accccccagag tccgtttgtc gtgcaactgc     120
aaaaaagctt cccgcaattt gaggtagtag cacagcaggt cactccaaat gaccatgcta     180
atgccagagc attttcgcat ctggccagta aactaatcga gctggaggtt cctaccacag     240
cgacgatctt ggacataggc agcgcaccgg ctcgtagaat gttttccgag caccagtatc     300
attgtgtctg ccccatgcgt agtccagaag acccggaccg catgatgaaa tatgccagta     360
aactggcgga aaaagcgtgc aagattacaa acaagaactt gcatgagaag attaaggatc     420
tccggaccgt acttgatacg ccggatgctg aaacaccatc gctctgcttt cacaacgatg     480
ttacctgcaa catgcgtgcc gaatattccg tcatgcagga cgtgtatatc aacgctcccg     540
gaactatcta tcatcaggct atgaaaggcg tgcggaccct gtactggatt ggcttcgaca     600
ccacccagtt catgttctcg gctatggcag gttcgtaccc tgcgtacaac accaactggg     660
ccgacgagaa agtccttgaa gcgcgtaaca tcggactttg cagcacaaag ctgagtgaag     720
gtaggacagg aaaattgtcg ataatgagga agaaggagtt gaagcccggg tcgcgggttt     780
atttctccgt aggatcgaca ctttatccag aacacagagc cagcttgcag agctggcatc     840
ttccatcggt gttccacttg aatggaaagc agtcgtacac ttgccgctgt gatacagtgg     900
tgagttgcga aggctacgta gtgaagaaaa tcaccatcag tcccgggatc acgggagaaa     960
ccgtgggata cgcggttaca cacaatagcg agggcttctt gctatgcaaa gttactgaca    1020
cagtaaaagg agaacgggta tcgttccctg tgtgcacgta catcccggcc accatatgcg    1080
atcagatgac tggtctaatg gccacggata tatcacctga cgatgcacaa aaacttctgg    1140
ttgggctcaa ccagcgaatt gtcattaacg gtaggactaa caggaacacc aacaccatgc    1200
aaaattacct tctgccgatc atagcacaag ggttcagcaa atgggctaag gagcgcaagg    1260
atgatcttga taacgagaaa atgctgggta ctagagaacg caagcttacg tatggctgct    1320
```

```
tgtgggcgtt tcgcactaag aaagtacatt cgttttatcg cccacctgga acgcagacct    1380
gcgtaaaagt cccagcctct tttagcgctt tccccatgtc gtccgtatgg acgacctctt    1440
tgcccatgtc gctgaggcag aaattgaaac tggcattgca accaaagaag gaggaaaaac    1500
tgctgcaggt ctcggaggaa ttagtcatgg aggccaaggc tgcttttgag gatgctcagg    1560
aggaagccag agcggagaag ctccgagaag cacttccacc attagtggca gacaaaggca    1620
tcgaggcagc cgcagaagtt gtctgcgaag tggaggggct ccaggcggac atcggagcag    1680
cattagttga aaccccgcgc ggtcacgtaa ggataatacc tcaagcaaat gaccgtatga    1740
tcggacagta tatcgttgtc tcgccaaact ctgtgctgaa gaatgccaaa ctcgcaccag    1800
cgcacccgct agcagatcag gttaagatca taacacactc cggaagatca ggaaggtacg    1860
cggtcgaacc atacgacgct aaagtactga tgccagcagg aggtgccgta ccatggccag    1920
aattcctagc actgagtgag agcgccacgt tagtgtacaa cgaaagagag tttgtgaacc    1980
gcaaactata ccacattgcc atgcatggcc ccgccaagaa tacagaagag gggcagtaca    2040
aggttacaaa ggcagagctt gcagaaacag agtacgtgtt tgacgtggac aagaagcgtt    2100
gcgttaagaa ggaagaagcc tcaggtctgg tcctctcggg agaactgacc aaccctccct    2160
atcatgagct agctctggag ggactgaaga cccgacctgc ggtcccgtac aaggtcgaaa    2220
caataggagt gataggcaca ccggggtcgg gcaagtccgc tattatcaag tcaactgtca    2280
cggcacgaga tcttgttacc agcggaaaga agaaaattg tcgcgaaatt gaggccgacg    2340
tgctaagact gaggggtatg cagattacgt cgaagacagt agattcggtt atgctcaacg    2400
gatgccacaa agccgtagaa gtgctgtacg ttgacgaagc gttcgcgtgc cacgcaggag    2460
cactacttgc cttgattgct atcgtcaggc cccgcaagaa ggtagtacta tgcggagacc    2520
ccatgcaatg cggattcttc aacatgatgc aactaaaggt acatttcaat caccctgaaa    2580
aagacatatg caccaagaca ttctacaagt atatctcccg gcgttgcaca cagccagtta    2640
cagctattgt atcgacactg cattacgatg aaagatgaa accacgaac ccgtgcaaga    2700 agaacattga aatcgatatt acaggggcca caaagccgaa gccagggat atcatcctga    2760 catgtttccg cgggtgggtt aagcaattgc aaatcgacta tcccggacat gaagtaatga    2820
cagccgcggc ctcacaaggg ctaaccagaa aaggagtgta tgccgtccgg cagaaagtca    2880
atgaaaaccc actgtacgcg atcacatcag agcatgtgaa cgtgttgctc acccgcactg    2940
aggacaggct agtgtggaaa accttgcagg gcgacccatg gattaagcag ctcactaaca    3000
tacctaaagg aaacttcag gctactatag aggactggga agctgaacac aagggaataa    3060
ttgctgcaat aaacagcccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttttcggca tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat ctctgcacag cataacctgg tcccggtgaa ccgcaatctt cctcacgcct    3540
tagcccccga gtacaaggag aagcaacccg gcccggtcga aaaattcttg aaccagttca    3600
aacaccactc agtacttgtg gtatcagagg aaaaaattga agctcccgt aagagaatcg    3660 aatggatcgc cccgattggc ataagccggtg cagataagaa ctacaacctg gctttcgggt    3720
```

```
ttccgccgca ggcacggtac gacctggtgt tcatcaacat tggaactaaa tacagaaacc    3780
accactttca gcagtgcgaa gaccatgcgg cgaccttaaa agcccttcg cgttcggccc    3840 tgaattgcct caacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga attgcgtgat ttcgtccgtg tatgagggta    4080
caagagatgg agttggagcc gcgccgtcat accgcaccaa aagggagaat attgctgact    4140
gtcaaggaga agcagttgtc aacgcagcca atccgctggg tagaccaggc gaaggagtct    4200
gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
cggcactcca acttaaggag tctgtaacag agctgaagga tgaagatatg gagatcgacg    4620
atgagttagt atggatccat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gccaaaacg ttgccgtgcc tttgcatgta tgccatgacg ccagaaaggg    4920
tccacagact tagaagcaat aacgtcaaag aagttacagt atgctcctcc acccccttc    4980 ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca tgagcctgcc cctattccac cgccaaggct aaagaagatg gcccgcctgg    5400
cagcggcaag aaaagagccc actccaccgg caagcaatag ctctgagtcc ctccacctct    5460
cttttggtgg ggtatccatg tccctcggat caattttcga cggagagacg gcccgccagg    5520
cagcggtaca accctggca acaggcccca cggatgtgcc tatgtctttc ggatcgtttt    5580
ccgacggaga gattgatgag ctgagccgca gagcaactga gtccgaaccc gtcctgtttg    5640
gatcatttga accgggcgaa gtgaactcaa ttatatcgtc ccgatcagcc gtatctttc    5700 cactacgcaa gcagagacgt agacgcagga gcaggaggac tgaatactga ctaaccgggg    5760
taggtgggta catatttcg acggacacag gccctgggca cttgcaaaag aagtccgttc    5820
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa aagtaggtac cagtctcgta aagtagaaaa tcagaaagcc ataaccactg    6000
agcgactact gtcaggacta cgactgtata actctgccac agatcagcca gaatgctata    6060
agatcaccta tccgaaacca ttgtactcca gtagcgtacc ggcgaactac tccgatccac    6120
```

```
agttcgctgt agctgtctgt aacaactatc tgcatgagaa ctatccgaca gtagcatctt    6180
atcagattac tgacgagtac gatgcttact tggatatggt agacgggaca gtcgcctgcc    6240
tggatactgc aaccttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccacactat ttgcaaagac gtataatttg gtcccattgc    6600
aagaagtgcc tatggataga ttcgtcatgg acatgaaaag agacgtgaaa gttacaccag    6660
gcacgaaaca cacagaagaa agaccgaaag tacaagtgat acaagccgca gaaccccctgg   6720 cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca ctttttgtca    7080
acacagtttt gaatgtcgtt atcgccagca gagtactaga agagcggctt aaaacgtcca    7140
gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
cgtgccgcgt ggcggatccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt ttgcccagag caaaagagca ttccaagcca    7560
tcagagggga aataaagcat ctctacggtg gtcctaaata gtcagcatag tacatttcat    7620
ctgactaata ctacaacacc accaccatga atagaggatt ctttaacatg ctcggccgcc    7680
gccccttccc ggccccact gccatgtgga ggccgcggag aaggaggcag gcggcccga    7740 tgcctgcccg caacgggctg gcttctcaaa tccagcaact gaccacagcc gtcagtgccc    7800
tagtcattgg acaggcaact agacctcaac ccccacgtcc acgcccgcca ccgcgccaga    7860
agaagcaggc gcccaagcaa ccaccgaagc cgaagaaacc aaaaacgcag gagaagaaga    7920
agaagcaacc tgcaaaaccc aaacccggaa agagacagcg catggcactt aagttggagg    7980
ccgacagatt gttcgacgtc aagaacgagg acggagatgt catcgggcac gcactggcca    8040
tggaaggaaa ggtaatgaaa cctctgcacg tgaaggaac catcgaccac cctgtgctat    8100
caaagctcaa atttaccaag tcgtcagcat acgacatgga gttcgcacag ttgccagtca    8160
acatgagaag tgaggcattc acctacacca gtgaacaccc cgaaggattc tataactggc    8220
accacggagc ggtgcagtat agtggaggta gatttaccat ccctcgcgga gtaggaggca    8280
gaggagacag cggtcgtccg atcatggata actccggtcg ggttgtcgcg atagtcctcg    8340
gtggcgctga tgaaggaaca cgaactgccc tttcggtcgt cacctggaat agtaaaggga    8400
agacaattaa gacgacccg gaagggacag aagagtggtc cgcagcacca ctggtcacgg    8460
caatgtgttt gctcggaaat gtgagcttcc catgcgaccg cccgcccaca tgctataccc    8520
```

```
gcgaaccttc cagagccctc gacatccttg aagagaacgt gaaccatgag gcctacgata    8580
ccctgctcaa tgccatattg cggtgcggat cgtctggcag aagcaaaaga agcgtcgttg    8640
acgactttac cctgaccagc ccctacttgg gcacatgctc gtactgccac catactgaac    8700
cgtgcttcag ccctgttaag atcgagcagg tctgggacga agcggacgat aacaccatac    8760
gcatacagac ttccgcccag tttggatacg accaaagcgg agcagcaagc gcaaacaagt    8820
accgctacat gtcgcttaag caggatcaca ccgttaaaga aggcaccatg gatgacatca    8880
agattagcac ctcaggaccg tgtagaaggc ttagctacaa aggatacttt ctcctcgcaa    8940
aatgccctcc aggggacagc gtaacggtta gcatagtgag tagcaactca gcaacgtcat    9000
gtacactggc ccgcaagata aaaccaaaat tcgtgggacg ggaaaaatat gatctacctc    9060
ccgttcacgg taaagaatt ccttgcacag tgtacgaccg tctgaaaaca actgcaggct     9120
acatcactat gcacaggccg ggaccgcacg cttatacatc ctacctggaa gaatcatcag    9180
ggaaagttta cgcaaagccg ccatctggga agaacattac gtatgagtgc aagtgcggcg    9240
actacaagac cggaaccgtt tcgacccgca ccgaaatcac tggttgcacc gccatcaagc    9300
agtgcgtcgc ctataagagc gaccaaacga agtgggtctt caactcaccg gacttgatca    9360
gacatgacga ccacacggcc caagggaaat tgcatttgcc tttcaagttg atcccgggtg    9420
cctgcatggt ccctgttgcc cacgcgccga atgtaataca tggctttaaa cacatcagcc    9480
tccaattaga tacagaccac ttgacattgc tcaccaccag gagactaggg gcaaacccgg    9540
aaccaaccac tgaatggatc gtcggaaaga cggtcagaaa cttcaccgtc gaccgagatg    9600
gcctggaata catatgggga aatcatgagc cagtgagggt ctatgcccaa gagtcagcac    9660
caggagaccc tcacggatgg ccacacgaaa tagtacagca ttactaccat cgccatcctg    9720
tgtacaccat cttagccgtc gcatcagcta ccgtggcgat gatgattggc gtaactgttg    9780
cagtgttatg tgcctgtaaa gcgcgccgtg agtgcctgac gccatacgcc ctggcccaa    9840
acgccgtaat cccaacttcg ctggcactct tgtgctgcgt taggtcggcc aatgctgaaa    9900
cgttcaccga gaccatgagt tacttgtggt cgaacagtca gccgttcttc tgggtccagt    9960
tgtgcatacc tttggccgcg ttcatcgttc taatgcgcta ctgctcctgc tgcctgcctt   10020
ttttagtggt tgccggcgcc tacctggcga aggtagacgc ctacgaacat gcgaccactg   10080
ttccaaatgt gccacagata ccgtataagg cacttgttga aagggcaggg tatgccccgc   10140
tcaatttgga gatcactgtc atgtcctcgg aggttttgcc ttccaccaac caagagtaca   10200
ttacctgcaa attcaccact gtggtcccct ccccaaaaat caaatgctgc ggctccttgg   10260
aatgtcagcc ggccgctcat gcagactata cctgcaaggt cttcggaggg gtctaccct    10320
ttatgtgggg aggagcgcaa tgtttttgcg acagtgagaa cagccagatg agtgaggcgt   10380
acgtcgaatt gtcagcagat tgcgcgtctg accacgcgca ggcgattaag gtgcacactg   10440
ccgcgatgaa agtaggactg cgtatagtgt acgggaacac taccagtttc ctagatgtgt   10500
acgtgaacgg agtcacacca ggaacgtcta aagacttgaa agtcatagct ggaccaattt   10560
cagcatcgtt tacgccattc gatcataagg tcgttatcca tcgcggcctg gtgtacaact   10620
atgacttccc ggaatatgga gcgatgaaac caggagcgtt cggagacatt caagctacct   10680
ccttgactag caaggatctc atcgccagca cagacattag gctactcaag ccttccgcca   10740
agaacgtgca tgtcccgtac acgcaggccg catcaggatt tgagatgtgg aaaaacaact   10800
caggccgccc actgcaggaa accgcacctt cgggtgtaa gattgcagta aatccgctcc    10860
gagcggtgga ctgttcatac gggaacattc ccatttctat tgacatcccg aacgctgcct   10920
```

```
ttatcaggac atcagatgca ccactggtct caacagtcaa atgtgaagtc agtgagtgca   10980
cttattcagc agacttcggc gggatggcca ccctgcagta tgtatccgac cgcgaaggtc   11040
aatgccccgt acattcgcat tcgagcacag caactctcca agagtcgaca gtacatgtcc   11100
tggagaaagg agcggtgaca gtacacttta gcaccgcgag tccacaggcg aactttatcg   11160
tatcgctgtg tgggaagaag acaacatgca atgcagaatg taaaccacca gctgaccata   11220
tcgtgagcac cccgcacaaa aatgaccaag aatttcaagc cgccatctca aaaacatcat   11280
ggagttggct gtttgccctt ttcggcggcg cctcgtcgct attaattata ggacttatga   11340
tttttgcttg cagcatgatg ctgactagca cacgaagatg accgctacgc cccaatgatc   11400
cgaccagcaa aactcgatgt acttccgagg aactgatgtg cataatgcat caggctggta   11460
cattagatcc ccgcttaccg cgggcaatat agcaacacta aaaactcgat gtacttccga   11520
ggaagcgcag tgcataatgc tgcgcagtgt tgccacataa ccactatatt aaccatttat   11580
ctagcggacg ccaaaaactc aatgtatttc tgaggaagcg tggtgcataa tgccacgcag   11640
cgtctgcata acttttatta tttctttat taatcaacaa aattttgttt ttaacatttc   11700
aaaaaaaaaa aaaaaaaaaa aaaaatctag agggccctat tctatagtgt cacctaaatg   11760
ctagagctcg ctgatcagcc tcgactgtgc cttctagttg ccagccatct gttgtttgcc   11820
cctcccccgt gccttccttg accctggaag gtgccactcc cactgtcctt tcctaataaa   11880
atgaggaaat tgcatcgcat tgtctgagta ggtgtcattc tattctgggg ggtggggtgg   11940
ggcaggacag caaggggag gattgggaag acaatagcag gcatgctggg gatgcggtgg   12000
gctctatggc ttctgaggcg gaaagaacca gctgggctc taggggggtat ccccacgcgc   12060
cctgtagcgg cgcattaagc gcggcgggtg tggtggttac gcgcagcgtg accgctacac   12120
ttgccagcgc cctagcgccc gctcctttcg ctttcttccc ttcctttctc gccacgttcg   12180
ccggcttttcc ccgtcaagct ctaaatcggg gcatcccttt agggttccga tttagtgctt   12240
tacggcacct cgaccccaaa aaacttgatt agggtgatgg ttcacgtagt gggccatcgc   12300
cctgatagac ggttttttcgc cctttgacgt tggagtccac gttctttaat agtggactct   12360
tgttccaaac tggaacaaca ctcaacccta tctcggtcta ttcttttgat ttataaggga   12420
ttttggggat tcggcctat tggttaaaaa atgagctgat ttaacaaaaa tttaacgcga   12480
attaattctg tggaatgtgt gtcagttagg gtgtggaaag tccccaggct ccccaggcag   12540
gcagaagtat gcaaagcatg catctcaatt agtcagcaac caggtgtgga aagtccccag   12600
gctccccagc aggcagaagt atgcaaagca tgcatctcaa ttagtcagca accatagtcc   12660
cgcccctaac tccgcccatc ccgcccctaa ctccgcccag ttccgcccat tctccgcccc   12720
atggctgact aattttttt atttatgcag aggccgaggc cgcctctgcc tctgagctat   12780
tccagaagta gtgaggaggc ttttttggag gcctaggctt ttgcaaaaag ctcccgggag   12840
cttgtatatc cattttcgga tctgatcaag agacaggatg aggatcgttt cgcatgattg   12900
aacaagatgg attgcacgca ggttctccgg ccgcttgggt ggagaggcta ttcggctatg   12960
actgggcaca acagacaatc ggctgctctg atgccgccgt gttccggctg tcagcgcagg   13020
ggcgcccggt tctttttgtc aagaccgacc tgtccggtgc cctgaatgaa ctgcaggacg   13080
aggcagcgcg gctatcgtgg ctggccacga cgggcgttcc ttgcgcagct gtgctcgacg   13140
ttgtcactga agcgggaagg gactggctgc tattgggcga agtgccgggg caggatctcc   13200
tgtcatctca ccttgctcct gccgagaaag tatccatcat ggctgatgca atgcggcggc   13260
tgcatacgct tgatccggct acctgcccat tcgaccacca agcgaaacat cgcatcgagc   13320
```

```
gagcacgtac tcggatggaa gccggtcttg tcgatcagga tgatctggac gaagagcatc    13380
aggggctcgc gccagccgaa ctgttcgcca ggctcaaggc gcgcatgccc gacggcgagg    13440
atctcgtcgt gacccatggc gatgcctgct tgccgaatat catggtggaa aatggccgct    13500
tttctggatt catcgactgt ggccggctgg gtgtggcgga ccgctatcag gacatagcgt    13560
tggctacccg tgatattgct gaagagcttg gcggcgaatg ggctgaccgc ttcctcgtgc    13620
tttacggtat cgccgctccc gattcgcagc gcatcgcctt ctatcgcctt cttgacgagt    13680
tcttctgagc gggactctgg ggttcgaaat gaccgaccaa gcgacgccca acctgccatc    13740
acgagatttc gattccaccg ccgccttcta tgaaaggttg ggcttcggaa tcgttttccg    13800
ggacgccggc tggatgatcc tccagcgcgg ggatctcatg ctggagttct tcgcccaccc    13860
caacttgttt attgcagctt ataatggtta caaataaagc aatagcatca caaatttcac    13920
aaataaagca ttttttttcac tgcattctag ttgtggtttg tccaaactca tcaatgtatc    13980
ttatcatgtc tgtataccgt cgacctctag ctagagcttg gcgtaatcat ggtcatagct    14040
gtttcctgtg tgaaattgtt atccgctcac aattccacac aacatacgag ccggaagcat    14100
aaagtgtaaa gcctggggtg cctaatgagt gagctaactc acattaattg cgttgcgctc    14160
actgcccgct ttccagtcgg gaaacctgtc gtgccagctg cattaatgaa tcggccaacg    14220
cgcggggaga ggcggtttgc gtattgggcg ctcttccgct tcctcgctca ctgactcgct    14280
gcgctcggtc gttcggctgc ggcgagcggt atcagctcac tcaaaggcgg taatacggtt    14340
atccacagaa tcaggggata acgcaggaaa gaacatgtga gcaaaaggcc agcaaaaggc    14400
caggaaccgt aaaaaggccg cgttgctggc gtttttccat aggctccgcc cccctgacga    14460
gcatcacaaa aatcgacgct caagtcagag gtggcgaaac ccgacaggac tataaagata    14520
ccaggcgttt ccccctggaa gctccctcgt gcgctctcct gttccgaccc tgccgcttac    14580
cggatacctg tccgcctttc tcccttcggg aagcgtggcg ctttctcaat gctcacgctg    14640
taggtatctc agttcggtgt aggtcgttcg ctccaagctg ggctgtgtgc acgaaccccc    14700
cgttcagccc gaccgctgcg ccttatccgg taactatcgt cttgagtcca acccggtaag    14760
acacgactta tcgccactgg cagcagccac tggtaacagg attagcagag cgaggtatgt    14820
aggcggtgct acagagttct tgaagtggtg gcctaactac ggctacacta agaggacagt    14880
atttggtatc tgcgctctgc tgaagccagt taccttcgga aaaagagttg gtagctcttg    14940
atccggcaaa caaaccaccg ctggtagcgg tggtttttt gtttgcaagc agcagattac    15000
gcgcagaaaa aaaggatctc aagaagatcc tttgatcttt tctacggggt ctgacgctca    15060
gtggaacgaa aactcacgtt aagggatttt ggtcatgaga ttatcaaaaa ggatcttcac    15120
ctagatcctt ttaaattaaa aatgaagttt taaatcaatc taaagtatat atgagtaaac    15180
ttggtctgac agttaccaat gcttaatcag tgaggcacct atctcagcga tctgtctatt    15240
tcgttcatcc atagttgcct gactccccgt cgtgtagata actacgatac gggagggctt    15300
accatctggc cccagtgctg caatgatacc gcgagaccca cgctcaccgg ctccagattt    15360
atcagcaata aaccagccag ccggaagggc cgagcgcaga agtggtcctg caactttatc    15420
cgcctccatc cagtctatta attgttgccg ggaagctaga gtaagtagtt cgccagttaa    15480 tagtttcgc aacgttgttg ccattgctac aggcatcgtg gtgtcacgct cgtcgtttgg    15540
tatggcttca ttcagctccg gttcccaacg atcaaggcga gttacatgat cccccatgtt    15600
gtgcaaaaaa gcggttagct ccttcggtcc tccgatcgtt gtcagaagta agttggccgc    15660
agtgttatca ctcatggtta tggcagcact gcataattct cttactgtca tgccatccgt    15720
```

```
aagatgcttt tctgtgactg gtgagtactc aaccaagtca ttctgagaat agtgtatgcg    15780
gcgaccgagt tgctcttgcc cggcgtcaat acgggataat accgcgccac atagcagaac    15840
tttaaaagtg ctcatcattg gaaaacgttc ttcggggcga aaactctcaa ggatcttacc    15900
gctgttgaga tccagttcga tgtaacccac tcgtgcaccc aactgatctt cagcatcttt    15960
tactttcacc agcgtttctg ggtgagcaaa acaggaagg  caaaatgccg caaaaaggg     16020 aataagggcg acacggaaat gttgaatact catactcttc cttttcaat  attattgaag    16080 catttatcag ggttattgtc tcatgagcgg atacatattt gaatgtattt agaaaaataa    16140
acaaataggg gttccgcgca catttccccg aaaagtgcca cctgacgtcg acggatcggg    16200
agatctaatg aaagacccca cctgtaggtt tggcaagcta gcttaagtaa cgccattttg    16260
caaggcatgg aaaatacat  aactgagaat agagaagttc agatcaaggt caggaacaga    16320
tggaacagct gaatatgggc caaacaggat atctgtggta agcagttcct gccccggctc    16380
agggccaaga acagatggaa cagctgaata tgggccaaac aggatatctg tggtaagcag    16440
ttcctgcccc ggctcagggc caagaacaga tggtccccag atgcggtcca gccctcagca    16500
gtttctagag aaccatcaga tgtttccagg gtgcccaag  gacctgaaat gaccctgtgc    16560
cttatttgaa ctaaccaatc agttcgcttc tcgcttctgt tcgcgcgctt ctgctccccg    16620
agctcaataa aagagcccac aaccctcac tcgggg                              16656

<210> SEQ ID NO 2
<211> LENGTH: 24
<212> TYPE: DNA
<213> ORGANISM: Artificial Sequence
<220> FEATURE:
<223> OTHER INFORMATION: Minimal junction region core

<400> SEQUENCE: 2
atctctacgg tggtcctaaa tagt                                           24

<210> SEQ ID NO 3
<211> LENGTH: 42
<212> TYPE: DNA
<213> ORGANISM: Artificial Sequence
<220> FEATURE:
<223> OTHER INFORMATION: cDNA primer

<400> SEQUENCE: 3
tatattctag attttttttt tttttttttt tttttttgaaa tg                      42

<210> SEQ ID NO 4
<211> LENGTH: 48
<212> TYPE: DNA
<213> ORGANISM: Artificial Sequence
<220> FEATURE:
<223> OTHER INFORMATION: primer SP6-1A

<400> SEQUENCE: 4
tatatgggcc cgatttaggt gacactatag attgacggcg tagtacac                 48

<210> SEQ ID NO 5
<211> LENGTH: 23
<212> TYPE: DNA
<213> ORGANISM: Artificial Sequence
<220> FEATURE:
<223> OTHER INFORMATION: primer 1B

<400> SEQUENCE: 5
ctggcaaccg gtaagtacga tac                                            23
```

```
<210> SEQ ID NO 6
<211> LENGTH: 21
<212> TYPE: DNA
<213> ORGANISM: Artificial Sequence
<220> FEATURE:
<223> OTHER INFORMATION: Primer 2A

<400> SEQUENCE: 6
atactagcca cggccggtat c                                          21

<210> SEQ ID NO 7
<211> LENGTH: 21
<212> TYPE: DNA
<213> ORGANISM: Artificial Sequence
<220> FEATURE:
<223> OTHER INFORMATION: Primer 2B

<400> SEQUENCE: 7
tcctctttcg acgtgtcgag c                                          21

<210> SEQ ID NO 8
<211> LENGTH: 21
<212> TYPE: DNA
<213> ORGANISM: Artificial Sequence
<220> FEATURE:
<223> OTHER INFORMATION: Primer 3A

<400> SEQUENCE: 8
accttggagc gcaatgtcct g                                          21

<210> SEQ ID NO 9
<211> LENGTH: 21
<212> TYPE: DNA
<213> ORGANISM: Artificial Sequence
<220> FEATURE:
<223> OTHER INFORMATION: Primer 7349R

<400> SEQUENCE: 9
ccttttcagg ggatccgcca c                                          21

<210> SEQ ID NO 10
<211> LENGTH: 21
<212> TYPE: DNA
<213> ORGANISM: Artificial Sequence
<220> FEATURE:
<223> OTHER INFORMATION: Primer 7328F

<400> SEQUENCE: 10
gtggcggatc ccctgaaaag g                                          21

<210> SEQ ID NO 11
<211> LENGTH: 20
<212> TYPE: DNA
<213> ORGANISM: Artificial Sequence
<220> FEATURE:
<223> OTHER INFORMATION: Primer 3B

<400> SEQUENCE: 11
tgggccgtgt ggtcgtcatg                                            20

<210> SEQ ID NO 12
<211> LENGTH: 21
<212> TYPE: DNA
<213> ORGANISM: Artificial Sequence
<220> FEATURE:
<223> OTHER INFORMATION: Primer 4A
```

```
<400> SEQUENCE: 12
tgggtcttca actcaccgga c                                              21

<210> SEQ ID NO 13
<211> LENGTH: 22
<212> TYPE: DNA
<213> ORGANISM: Artificial Sequence
<220> FEATURE:
<223> OTHER INFORMATION: Primer 10394R

<400> SEQUENCE: 13
caattcgacg tacgcctcac tc                                             22

<210> SEQ ID NO 14
<211> LENGTH: 22
<212> TYPE: DNA
<213> ORGANISM: Artificial Sequence
<220> FEATURE:
<223> OTHER INFORMATION: Primer 10373F

<400> SEQUENCE: 14
gagtgaggcg tacgtcgaat tg                                             22

<210> SEQ ID NO 15
<211> LENGTH: 33
<212> TYPE: DNA
<213> ORGANISM: Artificial Sequence
<220> FEATURE:
<223> OTHER INFORMATION: Forward Primer BAGbg12F1

<400> SEQUENCE: 15
tatatagatc taatgaaaga ccccacctgt agg                                 33

<210> SEQ ID NO 16
<211> LENGTH: 40
<212> TYPE: DNA
<213> ORGANISM: Artificial Sequence
<220> FEATURE:
<223> OTHER INFORMATION: Reverse primer BAGwt441R2

<400> SEQUENCE: 16
tcaatccccg agtgaggggt tgtgggctct tttattgagc                          40

<210> SEQ ID NO 17
<211> LENGTH: 36
<212> TYPE: DNA
<213> ORGANISM: Artificial Sequence
<220> FEATURE:
<223> OTHER INFORMATION: Forward Primer Mo-MLV LTR

<400> SEQUENCE: 17
ccacaacccc tcactcgggg attgacggcg tagtac                              36

<210> SEQ ID NO 18
<211> LENGTH: 23
<212> TYPE: DNA
<213> ORGANISM: Artificial Sequence
<220> FEATURE:
<223> OTHER INFORMATION: Reverse Primer SIN 3182-3160

<400> SEQUENCE: 18
ctggcaaccg gtaagtacga tac                                            23

<210> SEQ ID NO 19
<211> LENGTH: 22
<212> TYPE: DNA
```

```
<213> ORGANISM: Artificial Sequence
<220> FEATURE:
<223> OTHER INFORMATION: Reverse Primer SIN 2300-2278

<400> SEQUENCE: 19
ggtaacaaga tctcgtgccg tg                                              22

<210> SEQ ID NO 20
<211> LENGTH: 53
<212> TYPE: DNA
<213> ORGANISM: Artificial Sequence
<220> FEATURE:
<223> OTHER INFORMATION: Forward Primer SIN11664F

<400> SEQUENCE: 20
tatatatata tgcggccgct ttcttttatt aatcaacaaa attttgtttt taa            53

<210> SEQ ID NO 21
<211> LENGTH: 48
<212> TYPE: DNA
<213> ORGANISM: Artificial Sequence
<220> FEATURE:
<223> OTHER INFORMATION: Reverse Primer SINSac11700R

<400> SEQUENCE: 21
tatatgagct cttttttttt ttttttttt tttttgaaa tgttaaaa                    48

<210> SEQ ID NO 22
<211> LENGTH: 34
<212> TYPE: DNA
<213> ORGANISM: Artificial Sequence
<220> FEATURE:
<223> OTHER INFORMATION: Reverse Primer SINXho7643R

<400> SEQUENCE: 22
tatatctcga gggtggtgtt gtagtattag tcag                                 34

<210> SEQ ID NO 23
<211> LENGTH: 43
<212> TYPE: DNA
<213> ORGANISM: Artificial Sequence
<220> FEATURE:
<223> OTHER INFORMATION: Reverse primer SIN 7597-7566

<400> SEQUENCE: 23
tatatgggcc cttaagacca tcggagcgat gctttatttc ccc                       43

<210> SEQ ID NO 24
<211> LENGTH: 18
<212> TYPE: DNA
<213> ORGANISM: Artificial Sequence
<220> FEATURE:
<223> OTHER INFORMATION: 3' end of NSP 4

<400> SEQUENCE: 24
tctctacggt ggtcctaa                                                   18

<210> SEQ ID NO 25
<211> LENGTH: 5
<212> TYPE: PRT
<213> ORGANISM: Artificial Sequence
<220> FEATURE:
<223> OTHER INFORMATION: amino acids at 3' end of NSP 4

<400> SEQUENCE: 25

Ser Leu Arg Trp Ser
1               5
```

<210> SEQ ID NO 26
<211> LENGTH: 26
<212> TYPE: DNA
<213> ORGANISM: Artificial Sequence
<220> FEATURE:
<223> OTHER INFORMATION: recognition oligonucleotide 1

<400> SEQUENCE: 26
catctctacg gtggtcctaa atagtc                                    26

<210> SEQ ID NO 27
<211> LENGTH: 34
<212> TYPE: DNA
<213> ORGANISM: Artificial Sequence
<220> FEATURE:
<223> OTHER INFORMATION: recognition oligonucleotide 2

<400> SEQUENCE: 27
tcgagactat ttaggaccac cgtagagatg ggcc                           34

<210> SEQ ID NO 28
<211> LENGTH: 25
<212> TYPE: DNA
<213> ORGANISM: Artificial Sequence
<220> FEATURE:
<223> OTHER INFORMATION: oligonucleotide 1 SIN7598

<400> SEQUENCE: 28
cccttgtacg gctaacctaa aggac                                     25

<210> SEQ ID NO 29
<211> LENGTH: 33
<212> TYPE: DNA
<213> ORGANISM: Artificial Sequence
<220> FEATURE:
<223> OTHER INFORMATION: oligonucleotide 2 SIN7598

<400> SEQUENCE: 29
tcgagtcctt taggttagcc gtacaagggg gcc                            33

<210> SEQ ID NO 30
<211> LENGTH: 26
<212> TYPE: DNA
<213> ORGANISM: Artificial Sequence
<220> FEATURE:
<223> OTHER INFORMATION: oligonucleotide 1 SIN7582

<400> SEQUENCE: 30
catcgctacg gtggtcctaa atagtc                                    26

<210> SEQ ID NO 31
<211> LENGTH: 34
<212> TYPE: DNA
<213> ORGANISM: Artificial Sequence
<220> FEATURE:
<223> OTHER INFORMATION: oligonucleotide 2 SIN7582

<400> SEQUENCE: 31
tcgagactat ttaggaccac cgtagcgatg ggcc                           34

<210> SEQ ID NO 32
<211> LENGTH: 48
<212> TYPE: DNA
<213> ORGANISM: Artificial Sequence
<220> FEATURE:
<223> OTHER INFORMATION: 46 SINnts 1

```
<400> SEQUENCE: 32
cggaaataaa gcatctctac ggtggtccta aatagtcagc atagtacc                    48

<210> SEQ ID NO 33
<211> LENGTH: 56
<212> TYPE: DNA
<213> ORGANISM: Artificial Sequence
<220> FEATURE:
<223> OTHER INFORMATION: 46 SINnts 2

<400> SEQUENCE: 33
tcgaggtact atgctgacta tttaggacca ccgtagagat gctttatttc cgggcc           56

<210> SEQ ID NO 34
<211> LENGTH: 41
<212> TYPE: DNA
<213> ORGANISM: Artificial Sequence
<220> FEATURE:
<223> OTHER INFORMATION: reverse primer LucStop

<400> SEQUENCE: 34
tatatgcggc cgctctagat tacaatttgg actttccgcc c                           41

<210> SEQ ID NO 35
<211> LENGTH: 44
<212> TYPE: DNA
<213> ORGANISM: Artificial Sequence
<220> FEATURE:
<223> OTHER INFORMATION: forward primer SSVTT 2643

<400> SEQUENCE: 35
tatatatgag ctcttacaaa taaagcaata gcatcacaaa tttc                        44

<210> SEQ ID NO 36
<211> LENGTH: 36
<212> TYPE: DNA
<213> ORGANISM: Artificial Sequence
<220> FEATURE:
<223> OTHER INFORMATION: reverse primer RSVTT2563R

<400> SEQUENCE: 36
tatatgaatt cgtttggaca aaccacaact agaatg                                 36

<210> SEQ ID NO 37
<211> LENGTH: 44
<212> TYPE: DNA
<213> ORGANISM: Artificial Sequence
<220> FEATURE:
<223> OTHER INFORMATION: forward primer BGHTTF

<400> SEQUENCE: 37
tatatatgag ctctaataaa atgaggaaat tgcatcgcat tgtc                        44

<210> SEQ ID NO 38
<211> LENGTH: 43
<212> TYPE: DNA
<213> ORGANISM: Artificial Sequence
<220> FEATURE:
<223> OTHER INFORMATION: reverse primer BGHTTR

<400> SEQUENCE: 38
tatatgaatt catagaatga cacctactca gacaatgcga tgc                         43

<210> SEQ ID NO 39
<211> LENGTH: 46
```

-continued

```
<212> TYPE: DNA
<213> ORGANISM: Artificial Sequence
<220> FEATURE:
<223> OTHER INFORMATION: forward primer SHDV1F

<400> SEQUENCE: 39
tatatgagct cgggtcggca tggcatctcc acctcctcgc ggtccg              46

<210> SEQ ID NO 40
<211> LENGTH: 52
<212> TYPE: DNA
<213> ORGANISM: Artificial Sequence
<220> FEATURE:
<223> OTHER INFORMATION: nested primer HDV17-68

<400> SEQUENCE: 40
tccacctcct cgcggtccga cctgggcatc cgaaggagga cgcacgtcca ct        52

<210> SEQ ID NO 41
<211> LENGTH: 48
<212> TYPE: DNA
<213> ORGANISM: Artificial Sequence
<220> FEATURE:
<223> OTHER INFORMATION: reverse primer SHDV84R

<400> SEQUENCE: 41
tatatgagct cctcccttag ccatccgagt ggacgtgcgt cctccttc            48

<210> SEQ ID NO 42
<211> LENGTH: 47
<212> TYPE: DNA
<213> ORGANISM: Artificial Sequence
<220> FEATURE:
<223> OTHER INFORMATION: forward primer SIN11664F

<400> SEQUENCE: 42
tatatgcggc cgctttcttt tattaatcaa caaaattttg tttttaa              47

<210> SEQ ID NO 43
<211> LENGTH: 37
<212> TYPE: DNA
<213> ORGANISM: Artificial Sequence
<220> FEATURE:
<223> OTHER INFORMATION: reverse primer SSIN11700R

<400> SEQUENCE: 43
tatatgagct cgaaatgtta aaacaaaat tttgttg                          37

<210> SEQ ID NO 44
<211> LENGTH: 34
<212> TYPE: DNA
<213> ORGANISM: Artificial Sequence
<220> FEATURE:
<223> OTHER INFORMATION: forward primer pCBgl233F

<400> SEQUENCE: 44
tatatataga tctttgacat tgattattga ctag                            34

<210> SEQ ID NO 45
<211> LENGTH: 42
<212> TYPE: DNA
<213> ORGANISM: Artificial Sequence
<220> FEATURE:
<223> OTHER INFORMATION: reverse primer SNCMV1142R

<400> SEQUENCE: 45
ccgtcaatac ggttcactaa acgagctctg cttatataga cc                   42
```

<210> SEQ ID NO 46
<211> LENGTH: 38
<212> TYPE: DNA
<213> ORGANISM: Artificial Sequence
<220> FEATURE:
<223> OTHER INFORMATION: forward primer CMVSIN1F

<400> SEQUENCE: 46
gctcgtttag tgaaccgtat tgacggcgta gtacacac                                    38

<210> SEQ ID NO 47
<211> LENGTH: 33
<212> TYPE: DNA
<213> ORGANISM: Artificial Sequence
<220> FEATURE:
<223> OTHER INFORMATION: forward primer B2SVpr250F

<400> SEQUENCE: 47
tatatataga tctggtgtgg aaagtcccca ggc                                         33

<210> SEQ ID NO 48
<211> LENGTH: 31
<212> TYPE: DNA
<213> ORGANISM: Artificial Sequence
<220> FEATURE:
<223> OTHER INFORMATION: reverse primer SINSV5235R

<400> SEQUENCE: 48
ctacgccgtc aatgccgagg cggcctcggc c                                           31

<210> SEQ ID NO 49
<211> LENGTH: 37
<212> TYPE: DNA
<213> ORGANISM: Artificial Sequence
<220> FEATURE:
<223> OTHER INFORMATION: forward primer SVSIN1F

<400> SEQUENCE: 49
ggccgcctcg gcattgacgg cgtagtacac actattg                                     37

<210> SEQ ID NO 50
<211> LENGTH: 41
<212> TYPE: DNA
<213> ORGANISM: Artificial Sequence
<220> FEATURE:
<223> OTHER INFORMATION: forward primer XSVSD4647F

<400> SEQUENCE: 50
tatatatctc gagaagctct aaggtaaata taaaatttac c                                 41

<210> SEQ ID NO 51
<211> LENGTH: 38
<212> TYPE: DNA
<213> ORGANISM: Artificial Sequence
<220> FEATURE:
<223> OTHER INFORMATION: reverse primer XSVSA4562R

<400> SEQUENCE: 51
tatatatctc gagaggttgg aatctaaaat acacaaac                                    38

<210> SEQ ID NO 52
<211> LENGTH: 43
<212> TYPE: DNA
<213> ORGANISM: Artificial Sequence
<220> FEATURE:
<223> OTHER INFORMATION: forward primer NSVSD4647F

```
<400> SEQUENCE: 52
tatatatgcg gccgcaagct ctaaggtaaa tataaaattt acc            43

<210> SEQ ID NO 53
<211> LENGTH: 40
<212> TYPE: DNA
<213> ORGANISM: Artificial Sequence
<220> FEATURE:
<223> OTHER INFORMATION: reverse primer XSVSA4562R

<400> SEQUENCE: 53
tatatatgcg gccgcaggtt ggaatctaaa atacacaaac                40

<210> SEQ ID NO 54
<211> LENGTH: 35
<212> TYPE: DNA
<213> ORGANISM: Artificial Sequence
<220> FEATURE:
<223> OTHER INFORMATION: SINBVLinkF

<400> SEQUENCE: 54
tcgagcacgt ggcgcgcctg atcacgcgta ggcct                    35

<210> SEQ ID NO 55
<211> LENGTH: 35
<212> TYPE: DNA
<213> ORGANISM: Artificial Sequence
<220> FEATURE:
<223> OTHER INFORMATION: SINBVLinkR

<400> SEQUENCE: 55
ctagaggcct acgcgtgatc aggcgcgcca cgtgc                    35

<210> SEQ ID NO 56
<211> LENGTH: 35
<212> TYPE: DNA
<213> ORGANISM: Artificial Sequence
<220> FEATURE:
<223> OTHER INFORMATION: Ad 2 E3 forward primer

<400> SEQUENCE: 56
tatatctcca gatgaggtac atgattttag gcttg                    35

<210> SEQ ID NO 57
<211> LENGTH: 40
<212> TYPE: DNA
<213> ORGANISM: Artificial Sequence
<220> FEATURE:
<223> OTHER INFORMATION: Ad 2 E3 reverse primer

<400> SEQUENCE: 57
tatatatcga ttcaaggcat tttcttttca tcaataaaac                40

<210> SEQ ID NO 58
<211> LENGTH: 35
<212> TYPE: DNA
<213> ORGANISM: Artificial Sequence
<220> FEATURE:
<223> OTHER INFORMATION: HCMV H301 forward primer

<400> SEQUENCE: 58
tatatctcca gatgatgaca atgtggtgtc tgacg                    35

<210> SEQ ID NO 59
<211> LENGTH: 32
```

```
<212> TYPE: DNA
<213> ORGANISM: Artificial Sequence
<220> FEATURE:
<223> OTHER INFORMATION: HCMV H301 reverse primer

<400> SEQUENCE: 59
tatatatcga ttcatgacga ccggaccttg cg                                    32

<210> SEQ ID NO 60
<211> LENGTH: 28
<212> TYPE: DNA
<213> ORGANISM: Artificial Sequence
<220> FEATURE:
<223> OTHER INFORMATION: EMCV IRES forward primer A

<400> SEQUENCE: 60
tatatgggcc ccccccccc ccccaacg                                          28

<210> SEQ ID NO 61
<211> LENGTH: 30
<212> TYPE: DNA
<213> ORGANISM: Artificial Sequence
<220> FEATURE:
<223> OTHER INFORMATION: EMCV IRES forward primer B

<400> SEQUENCE: 61
tatatatcga tcccccccccc cccccaacg                                       30

<210> SEQ ID NO 62
<211> LENGTH: 34
<212> TYPE: DNA
<213> ORGANISM: Artificial Sequence
<220> FEATURE:
<223> OTHER INFORMATION: EMCV IRES reverse primer

<400> SEQUENCE: 62
tatatccatg gcttacaatc gtggttttca aagg                                  34

<210> SEQ ID NO 63
<211> LENGTH: 33
<212> TYPE: DNA
<213> ORGANISM: Artificial Sequence
<220> FEATURE:
<223> OTHER INFORMATION: Polio IRES forward primer A

<400> SEQUENCE: 63
tatatgggcc ctcgatgagt ctggacgttc ctc                                   33

<210> SEQ ID NO 64
<211> LENGTH: 33
<212> TYPE: DNA
<213> ORGANISM: Artificial Sequence
<220> FEATURE:
<223> OTHER INFORMATION: Polio IRES forward primer B

<400> SEQUENCE: 64
tatatatcga ttcgatgagt ctggacgttc ctc                                   33

<210> SEQ ID NO 65
<211> LENGTH: 37
<212> TYPE: DNA
<213> ORGANISM: Artificial Sequence
<220> FEATURE:
<223> OTHER INFORMATION: Polio IRES reverse primer

<400> SEQUENCE: 65
tatatccatg gatccaattt gctttatgat aacaatc                               37
```

```
<210> SEQ ID NO 66
<211> LENGTH: 30
<212> TYPE: DNA
<213> ORGANISM: Artificial Sequence
<220> FEATURE:
<223> OTHER INFORMATION: pGEM5ZBiP 5' forward primer

<400> SEQUENCE: 66
tatatgggcc cggtcgacgc cggccaagac                                    30

<210> SEQ ID NO 67
<211> LENGTH: 30
<212> TYPE: DNA
<213> ORGANISM: Artificial Sequence
<220> FEATURE:
<223> OTHER INFORMATION: BiP forward primer

<400> SEQUENCE: 67
tatatatcga tggtcgacgc cggccaagac                                    30

<210> SEQ ID NO 68
<211> LENGTH: 32
<212> TYPE: DNA
<213> ORGANISM: Artificial Sequence
<220> FEATURE:
<223> OTHER INFORMATION: amplification reverse primer

<400> SEQUENCE: 68
tatatccatg gtgccagcca gttgggcagc ag                                 32

<210> SEQ ID NO 69
<211> LENGTH: 23
<212> TYPE: DNA
<213> ORGANISM: Artificial Sequence
<220> FEATURE:
<223> OTHER INFORMATION: ribosomal spanning sequence

<400> SEQUENCE: 69
ttaattaacg gccgccacca tgg                                           23

<210> SEQ ID NO 70
<211> LENGTH: 13
<212> TYPE: DNA
<213> ORGANISM: Artificial Sequence
<220> FEATURE:
<223> OTHER INFORMATION: read through sense oligonucleotide

<400> SEQUENCE: 70
taacggccgc cac                                                      13

<210> SEQ ID NO 71
<211> LENGTH: 20
<212> TYPE: DNA
<213> ORGANISM: Artificial Sequence
<220> FEATURE:
<223> OTHER INFORMATION: read through antisense oligonucleotide

<400> SEQUENCE: 71
ccatggtggc ggccgttaat                                               20

<210> SEQ ID NO 72
<211> LENGTH: 16
<212> TYPE: DNA
<213> ORGANISM: Artificial Sequence
<220> FEATURE:
<223> OTHER INFORMATION: 12 mer oligonucleotide
```

```
<400> SEQUENCE: 72
ggtttaaaca ggagct                                                   16

<210> SEQ ID NO 73
<211> LENGTH: 16
<212> TYPE: DNA
<213> ORGANISM: Artificial Sequence
<220> FEATURE:
<223> OTHER INFORMATION: 12 mer oligonucleotide

<400> SEQUENCE: 73 cctgttttaaa ccagct                                                  16

<210> SEQ ID NO 74
<211> LENGTH: 47
<212> TYPE: DNA
<213> ORGANISM: Artificial Sequence
<220> FEATURE:
<223> OTHER INFORMATION: forward primer 7638F

<400> SEQUENCE: 74
tatatgcggc cgcaccacca ccatgaatag aggattcttt aacatgc                 47

<210> SEQ ID NO 75
<211> LENGTH: 34
<212> TYPE: DNA
<213> ORGANISM: Artificial Sequence
<220> FEATURE:
<223> OTHER INFORMATION: reverse primer 11384R

<400> SEQUENCE: 75
tatatgcggc cgctcatctt cgtgtgctag tcag                               34

<210> SEQ ID NO 76
<211> LENGTH: 61
<212> TYPE: DNA
<213> ORGANISM: Artificial Sequence
<220> FEATURE:
<223> OTHER INFORMATION: forward primer JUN7638F

<400> SEQUENCE: 76
tatatgcggc cgcatctcta cggtggtcct aaatagtacc accaccatga atagaggatt   60
c                                                                   61

<210> SEQ ID NO 77
<211> LENGTH: 25
<212> TYPE: DNA
<213> ORGANISM: Artificial Sequence
<220> FEATURE:
<223> OTHER INFORMATION: SinMCSI

<400> SEQUENCE: 77
ctcatcgatc agatctgact agttg                                         25

<210> SEQ ID NO 78
<211> LENGTH: 33
<212> TYPE: DNA
<213> ORGANISM: Artificial Sequence
<220> FEATURE:
<223> OTHER INFORMATION: SinMCSII

<400> SEQUENCE: 78
gatccaacta gtcagatctg atcgatgagg gcc                                33
```

```
<210> SEQ ID NO 79
<211> LENGTH: 56
<212> TYPE: DNA
<213> ORGANISM: Artificial Sequence
<220> FEATURE:
<223> OTHER INFORMATION: forward primer HDV49-XC

<400> SEQUENCE: 79
acttatcgat ggttctagac tcccttagcc atccgagtgg acgtgcgtcc tccttc          56

<210> SEQ ID NO 80
<211> LENGTH: 52
<212> TYPE: DNA
<213> ORGANISM: Artificial Sequence
<220> FEATURE:
<223> OTHER INFORMATION: reverse primer HKV17-68

<400> SEQUENCE: 80
tccacctcct cgcggtccga cctgggcatc cgaaggagga cgcacgtcca ct              52

<210> SEQ ID NO 81
<211> LENGTH: 57
<212> TYPE: DNA
<213> ORGANISM: Artificial Sequence
<220> FEATURE:
<223> OTHER INFORMATION: forward primer SIN-HDV

<400> SEQUENCE: 81
tcggaccgcg aggaggtgga gatgccatgc cgacccattg acggcgtagt acacact         57

<210> SEQ ID NO 82
<211> LENGTH: 36
<212> TYPE: DNA
<213> ORGANISM: Artificial Sequence
<220> FEATURE:
<223> OTHER INFORMATION: reverse primer SIN276-SPE

<400> SEQUENCE: 82
ctggactagt taatactggt gctcggaaaa cattct                                36

<210> SEQ ID NO 83
<211> LENGTH: 40
<212> TYPE: DNA
<213> ORGANISM: Artificial Sequence
<220> FEATURE:
<223> OTHER INFORMATION: forward primer Sin7632F

<400> SEQUENCE: 83
gtcaagcttg ctagctacaa caccaccacc atgaatagag                            40

<210> SEQ ID NO 84
<211> LENGTH: 40
<212> TYPE: DNA
<213> ORGANISM: Artificial Sequence
<220> FEATURE:
<223> OTHER INFORMATION: reverse primer Sin8439R

<400> SEQUENCE: 84
cagtctcgag ttactaccac tcttctgtcc cttccggggt                            40

<210> SEQ ID NO 85
<211> LENGTH: 43
<212> TYPE: DNA
<213> ORGANISM: Artificial Sequence
<220> FEATURE:
<223> OTHER INFORMATION: forward primer 8440F

<400> SEQUENCE: 85
```
tatatgcggc cgcaccacca tgtccgcagc accactggtc acg            43

<210> SEQ ID NO 86
<211> LENGTH: 34
<212> TYPE: DNA
<213> ORGANISM: Artificial Sequence
<220> FEATURE:
<223> OTHER INFORMATION: forward primer Pybg15021F

<400> SEQUENCE: 86
tatatagatc tcttgatcag cttcagaaga tggc            34

<210> SEQ ID NO 87
<211> LENGTH: 24
<212> TYPE: DNA
<213> ORGANISM: Artificial Sequence
<220> FEATURE:
<223> OTHER INFORMATION: reverse primer SINPy152R

<400> SEQUENCE: 87
tcaatggcgg gaagaggcgg ttgg            24

<210> SEQ ID NO 88
<211> LENGTH: 31
<212> TYPE: DNA
<213> ORGANISM: Artificial Sequence
<220> FEATURE:
<223> OTHER INFORMATION: forward primer Py nts 138-152/SIN nts 1-16

<400> SEQUENCE: 88
ccgcctcttc ccgccattga cggcgtagta c            31

<210> SEQ ID NO 89
<211> LENGTH: 34
<212> TYPE: DNA
<213> ORGANISM: Artificial Sequence
<220> FEATURE:
<223> OTHER INFORMATION: forward primer Pybg15021F

<400> SEQUENCE: 89
tatatagatc tcttgatcag cttcagaaga tggc            34

<210> SEQ ID NO 90
<211> LENGTH: 44
<212> TYPE: DNA
<213> ORGANISM: Artificial Sequence
<220> FEATURE:
<223> OTHER INFORMATION: forward primer VEE 7553F

<400> SEQUENCE: 90
tatatatatg cggccgcacc gccaagatgt tcccgttcca gcca            44

<210> SEQ ID NO 91
<211> LENGTH: 38
<212> TYPE: DNA
<213> ORGANISM: Artificial Sequence
<220> FEATURE:
<223> OTHER INFORMATION: reverse primer VEE 11206R

<400> SEQUENCE: 91
tatatatatg cggccgctca attatgtttc tggttggt            38

<210> SEQ ID NO 92
<211> LENGTH: 35
<212> TYPE: DNA
<213> ORGANISM: Artificial Sequence

```
<220> FEATURE:
<223> OTHER INFORMATION: sense primer sequence

<400> SEQUENCE: 92
ctcgagctcg aggcaccagc accatgcaac ttttt                          35

<210> SEQ ID NO 93
<211> LENGTH: 29
<212> TYPE: DNA
<213> ORGANISM: Artificial Sequence
<220> FEATURE:
<223> OTHER INFORMATION: anti-sense nucleotide sequence

<400> SEQUENCE: 93
ctactagatc cctagatgct ggatcttcc                                 29

<210> SEQ ID NO 94
<211> LENGTH: 29
<212> TYPE: DNA
<213> ORGANISM: Artificial Sequence
<220> FEATURE:
<223> OTHER INFORMATION: sense primer 2130-2158

<400> SEQUENCE: 94
ggaagatcca gcatctaggg atctagtag                                 29

<210> SEQ ID NO 95
<211> LENGTH: 26
<212> TYPE: DNA
<213> ORGANISM: Artificial Sequence
<220> FEATURE:
<223> OTHER INFORMATION: anti-sense nucleotide sequence SK+

<400> SEQUENCE: 95
gggcgatatc aagcttatcg ataccg                                    26

<210> SEQ ID NO 96
<211> LENGTH: 26
<212> TYPE: DNA
<213> ORGANISM: Artificial Sequence
<220> FEATURE:
<223> OTHER INFORMATION: anti-sense nucleotide sequence sk+

<400> SEQUENCE: 96
gggcgatatc aagcttatcg ataccg                                    26

<210> SEQ ID NO 97
<211> LENGTH: 19
<212> TYPE: DNA
<213> ORGANISM: Artificial Sequence
<220> FEATURE:
<223> OTHER INFORMATION: sense primer T7

<400> SEQUENCE: 97
aatacgactc actataggg                                            19

<210> SEQ ID NO 98
<211> LENGTH: 29
<212> TYPE: DNA
<213> ORGANISM: Artificial Sequence
<220> FEATURE:
<223> OTHER INFORMATION: anti-sense sequence T7

<400> SEQUENCE: 98
ctactagatc cctagatgct ggatcttcc                                 29
```

```
<210> SEQ ID NO 99
<211> LENGTH: 17
<212> TYPE: DNA
<213> ORGANISM: Artificial Sequence
<220> FEATURE:
<223> OTHER INFORMATION: anti-sense primer T7

<400> SEQUENCE: 99 attaccctc actaaag                                                    17

<210> SEQ ID NO 100
<211> LENGTH: 29
<212> TYPE: DNA
<213> ORGANISM: Artificial Sequence
<220> FEATURE:
<223> OTHER INFORMATION: sense primer T3

<400> SEQUENCE: 100
ggaagatcca gcatctaggg atctagtag                                      29

<210> SEQ ID NO 101
<211> LENGTH: 17
<212> TYPE: DNA
<213> ORGANISM: Artificial Sequence
<220> FEATURE:
<223> OTHER INFORMATION: anti-sense primer T3

<400> SEQUENCE: 101 attaccctc actaaag                                                    17

<210> SEQ ID NO 102
<211> LENGTH: 19
<212> TYPE: DNA
<213> ORGANISM: Artificial Sequence
<220> FEATURE:
<223> OTHER INFORMATION: sense primer T7

<400> SEQUENCE: 102
aatacgactc actataggg                                                 19

<210> SEQ ID NO 103
<211> LENGTH: 34
<212> TYPE: DNA
<213> ORGANISM: Artificial Sequence
<220> FEATURE:
<223> OTHER INFORMATION: sense primer 1885-1905

<400> SEQUENCE: 103
cctcgagctc gagcttgggt ggctttgggg catg                                34

<210> SEQ ID NO 104
<211> LENGTH: 17
<212> TYPE: DNA
<213> ORGANISM: Artificial Sequence
<220> FEATURE:
<223> OTHER INFORMATION: anti-sense primer T3

<400> SEQUENCE: 104
attacccctc actaaag                                                   17

<210> SEQ ID NO 105
<211> LENGTH: 44
<212> TYPE: DNA
<213> ORGANISM: Artificial Sequence
<220> FEATURE:
<223> OTHER INFORMATION: sense primer sequence

<400> SEQUENCE: 105
```
ccctcgagct cgagggtca ctgagaaact agaaaaagaa ttag            44

<210> SEQ ID NO 106
<211> LENGTH: 37
<212> TYPE: DNA
<213> ORGANISM: Artificial Sequence
<220> FEATURE:
<223> OTHER INFORMATION: antisense primer sequence

<400> SEQUENCE: 106
ccgcggccgc gtatctgtgg gagcctcaag ggagaac                  37

<210> SEQ ID NO 107
<211> LENGTH: 44
<212> TYPE: DNA
<213> ORGANISM: Artificial Sequence
<220> FEATURE:
<223> OTHER INFORMATION: Apa I

<400> SEQUENCE: 107
cgcgcgggcc ctgtgacatt gaatagagtg agggtcctgt tggg          44

<210> SEQ ID NO 108
<211> LENGTH: 45
<212> TYPE: DNA
<213> ORGANISM: Artificial Sequence
<220> FEATURE:
<223> OTHER INFORMATION: CEA 651

<400> SEQUENCE: 108
aaaggtttca catttgtagc ttgctgtgtc attgcgatct ctacg         45

<210> SEQ ID NO 109
<211> LENGTH: 45
<212> TYPE: DNA
<213> ORGANISM: Artificial Sequence
<220> FEATURE:
<223> OTHER INFORMATION: Junction Core

<400> SEQUENCE: 109
gtggtcctaa atagttcact ctattcaatg tcacactcga gccgg         45

<210> SEQ ID NO 110
<211> LENGTH: 33
<212> TYPE: DNA
<213> ORGANISM: Artificial Sequence
<220> FEATURE:
<223> OTHER INFORMATION: forward primer

<400> SEQUENCE: 110
tatattctag agcaagcaac agttactgcg acg                      33

<210> SEQ ID NO 111
<211> LENGTH: 33
<212> TYPE: DNA
<213> ORGANISM: Artificial Sequence
<220> FEATURE:
<223> OTHER INFORMATION: reverse primer

<400> SEQUENCE: 111
tatatatcga tccgaagcgt agagtcacac ttg                      33

<210> SEQ ID NO 112
<211> LENGTH: 18
<212> TYPE: DNA
<213> ORGANISM: Artificial Sequence

```
<220> FEATURE:
<223> OTHER INFORMATION: HPV 16 E6 RNA (nts 414-431)

<400> SEQUENCE: 112
ttaactgtca aaagccac                                                  18

<210> SEQ ID NO 113
<211> LENGTH: 68
<212> TYPE: DNA
<213> ORGANISM: Artificial Sequence
<220> FEATURE:
<223> OTHER INFORMATION: HPV 16 E6 HRBZ, sense strand

<400> SEQUENCE: 113
cgatgtggct tttagatgtt aaaccagaga acacacgga cttcggtccg tggtatatta     60
gctggtat                                                             68

<210> SEQ ID NO 114
<211> LENGTH: 70
<212> TYPE: DNA
<213> ORGANISM: Artificial Sequence
<220> FEATURE:
<223> OTHER INFORMATION: HPV 16 E6 HBRZ, antisense strand

<400> SEQUENCE: 114
ctagatacca gctaatatac cacggaccga agtccgtgtg tttctctggt ttaacatcta    60
aaagccacat                                                           70

<210> SEQ ID NO 115
<211> LENGTH: 42
<212> TYPE: DNA
<213> ORGANISM: Artificial Sequence
<220> FEATURE:
<223> OTHER INFORMATION: forward primer AM-MSP-2F

<400> SEQUENCE: 115
tatatctcga gaccaccatg agtgctgtaa gtaataggaa gc                       42

<210> SEQ ID NO 116
<211> LENGTH: 36
<212> TYPE: DNA
<213> ORGANISM: Artificial Sequence
<220> FEATURE:
<223> OTHER INFORMATION: reverse primer AM-MSP-2R

<400> SEQUENCE: 116
tatatctcga gctagaaggc aaacctaaca cccaac                              36

<210> SEQ ID NO 117
<211> LENGTH: 31
<212> TYPE: DNA
<213> ORGANISM: Artificial Sequence
<220> FEATURE:
<223> OTHER INFORMATION: forward primer HBVpkgF

<400> SEQUENCE: 117
tatatgggcc ctacatgtcc cactgttcaa g                                   31

<210> SEQ ID NO 118
<211> LENGTH: 31
<212> TYPE: DNA
<213> ORGANISM: Artificial Sequence
<220> FEATURE:
<223> OTHER INFORMATION: reverse primer HBVpkgR

<400> SEQUENCE: 118
```
tatatgggcc cgtacggaag gaaagaagtc a                                      31

<210> SEQ ID NO 119
<211> LENGTH: 32
<212> TYPE: DNA
<213> ORGANISM: Artificial Sequence
<220> FEATURE:
<223> OTHER INFORMATION: forward primer MHVpkgF

<400> SEQUENCE: 119
tatatgggcc cattttggtt ttgctatgcg ta                                     32

<210> SEQ ID NO 120
<211> LENGTH: 16
<212> TYPE: DNA
<213> ORGANISM: Artificial Sequence
<220> FEATURE:
<223> OTHER INFORMATION: IFN-alpha 4b

<400> SEQUENCE: 120
tctctgtcct ccatga                                                      16

<210> SEQ ID NO 121
<211> LENGTH: 66
<212> TYPE: DNA
<213> ORGANISM: Artificial Sequence
<220> FEATURE:
<223> OTHER INFORMATION: IFN-alpha HRBZ, sense strand

<400> SEQUENCE: 121
tcgagtcatg gagagaggag aaccagagaa acacacggac ttcggtccgt ggtatattac       60
ctggat                                                                 66

<210> SEQ ID NO 122
<211> LENGTH: 64
<212> TYPE: DNA
<213> ORGANISM: Artificial Sequence
<220> FEATURE:
<223> OTHER INFORMATION: IFN-alpha HBRZ, antisense strand

<400> SEQUENCE: 122
cgatccaggt aatataccac ggaccgaagt ccgtgtgttt ctctggttct cctctctcca       60
tgac                                                                   64

<210> SEQ ID NO 123
<211> LENGTH: 35
<212> TYPE: DNA
<213> ORGANISM: Artificial Sequence
<220> FEATURE:
<223> OTHER INFORMATION: 5' hIL-2

<400> SEQUENCE: 123
gcctcgagac aatgtacagg atgcaactcc tgtct                                  35

<210> SEQ ID NO 124
<211> LENGTH: 36
<212> TYPE: DNA
<213> ORGANISM: Artificial Sequence
<220> FEATURE:
<223> OTHER INFORMATION: 3' hIL-2

<400> SEQUENCE: 124
gaatcgattt atcaagtcag tgttggagat gatgct                                 36

```
<210> SEQ ID NO 125
<211> LENGTH: 31
<212> TYPE: DNA
<213> ORGANISM: Artificial Sequence
<220> FEATURE:
<223> OTHER INFORMATION: reverse primer MHVpkgF

<400> SEQUENCE: 125
tatatgggcc catcgaggtg agaaagagga c                                  31

<210> SEQ ID NO 126
<211> LENGTH: 31
<212> TYPE: DNA
<213> ORGANISM: Artificial Sequence
<220> FEATURE:
<223> OTHER INFORMATION: forward primer MLVpkgF

<400> SEQUENCE: 126
tatatgggcc ctgtatctgg cggacccgtg g                                  31

<210> SEQ ID NO 127
<211> LENGTH: 31
<212> TYPE: DNA
<213> ORGANISM: Artificial Sequence
<220> FEATURE:
<223> OTHER INFORMATION: reverse primer MLVpkgR

<400> SEQUENCE: 127
tatatgggcc cgcagacaag acgcgcggcg c                                  31

<210> SEQ ID NO 128
<211> LENGTH: 24
<212> TYPE: RNA
<213> ORGANISM: Artificial Sequence
<220> FEATURE:
<223> OTHER INFORMATION: Minimum Junction Region

<400> SEQUENCE: 128
aucucuacgg ugguccuaaa uagu                                          24

<210> SEQ ID NO 129
<211> LENGTH: 24
<212> TYPE: RNA
<213> ORGANISM: Artificial Sequence
<220> FEATURE:
<223> OTHER INFORMATION: Artificial RNA sequence for modified Sindbis
      Junction.
<220> FEATURE:
<221> NAME/KEY: misc_feature
<222> LOCATION: (4)..(4)
<223> OTHER INFORMATION: n is u or g
<220> FEATURE:
<221> NAME/KEY: misc_feature
<222> LOCATION: (7)..(7)
<223> OTHER INFORMATION: n is a or c
<220> FEATURE:
<221> NAME/KEY: misc_feature
<222> LOCATION: (10)..(10)
<223> OTHER INFORMATION: n is g or a

<400> SEQUENCE: 129
aucncuncgn ugguccuaaa uagu                                          24
```

EUKARYOTIC LAYERED VECTOR INITIATION SYSTEMS

This application is a continuation of Ser. No. 10/346,880 filed Jan. 16, 2003, pending, which is a continuation of Ser. No. 09/503,138, filed Feb. 11, 2000, now abandoned, which is a continuation of Ser. No. 09/191,747 filed Nov. 12, 1998, now abandoned, which is a continuation of Ser. No. 08/739,199 filed Oct. 30, 1996, now abandoned, which is a division of Ser. No. 08/404,796 filed Mar. 15, 1995, now U.S. Pat. No. 6,015,686, which is a continuation-in-part of Ser. No. 08/376,184 filed Jan. 18, 1995, now abandoned, which is a continuation-in-part of Ser. No. 08/348,472 filed Nov. 30, 1994, now abandoned, which is a continuation-in-part of Ser. No. 08/198,450, filed Feb. 18, 1994, now abandoned, which is a continuation-in-part of Ser. No. 08/122,791, filed Sep. 15, 1993, now abandoned. Each of these applications is incorporated herein in its entirety by reference.

This application incorporates by reference the contents of a 46.9 kb text file created on Jul. 24, 2009 and named "51250_US_seq_list.txt," which is the sequence listing for this application.

TECHNICAL FIELD

The present invention relates generally to use of recombinant viruses as vectors, and more specifically, to recombinant alphaviruses which are capable of expressing a heterologous sequence in target cells.

BACKGROUND OF THE INVENTION

Alphaviruses comprise a set of serologically related arthropod-borne viruses of the Togavirus family. Briefly, alphaviruses are distributed worldwide, and persist in nature through a mosquito to vertebrate cycle. Birds, rodents, horses, primates, and humans are among the defined alphavirus vertebrate reservoir/hosts.

Twenty-six known viruses and virus subtypes have been classified within the alphavirus genus utilizing the hemagglutination inhibition (HI) assay. Briefly, the HI test segregates the 26 alphaviruses into three major complexes: the Venezuelan encephalitis (VE) complex, the Semliki Forest (SF) complex, and the western encephalitis (WE) complex. In addition, four additional viruses, eastern encephalitis (EE), Barmah Forest, Middelburg, and Ndumu, receive individual classification based on the HI serological assay.

Members of the alphavirus genus are also classified based on their relative clinical features in humans: alphaviruses associated primarily with encephalitis, and alphaviruses associated primarily with fever, rash, and polyarthritis. Included in the former group are the VE and WE complexes, and EE. In general, infection with this group can result in permanent sequelae, including behavior changes and learning disabilities, or death. In the latter group is the SF complex, comprised of the individual alphaviruses Chikungunya, O'nyong-nyong, Sindbis, Ross River, and Mayaro. With respect to this group, although serious epidemics have been reported, infection is in general self-limiting, without permanent sequelae.

Sindbis virus is the prototype member of the alphavirus genus of the Togavirus family. Although not usually apparent, clinical manifestations of Sindbis virus infection may include fever, arthritis, and rash. Sindbis virus is distributed over Europe, Africa, Asia, and Australia, with the best epidemiological data coming from South Africa, where 20% of the population is seropositive. (For a review, see Peters and Dalrymple, *Fields Virology* (2d ed), Fields et al. (eds.), B.N. Raven Press, New York, N.Y., chapter 26, pp. 713-762). Infectious Sindbis virus has been isolated from human serum only during an outbreak in Uganda and in a single case from Central Africa.

The morphology and morphogenesis of the alphavirus genus is generally quite uniform. In particular, the enveloped 60-65 nm particles infect most vertebrate cells, where productive infection is cytopathic. On the other hand, infection of invertebrate cells, for example, those derived from mosquitoes, does not result in any overt cytopathology. Typically, alphaviruses are propagated in BHK-21 or vero cells, where growth is rapid, reaching a maximum yield within 24 hours of infection. Field strains are usually isolated on primary avian embryo, for example chicken fibroblast cultures (CEF).

The genomic RNA (49S RNA) of alphaviruses is unsegmented, of positive polarity, approximately 11-12 kb in length, and contains a 5' cap and a 3' polyadenylate tail. Infectious enveloped virus is produced by assembly of the viral nucleocapsid proteins onto genomic RNA in the cytoplasm, and budding through the cell membrane embedded with viral-encoded glycoproteins. Entry of virus into cells appears to occur by endocytosis through clatherin-coated pits, fusion of the viral membrane with the endosome, release of the nucleocapsid and uncoating of the viral genome. During viral replication, the genomic 49S RNA serves as template for synthesis of a complementary negative strand. The negative strand in turn serves as template for full-length genomic RNA and for an internally initiated positive-strand 26S subgenomic RNA. The nonstructural proteins are translated from the genomic RNA. Alphaviral structural proteins are translated from the subgenomic 26S RNA. All viral genes are expressed as polyproteins and processed into individual proteins by proteolytic cleavage post-translation.

The use of recombinant virus vectors (in particular, alphavirus vectors) to treat individuals requires that they be able to be transported and stored for long periods at a desired temperature, such that infectivity and viability of the recombinant virus is retained. Current methods for storing recombinant viruses generally involve storage as liquids and at low temperatures. Such methods present problems in Third World countries, which typically do not have adequate refrigeration capabilities. For example, each year in Africa, millions of children die from infectious diseases such as measles. Vaccines necessary for the prevention of these diseases cannot be distributed to the majority of these countries because refrigeration is not readily accessible.

In addition to storage as liquids and at low temperatures, present viral formulations often contain media components that are not desirable for injection into patients. Consequently, there is a need in the art for a method of preserving purified recombinant viral vector (and in particular, alphavirus vectors) in a lyophilized form at elevated temperatures, and for this form to be suitable for injection into patients.

The present invention discloses recombinant alphavirus vectors which are suitable for use in a variety of applications, including for example, gene therapy, and further provides other related advantages.

SUMMARY OF THE INVENTION

Briefly stated, the present invention provides alphavirus vector constructs and alphavirus particles, as well as methods of making and utilizing the same. Within one aspect of the present invention, alphavirus vector constructs are provided comprising a 5' promoter which is capable of initiating the synthesis of viral RNA in vitro from cDNA, a 5' sequence which is capable of initiating transcription of an alphavirus, a nucleotide sequence encoding alphavirus non-structural proteins, a viral junction region which has been inactivated such that viral transcription of the subgenomic fragment is prevented, and an alphavirus RNA polymerase recognition sequence. Within other aspects of the present invention, the viral junction region has been modified such that viral transcription of the subgenomic fragment is reduced.

Within yet other aspects of the present invention, alphavirus vector constructs are provided comprising a 5' promoter which is capable of initiating the synthesis of viral RNA in vitro from cDNA, a 5' sequence which is capable of initiating transcription of an alphavirus, a nucleotide sequence encoding alphavirus non-structural proteins, a first viral junction region which has been inactivated such that viral transcription of the subgenomic fragment is prevented, a second viral junction region which is active, or which has been modified such that viral transcription of the subgenomic fragment is reduced, and an alphavirus RNA polymerase recognition sequence.

Within still other aspects of the present invention, alphavirus cDNA vector constructs are provided, comprising a 5' promoter which is capable of initiating the synthesis of viral RNA from cDNA, followed by a 5' sequence which is capable of initiating transcription of an alphavirus, a nucleotide sequence encoding alphavirus non-structural proteins, a viral junction region which has been inactivated such that viral transcription of the subgenomic fragment is prevented, an alphavirus RNA polymerase recognition sequence, and a 3' sequence which controls transcription termination.

Within another aspect of the present invention, alphavirus cDNA vector constructs are provided, comprising a 5' promoter which is capable of initiating the synthesis of viral RNA from cDNA, followed by a 5' sequence which is capable of initiating transcription of an alphavirus, a nucleotide sequence encoding alphavirus non-structural proteins, a viral junction region which is active, or which has been modified such that viral transcription of the subgenomic fragment is reduced, an alphavirus RNA polymerase recognition sequence, and a 3' sequence which controls transcription termination.

Within another aspect of the present invention, alphavirus cDNA vector constructs are provided, comprising a promoter which is capable of initiating the synthesis of viral RNA from cDNA followed by a 5' sequence which is capable of initiating transcription of an alphavirus, a nucleotide sequence encoding alphavirus non-structural proteins, a first viral junction region which has been inactivated such that viral transcription of the subgenomic fragment is prevented, followed by a second viral junction region which is active, or which has been modified such that viral transcription of the subgenomic fragment is reduced, an alphavirus RNA polymerase recognition sequence, and a 3' sequence which controls transcription termination.

Within other aspects of the present invention, eukaryotic layered vector initiation systems are provided which are capable of expressing a heterologous nucleic acid sequence in a eukaryotic cell transformed or transfected therewith. In particular embodiments, eukaryotic layered vector initiation systems are provided, comprising a promoter which is capable of initiating the 5' synthesis of RNA from cDNA, a vector construct which is capable of autonomous replication in a cell, the vector construct being capable of expressing a heterologous nucleic acid sequence, and a 3' sequence which controls transcription termination.

Within a related aspect, eukaryotic layered vector initiation systems are provided, comprising a DNA promoter which is capable of initiating the 5' synthesis of RNA from cDNA, a vector construct which is capable of autonomous replication in a cell, the vector construct being capable of expressing a heterologous ribonucleic acid sequence, and a 3' DNA sequence which controls transcription termination.

Within one embodiment, the vector construct within the eukaryotic layered vector initiation systems of the present invention is an alphavirus vector construct. Within other embodiments, the construct is derived from a virus selected from the group consisting of poliovirus, rhinovirus, coxsackieviruses, rubella, yellow fever, HCV, TGEV, IBV, MHV, BCV, parainfluenza virus, mumps virus, measles virus, respiratory syncytial virus, influenza virus, RSV, MoMLV, HIV, HTLV, hepatitis delta virus and Astrovirus. Within yet other embodiments, the promoter which is capable of initiating the 5' synthesis of RNA from cDNA is selected from the group consisting of the MoMLV promoter, metallothionein promoter, glucocorticoid promoter, SV40 promoter, and the CMV promoter. Within further embodiments, the eukaryotic layered vector initiation systems further comprise a polyadenylation sequence.

In further embodiments of the invention, in any of the above aspects, the vectors (e.g., alphavirus vector construct, alphavirus cDNA vector construct, or eukaryotic layered vector initiation system) may be derived from an alphavirus selected from the group consisting of Aura, Fort Morgan, Venezuelan Equine Encephalitis, Ross River, Semliki Forest, Sindbis, and Mayaro.

In other embodiments, the vectors described above contain a heterologous sequence. Typically, such vectors contain a heterologous nucleotide sequence of greater than 100 bases, generally the heterologous nucleotide sequence is greater than 3 kb, and sometimes greater than 5 kb, or even 8 kb. In various embodiments, the heterologous sequence is a sequence encoding a protein selected from the group consisting of IL-1, IL-2, IL-3, IL-4, IL-5, IL-6, IL-7, IL-8, IL-9, IL-10, IL-11, IL-12, IL-13, IL-14, IL-15, alpha-, beta-, or gamma-WN, G-CSF, and GM-CSF. Within other embodiments of the invention, the heterologous sequence may encode a lymphokine receptor. Representative examples of such receptors include receptors for any of the lymphokines set forth above.

In still other embodiments, the vectors described above include a selected heterologous sequence which may be obtained from a virus selected from the group consisting of influenza virus, HPV, HBV, HCV, EBV, HIV, HSV, FeLV, FIV, Hanta virus, HTLV I, HTLV II and CMV. Within one preferred embodiment, the heterologous sequence obtained from HPV encodes a protein selected from the group consisting of E5, E6, E7 and L1. In yet other embodiments, the vectors described above include a selected heterologous sequence encoding an HIV protein selected from the group consisting of HIV gp120 and gag.

The selected heterologous sequences described above also may be an antisense sequence, noncoding sense sequence, or ribozyme sequence. In preferred embodiments, the antisense or noncoding sense sequence is selected from the group consisting of sequences which are complementary to influenza virus, HPV, HBV, HCV, EBV, HIV, HSV, FeLV, FIV, Hanta virus, HTLV I, HTLV II, and CMV sequences.

In another embodiment, the vectors described above contain no alphavirus structural protein genes. Within other embodiments, the selected heterologous sequence is located downstream from a viral junction region. In the vectors described above having a second viral junction, the selected heterologous sequence may, within certain embodiments, be located downstream from the second viral junction region.

Where the heterologous sequence is located downstream from a viral junction region, the vector construct may further comprise a polylinker located subsequent to the viral junction region. Within preferred embodiments, such polylinkers do not contain a restriction endonuclease recognition sequence present in the wild-type alphavirus sequence.

In yet another embodiment, in the vectors described above the selected heterologous sequence may be located within the nucleotide sequence encoding alphavirus non-structural proteins.

In particular embodiments, the vectors described above include a viral junction region consisting of the nucleotide sequence as shown in FIG. 3, from nucleotide number 7579, to nucleotide number 7597 (SEQ. ID NO. 1). In alternative embodiments, where the vector includes a second viral junction, an E3 adenovirus gene may be located downstream from the second viral junction region. Vectors of the present invention may also further comprise a non-alphavirus (for example retrovirus, coronavirus, hepatitis B virus) packaging sequence located between the first viral junction region and the second viral junction region, or in the nonstructural protein coding region.

In further aspects, the present invention provides an isolated recombinant alphavirus vector which does not contain a functional viral junction region, and which in preferred embodiments produces reduced viral transcription of the subgenomic fragment.

In still a further aspect, the present invention provides an alphavirus structural protein expression cassette, comprising a promoter and one or more alphavirus structural protein genes, the promoter being capable of directing the expression of alphavirus structural proteins. In various embodiments, the expression cassette is capable of expressing alphavirus structural proteins, such as an alphavirus structural protein selected from the group consisting of C, 6K, E3, E2, and E1.

Within other embodiments, the alphavirus structural protein is derived from an alphavirus selected from the group consisting of Aura, Fort Morgan, Venezuelan Equine Encephalitis, Ross River, Semliki Forest, Sindbis and Mayaro viruses.

In yet another aspect, the present invention provides an alphavirus structural protein expression cassette, comprising a promoter, one or more alphavirus structural proteins, and a heterologous ligand sequence, the promoter being capable of directing the expression of the alphavirus structural proteins and the heterologous sequence. In various embodiments, the heterologous ligand sequence is selected from the group consisting of VSVG, HIV gp120, antibody, insulin, and CD4.

In certain embodiments, the expression cassettes described above include a promoter selected from the group consisting of metallothionein, *Drosophila* actin 5C distal, SV40, heat shock protein 65, heat shock protein 70, Py, RSV, BK, JC, MuLV, MMTV, alphavirus junction region, CMV and VA1RNA.

The present invention also provides packaging cell lines and producer cell lines suitable for producing recombinant alphavirus particles. Such packaging or producer cell lines may be either mammalian or non-mammalian (e.g., insect cells, such as mosquito cells). In certain embodiments, the packaging cell lines and producer cell lines contain an integrated alphavirus structural protein expression cassette.

Within one embodiment, packaging cell lines are provided which, upon introduction of a vector construct, produce alphavirus particles capable of infecting human cells. Within other embodiments, the packaging cell line produces alphavirus particles in response to one or more factors. Within certain embodiments, an alphavirus inhibitory protein is not produced within the packaging cell line.

Within other aspects, retroviral-derived packaging cell lines are provided which are suitable for packaging and production of an alphavirus vector. Within one embodiment, a retroviral-derived producer cell line suitable for packaging and production of an alphavirus vector is provided, comprising an expression cassette which directs the expression of gag/pol, an expression cassette which directs the expression of env, and alphavirus vector construct containing a retroviral packaging sequence.

Within another aspect, HBV-derived and coronavirus-derived packaging cell lines are provided which are suitable for packaging and production of and alphavirus vector. Within one embodiment, an HBV-derived packaging cell line is provided, comprising an expression cassette which directs the expression of HBV core, preS/S, and P proteins. Within another embodiment, a coronavirus-derived packaging cell line is provided, comprising an expression cassette which directs the expression of coronavirus N, M, and S proteins.

Within another aspect, a VSV-G derived packaging cell is provided which is suitable for packaging and production of an alphavirus vector, comprising a stably integrated expression cassette which directs the expression of VSV-G. Within a further embodiment, such packaging cell lines comprise a stably integrated expression cassette which directs the expression of one or more alphavirus structural proteins.

Within yet other aspects, producer cell lines are provided based upon the above packaging cell lines. Within one embodiment, such producer cell lines produce recombinant alphavirus particles in response to a differentiation state of the producer cell line. Within other embodiments, such producer cell lines produce recombinant alphavirus particles in response to one or more factors.

As utilized with the context of the present invention, alphavirus producer cell line refers to a cell line which is capable of producing recombinant alphavirus particles. The producer cell line should include an integrated alphavirus structural protein expression cassette capable of directing the expression of alphavirus structural protein(s), and also, an alphavirus vector construct. Preferably, the alphavirus vector construct is a cDNA vector construct. More preferably, the alphavirus vector construct is an integrated cDNA vector construct. When the alphavirus vector construct is an integrated cDNA vector construct, it may, in some instances, function only in response to one or more factors, or the differentiation state of the alphavirus producer cell line.

In still yet another aspect, the present invention provides alphavirus particles which, upon introduction into a BHK cell, produces an infected cell which is viable at least 24 hours and as much as 48, 72, or 96 hours, or 1 week after infection. Also provided are mammalian cells which contain such alphavirus particles. In addition, recombinant alphavirus particles capable of infecting human cells are provided.

In another aspect, the present invention provides recombinant alphavirus particles which, upon introduction into a BHK cell, produces an infected cell which is viable at least 24 hours after infection, the particle also carrying a vector construct which directs the expression of at least one antigen or modified form thereof in target cells infected with the alphavirus particle, the antigen or modified form thereof being capable of stimulating an immune response within an animal. In various embodiments, the expressed antigen or modified form thereof elicits a cell-mediated immune response, preferably an HLA class 1-restricted immune response.

In still another aspect, the present invention provides recombinant alphavirus particles which carry a vector capable of directing the expression of a palliative in cells infected with the alphavirus particle, the palliative being capable of inhibiting a function of a pathogenic agent necessary for pathogenicity. In various embodiments, the pathogenic agent is a virus, fungi, protozoa, or bacteria, and the inhibited function is selected from the group consisting of adsorption, replication, gene expression, assembly, and exit of the pathogenic agent from infected cells. In other embodiments, the pathogenic agent is a cancerous cell, cancer-promoting growth factor, autoimmune disorder, cardiovascular disorders such as restenosis, osteoporosis and male pattern baldness, and the inhibited function is selected from the group consisting of cell viability and cell replication. In further embodiments, the vector directs the expression of a toxic palliative in infected target cells in response to the presence in such cells of an entity associated with the pathogenic agent; preferably the palliative is capable of selectively inhibiting the expression of a pathogenic gene or inhibiting the activity of a protein produced by the pathogenic agent. In still further embodiments, the palliative comprises an inhibiting peptide specific for viral protease, an antisense RNA complementary to RNA sequences necessary for pathogenicity, a sense RNA complementary to RNA sequences necessary for pathogenicity, or a defective structural protein of a pathogenic agent, such protein being capable of inhibiting assembly of the pathogenic agent.

In yet further embodiments, recombinant alphavirus particles described above direct the expression of a palliative, more particularly, direct the expression of a gene product capable of activating an otherwise inactive precursor into an active inhibitor of the pathogenic agent, for example, the herpes thymidine kinase gene product, a tumor suppressor gene, or a protein that activates a compound with little or no cytotoxicity into a toxic product in the presence of a pathogenic agent, thereby effecting localized therapy to the pathogenic agent. Alternatively, the recombinant alphavirus particle directs the expression of a protein that is toxic upon processing or modification by a protein derived from a pathogenic agent, a reporting product on the surface of target cells infected with the alphavirus and containing the pathogenic agent, or an RNA molecule which functions as an antisense or ribozyme specific for a pathogenic RNA molecule required for pathogens. In certain embodiments, in the alphavirus particles described above, the protein is herpes thymidine kinase or CD4.

In yet further aspects, the present invention provides recombinant alphavirus particles which direct the expression of a gene capable of suppressing one or more elements of the immune system in target cells infected with the alphavirus vector, and an alphavirus particle which directs the expression of a blocking element in cells infected with the alphavirus vector, the blocking element being capable of binding to either a receptor or an agent such that the receptor/agent interaction is blocked.

In further aspects, methods are provided for administering any of the above-described recombinant alphavirus particles or vectors, for a prophylactic or therapeutic effect. For example, within one aspect, the present invention provides methods of stimulating an immune response to an antigen, comprising the step of infecting susceptible target cells with a recombinant alphavirus particle which directs the expression of at least one antigen or modified form thereof in target cells infected with the alphavirus, the antigen or modified form thereof being capable of stimulating an immune response within an animal. In one embodiment, the target cells are infected in vivo, although within other embodiments the target cells are removed, infected ex vivo, and returned to the animal.

In still further aspects of the present invention, methods of stimulating an immune response to a pathogenic antigen are provided, comprising the step of infecting susceptible target cells with a recombinant alphavirus particle which directs the expression of a modified form of a pathogenic antigen in target cells infected with the alphavirus, the modified antigen being capable of stimulating an immune response within an animal but having reduced pathogenicity relative to the pathogenic antigen.

In even further aspects of the present invention, methods of stimulating an immune response to an antigen are provided, comprising infecting susceptible target cells with a recombinant alphavirus particle which directs the expression of a peptide having multiple epitopes, one or more of the epitopes derived from different proteins.

In yet another aspect of the invention, methods of stimulating an immune response within a warm-blooded animal are provided, comprising infecting susceptible target cells associated with a warm-blooded animal with nucleic acid sequences coding for either individual class I or class II MHC protein, or combinations thereof, and infecting the cells with an alphavirus particle which directs the expression of at least one antigen or modified form thereof in target cells infected with the alphavirus particle, the antigen or modified form thereof being capable of stimulating an immune response within the animal.

In another aspect of the present invention, methods of inhibiting a pathogenic agent are provided, comprising infecting susceptible target cells with an alphavirus particle which directs the expression of a palliative in cells infected with the alphavirus particle, the palliative being capable of inhibiting a function of a pathogenic agent necessary for pathogenicity.

As utilized within the context of the present invention, vector or vector constructs which direct the expression of a heterologous sequence of interest in fact refers to the transcribed vector RNA, which directs the expression of the heterologous sequence of interest. In addition, although "animals" are generally referred to, it should be understood that the present invention may be readily applied to a wide variety of animals (both mammalian and non-mammalian), including for example, humans, chimps, macaques, cows, horses, sheep, dogs, birds, cats, fish, rats, and mice. Further, although alphaviruses such as Sindbis may be specifically described herein, it should be understood that a wide variety of other alphaviruses may also be utilized including, for example, Aura, Venezuelan Equine Encephalitis, Fort Morgan, Ross River, Semliki Forest, and Mayaro.

Within other aspects of the present invention, methods are provided for delivering a heterologous nucleic acid sequence to an animal comprising the steps of administering to the warm-blooded animal a eukaryotic layered vector initiation system as described above. Within certain embodiments, the eukaryotic layered vector initiation system may be introduced into the target cells directly as a DNA molecule by physical means, as a complex with various liposome formulations, or as a DNA-ligand complex including the vector molecule (e.g., along with a polycation compound such as polylysine, a receptor specific ligand, or a psoralen inactivated virus such as Sendai or Adenovirus).

Within yet other aspects of the invention, ex vivo cells are infected with any of the above-described recombinant alphaviruses are provided. Within yet other aspects, recombinant alphavirus particles are provided which are resistant to inactivation in serum. As utilized herein, recombinant alphavirus particles are considered to be resistant to inactivation in serum if the ratio of surviving particles to input/starting particles in a complement inactivation assay is greater in a statistically significant manner, preferably at least 5-fold, and as much as 10- to 20-fold, as compared to a reference sample produced in BHK cells. Within further aspects, pharmaceutical compositions are provided comprising any of the above-described vectors, or recombinant alphavirus particles, in combination with a physiologically acceptable carrier or diluent.

In yet another aspect of the invention, the eukaryotic layered vector initiation systems provided enable new methods for large scale recombinant protein expression.

These and other aspects of the present invention will become evident upon reference to the following detailed description and attached drawings. In addition, various references are set forth below which describe in more detail certain procedures or compositions (e.g., plasmids, etc.). These references are incorporated herein by reference in their entirety.

BRIEF DESCRIPTION OF THE DRAWINGS

Figure 3A:
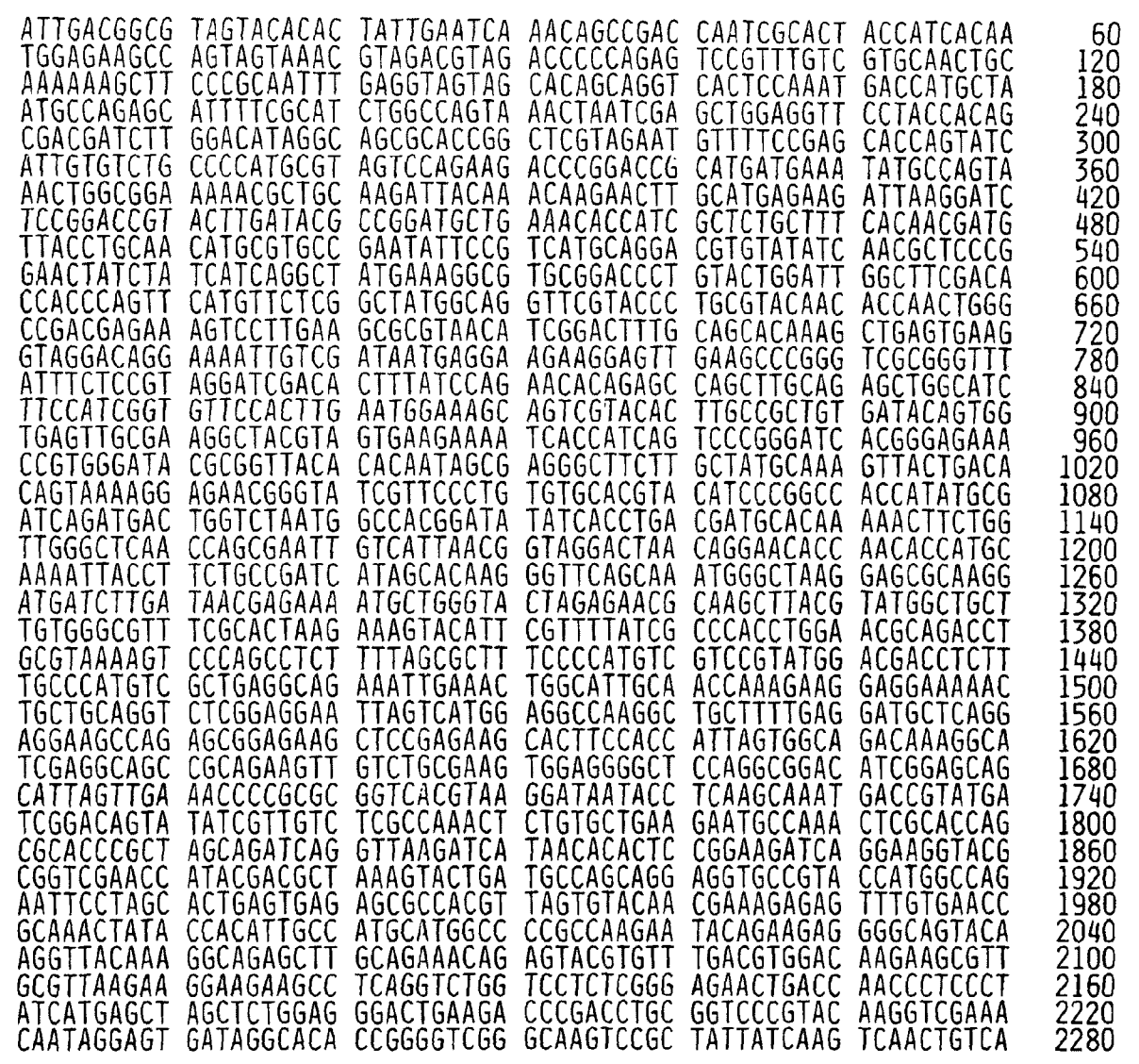
Figure 3B:
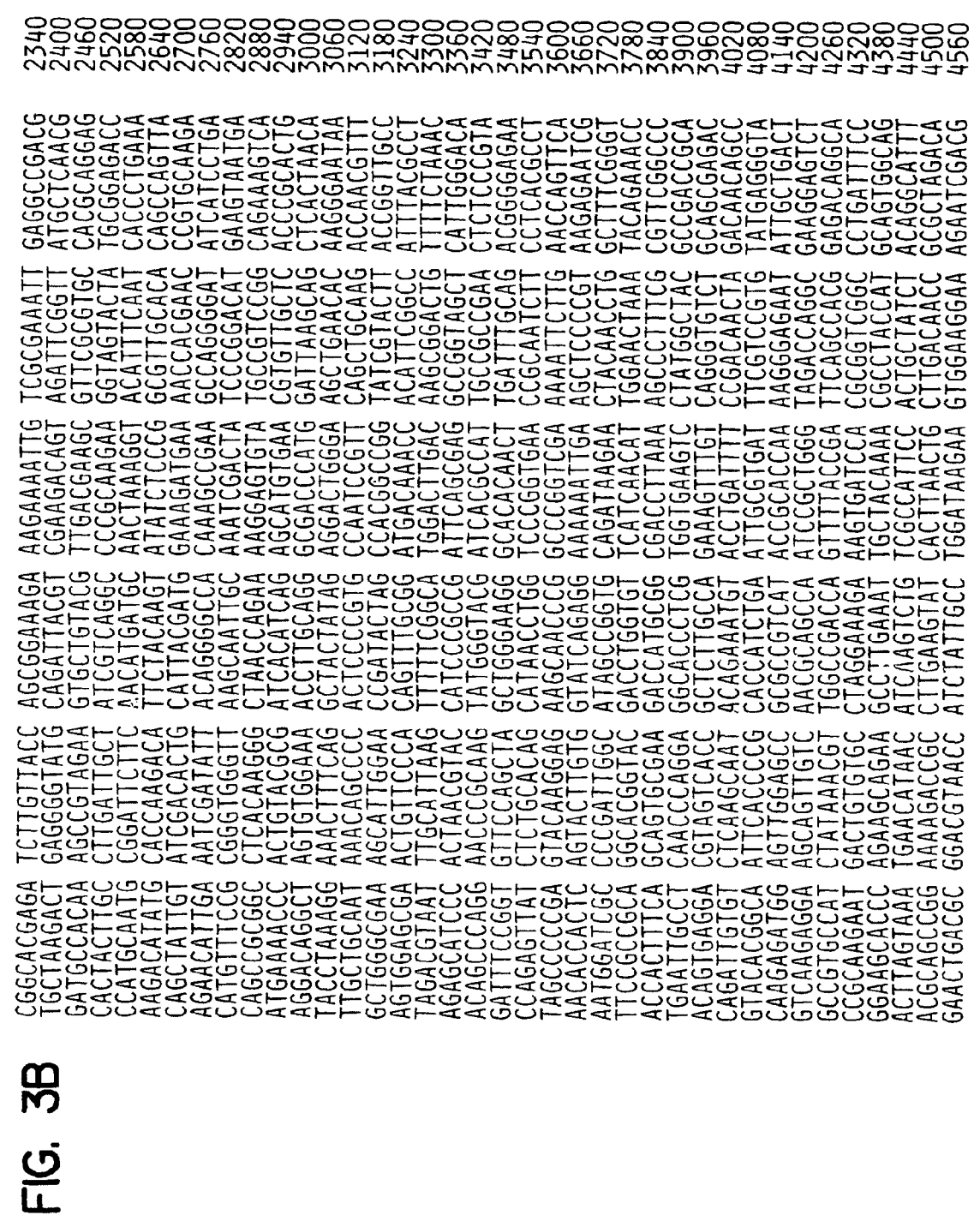
Figure 3C:
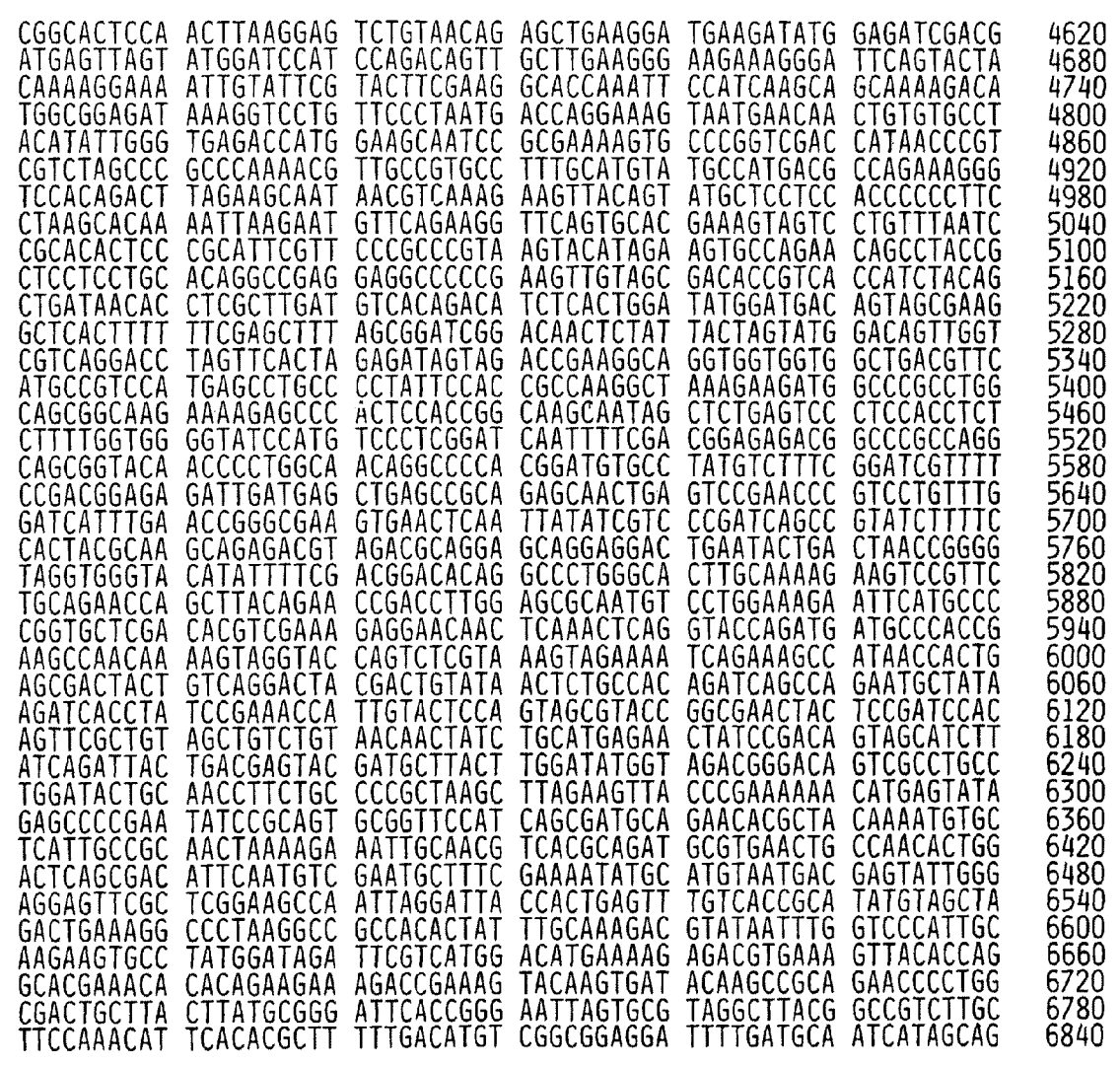
Figure 3E:
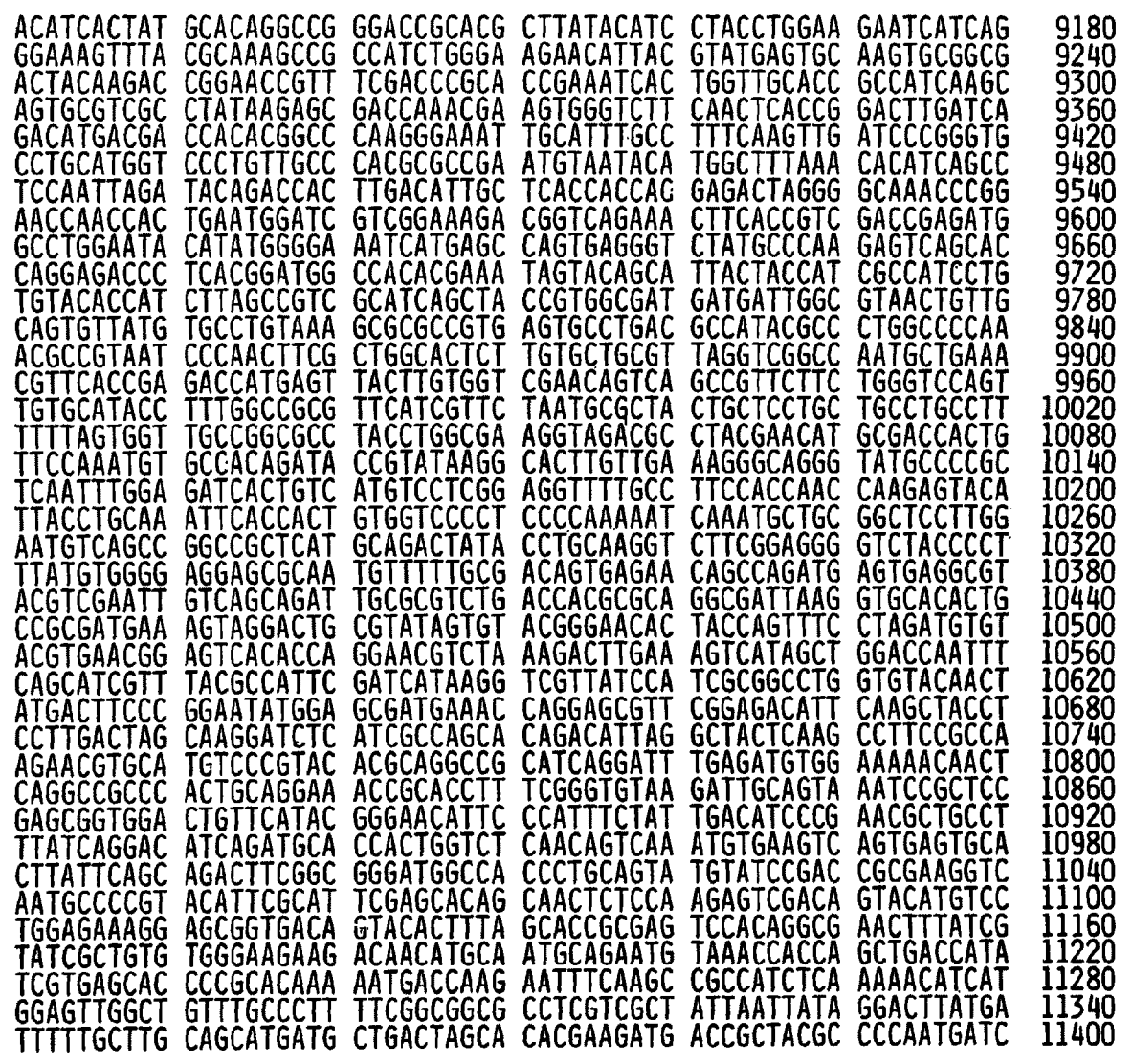
Figure 3F:
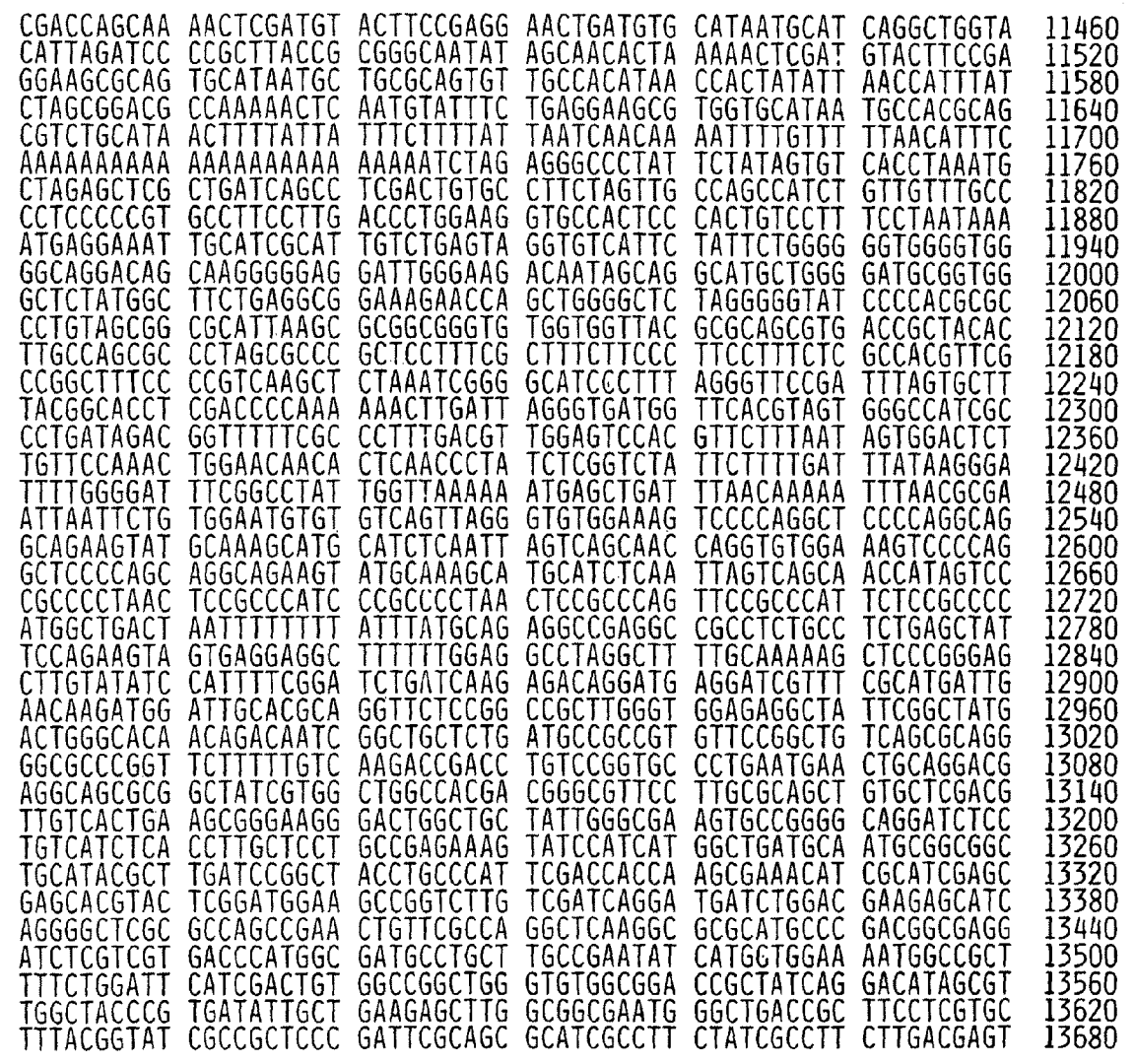
Figure 3G:
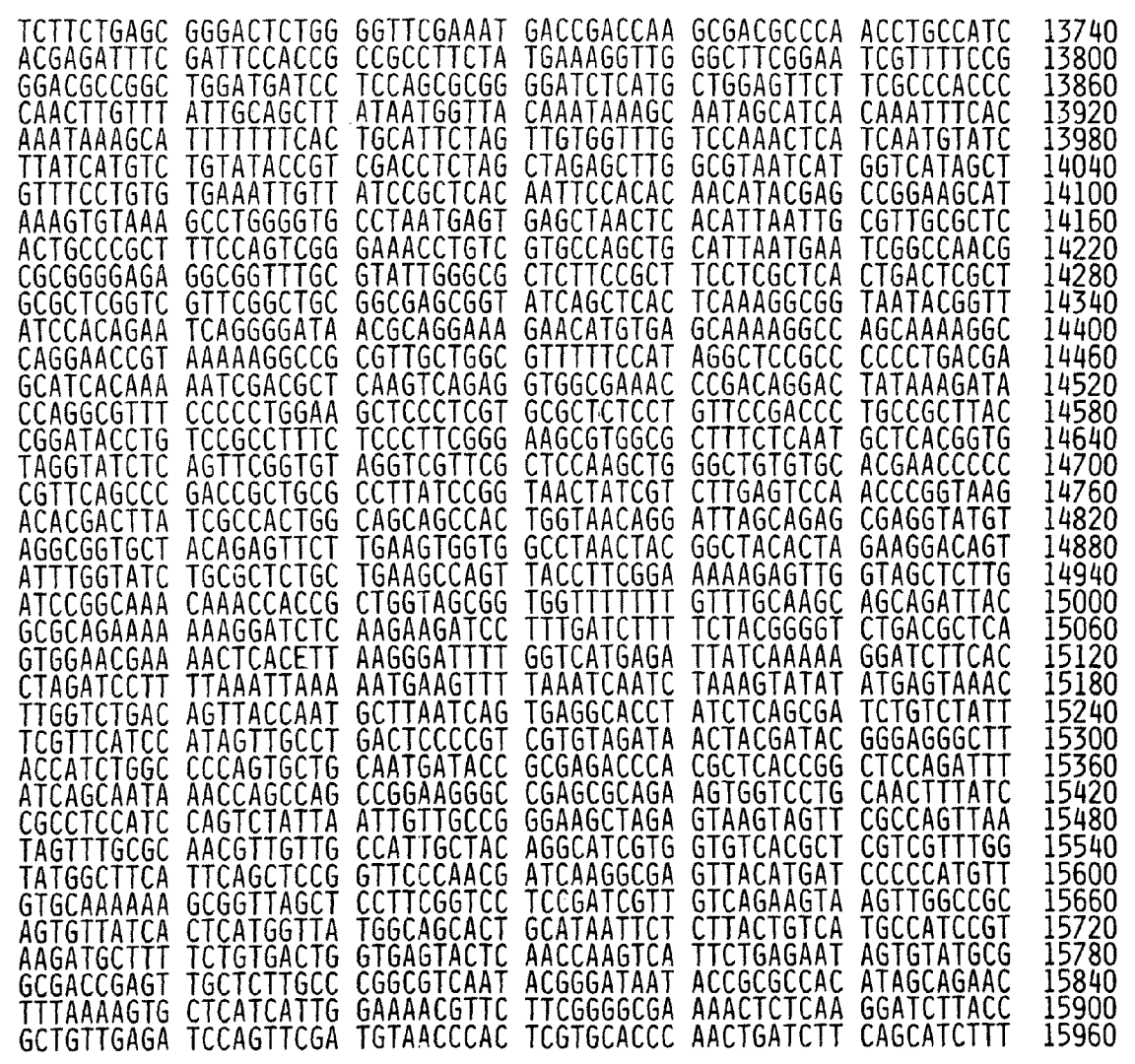

FIGS. 3A-H set forth the sequence of a representative Eukaryotic Layered Vector Initiation System derived from Sindbis (see also SEQ ID NO:1).

DETAILED DESCRIPTION OF THE INVENTION

Figure 1:
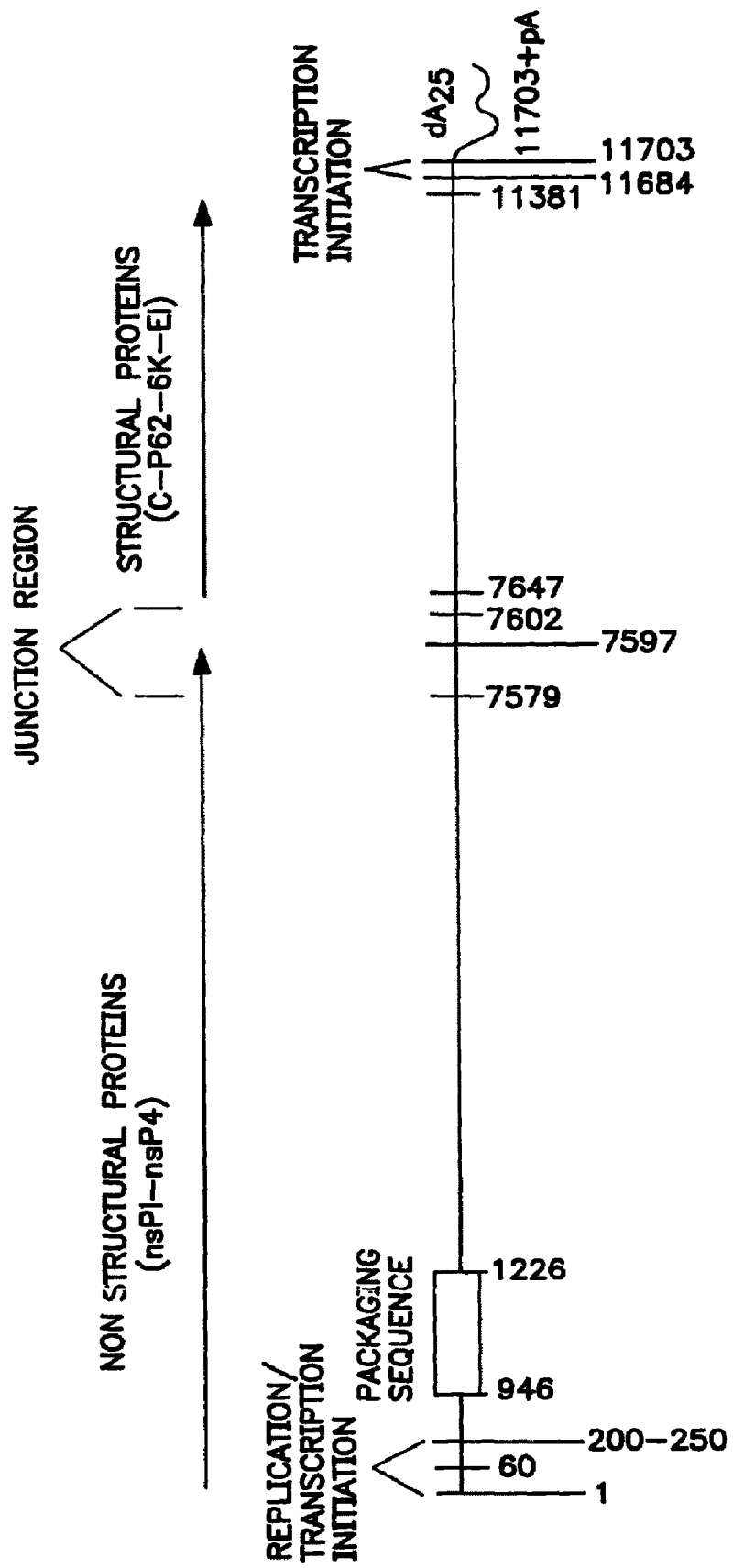
FIG. 1 is a schematic illustration of Sindbis virus genomic organization.
Figure 2:
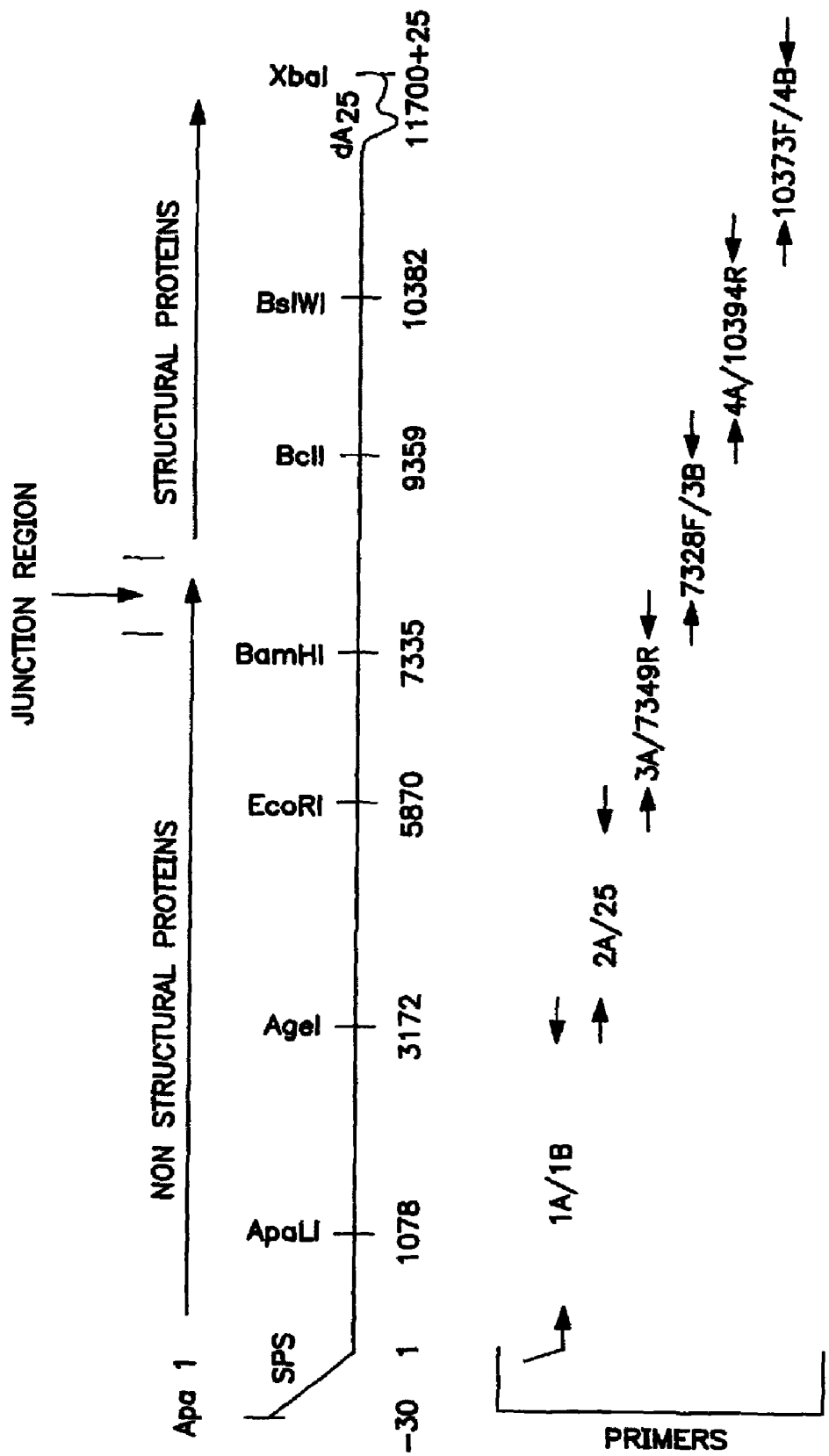
FIG. 2 is an illustration which depicts a method for amplification of a Sindbis RNA genome by RT-PCR.

Prior to setting forth the invention, it may be helpful to an understanding thereof to first set forth definitions of certain terms that will be used hereinafter.

"Alphavirus vector construct" refers to an assembly which is capable of directing the expression of a sequence(s) or gene(s) of interest. The vector construct should include a 5' sequence which is capable of initiating transcription of an alphavirus, as well as sequence(s) which, when expressed, code for biologically active alphavirus non-structural proteins (e.g., NSP1, NSP2, NSP3, and NSP4), and an alphavirus RNA polymerase recognition sequence. In addition, the vector construct should include a viral junction region which may, in certain embodiments, be modified in order to prevent, increase, or reduce viral transcription of the subgenomic fragment, and an alphavirus RNA polymerase recognition sequence. The vector may also include nucleic acid molecule(s) which are of a size sufficient to allow production of viable virus, a 5' promoter which is capable of initiating the synthesis of viral RNA in vitro from cDNA, as well as one or more restriction sites, and a polyadenylation sequence.

"Alphavirus cDNA vector construct" refers to an assembly which is capable of directing the expression of a sequence(s) or gene(s) of interest. The vector construct should include a 5' sequence which is capable of initiating transcription of an alphavirus, as well as sequence(s) which, when expressed, code for biologically active alphavirus non-structural proteins (e.g., NSP1, NSP2, NSP3, and NSP4), and an alphavirus RNA polymerase recognition sequence. In addition, the vector construct should include a 5' promoter which is capable of initiating the synthesis of viral RNA from cDNA, a viral junction region which may, in certain embodiments, be modified in order to prevent, increase, or reduce viral transcription of the subgenomic fragment, an alphavirus RNA polymerase recognition sequence, and a 3' sequence which controls transcription termination. The vector may also include nucleic acid molecule(s) which are of a size sufficient to allow production of viable virus, splice recognition sequences, a catalytic ribozyme processing sequence, as well as a polyadenylation sequence.

"Expression cassette" refers to a recombinantly produced nucleic acid molecule which is capable of directing the expression of one or more proteins. The expression cassette must include a promoter capable of directing the expression of said proteins, and a sequence encoding one or more proteins, said proteins preferably comprising alphavirus structural protein(s). Optionally, the expression cassette may include transcription termination, splice recognition, and polyadenylation addition sites. Preferred promoters include the CMV, MMTV, MoMLV, and adenovirus VA1RNA promoters. In addition, the expression cassette may contain selectable markers such as Neo, SV2 Neo, hygromycin, phleomycin, histidinol, and DHFR.

"Alphavirus producer cell line" refers to a cell line which is capable of producing recombinant alphavirus particles. The producer cell line should include an integrated alphavirus structural protein expression cassette capable of directing the expression of alphavirus structural protein(s), and also, an alphavirus vector construct. Preferably, the alphavirus vector construct is a cDNA vector construct. More preferably, the alphavirus vector construct is an integrated cDNA vector construct. When the alphavirus vector construct is an integrated cDNA vector construct, it may, in some instances, function only in response to one or more factors, or the differentiation state of the alphavirus producer cell line.

"Recombinant alphavirus particle" refers to a capsid which contains an alphavirus vector construct. Preferably, the capsid is an alphavirus capsid and is contained within a lipid bilayer, such as a cell membrane, in which viral-encoded proteins are embedded. In some instances, the alphavirus vector construct may be contained in a capsid derived from viruses other than alphaviruses (for example, retroviruses, coronaviruses, and hepatitis B virus). A variety of alphavirus vectors may be contained within the recombinant alphavirus particle, including the alphavirus vector constructs of the present invention.

A. Sources of Alphavirus

As noted above, the present invention provides alphavirus vector constructs, alphavirus particles containing such constructs, as well as methods for utilizing such vector constructs and particles. Briefly, sequences encoding wild-type alphavirus suitable for use in preparing the above-described vector constructs and particles may be readily obtained given the disclosure provided herein from naturally-occurring sources, or from depositories (e.g., the American Type Culture Collection, Rockville, Md.).

Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC \TR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

B. Sequences which Encode Wild-Type Sindbis Virus

Within one particularly preferred aspect of the present invention, the sequences which encode wild-type alphavirus may be obtained from Sindbis virus. In particular, within one embodiment of the invention (and as described in more detail below in Example 1), a Sindbis full-length genomic cDNA clone may be obtained by linking the 5' end of a Sindbis virus cDNA clone to a bacteriophage RNA polymerase promoter, and the 3' end of the cDNA clone to a polyadenosine (poly A) tract of at least 25 nucleotides. In particular, synthesis of the first cDNA strand from the viral RNA template may be accomplished with a 3' oligonucleotide primer having a consecutive sequence comprising an enzyme recognition sequence, a sequence of 25 deoxythymidine nucleotides, and a stretch of approximately 18 nucleotides which is complementary to the viral 3' end, and with a 5' primer containing buffer nucleotides, an enzyme recognition sequence, a bacteriophage promoter, and a sequence complimentary to the viral 5' end. The enzyme recognition sites present on each of these primers should be different from each other, and not found in the Sindbis virus. Further, the first nucleotide linked to the 3' end of the bacteriophage RNA polymerase promoter may be the authentic first nucleotide of the RNA virus, or may contain one or more additional non-viral nucleotides. RNA transcribed in vitro from the viral cDNA clone, having the construction described above and linearized by digestion with the unique dT:dA 3' distal restriction enzyme will, after introduction into the appropriate eukaryotic cell, initiate the same infection cycle which is characteristic of infection by the wild-type virus from which the cDNA was cloned. This viral cDNA clone, which yields RNA able to initiate infection after in vitro transcription, is referred to below as an "infectious cDNA clone."

C. Production of Recombinant Alphavirus Vector Constructs with Inactivated Viral Junction Regions An infectious cDNA clone prepared as described above (or utilizing sequences encoding an alphavirus obtained from other sources) may be readily utilized to prepare alphavirus vector constructs of the present invention. Briefly, within one aspect of the present invention, recombinant alphavirus vector constructs are provided, comprising a 5' sequence which is capable of initiating transcription of an alphavirus, a nucleotide sequence encoding alphavirus nonstructural proteins, a viral junction region which has been inactivated such that viral transcription of the subgenomic fragment is prevented, and an alphavirus RNA polymerase recognition sequence. As will be discussed in greater detail below, alphavirus vector constructs which have inactivated viral junction regions do not transcribe the subgenomic fragment, making them suitable for a wide variety of applications.

1. RNA Polymerase Promoter

As noted above, within certain embodiments of the invention alphavirus vector constructs are provided which contain a 5' promoter which is capable of initiating the synthesis of viral RNA in vitro from cDNA. Particularly, preferred 5' promoters include both eukaryotic and prokaryotic promoters, such as, for example, the β-galactosidase promoter, trpE promoter, lacZ promoter, T7 promoter, T3 promoter, SP6 promoter, SV40 promoter, CMV promoter, and MoMLV LTR.

2. Sequences which Initiate Transcription

As noted above, within preferred embodiments the alphavirus vector constructs of the present invention contain a 5' sequence which is capable of initiating transcription of an alphavirus. Representative examples of such sequences include nucleotides 1-60, and to a lesser extent nucleotides 150-210, of the wild-type Sindbis virus (see FIG. 3), nucleotides 10-75 for tRNA Asparagine (Schlesinger et al., U.S. Pat. No. 5,091,309), and 5' sequences from other Togaviruses which initiate transcription.

3. Alphavirus Nonstructural Proteins

Alphavirus vector constructs of the present invention should also contain sequences which encode alphavirus nonstructural proteins (NSPs). As an example, for Sindbis virus there are four nonstructural proteins, NSP1, NSP2, NSP3 and NSP4, which encode proteins that enable the virus to self-replicate. Nonstructural proteins 1 through 3 (NSP1-NSP3) are, within one embodiment of the invention, encoded by nucleotides 60 to 5750 of the wild-type Sindbis virus (see FIG. 3). These proteins are produced as a polyprotein and later cleaved into nonstructural proteins NSP1, NSP2, and NSP3. NSP4 is, within one embodiment, encoded by nucleotides 5928 to 7579 (see FIG. 3).

It will be evident to one of ordinary skill in the art that a wide variety of sequences which encode alphavirus nonstructural proteins, in addition to those discussed above, may be utilized in the present invention, and are therefore deemed to fall within the scope of the phrase "Alphavirus Nonstructural Proteins." For example, within one embodiment of the invention, due to the degeneracy of the genetic code, more than one codon may code for a given amino acid. Therefore, a wide variety of nucleic acid sequences which encode alphavirus nonstructural proteins may be generated. Within other embodiments of the invention, a variety of other nonstructural protein derivatives may be made, including for example, various substitutions, insertions, or deletions, the net result of which do not alter the biological activity of the alphavirus nonstructural proteins. Within the context of the present invention, alphavirus nonstructural proteins are deemed to be "biologically active" in tow if they promote the self-replication of the vector construct. Self-replication, which refers to replication of viral nucleic acids and not the production of infectious virus, may be readily determined by metabolic labelling or RNase protection assays performed over a course of time. Methods for making such derivatives may be readily accomplished by one of ordinary skill in the art given the disclosure provided herein (see also, *Molecular Cloning: A Laboratory Manual* (2d. ed.), Cold Spring Harbor Laboratory Press).

4. Viral Junction Regions

Within this aspect of the invention, the alphavirus vector constructs may also include a viral junction region which has been inactivated, such that viral transcription of the subgenomic fragment is prevented. Briefly, the alphavirus viral junction region normally controls transcription initiation of the subgenomic mRNA. In the case of the Sindbis virus, the normal viral junction region typically begins at approximately nucleotide number 7579 and continues through at least nucleotide number 7612 (and possibly beyond). At a minimum, nucleotides 7579 to 7602 (5'-ATC TCT ACG GTG GTC CTA AAT AGT—SEQ. ID NO. 2) are believed necessary for transcription of the subgenomic fragment. This region (nucleotides 7579 to 7602) is hereinafter referred to as the "minimal junction region core."

Within preferred embodiments of the invention (and as described in more detail below), the viral junction region is inactivated in order to prevent viral transcription of the subgenomic fragment. As utilized within the context of the present invention, "inactivated" means that the fragment corresponding to the initiation point of the subgenomic fragment, as measured by a RNase protection assay, is not detected. (Representative assays are described by Melton et al., *Nuc. Acids Res.* 12:7035-7056, 1984; Calzon et al., *Methods in Enz.* 152:611-632, 1987; and Kekula et al., *Nature* 343:457-461, 1990.)

Within one embodiment of the invention, the viral junction region is inactivated by truncating the viral junction region at nucleotide 7597 (i.e., the viral junction region will then consist of the sequence as shown in FIG. 3, from nucleotide 7579 to nucleotide 7597). This truncation prevents transcription of the subgenomic fragment, and additionally permits synthesis of the complete NSP4 region (which is encoded by nucleotides 5928 to 7579).

As will be evident to one of ordinary skill in the art given the disclosure provided herein, a wide variety of other deletions, substitutions or insertions may also be made in order to inactivate the viral junction region. For example, within other embodiments of the invention the viral junction region may be further truncated into the region which encodes NSP4, thereby preventing viral transcription from the subgenomic fragment while retaining the biological activity of NSP4. Alternatively, within other embodiments, due to the redundancy of the genetic code, nucleotide substitutions may be made in the sequence encoding NSP4, the net effect of which does not alter the biological activity of NSP4 yet, nevertheless, prevents transcription of the subgenomic fragment.

5. Alphavirus RNA Polymerase Recognition Sequence and Poly-A Tail

As noted above, alphavirus vector constructs of the present invention should also include an alphavirus RNA polymerase recognition sequence (also termed "alphavirus replicase recognition sequence"). Briefly, the alphavirus RNA polymerase recognition sequence provides a recognition site at which the virus begins replication by synthesis of the negative strand. A wide variety of sequences may be utilized as an alphavirus RNA polymerase recognition sequence. For example, within one embodiment, Sindbis vector constructs of the present invention include a Sindbis polymerase recognition sequence which is encoded by nucleotides 11,647 to 11,703 (see FIG. 3). Within other embodiments, the Sindbis polymerase recognition is truncated to the smallest region which can still function as a recognition sequence (e.g., nucleotides 11,684 to 11,703 of FIG. 3).

Within preferred embodiments of the invention, the vector construct may additionally contain a polyA tail. Briefly, the polyA tail may be of any size which is sufficient to promote stability in the cytoplasm, thereby increasing the efficiency of initiating the viral life cycle. Within various embodiments of the invention, the polyA Nil comprises at least 10 adenosine nucleotides, and most preferably, at least 25 adenosine nucleotides.

D. Other Alphavirus Vector Constructs

In addition to the vector constructs which are generally described above, a wide variety of other alphavirus vector constructs may also be prepared utilizing the disclosure provided herein.

1. Modified Viral Junction Regions

As noted above, the present invention provides viral junction regions which have been modified from the wild-type sequence. Within the context of the present invention, modified viral junction regions should be understood to include junction regions which have wild-type activity, but a non-wild-type sequence, as well as junction regions with increased, decreased, or no activity. For example, within one aspect of the invention, alphavirus vector constructs are provided wherein the viral junction region has been modified, such that viral transcription of the subgenomic fragment is reduced. Briefly, infection of cells with wild-type alphavirus normally results in cell death as a result of abundant viral transcription of the subgenomic fragment initiated from the viral junction region. This large abundance of RNA molecules can overwhelm the transcriptional machinery of the infected cell, ultimately resulting in death of the cell. In applications where it is desired that infection of a target cell should result in a therapeutic effect (e.g., strand scission of a target nucleic acid or prolonged expression of a heterologous protein) rather than cell death, several modifications to the alphavirus vector construct (in addition to inactivating the vector construct, as described above) may be made in order to reduce the level of viral transcription of the subgenomic fragment, and thereby prolong the life of the vector infected target cell. Within the context of the present invention, viral transcription of the subgenomic fragment is considered to be "reduced" if it produces less subgenomic fragment than a standard wild-type alphavirus (e.g., Sindbis virus ATCC No. VR-1248) as determined by a RNase protection assay.

Viral junction regions may be modified by a variety of methods in order to reduce the level of viral transcription of the subgenomic fragment. For example, within one embodiment of the invention, due to the redundancy of the genetic code nucleotide substitutions may be made in the viral junction region 7579 to 7597, the net effect of which does not alter the amino acid sequence NSP4 (or, within other embodiments, the biological activity of NSP4), and yet reduces the level of viral transcription of the subgenomic fragment. If the modified vector construct includes nucleotides beyond 7597 (e.g., to 7602 or 7612), further nucleotide substitutions may likewise be made, although, since NSP4 terminates at 7597, such substitutions need not be based upon genetic redundancy. Representative examples of modified viral junction regions are described in more detail below in Example 3.

2. Tandem Viral Junction Regions

Within other aspects of the invention, alphavirus vector constructs are provided, which comprise a 5' sequence which is capable of initiating transcription of an alphavirus, a nucleotide sequence encoding alphavirus non-structural proteins, a first viral junction region which has been inactivated such that viral transcription of the subgenomic fragment is prevented, a second viral junction region which is active, or which has been modified such that viral transcription of the subgenomic fragment is reduced, and an alphavirus RNA polymerase recognition sequence. Such vector constructs are referred to as "tandem" vector constructs because they comprise a first inactivated (or "disabled") viral junction region, as well as a second modified ("synthetic") or unmodified viral junction region. Within preferred embodiments of the invention, the inactivated junction region is followed directly by the second viral junction region.

In applications where a low level of subgenomic transcription is required, a minimal junction region core may be inserted downstream in tandem to the inactivated junction region. In order to gradually increase the level of subgenomic transcription for the desired effect, sequences corresponding to the entire junction region may be added to the in-tandem junction region, in increments.

3. The adenovirus E3 Gene

Within another aspect of the invention, an adenovirus E3 gene is inserted into a tandem vector construct following the second viral junction region, in order to down-regulate HLA expression in alphavirus infected cells. Briefly, within various embodiments of the invention, repeated inoculations of a gene therapeutic into the same individual is desirable. However, repeated inoculations of alphaviruses such as the Sindbis virus may lead to the development of specific antibodies or cell-mediated immune response against Sindbis viral nonstructural proteins (NSPs). Thus, it may be necessary to mitigate the host immune response targeted to vector-specific proteins in order to administer repeated doses to the same individual.

Therefore, within one embodiment of the invention, products of the Adenovirus type 2 early region gene 3 are utilized in order to down-regulate the expression of integral histocompatibility antigens expressed on the surface of infected cells. Briefly, the E3 19,000 dalton (E3/19K) protein binds to, and forms a molecular complex with, class I H-2/HLA antigens in the endoplasmic reticulum, preventing terminal glycosylation pathways necessary for the full maturation and subsequent transport of the class I H-2/HLA antigens to the cell membrane. In target cells infected with an alphavirus vector encoding the Ad 2 E3 protein, co-expression of the viral nonstructural proteins in the context of class I antigens will not occur. Thus, it is possible to administer repeated doses of an alphavirus vector which expresses the Ad 2 E3 protein as a component of its therapeutic palliative to the same individual. A representative example of the use of the Adenovirus E3 gene is set forth in more derail below in Example 4A.

4. The CMV H301 Gene

Other methods may also be utilized in order to mitigate a host's immune response against viral NSPs. For example, within another aspect of the invention, the human cytomegalovirus ("HCMV") H301 gene is cloned into an alphavirus vector construct, preferably immediately following the second viral junction region in a tandem vector, in order to inhibit host CTL response directed against viral specific proteins expressed in vector infected cells.

Briefly, 2-Microglobulin (2 m) protein binds to the 1, 2 and 3 domains of the alpha-chain of the class I major histocompatibility molecules of higher eukaryotes. Preventing the interaction between 2 m and MHC class I products renders infected cells unrecognizable by cytotoxic T cells. Therefore, as described in greater detail below in Example 4B, expression of the HCMV H301 gene product as a component of a therapeutic palliative may be utilized in order to mitigate the host immune response to viral NSP.

5. Nonalphavirus Packaging Sequence

Within another aspect of the invention, a packaging sequence derived from a virus other than an alphavirus (for example, retrovirus, coronavirus, hepatitis B virus) is inserted into a tandem vector and positioned between the first (inactivated) viral junction region and the second, modified viral junction region. Briefly, nonalphavirus packaging sequences signal the packaging of an RNA genome into a virus particle corresponding to the source of the packaging sequence. For example, and as described in more detail below, a retroviral packaging sequence may be utilized in order to package an alphavirus vector into a retroviral particle using a retroviral packaging cell line. This is performed in order to increase the efficiency of alphavirus vector transfer into an alphavirus packaging cell line, or to alter the cell or tissue tropism of the alphavirus vector.

6. Expression of Multiple Heterologous Genes

The genomic length and subgenomic length of mRNAs transcribed in wild-type alphavirus infected cells are polycistronic, coding for, respectively, the viral four non-structural proteins (NSPs) and four structural proteins (SPs). The genomic and subgenomic mRNAs are translated as polyproteins, and processing into the individual nonstructural and structural proteins is accomplished by post-translational proteolytic cleavage, catalyzed by viral encoded NSP- and SP-specific proteases, as well as cellular proteases.

In certain applications of the alphavirus vectors described herein, the expression of more than one heterologous gene is desired. For example, in order to treat metabolic disorders such as Gaucher's syndrome, multiple administrations of alphavirus vectors or particles may be required, since duration of the therapeutic palliative may be limited. Therefore, with certain embodiments of the invention it may be desirable to co-express in a target cell the Ad 2 E3 gene (see Example 4), along with a therapeutic palliative, such as the glucocerebrosidase gene (see Example 17). In wild-type virus, however, the structural protein ("SP") polycistronic message is translated into a single polyprotein which is subsequently processed into individual proteins by cleavage with SP-encoded proteases. Thus, expression of multiple heterologous genes from a polycistronic message requires a mechanism different from the wild-type virus, since the SP protease gene, or the peptides recognized for cleavage, are not present in the replacement region of the alphavirus vectors.

Therefore, within one embodiment of the invention alphavirus vectors may be constructed by placing appropriate signals either ribosome readthrough or internal ribosome entry between cistrons. One such representative method of expressing multiple heterologous genes is set forth below in Example 5.

In yet another embodiment of the invention, the placement of signals promoting either ribosome readthrough or internal ribosome entry immediately downstream of the disabled junction region vector pKSSINBVdlJR is described (see Examples 3 and 5). In this vector configuration, synthesis of subgenomic message cannot occur, however, the heterologous proteins are expressed from genomic length mRNA by either ribosomal readthrough (scanning) or internal ribosome entry. Relative to wild-type, the low level of viral transcription with this alphavirus vector would prolong the life of the infected target cell.

In still another embodiment of the invention, placement of signals promoting either ribosome readthrough or internal ribosome entry immediately downstream of the pKSSINBVdlJRsjr or pKSSINBV vectors is described. Briefly, since synthesis of subgenomic mRNA occurs in cells infected with the pKSSINBVdlJRsjr and pKSSINBV vectors, placement of either a ribosome readthrough sequence or an internal ribosome entry sequence between the two heterologous genes permits translation of both proteins encoded by the subgenomic mRNA polycistronic message. Further, additional heterologous genes can be placed in the subgenomic mRNA region, provided that a suitable translation initiation signal resides at the 5' end of the translational AUG start codon. The number of heterologous gene(s) which can be inserted into the subgenomic mRNA region, as described here, is limited only by the packaging constraints of the vector.

Different sequences which allow either ribosome readthrough, cap-independent translation, or internal ribosome entry may be placed into Sindbis vectors pKSSINBVdlJR, pKSSINBV, pKSSINBVdlJRsjrc, or vectors encompassed by the eukaryotic layered vector initiation system, in the configurations as discussed above. The source of these translation control sequences are the picornaviruses polio and EMCV, the 5' noncoding region of the human immunoglobulin heavy-chain binding protein, and a synthetic sequence of at least 15 bps corresponding in part to the Kozak consensus sequence for efficient translational initiation. Although not described in detail here, these signals which affect translation initiation can also be placed downstream of the junction region and between heterologous genes in all of the Modified junction region vectors described in Example 3.

As noted above, the alphavirus cDNA vector construct also includes a 3' sequence which controls transcription termination. A representative example of such a sequence is set forth in more detail below in Examples 2 and 3.

7. Tissue Specific Expression

Figure 20A:
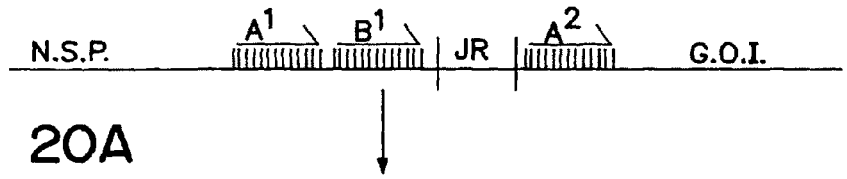
FIG. 20A-D is a schematic illustration of several representative mechanisms for activating a disabled viral junction region by "RNA loop-out."
Figure 20B:
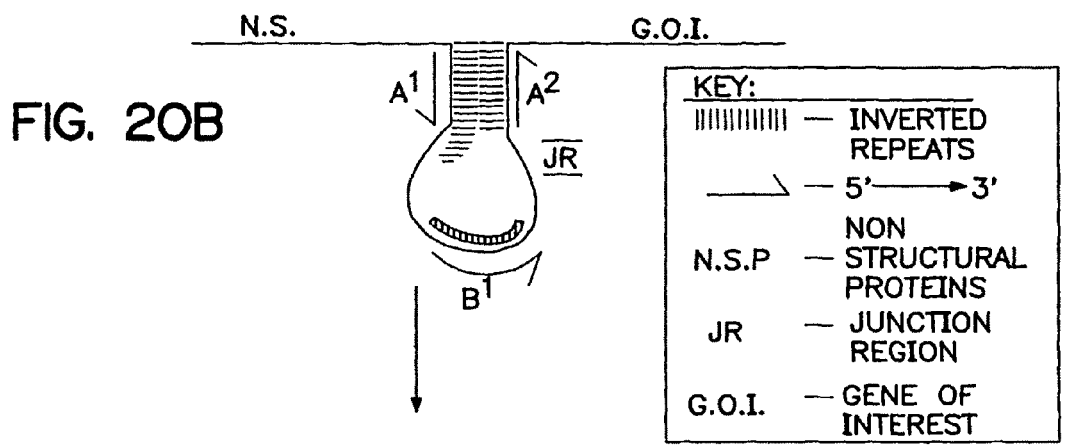

Within other aspects of the present invention, alphavirus vector constructs are provided which are capable of expressing a desired heterologous sequence only in a selected tissue. One such representative example is shown in FIG. 20. Briefly, as shown in FIG. 20A, a recombinant alphavirus vector is constructed such that upon introduction of the vector (FIG. 20A) into a target cell, internal inverted repeat sequences which flank the transcriptional control regions (e.g., modified junction region) loop out (see FIG. 20B), thereby preventing viral transcription of subgenomic sequences ("G.O.I.") from the synthetic junction region.

Figure 20C:
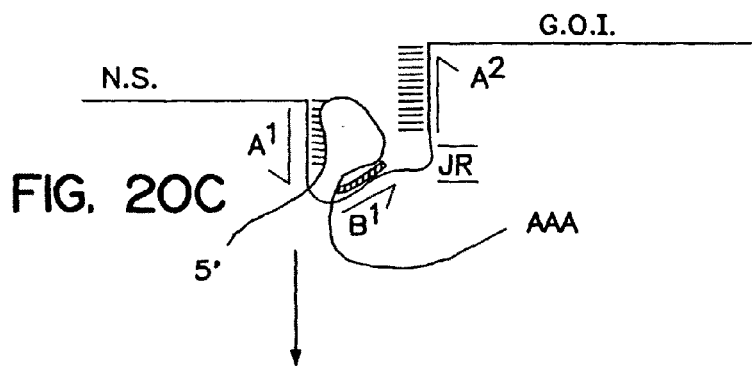
Figure 20D:
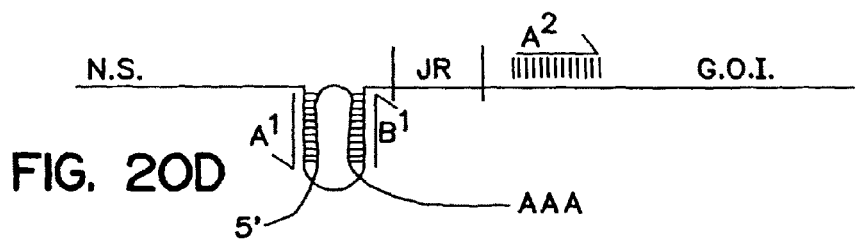
Figure 21:
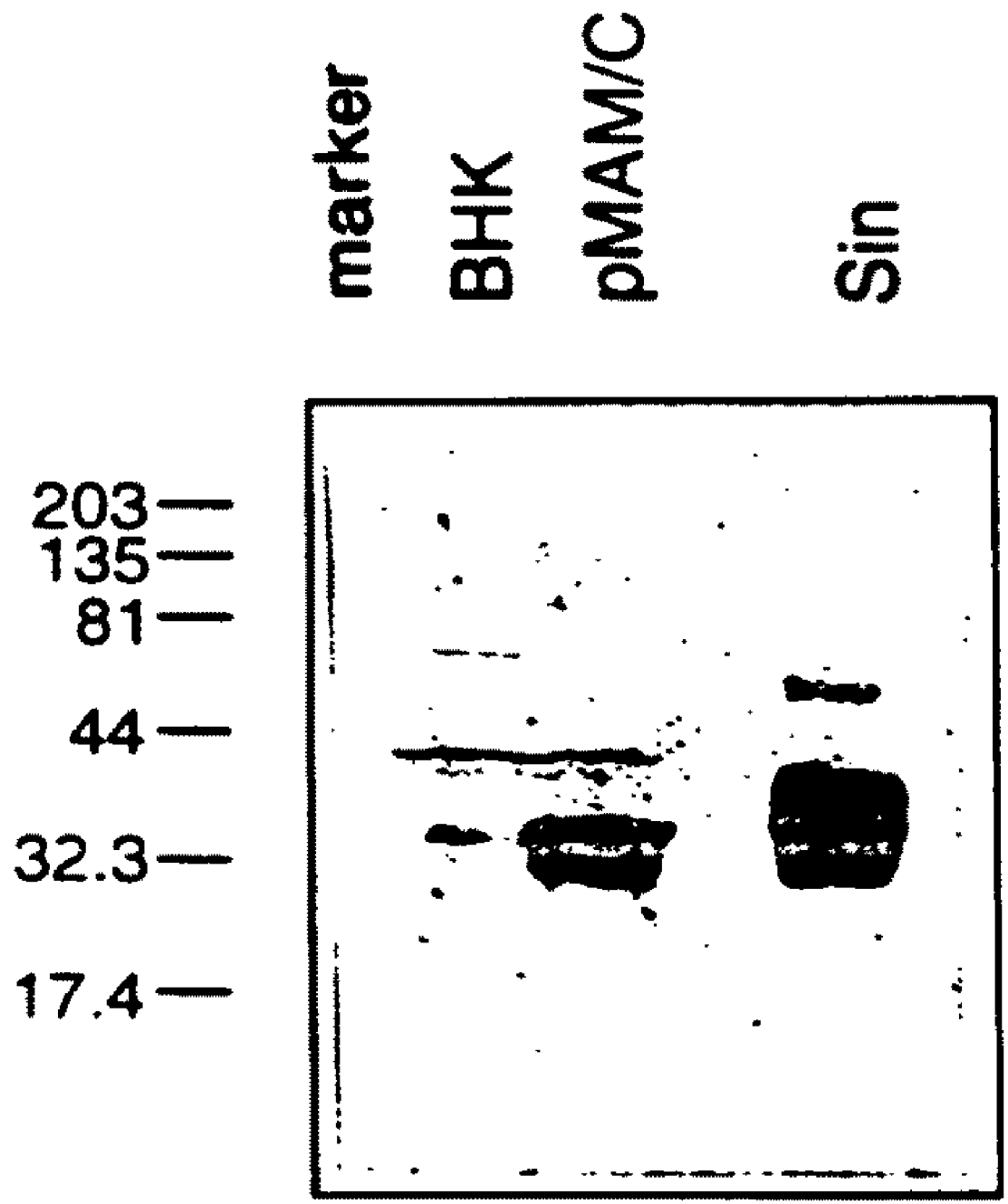
FIG. 21 is a western blot demonstrating expression of capsid protein after transfection with pMAM/C, selection in HAT media, and induction with dexamethasone.

On the other hand, activation of the vector can be attained if the inverted repeats are designed to also hybridize to a specific cellular RNA sequence which is characteristic of a selected tissue or cell type. Such cellular RNA disrupts the disabling stem loop structure, thereby allowing the formation of a more stable secondary stem loop structure (FIGS. 20C and 20D). This secondary stem loop structure allows transcription of the sub-genomic message by placing the junction region back into its correct positional configuration.

Full-length alphavirus vectors can also be transcribed using the secondary stem loop structure by taking advantage of the ability of the viral polymerase to switch templates during synthesis of the negative strand using a strand hopping mechanism termed copy choice (King, *RNA genetics II*, CRC Press, Inc., Boca Raton Fla., Domingo et al. (ed.), pp. 150-185, 1988). Once a single successful round of transcription has occurred, the resulting RNA transcript does not contain inverted repeats because they are deleted as a result of the polymerase copy choice event. This newly synthesized RNA molecule now functions as the primary RNA vector transcript which will transcribe and express as any other non-disabled genomic alphavirus vector previously described. In this RNA vector configuration, tissue or cell-specific activation of the disabled Sindbis vector can be achieved if specific RNA sequences, present only in the targeted cell or tissue types, are used in the design of the inverted repeats. In this fashion alphaviruses such as Sindbis can be engineered to be tissue-specific expression vectors using similar inverted sequences described above.

Using this vector system to achieve tissue specific expression enables a therapeutic alphavirus vector or particle to be delivered systemically into a patient. If the vector should infect a cell which does not express the appropriate RNA species, the vector will only be capable of expressing non-structural proteins and not the gene of interest. Eventually, the vector will be harmlessly degraded.

Use of the above-described vectors enables virtual tissue-specific expression possible for a variety of therapeutic applications, including for example, targeting vectors for the treatment for various types of cancers. This rationale relies on specific expression of tumor-specific markers such as the carcinoembryonic tumor specific antigen (CEA) and the alpha-fetoprotein tumor marker. Briefly, utilizing such tumor-specific RNA to target specific tumors allows for the tumor-specific expression of toxic molecules, lymphokines or pro-drugs discussed below. Such methods may be utilized for a wide variety of tumors, including for example, colorectal, lung, breast, ovary, bladder and prostate cancers because all these tumors express the CEA. One representative illustration of vectors suitable for use within this aspect of the present invention is set forth in more detail below in Example 16.

Briefly, CEA was one of the first tumor-specific markers to be described, along with the alpha-fetoprotein tumor marker. CEA is a normal glycoprotein in the embryonic tissue of the gut, pancreas and liver during the first two trimesters of fetal development (*Pathologic Basis of Disease,* 3rd edition 1984, Robbins et al. (eds.)). Previously, CEA was believed to be specific for adenocarcinomas of the colon, however, with the subsequent development of more sensitive radioimmunoassays it became apparent that CEA was presented in the plasma with many endodermally derived cancers, particularly pancreatic, gastric and broncogenic.

Within related aspects of the present invention, alphavirus cell-specific expression vectors may be constructed to express viral antigens, ribozyme, antisense sequences or immunostimulatory factors such as gamma-interferon (γ-IFN), IL-2 or IL-5 for the targeted treatment of virus infected cell types. In particular, in order to target alphavirus vectors to specific foreign organism or pathogen-infected cells, inverted repeats of the alphavirus vector may be selected to hybridize to any pathogen-specific RNA, for instance target cells infected by pathogens such as HIV, CMV, HBV, HPV and HSV.

Within yet other aspects of the invention, specific organ tissues may be targeted for the treatment of tissue-specific metabolic diseases utilizing gene replacement therapies. For example, the liver is an important target tissue because it is responsible for many of the body's metabolic functions and is associated with many metabolic genetic disorders. Such diseases include many of the glycogen storage diseases, phenylketonuria, Gaucher's disease and familial hypercholesterolemia. Presently there are many liver-specific enzymes and markers which have been sequenced which may be used to engineer appropriate inverted repeats for alphavirus vectors. Such liver-specific cDNAs include sequences encoding for S-adenosylmethione synthetase (Horikawa et al., *Biochem. Int.* 25:81, 1991); lecithin: cholesterolacyl transferase (Rogue et al., *Biochem. Biophys. Res. Commun.* 148:161, 1987); as well as other liver-specific cDNAs (Chin et al., *Ann. N.Y. Acad. Sci.* 478:120, 1986). Such a liver-specific alphavirus vector could be used to deliver the low density lipoprotein receptor (Yamamoto et al., *Cell* 39:27, 1984) to liver cells for the treatment of familial hypercholesterolemia (Wilson et al., *Mol. Biol. Med.* 7:223, 1990).

E. Heterologous Sequences

As noted above, a wide variety of nucleotide sequences may be carried by the alphavirus vector constructs of the present invention. Preferably, the nucleotide sequences should be of a size sufficient to allow production of viable virus. Within the context of the present invention, the production of any measurable titer, for example, by plaque assay, luciferase assay, or β-galactosidase assay, of infectious virus on appropriate susceptible monolayers, is considered to be "production of viable virus." This may be, at a minimum, an alphavirus vector construct which does not contain any additional heterologous sequence. However, within other embodiments, the vector construct may contain additional heterologous or foreign sequences. Within preferred embodiments, the heterologous sequence will comprise a heterologous sequence of at least about 100 bases, 2 kb, 3.5 kb, 5 kb, 7 kb, or even a heterologous sequence of at least about 8 kb.

As will be evident to one of ordinary skill in the art given the disclosure provided herein, the efficiency of packaging and hence, viral titer, is to some degree dependent upon the size of the sequence to be packaged. Thus, in order to increase the efficiency of packaging and the production of viable virus, additional non-coding sequences may be added to the vector construct. Moreover, within certain embodiments of the invention it may be desired to increase or decrease viral titer. This increase or decrease may be accomplished by increasing or decreasing the size of the heterologous sequence, and hence the efficiency of packaging.

A wide variety of heterologous sequences may be included in the vector construct, including for example sequences which encode palliatives such as lymphokines, toxins, prodrugs, antigens which stimulate an immune response, ribozymes, and proteins which assist or inhibit an immune response, as well as antisense sequences (or sense sequences for "antisense applications"). As noted above, within various embodiments of the invention the alphavirus vector constructs provided herein may contain (and express, within certain embodiments) two or more heterologous sequences.

1. Lymphokines

Within one embodiment of the invention, the heterologous sequence encodes a lymphokine. Briefly, lymphokines act to proliferate, activate, or differentiate immune effectors cells. Representative examples of lymphokines include gamma interferon, tumor necrosis factor, IL-1, IL-2, IL-3, IL-4, IL-5, IL-6, IL-7, IL-8, IL-9, M-10, IL-11, IL-12, IL-13, IL-14, IL-15, GM-CSF, CSF-1 and G-CSF.

Within related embodiments of the invention, the heterologous sequence encodes an immunomodulatory cofactor. Briefly, as utilized within the context of the present invention, "immunomodulatory cofactor" refers to factors which, when manufactured by one or more of the cells involved in an immune response, or when added exogenously to the cells, causes the immune response to be different in quality or potency from that which would have occurred in the absence of the cofactor. The quality or potency of a response may be measured by a variety of assays known to one of skill in the art including, for example, in vitro assays which measure cellular proliferation (e.g., $^3$H thymidine uptake), and in vitro cytotoxic assays (e.g., which measure $^{51}$Cr release) (see Warner et al., *AIDS Res. and Human Retroviruses* 7:645-655, 1991).

Representative examples of immunomodulatory co-factors include alpha interferon (Finter et al., *Drugs* 42(5):749-765, 1991; U.S. Pat. No. 4,892,743; U.S. Pat. No. 4,966,843; WO 85/02862; Nagata et al., *Nature* 284:316-320, 1980; Familletti et al., *Methods in Enz.* 78:387-394, 1981; Twu et al., *Proc. Natl. Acad. Sci. USA* 86:2046-2050, 1989; Faktor et al., *Oncogene* 5:867-872, 1990), beta interferon (Seif et al., *J. Virol.* 65:664-671, 1991), gamma interferons (Radford et al., *American Society of Hepatology*:2008-2015, 1991; Watanabe et al., *PNAS* 86:9456-9460, 1989; Gansbacher et al., *Cancer Research* 50:7820-7825, 1990; Maio et al., *Can. Immunol. Immunother.* 30:3442, 1989; U.S. Pat. Nos. 4,762,791 and 4,727,138), G-CSF (U.S. Pat. Nos. 4,999,291 and 4,810,643), GM-CSF (WO 85/04188), TNFs (Jayaraman et al., *J. Immunology* 144:942-951, 1990), Interleukin-2 (IL-2) (Karupiah et al., *J. Immunology* 144:290-298, 1990; Weber et al., *J. Exp. Med.* 166:1716-1733, 1987; Gansbacher et al., *J. Exp. Med.* 172:1217-1224, 1990; U.S. Pat. No. 4,738,927), IL-4 (Tepper et al., *Cell* 57:503-512, 1989; Golumbek et al., *Science* 254:713-716, 1991; U.S. Pat. No. 5,017,691), IL-6 (Brakenhof et al., *J. Immunol.* 139:4116-4121, 1987; WO 90/06370), IL-12, IL-15 (Grabstein et al., *Science* 264:965-968, 1994; Genbank-EMBL Accession No. V03099), ICAM-1 (Altman et al., *Nature* 338:512-514, 1989), ICAM-2, LFA-1, LFA-3, MHC class I molecules, MHC class II molecules, 2-microglobulin, chaperones, CD3, B7/BB1, MHC linked transporter proteins or analogues thereof.

The choice of which immunomodulatory cofactor to include within a alphavirus vector construct may be based upon known therapeutic effects of the cofactor, or experimentally determined. For example, in chronic hepatitis B infections alpha interferon has been found to be efficacious in compensating a patient's immunological deficit and thereby assisting recovery from the disease. Alternatively, a suitable immunomodulatory cofactor may be experimentally determined. Briefly, blood samples are first taken from patients with a hepatic disease. Peripheral blood lymphocytes (PBLs)

are restimulated in vitro with autologous or HLA-matched cells (e.g., EBV transformed cells), and transduced with an alphavirus vector construct which directs the expression of an immunogenic portion of a hepatitis antigen and the immunomodulatory cofactor. Stimulated PBLs are used as effectors in a CTL assay with the HLA-matched transduced cells as targets. An increase in CTL response over that seen in the same assay performed using HLA-matched stimulator and target cells transduced with a vector encoding the antigen alone, indicates a useful immunomodulatory cofactor. Within one embodiment of the invention, the immunomodulatory cofactor gamma interferon is particularly preferred.

Another example of an immunomodulatory cofactor is the B7/BB1 costimulatory factor. Briefly, activation of the full functional activity of T cells requires two signals. One signal is provided by interaction of the antigen-specific T cell receptor with peptides which are bound to major histocompatibility complex (MHC) molecules, and the second signal, referred to as costimulation, is delivered to the T cell by antigen-presenting cells. Briefly, the second signal is required for interleukin-2 (IL-2) production by T cells and appears to involve interaction of the B7/BB1 molecule on antigen-presenting cells with CD28 and CTLA-4 receptors on T lymphocytes (Linsley et al., *J. Exp. Med.*, 173:721-730, 1991a, and *J. Exp. Med.*, 174:561-570, 1991). Within one embodiment of the invention, B7/BB1 may be introduced into tumor cells in order to cause costimulation of $CD8^+$ T cells, such that the $CD8^+$ T cells produce enough IL-2 to expand and become fully activated. These $CD8^+$ T cells can kill tumor cells that are not expressing B7 because costimulation is no longer required for further CTL function. Vectors that express both the costimulatory B7/BB1 factor and, for example, an immunogenic HBV core protein, may be made utilizing methods which are described herein. Cells transduced with these vectors will become more effective antigen-presenting cells. The HBV core-specific CTL response will be augmented from the fully activated $CD8^+$ T cell via the costimulatory ligand B7/BB1.

2. Toxins

Within another embodiment of the invention, the heterologous sequence encodes a toxin. Briefly, toxins act to directly inhibit the growth of a cell. Representative examples of toxins include ricin (Lamb et al., *Eur. J. Biochem.* 148:265-270, 1985), abrin (Wood et al., *Eur. J. Biochem.* 198:723-732, 1991; Evensen et al., *J. of Biol. Chem.* 266:6848-6852, 1991; Collins et al., *J. of Biol. Chem.* 265:8665-8669, 1990; Chen et al., *Fed. of Eur. Biochem Soc.* 309:115-118, 1992), diphtheria toxin (Tweten et al., *J. Biol. Chem.* 260:10392-10394, 1985), cholera toxin (Mekalanos et al., *Nature* 306:551-557, 1983; Sanchez and Holmgren, *PNAS* 86:481-485, 1989), gelonin (Stirpe et at, *J. Biol. Chem.* 255:6947-6953, 1980), pokeweed (Irvin, *Pharmac. Ther.* 21:371-387, 1983), antiviral protein (Barbieri et al., *Biochem. J.* 203:55-59, 1982; Irvin et al., *Arch. Biochem. & Biophys.* 200:418-425, 1980; Irvin, *Arch. Biochem. & Biophys.* 169:522-528, 1975), tritin, *Shigella* toxin (Calderwood et al., *PNAS* 84:436-44368, 1987; Jackson et al., *Microb. Path.* 2:147-153, 1987), *Pseudomonas* exotoxin A (Carroll and Collier, *J. Biol. Chem.* 262:8707-8711, 1987), herpes simplex virus thymidine kinase (HSVTK) (Field et at, *J. Gen. Virol.* 49:115-124, 1980), and *E. coli* guanine phosphoribosyl transferase.

3. Pro-Drugs

Within other embodiments of the invention, the heterologous sequence encodes a "pro-drug". Briefly, as utilized within the context of the present invention, "pro-drug" refers to a gene product that activates a compound with little or no cytotoxicity into a toxic product. Representative examples of such gene products include HSVTK and VZVTK (as well as analogues and derivatives thereof), which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAU, FIAC, DHPG) to HSVTK phosphorylates the drug into its corresponding active nucleotide triphosphate form.

Representative examples of other pro-drugs which may be utilized within the context of the present invention include: *E. coli* guanine phosphoribosyl transferase which converts thioxanthine into toxic thioxanthine monophosphate (Besnard et al., *Mol. Cell. Biol.* 7:4139-4141, 1987); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase, which will convert 5-fluorocytosine to the toxic compound 5-fluorouracil (Mullen, *PNAS* 89:33, 1992); carboxypeptidase G2, which will cleave the glutamic acid from para-N-bis(2-chloroethyl)aminobenzoyl glutamic acid, thereby creating a toxic benzoic acid mustard; and Penicillin-V amidase, which will convert phenoxyacetabide derivatives of doxorubicin and melphalan to toxic compounds (see generally, Vrudhula et al., *J. of Med. Chem.* 36(7):919-923, 1993; Kern et al., *Canc. Immun. Immunother.* 31(4):202-206, 1990).

4. Antisense Sequences

Within another embodiment of the invention, the heterologous sequence is an antisense sequence. Briefly, antisense sequences are designed to bind to RNA transcripts, and thereby prevent cellular synthesis of a particular protein or prevent use of that RNA sequence by the cell. Representative examples of such sequences include antisense thymidine kinase, antisense dihydrofolate reductase (Maher and Dolnick, *Arch. Biochem. & Biophys.* 253:214-220, 1987; Bzik et al., *PNAS* 84:8360-8364, 1987), antisense HER2 (Coussens et al., *Science* 230:1132-1139, 1985), antisense ABL (Fainstein et al., *Oncogene* 4:1477-1481, 1989), antisense Myc (Stanton et al., *Nature* 310:423-425, 1984) and antisense ras, as well as antisense sequences which block any of the enzymes in the nucleotide biosynthetic pathway. In addition, within other embodiments of the invention antisense sequences to interferon and 2 microglobulin may be utilized in order to decrease immune response.

In addition, within a further embodiment of the invention, antisense RNA may be utilized as an anti-tumor agent in order to induce a potent Class I restricted response. Briefly, in addition to binding RNA and thereby preventing translation of a specific mRNA, high levels of specific antisense sequences are believed to induce the increased expression of interferons (including gamma-interferon) due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

5. Ribozymes

Within other aspects of the present invention, alphavirus vectors are provided which produce ribozymes upon infection of a host cell. Briefly, ribozymes are used to cleave specific RNAs and are designed such that it can only affect one specific RNA sequence. Generally, the substrate binding sequence of a ribozyme is between 10 and 20 nucleotides long. The length of this sequence is sufficient to allow a hybridization with target RNA and disassociation of the ribozyme from the cleaved RNA. Representative examples for creating ribozymes include those described in U.S. Pat. Nos. 5,116,742; 5,225,337 and 5,246,921. Particularly preferred ribozymes for use within the present invention include those disclosed in more detail below in the Examples (e.g., Examples 18 and 19).

6. Proteins and Other Cellular Constituents

Within other aspects of the present invention, a wide variety of proteins or other cellular constituents may be carried by the alphavirus vector construct. Representative examples of such proteins include native or altered cellular components, as well as foreign proteins or cellular constituents, found in for example, viruses, bacteria, parasites or fungus.

(a) Altered Cellular Components

Within one embodiment, alphavirus vector constructs are provided which direct the expression of an immunogenic, non-tumorigenic, altered cellular component. As utilized herein, the term "immunogenic" refers to altered cellular components which are capable, under the appropriate conditions, of causing an immune response. This response must be cell-mediated, and may also include a humoral response. The term "non-tumorigenic" refers to altered cellular components which will not cause cellular transformation or induce tumor formation in nude mice. The phrase "altered cellular component" refers to proteins and other cellular constituents which are either associated with rendering a cell tumorigenic, or are associated with tumorigenic cells in general, but are not required or essential for rendering the cell tumorigenic.

Before alteration, the cellular components may be essential to normal cell growth and regulation and include, for example, proteins which regulate intracellular protein degradation, transcriptional regulation, cell-cycle control, and cell-cell interaction. After alteration, the cellular components no longer perform their regulatory functions and, hence, the cell may experience uncontrolled growth. Representative examples of altered cellular components include ras*, p53*, Rb*, altered protein encoded by the Wilms' tumor gene, ubiquitin*, mucin*, protein encoded by the DCC, APC, and MCC genes, the breast cancer gene BRCA1*, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Within one embodiment of the present invention, alphavirus vector constructs are provided which direct the expression of a non-tumorigenic, altered ras (ras*) gene. Briefly, the ras* gene is an attractive target because it is causally linked to the neoplastic phenotype, and indeed may be necessary for the induction and maintenance of tumorigenesis in a wide variety of distinct cancers, such as pancreatic carcinoma, colon carcinoma and lung adenocarcinoma. In addition, ras* genes are found in pre-neoplastic tumors and, therefore, immune intervention therapy may be applied prior to detection of a malignant tumor.

Normal ras genes are non-tumorigenic and ubiquitous in all mammals. They are highly conserved in evolution and appear to play an important role in maintenance of the cell cycle and normal growth properties. The normal ras protein is a G-protein which binds GTP and has GTPase activity, and is involved in transmitting signals from the external milieu to the inside of the cell, thereby allowing a cell to respond to its environment. Ras* genes on the other hand alter the normal growth regulation of neoplastic cells by uncoupling cellular behavior from the environment, thus leading to the uncontrolled proliferation of neoplastic cells. Mutation of the ras gene is believed to be an early event in carcinogenesis (Kumar et al., Science 248:1101-1104, 1990) which, if treated early, may prevent tumorigenesis.

Ras* genes occur in a wide variety of cancers, including for example, pancreatic, colon, and lung adenocarcinomas. The spectrum of mutations occurring in the ras* genes found in a variety of cancers is quite limited. These mutations alter the GTPase activity of the ras protein by converting the normal on/off switch to a constitutive ON position. Tumorigenic mutations in ras* occur primarily (in vivo) in only 3 codons: 12, 13 and 61. Codon 12 mutations are the most prevalent in both human and animal tumors.

Table 1 below summarizes known in vivo mutations (codons 12, 13 and 61) which activate human ras, as well as potential mutations which have in vitro transforming activity. Potential mutations with in vitro transforming activity were produced by the systematic substitution of amino acids for the normal codon (e.g., other amino acids were substituted for the normal glycine at position 12). In vitro mutations, while not presently known to occur in humans or animals, may serve as the basis for an anti-cancer immunotherapeutic if they are eventually found to arise in vivo.

TABLE 1

AMINO ACID SUBSTITUTIONS THAT ACTIVATE HUMAN RAS PROTEINS

| | Amino Acid | | | | | | |
|---|---|---|---|---|---|---|---|
| | Gly | Gly | Ala | Gln | Glu | Asn | Lys | Asp |
| Mutant Codon | 12 | 13 | 59 | 61 | 63 | 116 | 117 | 119 |
| In vivo | Val<br>Arg<br>Asp<br>Cys<br>Ala<br>Ser<br>Phe | Asp<br>Val<br>Arg | | Arg<br>His<br>Leu | | | | |
| In vitro | Ala<br>Asn<br>Gln<br>Glu<br>His<br>Ile<br>Leu<br>Lys<br>Met<br>Phe<br>Ser<br>Thr<br>Trp<br>Tyr | Ser | Thr | Val<br>Ala<br>Cys<br>Asn<br>Ile<br>Met<br>Thr<br>Tyr<br>Trp<br>Phe<br>Gly | Lys | His<br>Ile | Glu<br>Arg | His<br>Glu<br>Ala<br>Asn |

Alterations as described above result in the production of proteins containing novel coding sequence(s). The novel proteins encoded by these sequence(s) may be used as a marker of tumorigenic cells, and an immune response directed against these novel coding regions may be utilized to destroy tumorigenic cells containing the altered sequences (ras*).

Within another embodiment of the present invention, alphavirus vector constructs are provided which direct the expression of an altered p53 (p53*) gene. Briefly, p53 is a nuclear phosphoprotein which was originally discovered in extracts of transformed cells and thus was initially classified as an oncogene (Linzer and Levine, Cell 17:43-52, 1979; Lane and Crawford, Nature 278:261-263, 1979). It was later discovered that the original p53 cDNA clones were mutant forms of p53 (Hinds et al., J. Virol. 63:739-746, 1989). It now appears that p53 is a tumor suppressor gene which negatively regulates the cell cycle, and that mutation of this gene may lead to tumor formation. Of colon carcinomas that have been studied, 75%-80% show a loss of both p53 alleles, one through deletion and the other through point mutation. Similar mutations are found in lung cancer, and in brain and breast tumors.

The majority of p5g mutations (e.g., p53*[1], p53*[2], etc.) are clustered between amino acid residues 130 to 290 (see Levine et al., *Nature* 351:453-456, 1991; see also the following references which describe specific mutations in more detail: Baker et al., *Science* 244:217-221, 1989; Nigro et al., *Nature* 342:705-708, 1989 (p53 mutations cluster at four "hot spots" which coincide with the four highly conserved regions of the genes and these mutations are observed in human brain, breast, lung and colon tumors); Vogelstein, *Nature* 348:681-682, 1990; Takahashi et al., *Science* 246:491-494, 1989; Iggo et al., *Lancet* 335:675-679, 1990; James et al., *Proc. Natl. Acad. Sci. USA* 86:2858-2862, 1989; Mackay et al., *Lancet* 11:1384-1385, 1988; Kelman et al., *Blood* 74:2318-2324, 1989; Malkin et al., *Science* 250:1233-1238, 1990; Baker et al., *Cancer Res.* 50:7717-7722, 1991; Chiba et al., *Oncogene* 5:1603-1610, 1990 (pathogenesis of early stage non-small cell lung cancer is associated with somatic mutations in the p53 gene between codons 132 to 283); Prosser et al., *Oncogene* 5:1573-1579, 1990 (mutations in the p53 gene coding for amino acids 126 through 224 were identified in primary breast cancer); Cheng and Hass, *Mol. Cell. Biol.* 10:5502-5509, 1990; Bartek et al., *Oncogene* 5:893-899, 1990; Rodrigues et al., *Proc. Natl. Acad. Sci. USA* 87:7555-7559, 1990; Menon et al., *Proc. Natl. Acad. Sci. USA* 87:5435-5439, 1990; Mulligan et al., *Proc. Natl. Acad. Sci. USA* 87:5863-5867, 1990; and Romano et al., *Oncogene* 4:1483-1488, 1990 (identification of a p53 mutation at codon 156 in human osteosarcoma derived cell line HOS-SL)).

Certain alterations of the p53 gene may be due to certain specific toxins. For example, Bressac et al. (*Nature* 350:429-431, 1991) describes specific G to T mutations in codon 249 in patients affected with hepatocellular carcinoma. One suggested causative agent of this mutation is aflatoxin $B_1$, a liver carcinogen which is known to be a food contaminant in Africa.

Four regions of the gene that are particularly affected occur at residues 132-145, 171-179, 239-248, and 272-286. Three "hot spots" which are found within these regions that are of particular interest occur at residues 175, 248 and 273 (Levine et al., *Nature* 351:453-456, 1991). These alterations, as well as others which are described above, result in the production of protein(s) which contain novel coding sequence(s). The novel proteins encoded by these sequences may be used as a marker of tumorigenic cells and an immune response directed against these novel coding regions may be utilized to destroy tumorigenic cells containing the altered sequence (p53*).

Once a sequence encoding the altered cellular component has been obtained, it is necessary to ensure that the sequence encodes a non-tumorigenic protein. Various assays which assess the tumorigenicity of a particular cellular component are known and may easily be accomplished. Representative assays include a rat fibroblast assay, tumor formation in nude mice or rats, colony formation in soft agar, and preparation of transgenic animals, such as transgenic mice.

Tumor formation in nude mice or rats is a particularly important and sensitive method for determining the tumorigenicity of a particular cellular component. Nude mice lack a functional cellular immune system (i.e., do not possess CTLs), and therefore provide a useful in vivo model in which to test the tumorigenic potential of cells. Normal non-tumorigenic cells do not display uncontrolled growth properties if infected into nude mice. However, transformed cells will rapidly proliferate and generate tumors in nude mice. Briefly, in one embodiment the alphavirus vector construct is administered to syngeneic murine cells, followed by injection into nude mice. The mice are visually examined for a period of 2 to 8 weeks after injection in order to determine tumor growth. The mice may also be sacrificed and autopsied in order to determine whether tumors are present. (Giovanella et al., *J. Natl. Cancer Inst.* 48:1531-1533, 1972; Furesz et al., *Abnormal Cells, New Products and Risk*, Hopps and Petricciani (eds.), Tissue Culture Association, 1985; and Levenbook et al., *J. Biol. Std.* 13:135-141, 1985.)

Tumorigenicity may also be assessed by visualizing colony formation in soft agar (Macpherson and Montagnier, *Vir.* 23:291-294, 1964). Briefly, one property of normal non-tumorigenic cells is "contact inhibition" (i.e., cells will stop proliferating when they touch neighboring cells). If cells are plated in a semi-solid agar support medium, normal cells rapidly become contact inhibited and stop proliferating, whereas tumorigenic cells will continue to proliferate and form colonies in soft agar.

Transgenic animals, such as transgenic mice, may also be utilized to assess the tumorigenicity of an altered cellular component. (Stewart et al., *Cell* 38:627-637, 1984; Quaife et al., *Cell* 48:1023-1034, 1987; and Koike et al., *Proc. Natl. Acad. Sci. USA* 86:5615-5619, 1989.) In transgenic animals, the gene of interest may be expressed in all tissues of the animal. This dysregulated expression of the transgene may serve as a model for the tumorigenic potential of the newly introduced gene.

If the altered cellular component is associated with making the cell tumorigenic, then it is necessary to make the altered cellular component non-tumorigenic. For example, within one embodiment the sequence or gene of interest which encodes the altered cellular component is truncated in order to render the gene product non-tumorigenic. The gene encoding the altered cellular component may be truncated to a variety of sizes, although it is preferable to retain as much as possible of the altered cellular component. In addition, it is necessary that any truncation leave intact at least some of the immunogenic sequences of the altered cellular component. Alternatively, multiple translational termination codons may be introduced downstream of the immunogenic region. Insertion of termination codons will prematurely terminate protein expression, thus preventing expression of the transforming portion of the protein.

Within one embodiment, the ras* gene is truncated in order to render the ras* protein non-tumorigenic. Briefly, the carboxy-terminal amino acids of ras* functionally allow the protein to attach to the cell membrane. Truncation of these sequences renders the altered cellular component non-tumorigenic. Preferably, the ras* gene is truncated in the purine ring binding site, for example around the sequence which encodes amino acid number 110. The ras* gene sequence may be truncated such that as little as about 20 amino acids (including the altered amino acid(s)) are encoded by the alphavirus vector construct, although preferably, as many amino acids as possible should be expressed (while maintaining non-tumorigenicity).

Within another embodiment, the p53* protein is modified by truncation in order to render the cellular component non-tumorigenic. As noted above, not all mutations of the p53 protein are tumorigenic, and therefore, not all mutations would have to be truncated. Nevertheless, within a preferred embodiment, p53* is truncated to a sequence which encodes amino acids 100 to 300, thereby including all four major "hot spots."

Other altered cellular components which are oncogenic may also be truncated in order to render them non-tumorigenic. For example, both neu and bcr/abl may be truncated in order to render them non-tumorigenic. Non-tumorigenicity may be confirmed by assaying the truncated altered cellular component as described above.

It should be noted, however, that if the altered cellular component is only associated with non-tumorigenic cells in general, and is not required or essential for making the cell tumorigenic, then it is not necessary to render the cellular component non-tumorigenic. Representative examples of such altered cellular components which are not tumorigenic include Rb*, ubiquitin*, and mucin*.

As noted above, in order to generate an appropriate immune response, the altered cellular component must also be immunogenic. Immunogenicity of a particular sequence is often difficult to predict, although T cell epitopes often possess an immunogenic amphipathic alpha-helix component. In general, however, it is preferable to determine immunogenicity in an assay. Representative assays include an ELISA, which detects the presence of antibodies against the newly introduced vector, as well as assays which test for T helper cells such as gamma-interferon assays, IL-2 production assays, and proliferation assays.

As noted above, within another aspect of the present invention, several different altered cellular components may be co-expressed in order to form a general anti-cancer therapeutic. Generally, it will be evident to one of ordinary skill in the art that a variety of combinations can be made. Within preferred embodiments, this therapeutic may be targeted to a particular type of cancer. For example, nearly all colon cancers possess mutations in ras, p53, DCC APC or MCC genes. An alphavirus vector construct which co-expresses a number of these altered cellular components may be administered to a patient with colon cancer in order to treat all possible mutations. This methodology may also be utilized to treat other cancers. Thus, an alphavirus vector construct which co-expresses mucin*, ras*, neu, BRCA1* and p53* may be utilized to treat breast cancer.

(b) Antigens from Foreign Organisms or Other Pathogens

Within other aspects of the present invention, alphavirus vector constructs are provided which direct the expression of immunogenic portions of antigens from foreign organisms or other pathogens. Representative examples of such antigens include bacterial antigens (e.g., E. coli, streptococcal, staphylococcal, mycobacterial, etc.), fungal antigens, parasitic antigens, and viral antigens (e.g., influenza virus, Human Immunodeficiency Virus ("HIV"), Hepatitis A, B and C Virus ("HAV", "HBV" and "HCV", respectively), Human Papiloma Virus ("HPV"), Epstein-Barr Virus ("EBV"), Herpes Simplex Virus ("HSV"), Hantavirus, TTLV I, HTLV II and Cytomegalovirus ("CMV"). As utilized within the context of the present invention, "immunogenic portion" refers to a portion of the respective antigen which is capable, under the appropriate conditions, of causing an immune response (i.e., cell-mediated or humoral). "Portions" may be of variable size, but are preferably at least 9 amino acids long, and may include the entire antigen. Cell-mediated immune responses may be mediated through Major Histocompatability Complex ("MHC") class I presentation, MHC Class II presentation, or both.

Within one aspect of the invention, alphavirus vector constructs are provided which direct the expression of immunogenic portions of Hepatitis B antigens. Briefly, the Hepatitis B genome is comprised of circular DNA of about 3.2 kilobases in length and has been well characterized (Tiollais et al., Science 213:406-411, 1981; Tiollais et al., Nature 317:489-495, 1985; and Ganem and Varmus, Ann. Rev. Biochem. 56:651-693, 1987; see also EP 0 278,940, EP 0 241,021, WO 88/10301, and U.S. Pat. Nos. 4,696,898 and 5,024,938, which are hereby incorporated by reference). The Hepatitis B virus presents several different antigens, including among others, three HB "S" antigens (HBsAgs), an HBc antigen (HBcAg), an HBe antigen (HBeAg), and an HBx antigen (HBxAg) (see Blum et al., TIG 5(5):154-158, 1989). Briefly, the HBeAg results from proteolytic cleavage of a P22 pre-core intermediate and is secreted from the cell. HBeAg is found in serum as a 17 kD protein. The HBcAg is a protein of 183 amino acids, and the HBxAg is a protein of 145 to 154 amino acids, depending on subtype.

The HBsAgs (designated "large," "middle" and "small") are encoded by three regions of the Hepatitis B genome: S, pre-S2 and pre-S1. The large protein, which has a length varying from 389 to 400 amino acids, is encoded by pre-S1, pre-S2, and S regions, and is found in glycosylated and non-glycosylated forms. The middle protein is 281 amino acids long and is encoded by the pre-S2 and S regions. The small protein is 226 amino acids long and is encoded by the S region. It exists in two forms, glycosylated (GP $27^s$) and non-glycosylated (P$24^2$). If each of these regions are expressed separately, the pre-S1 region will code for a protein of approximately 119 amino acids, the pre-S2 region will code for a protein of approximately 55 amino acids, and the S region will code for a protein of approximately 226 amino acids.

As will be evident to one of ordinary skill in the art, various immunogenic portions of the above-described S antigens may be combined in order to induce an immune response when administered by one of the alphavirus vector constructs described herein. In addition, due to the large immunological variability that is found in different geographic regions for the S open reading frame of HBV, particular combinations of antigens may be preferred for administration in particular geographic regions. Briefly, epitopes that are found in all human hepatitis B virus S samples are defined as determinant "a". Mutually exclusive subtype determinants, however, have also been identified by two-dimensional double immunodiffusion (Ouchterlony, Progr. Allergy 5:1, 1958). These determinants have been designated "d" or and "w" or "r" (LeBouvier, J. Infect. 123:671, 1971; Bancroft et al., J. Immunol. 109:842, 1972; and Courouce et al., Bibl. Haematol. 42:1-158, 1976). The immunological variability is due to single nucleotide substitutions in two areas of the hepatitis B virus S open reading frame, resulting in the following amino acid changes: (1) exchange of lysine-122 to arginine in the Hepatitis B virus S open reading frame causes a subtype shift from d to y, and (2) exchange of arginine-160 to lysine causes the shift from subtype r to w. In Africans, subtype ayw is predominant, whereas in the U.S. and northern Europe the subtype adw$_2$ is more abundant (Molecular Biology of the Hepatitis B Virus, McLachlan (ed.), CRC Press, 1991). As will be evident to one of ordinary skill in the art, it is generally preferred to construct a vector for administration which is appropriate to the particular hepatitis B virus subtype which is prevalent in the geographical region of administration. Subtypes of a particular region may be determined by two-dimensional double immunodiffusion or, preferably, by sequencing the S open reading frame of HBV virus isolated from individuals within that region.

Also presented by HBV are pol ("HBV pol"), ORF 5, and ORF 6 antigens. Briefly, the polymerase open reading frame of HBV encodes reverse transcriptase activity found in virions and core-like particles in infected livers. The polymerase protein consists of at least two domains: the amino terminal domain which encodes the protein that primes reverse transcription, and the carboxyl terminal domain which encodes reverse transcriptase and RNase H activity. Immunogenic portions of HBV pol may be determined utilizing methods described herein (e.g., below and in Example 13), utilizing alphavirus vector constructs described below, and administered in order to generate an immune response within a warm-blooded animal. Similarly, other HBV antigens, such as ORF 5 and ORF 6 (Miller et al., *Hepatology* 9:322-327, 1989) may be expressed utilizing alphavirus vector constructs as described herein. Representative examples of alphavirus vector constructs utilizing ORF 5 and ORF 6 are set forth below in the examples.

As noted above, at least one immunogenic portion of a hepatitis B antigen is incorporated into an alphavirus vector construct. The immunogenic portion(s) which are incorporated into the alphavirus vector construct may be of varying length, although it is generally preferred that the portions be at least 9 amino acids long and may include the entire antigen. Immunogenicity of a particular sequence is often difficult to predict, although T cell epitopes may be predicted utilizing computer algorithms such as TSITES (MedImmune, Maryland), in order to scan coding regions for potential T-helper sites and CIL sites. From this analysis, peptides are synthesized and used as targets in an in vitro cytotoxic assay. Other assays, however, may also be utilized, including, for example, ELISA, which detects the presence of antibodies against the newly introduced vector, as well as assays which test for T helper cells, such as gamma-interferon assays, IL-2 production assays and proliferation assays.

Immunogenic portions may also be selected by other methods. For example, the HLA A2.1 transgenic mouse has been shown to be useful as a model for human T-cell recognition of viral antigens. Briefly, in the influenza and hepatitis B viral systems, the murine T cell receptor repertoire recognizes the same antigenic determinants recognized by human T cells. In both systems, the CTL response generated in the HLA A2.1 transgenic mouse is directed toward virtually the same epitope as those recognized by human CTLs of the HLA A2.1 haplotype (Vitiello et al., *J. Exp. Med.* 173:1007-1015, 1991; Vitiello et al., *Abstract of Molecular Biology of Hepatitis B Virus Symposia,* 1992).

Particularly preferred immunogenic portions for incorporation into alphavirus vector constructs include HBeAg, HBcAg and HBsAgs, as described in greater detail below in Example 13.

Additional immunogenic portions of the hepatitis B virus may be obtained by truncating the coding sequence at various locations including, for example, the following sites: Bst UI, Ssp I, Ppu M1, and Msp I (Valenzuela et al., *Nature* 280:815-19, 1979; Valenzuela et al., *Animal Virus Genetics: ICN/UCLA Symp. Mol. Cell. Biol.,* 1980, B. N. Fields and R. Jaenisch (eds.), pp. 57-70, New York: Academic). Further methods for determining suitable immunogenic portions as well as methods are also described below in the context of hepatitis C.

As noted above, more than one immunogenic portion may be incorporated into the alphavirus vector construct. For example, an alphavirus vector construct may express (either separately or as one construct) all or immunogenic portions of HBcAg, HBeAg, HBsAgs, HBxAg, as well as immunogenic portions of HCV antigens.

7. Sources for Heterologous Sequences

Sequences which encode the above-described proteins may be readily obtained from a variety of sources, including for example, depositories such as the American Type Culture Collection (ATCC, Rockville, Md.), or from commercial sources such as British Bio-Technology Limited (Cowley, Oxford, England). Representative examples include BBG 12 (containing the GM-CSF gene coding for the mature protein of 127 amino acids); BBG 6 (which contains sequences encoding gamma interferon), ATCC No. 39656 (which contains sequences encoding TNF), ATCC No. 20663 (which contain sequences encoding alpha interferon), ATCC Nos. 31902, 31902 and 39517 (which contains sequences encoding beta interferon), ATCC No 67024 (which contain a sequence which encodes Interleukin-1 b); ATCC Nos. 39405, 39452, 39516, 39626 and 39673 (which contains sequences encoding Interleukin-2); ATCC Nos. 59399, 59398, and 67326 (which contain sequences encoding Interleukin-3); ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Sequences which encode altered cellular components as described above may be readily obtained from a variety of sources. For example, plasmids which contain sequences that encode altered cellular products may be obtained from a depository such as the American Type Culture Collection (ATCC, Rockville, Md.), or from commercial sources such as Advanced Biotechnologies (Columbia, Md.). Representative examples of plasmids containing some of the above-described sequences include ATCC No. 41000 (containing a G to T mutation in the 12th codon of ras), and ATCC No. 41049 (containing a G to A mutation in the 12th codon).

Alternatively, plasmids which encode normal cellular components may also be obtained from depositories such as the ATCC (see, for example, ATCC No. 41001, which contains a sequence which encodes the normal ras protein; ATCC No. 57103, which encodes abl; and ATCC Nos. 59120 or 59121, which encode the bcr locus) and mutated to form the altered cellular component. Methods for mutagenizing particular sites may readily be accomplished using methods known in the art (see Sambrook et al., supra., 15.3 et seq.). In particular, point mutations of normal cellular components such as ras may readily be accomplished by site-directed mutagenesis of the particular codon, for example, codons 12, 13 or 61.

Sequences which encode the above-described viral antigens may likewise be obtained from a variety of sources. For example, molecularly cloned genomes which encode the hepatitis B virus may be obtained from sources such as the American Type Culture Collection (ATCC, Rockville, Md.). For example, ATCC No. 45020 contains the total genomic DNA of hepatitis B (extracted from purified Dane particles) (see FIG. 3 of Blum et al., *TIG* 5(5):154-158, 1989) in the Bam HI site of pBR322 (Moriarty et al., *Proc. Natl. Acad. Sci. USA* 78:2606-2610, 1981).

Alternatively, cDNA sequences which encode the above-described heterologous sequences may be obtained from cells which express or contain the sequences. Briefly, within one embodiment, mRNA from a cell which expresses the gene of interest is reverse transcribed with reverse transcriptase using oligonucleotide dT or random primers. The single stranded cDNA may then be amplified by PCR (see U.S. Pat. Nos. 4,683,202; 4,683,195 and 4,800,159. See also *PCR Technology: Principles and Applications for DNA Amplification*, Erlich (ed.), Stockton Press, 1989) utilizing oligonucleotide primers complementary to sequences on either side of desired sequences. In particular, a double-stranded DNA is denatured by heating in the presence of heat stable Taq polymerase, sequence-specific DNA primers, dATP, dCTP, dGTP and dTTP. Double-stranded DNA is produced when synthesis is complete. This cycle may be repeated many times, resulting in a factorial amplification of the desired DNA.

Sequences which encode the above-described proteins may also be synthesized, for example, on an Applied Biosystems Inc. DNA synthesizer (e.g., APB DNA synthesizer model 392 (Foster City, Calif.)).

F. Eukaryotic Layered Vector Initiation Systems

Due to the size of a full-length genomic alphavirus cDNA clone, in vitro transcription of full-length RNA molecules is rather inefficient. This results in a lowered transfection efficiency, in terms of infectious centers of virus (as measured by plaque formation), relative to the amount of in vitro transcribed RNA transfected. Such inefficiency is also relevant to the in vitro transcription of alphavirus expression vectors. Testing of candidate cDNA clones and other alphavirus cDNA expression vectors for their ability to initiate an infectious cycle or to direct the expression of a heterologous sequence would thus be greatly facilitated if a cDNA clone was transfected into susceptible cells as a DNA molecule, which then directed the synthesis of viral RNA in vivo.

Therefore, within one aspect of the present invention DNA-based vectors (referred to as "Eukaryotic Layered Vector Initiation Systems") are provided which are capable of directing the synthesis of viral RNA in vivo. In particular, eukaryotic layered vector initiation systems are provided comprising a promoter which is capable of initiating the 5' synthesis of RNA from cDNA, a construct which is capable of autonomous replication in a cell, the construct also being capable of expressing a heterologous nucleic acid sequence, and a 3' sequence which controls transcription termination. Briefly, such eukaryotic layered vector initiation systems provide a two-stage or "layered" mechanism which controls expression of heterologous nucleotide sequences. The first layer initiates transcription of the second layer, and comprises a promoter which is capable of initiating the 5' synthesis of RNA from cDNA (e.g., a 5' promoter), a 3' transcription termination site, as well as one or more splice sites and/or a polyadenylation site, if desired. Representative promoters suitable for use within the present invention include both eukaryotic (e.g., pol I, II, or III) and prokaryotic promoters, and inducible or non-inducible (i.e., constitutive) promoters, such as, for example, Murine Leukemia virus promoters (e.g., MoMLV), metallothionein promoters, the glucocorticoid promoter, Drosophila actin 5C distal promoter, SV 40 promoter, heat shock protein 65 promoter, heat shock protein 70 promoter, immunoglobulin promoters, Mouse polyoma virus promoter ("Py"), rous sarcoma virus ("RSV"), BK virus and JC virus promoters, MMTV promoter, alphavirus junction region, CMV promoter, Adenovirus VA1RNA, rRNA promoter, tRNA methionine promoter, CaMV 35S promoter, nopaline synthetase promoter, and the lac promoter. The second layer comprises a vector construct which is capable of expressing one or more heterologous nucleotide sequences and of replication in a cell, either autonomously or in response to one or more factors. Within one embodiment of the invention, the second layer construct may be an alphavirus vector construct as described above.

A wide variety of vector systems may be utilized as the first layer of the eukaryotic layered vector initiation system, including for example, viral vector constructs developed from DNA viruses such as those classified in the Poxyiridae, including for example canary pox virus or vaccinia virus (e.g., Fisher-Hoch et al., *PNAS* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603,112, 4,769,330 and 5,017,487; WO 89/01973); Papoviridae such as BKV, JCV or SV40 (e.g., Mulligan et al., *Nature* 277:108-114, 1979); Adenoviridae, such as adenovirus (e.g., Berkner, *Biotechniques* 6:616-627, 1988; Rosenfeld et al., *Science* 252:431-434, 1991); Parvoviridae, such as adeno-associated virus (e.g., Samulski et al., *J. Vir.* 63:3822-3828, 1989; Mendelson et al., *Virol.* 166:154-165, 1988; PA 7/222,684); Herpesviridae, such as Herpes Simplex Virus (e.g., Kit, *Adv. Exp. Med. Biol.* 215:219-236, 1989); and Hepadnaviridae (e.g., HBV), as well as certain RNA viruses which replicate through a DNA intermediate, such as the Retroviridae (see, e.g., U.S. Pat. No. 4,777,127, GB 2,200,651, EP 0,345,242 and WO91/02805; Retroviridae include leukemia in viruses such as MoMLV and immunodeficiency viruses such as HIV, e.g., Poznansky, *J. Virol.* 65:532-536, 1991).

Similarly, a wide variety of vector systems may be utilized as second layer of the eukaryotic layered vector initiation system, including for example, vector systems derived from viruses of the following families: Picornaviridae (e.g., poliovirus, rhinovirus, coxsackieviruses), Caliciviridae, Togaviridae (e.g. alphavirus, rubella), Flaviviridae (e.g., yellow fever), Coronaviridae (e.g., HCV, TGEV, IBV, MHV, BCV), Bunyaviridae, Arenaviridae, Retroviridae (e.g., RSV, MoMLV, HIV, HTLV), hepatitis delta virus and Astrovirus. In addition, non-mammalian RNA viruses (as well as components derived therefrom) may also be utilized, including for example, bacterial and bacteriophage replicases, as well as components derived from plant viruses, such as potexviruses (e.g., PVX), carlaviruses (e.g., PVM), tobraviruses (e.g., TRV, PEBV, PRV), Tobamoviruses (e.g., TMV, ToMV, PPMV), luteoviruses (e.g., PLRV), potyviruses (e.g., TEV, PPV, PVY), tombusviruses (e.g., CyRSV), nepoviruses (e.g., GFLV), bromoviruses (e.g., BMV), and topamoviruses.

The replication competency of the autocatalytic vector construct, contained within the second layer of the eukaryotic vector initiation system, may be measured by a variety of assays known to one of skill in the art including, for example, ribonuclease protection assays which measure increases in both positive-sense and negative-sense RNA over time, in transfected cells, in the presence of an inhibitor of cellular RNA synthesis, such as dactinomycin, and assays which measure the synthesis of a subgenomic RNA or expression of a heterologous reporter gene in transfected cells.

Within particularly preferred embodiments of the invention, eukaryotic layered vector initiation systems are provided that comprise a 5' promoter which is capable of initiating the synthesis of viral RNA from cDNA, followed by a 5' sequence which is capable of initiating transcription of an alphavirus, a nucleotide sequence encoding alphavirus nonstructural proteins, a viral junction region which is either active or which has been inactivated such that viral transcription of the subgenomic fragment is prevented, an alphavirus RNA polymerase recognition sequence, and a 3' sequence which controls transcription termination. Within various embodiments, the viral junction region may be modified, such that viral transcription of the subgenomic fragment is merely reduced, rather than inactivated. Within other embodiments, a second viral junction region may be inserted following the first inactivated viral junction region, the second viral junction region being either active or modified such that viral transcription of the subgenomic fragment is reduced.

Following transcription of an alphavirus cDNA vector construct, the resulting alphavirus RNA vector molecule is comprised of a 5' sequence which is capable of initiating transcription of an alphavirus, a nucleotide sequence encoding alphavirus nonstructural proteins, a viral junction region, a heterologous nucleotide sequence, an alphavirus RNA polymerase recognition sequence, and a polyadenylate sequence.

Various aspects of the alphavirus cDNA vector constructs have been discussed above, including the 5' sequence which is capable of initiating transcription of an alphavirus, the nucleotide sequence encoding alphavirus nonstructural proteins, the viral junction region, including junction regions which have been inactivated such that viral transcription of the subgenomic fragment is prevented, and the alphavirus RNA polymerase recognition sequence. In addition, modified junction regions and tandem junction regions have also been discussed above.

Within certain aspects of the present invention, methods are provided for delivering a heterologous nucleotide sequence to a warm-blooded animal, comprising the step of administering a eukaryotic layered vector initiation system as described above, to a warm-blooded animal. Eukaryotic layered vector initiation systems may be administered to warm-blooded animals either directly (e.g., intravenously, intramuscularly, intraperitoneally, subcutaneously, orally, rectally, intraocularly, intranasally), or by various physical methods such as lipofection (Felgner et al., *Proc. Natl. Acad. Sci. USA* 84:7413-7417, 1989), direct DNA injection (Acsadi et al., *Nature* 352:815-818, 1991); microprojectile bombardment (Williams et al., *PNAS* 88:2726-2730, 1991); liposomes of several types (see, e.g., Wang et al., *PNAS* 84:7851-7855, 1987); CaPO$_4$ (Dubensky et al., *PNAS* 81:7529-7533, 1984); DNA ligand (Wu et al, *J. of Biol. Chem.* 264:16985-16987, 1989); administration of nucleic acids alone (WO 90/11092); or administration of DNA linked to killed adenovirus (Curiel et al., *Hum. Gene Ther.* 3:147-154, 1992); via polycation compounds such as polylysine, utilising receptor specific ligands; as well as with psoralen inactivated viruses such as Sendai or Adenovirus. In addition, the eukaryotic layered vector initiation systems may either be administered directly (i.e., in vivo), or to cells which have been removed (ex vivo), and subsequently returned.

Eukaryotic layered vector initiation systems may be administered to a warm-blooded animal for any of the therapeutic uses described herein, including for example, for the purpose of stimulating a specific immune response; inhibiting the interaction of an agent with a host cell receptor, to express a toxic palliative, including for example, conditional toxic palliatives; to immunologically regulate the immune system; to express markers, and for replacement gene therapy. These and other uses are discussed in more detail below.

In another embodiment of this aspect of the invention, eukaryotic layered vector initiation systems can be utilized to direct the expression of one or more recombinant proteins by eukaryotic cells. As used herein, a "recombinant protein" refers to a protein, polypeptide, enzyme, or fragment thereof. Using this approach, proteins having therapeutic or other commercial application can be more cost-effectively produced. Furthermore, proteins produced in eukaryotic cells may be post-translationally modified (e.g., glycosylated, sulfated, acetylated, etc.), as compared to proteins produced in prokaryotic cells. In addition, such systems may be employed in the in vivo production of various chemical compounds, e.g., fine or specialty chemicals.

Within this embodiment, a eukaryotic layered vector initiation system encoding the desired protein, enzyme, or enzymatic pathway (as may be required for the production of a desired chemical) is transformed, transfected, or otherwise introduced into a suitable eukaryotic cell line. Representative examples of proteins which can be produced using such a system include, but are not limited to, insulin (see U.S. Pat. No. 4,431,740 and BE 885196A), hemoglobin (Lawn et al. *Cell* 21:647-51, 1980), erythropoietin (EPO; see U.S. Pat. No. 4,703,008), megakaryocyte growth and differentiation factor (MGDF), stem cell factor (SCF), G-CSF (Nagata et al. *Nature* 319:415-418, 1986), GM-CSF, M-CSF (see WO 8706954), the flt3 ligand (Lyman, et al. (1993), *Cell, vol.* 75, pp. 1157-1167), EGF, acidic and basic FGF, PDGF, members of the interleukin or interferon families, supra, neurotropic factors (e.g., BDNF; Rosenthal et al *Endocrinology* 129: 1289-1294, 1991, NT-3; see WO 9103569, CNTF; see WO 9104316, NGF; see WO 9310150), coagulation factors (e.g., factors VIII and IX), thrombolytic factors such as t-PA (see EP 292009, AU 8653302 and EP 174835) and streptokinase (see EP 407942), human growth hormone (see JP 94030582 and U.S. Pat. No. 4,745,069) and other animal somatotropins, and integrins and other cell adhesion molecules, such as ICAM-1 and ELAM. Genes encoding such recombinant proteins are among the heterologous nucleic acid sequences of the invention. As those in the art will appreciate, once characterized, any gene can be readily cloned into a eukaryotic layered vector initiation system according to the invention, followed by introduction into a suitable host cell and expression of the desired gene.

In a preferred embodiment of this and other aspects of the invention, the eukaryotic layered vector initiation system is one derived from an alphavirus vector, such as a Sindbis vector construct, which has been adapted to replicate in one or more cell lines from a particular eukaryotic species, especially a mammalian species, such as humans. For instance, if the gene encoding the recombinant protein to be expressed is of human origin and the protein is intended for human therapeutic use, production in a suitable human cell line may be preferred in order that the protein be post-translationally modified as would be expected to occur in humans. This approach may be useful in further enhancing recombinant protein production. Given the overall plasticity of an alphaviral genome due to the infidelity of the viral replicase, variant strains with an enhanced ability to establish high titer productive infection in selected eukaryotic cells (e.g., human, murine, canine, feline, etc.) can be isolated. Additionally, variant alphaviral strains having an enhanced ability to establish high titer persistent infection in eukaryotic cells may also be isolated using this approach. Alphavirus expression vectors can then be constructed from cDNA clones of these variant strains according to procedures provided herein.

Within another preferred embodiment of this aspect of the invention, the eukaryotic layered vector initiation system comprises a promoter for initial alphaviral vector transcription that is transcriptionally active only in a differentiated cell type. It is well established that alphaviral infection of cells in culture, in particular those derived from hamster (e.g., baby hamster kidney cells) or chicken (e.g., chicken embryo fibroblasts), may result in cytoxicity. Thus, to produce a stably transformed or transfected host cell line, the eukaryotic layered vector initiation system is preferably introduced into a host cell wherein the promoter which enables the initial vector amplification is a transcriptionally inactive, but inducible, promoter. In a particularly preferred embodiment, such a promoter is differentiation state dependent. In this configuration, activation of the promoter and subsequent activation of the alphavirus DNA vector coincides with induction of cell differentiation. Upon growth to a certain cell number of such a stably transformed or transfected host cell line, the appropriate differentiation stimulus is provided, thereby initiating transcription of the vector construct and amplified expression of the desired gene and encoded polypeptide(s). Many such differentiation state-dependent promoters are known to those in the art, as are cell lines which can be induced to differentiate by application of a specific stimulus. Representative examples include cell lines F9 and P19, HL60, and Freund erythroleukemic cell lines and HEL, which are activated by retinoic acid, horse serum, and DMSO, respectively.

G. Alphavirus Packaging Cell Lines

Within further embodiments of the invention, alphavirus packaging cell lines are provided. In particular, within one aspect of the present invention, alphavirus packaging cell lines are provided wherein the viral structural proteins, supplied in trans from one or more stably integrated expression vectors, are able to encapsidate transfected, transduced, or intracellularly produced vector RNA transcripts in the cytoplasm and release infectious packaged vector particles through the cell membrane, thus creating an alphavirus vector producing cell line. Alphavirus RNA vector molecules, capable of replicating in the cytoplasm of the packaging cell, can be produced initially utilizing, for example, an SP6 RNA polymerase system to transcribe in vitro a cDNA vector clone encoding the gene of interest and the alphavirus nonstructural proteins (described previously). Vector RNA transcripts are then transfected into the alphavirus packaging cell line, such that the vector RNA replicates to high levels, and is subsequently packaged by the viral structural proteins, yielding infectious vector particles. Because of the extended length of the alphavirus cDNA molecule, the in vitro transcription process is inefficient. Further, only a fraction of the cells contained in a monolayer are typically transfected by most procedures.

In an effort to optimize vector producing cell line performance and titer, two successive cycles of gene transfer may be performed. In particular, rather than directly transfecting alphavirus RNA vector molecules into the final producing cell line, the vector may first be transfected into a primary alphavirus packaging cell line. The transfected primary packaging cell line releases infectious vector particles into the culture supernatants and these vector-containing supernatants are subsequently used to transduce a fresh monolayer of alphavirus packaging cells. Transduction into the final alphavirus vector producing cells is preferred over transfection because of its higher RNA transfer efficiency into cells and optimized biological placement of the vector in the cell. This leads to higher expression and higher titer of packaged infectious recombinant alphavirus vector.

Within certain embodiments of the invention, alphavirus vector particles may fail to transduce the same packaging cell line because the cell line produces extracellular envelope proteins which block cellular receptors for alphavirus vector particle attachment, a second type of alphavirus vector particle is generated which maintains the ability to transduce the alphavirus packaging cells. This second type of viral particle is produced by a packaging cell line known as a "hopping cell line," which produces transient vector particles as the result of being transfected with in vitro transcribed alphavirus RNA vector transcripts. Briefly, the hopping cell line is engineered to redirect the receptor tropism of the transiently produced vector particles by providing alternative viral envelope proteins which redirect alphavirus vectors to different cellular receptors, in a process termed pseudotyping. Two primary approaches have been devised for alphavirus vector particle pseudotyping. The first approach consists of an alphavirus packaging cell line expressing the vesicular stomatitis virus G protein (VSV-G). The second approach for producing a pseudotyped alphavirus vector particle is to use currently available retroviral packaging cell lines containing retroviral gag/pol and env sequences which would be capable of packaging an alphavirus RNA vector containing a retroviral packaging sequence (e.g., WO 92/05266).

Within other embodiments of the invention, a second approach has also been devised in which a stably integrated DNA expression vector is used to produce the alphavirus vector RNA molecule, which, as in the first approach, maintains the autocatalytic ability to self-replicate. This approach allows for continued vector expression over extended periods of culturing because the integrated DNA vector expression system is maintained through a drug selection marker and the DNA system will constitutively express unaltered RNA vectors which cannot be diluted out by defective RNA copies. In this "alphavirus producer cell line" configuration, the DNA-based alphavirus vector is introduced initially into the packaging cell line by transfection, since size restrictions could prevent packaging of the expression vector into a viral vector particle for transduction. Also, for this configuration, the SP6 RNA polymerase recognition site of the plasmid, previously used to transcribe vector RNA in vitro, is replaced with another appropriate promoter sequence defined by the parent cell line used. In addition, this plasmid sequence also contains a selection marker different from that used to create the packaging cell line.

The expression of alphavirus proteins and/or vector RNA above certain levels may result in cytotoxic effects in packaging cell lines. Therefore, within certain embodiments of the invention, it may be desirable for these elements to be expressed only after the packaging/producer cells have been propagated to a certain critical density. For this purpose, additional packaging or producer cell line modifications are made whereby the structural proteins necessary for packaging are synthesized only after induction by the RNA vector itself or some other stimulus. Also, other modifications allow for the individual expression of these proteins under the control of separate inducible elements, by utilizing expression vectors which unlink the genes encoding these proteins. In addition, expression of the integrated vector molecule itself, in some instances, is controlled by yet another inducible system. This configuration results in a cascade of events following induction, that ultimately leads to the production of packaged vector particles.

H. Methods for Utilizing Alphavirus Vectors

1. Immunostimulation

Within other aspects of the present invention, compositions and methods are provided for administering an alphavirus vector construct which is capable of preventing, inhibiting, stabilizing or reversing infectious, cancerous, auto-immune or immune diseases. Representative examples of such diseases include viral infections such as HIV, HBV HTLV I, HTLV II, CMV, EBV and HPV, melanomas, diabetes, graft vs. host disease, Alzheimer's disease and heart disease.

More specifically, within one aspect of the present invention, compositions and methods are provided for stimulating an immune response (either humoral or cell-mediated) to a pathogenic agent, such that the pathogenic agent is either killed or inhibited. Representative examples of pathogenic agents include bacteria, fungi, parasites, viruses and cancer cells.

Within one embodiment of the invention the pathogenic agent is a virus, and methods are provided for stimulating a specific immune response and inhibiting viral spread by using recombinant alphavirus viral particles designed to deliver a vector construct that directs the expression of an antigen or modified form thereof to susceptible target cells capable of either (1) initiating an immune response to the viral antigen or (2) preventing the viral spread by occupying cellular receptors required for viral interactions. Expression of the vector nucleic acid encoded protein may be transient or stable with time. Where an immune response is to be stimulated to a pathogenic antigen, the recombinant alphavirus is preferably designed to express a modified form of the antigen which will stimulate an immune response and which has reduced pathogenicity relative to the native antigen. This immune response is achieved when cells present antigens in the correct manner, i.e., in the context of the MHC class I and/or II molecules along with accessory molecules such as CD3, ICAM-1, ICAM-2, LFA-1, or analogues thereof (e.g., Altmann et al., *Nature* 338:512, 1989). Cells infected with alphavirus vectors are expected to do this efficiently because they closely mimic genuine viral infection and because they: (a) are able to infect non-replicating cells, (b) do not integrate into the host cell genome, (c) are not associated with any life threatening diseases, and (d) express high levels of heterologous protein. Because of these differences, alphavirus vectors can easily be thought of as safe viral vectors which can be used on healthy individuals for vaccine use.

This aspect of the invention has a further advantage over other systems that might be expected to function in a similar manner, in that the presenter cells are fully viable and healthy, and low levels of viral antigens, relative to heterologous genes, are expressed. This presents a distinct advantage since the antigenic epitopes expressed can be altered by selective cloning of sub-fragments of the gene for the antigen into the recombinant alphavirus, leading to responses against immunogenic epitopes which may otherwise be overshadowed by immunodominant epitopes. Such an approach may be extended to the expression of a peptide having multiple epitopes, one or more of the epitopes being derived from different proteins. Further, this aspect of the invention allows efficient stimulation of cytotoxic T lymphocytes (CTL) directed against antigenic epitopes, and peptide fragments of antigens encoded by sub-fragments of genes, through intracellular synthesis and association of these peptide fragments with MHC Class I molecules. This approach may be utilized to map major immunodominant epitopes for CTL induction.

An immune response may also be achieved by transferring to an appropriate immune cell (such as a T lymphocyte) the gene for the specific T cell receptor which recognizes the antigen of interest (in the context of an appropriate MHC molecule if necessary), for an immunoglobulin which recognizes the antigen of interest, or for a hybrid of the two which provides a CTL response in the absence of the MHC context. Thus, the recombinant alphavirus infected cells may be used as an immunostimulant, immunomodulator, or vaccine.

In another embodiment of the invention, methods are provided for producing inhibitor palliatives wherein alphavirus vectors deliver and express defective interfering viral structural proteins, which inhibit viral assembly. Such vectors may encode defective gag, pol, env or other viral particle proteins or peptides and these would inhibit in a dominant fashion the assembly of viral particles. This occurs because the interaction of normal subunits of the viral particle is disturbed by interaction with the defective subunits.

In another embodiment of the invention, methods are provided for the expression of inhibiting peptides or proteins specific for viral protease. Briefly, viral protease cleaves the viral gag and gag/pol proteins into a number of smaller peptides. Failure of this cleavage in all cases leads to complete inhibition of production of infectious retroviral particles. As an example, the HIV protease is known to be an aspartyl protease and these are known to be inhibited by peptides made from amino acids from protein or analogues. Vectors to inhibit HIV will express one or multiple fused copies of such peptide inhibitors.

Another embodiment involves the delivery of suppressor genes which, when deleted, mutated, or not expressed in a cell type, lead to tumorigenesis in that cell type. Reintroduction of the deleted gene by means of a viral vector leads to regression of the tumor phenotype in these cells. Examples of such cancers are retinoblastoma and Wilms Tumor. Since malignancy can be considered to be an inhibition of cellular terminal differentiation compared with cell growth, the alphavirus vector delivery and expression of gene products which lead to differentiation of a tumor should also, in general, lead to regression.

In yet another embodiment, the alphavirus vector provides a therapeutic effect by transcribing a ribozyme (an RNA enzyme) (Haseloff and Gerlach, *Nature* 334:585, 1989) which will cleave and hence inactivate RNA molecules corresponding to a pathogenic function. Since ribozymes function by recognizing a specific sequence in the target RNA and this sequence is normally 12 to 17 bp, this allows specific recognition of a particular RNA species such as a RNA or a retroviral genome. Additional specificity may be achieved in some cases by making this a conditional toxic palliative (see below).

One way of increasing the effectiveness of inhibitory palliatives is to express viral inhibitory genes in conjunction with the expression of genes which increase the probability of infection of the resistant cell by the virus in question. The result is a nonproductive "dead-end" event which would compete for productive infection events. In the specific case of HIV, vectors may be delivered which inhibit HIV replication (by expressing anti-sense tat, etc., as described above) and also overexpress proteins required for infection, such as CD4. In this way, a relatively small number of vector-infected HIV-resistant cells act as a "sink" or "magnet" for multiple nonproductive fusion events with free virus or virally infected cells.

2. Blocking Agents

Many infectious diseases, cancers, autoimmune diseases, and other diseases involve the interaction of viral particles with cells, cells with cells, or cells with factors. In viral infections, viruses commonly enter cells via receptors on the surface of susceptible cells. In cancers, cells may respond inappropriately or not at all to signals from other cells or factors. In autoimmune disease, there is inappropriate recognition of "self" markers. Within the present invention, such interactions may be blocked by producing, in vivo, an analogue to either of the partners in an interaction.

This blocking action may occur intracellularly, on the cell membrane, or extracellularly. The blocking action of a viral or, in particular, an alphavirus vector carrying a gene for a blocking agent, can be mediated either from inside a susceptible cell or by secreting a version of the blocking protein to locally block the pathogenic interaction.

In the case of HIV, the two agents of interaction are the gp120/gp 41 envelope protein and the CD4 receptor molecule. Thus, an appropriate blocker would be a vector construct expressing either an HIV env analogue that blocks HIV entry without causing pathogenic effects, or a CD4 receptor analogue. The CD4 analogue would be secreted and would function to protect neighboring cells, while the gp120/gp 41 is secreted or produced only intracellularly so as to protect only the vector-containing cell. It may be advantageous to add human immunoglobulin heavy chains or other components to CD4 in order to enhance stability or complement lysis. Delivery of an alphavirus vector encoding such a hybrid-soluble CD4 to a host results in a continuous supply of a stable hybrid molecule. Efficacy of treatment can be assayed by measuring the usual indicators of disease progression, including antibody level, viral antigen production, infectious HIV levels, or levels of nonspecific infections.

3. Expression of Palliatives

Techniques similar to those described above can be used to produce recombinant alphavirus vector constructs which direct the expression of an agent (or "palliative") which is capable of inhibiting a function of a pathogenic agent or gene. Within the present invention, "capable of inhibiting a function" means that the palliative either directly inhibits the function or indirectly does so, for example, by converting an agent present in the cells from one which would not normally inhibit a function of the pathogenic agent to one which does. Examples of such functions for viral diseases include adsorption, replication, gene expression, assembly, and exit of the virus from infected cells. Examples of such functions for a cancerous cell or cancer-promoting growth factor include viability, cell replication, altered susceptibility to external signals (e.g., contact inhibition), and lack of production or production of mutated forms of anti-oncogene proteins.

(a) Inhibitor Palliatives

In one aspect of the present invention, the alphavirus vector construct directs the expression of a gene which can interfere with a function of a pathogenic agent, for instance in viral or malignant diseases. Such expression may either be essentially continuous or in response to the presence in the cell of another agent associated either with the pathogenic condition or with a specific cell type (an "identifying agent"). In addition, vector delivery may be controlled by targeting vector entry specifically to the desired cell type (for instance, a virally infected or malignant cell) as discussed above.

One method of administration is leukophoresis, in which about 20% of an individual's PBLs are removed at any one time and manipulated in vitro. Thus, approximately $2 \times 10^9$ cells may be treated and replaced. Repeat treatments may also be performed. Alternatively, bone marrow may be treated and allowed to amplify the effect as described above. In addition, packaging cell lines producing a vector may be directly injected into a subject, allowing continuous production of recombinant virions.

In one embodiment, alphavirus vectors which express RNA complementary to key pathogenic gene transcripts (for example, a viral gene product or an activated cellular oncogene) can be used to inhibit translation of that transcript into protein, such as the inhibition of translation of the HIV tat protein. Since expression of this protein is essential for viral replication, cells containing the vector would be resistant to HIV replication.

In a second embodiment, where the pathogenic agent is a single-stranded virus having a packaging signal, RNA complementary to the viral packaging signal (e.g., an HIV packaging signal when the palliative is directed against HIV) is expressed, so that the association of these molecules with the viral packaging signal will, in the case of retroviruses, inhibit stem loop formation or tRNA primer binding required for proper encapsidation or replication of the alphavirus RNA genome.

In a third embodiment, an alphavirus vector may be introduced which expresses a palliative capable of selectively inhibiting the expression of a pathogenic gene, or a palliative capable of inhibiting the activity of a protein produced by the pathogenic agent. In the case of HIV, one example is a mutant tat protein which lacks the ability to transactivate expression from the HIV LTR and interferes (in a transdominant manner) with the normal functioning of tat protein. Such a mutant has been identified for HTLV II tat protein ("XII Leu$^5$" mutant; see Wachsman et al., *Science* 235:674, 1987). A mutant transrepressor tat should inhibit replication much as has been shown for an analogous mutant repressor in HSV-1 (Friedmann et al., *Nature* 335:452, 1988).

Such a transcriptional repressor protein may be selected for in tissue culture using any viral-specific transcriptional promoter whose expression is stimulated by a virus-specific transactivating protein (as described above). In the specific case of HIV, a cell line expressing HIV tat protein and the HSVTK gene driven by the HIV promoter will die in the presence of ACV. However, if a series of mutated tat genes are introduced to the system, a mutant with the appropriate properties (i.e., represses transcription from the HIV promoter in the presence of wild-type tat) will grow and be selected. The mutant gene can then be reisolated from these cells. A cell line containing multiple copies of the conditionally lethal vector/tat system may be used to assure that surviving cell clones are not caused by endogenous mutations in these genes. A battery of randomly mutagenized tat genes are then introduced into these cells using a "rescuable" alphavirus vector (i.e., one that expresses the mutant tat protein and contains a bacterial origin of replication and drug resistance marker for growth and selection in bacteria). This allows a large number of random mutations to be evaluated and permits facile subsequent molecular cloning of the desired mutant cell line. This procedure may be used to identify and utilize mutations in a variety of viral transcriptional activator/viral promoter systems for potential antiviral therapies.

4. Conditional Toxic Palliatives

Another approach for inhibiting a pathogenic agent is to express a palliative which is toxic for the cell expressing the pathogenic condition. In this case, expression of the palliative from the vector should be limited by the presence of an entity associated with the pathogenic agent, such as a specific viral RNA sequence identifying the pathogenic state, in order to avoid destruction of nonpathogenic cells.

In one embodiment of this method, a recombinant alphavirus vector carries a vector construct containing a toxic gene (as discussed above) expressed from a cell-specific responsive vector. In this manner, rapidly replicating cells, which contain the RNA sequences capable of activating the cell-specific responsive vectors, are preferentially destroyed by the cytotoxic agent produced by the alphavirus vector construct.

In a similar manner to the preceding embodiment, the alphavirus vector construct can carry a gene for phosphorylation, phosphoribosylation, ribosylation, or other metabolism of a purine- or pyrimidine-based drug. This gene may have no equivalent in mammalian cells and might come from organisms such as a virus, bacterium, fungus, or protozoan. An example of this would be the *E. coli* guanine phosphoribosyl transferase gene product, which is lethal in the presence of thioxanthine (see Besnard et al., *Mol. Cell. Biol.* 7:4139-4141, 1987). Conditionally lethal gene products of this type (also referred to as "pro-drugs" above) have application to many presently known purine- or pyrimidine-based anticancer drugs, which often require intracellular ribosylation or phosphorylation in order to become effective cytotoxic agents. The conditionally lethal gene product could also metabolize a nontoxic drug which is not a purine or pyrimidine analogue to a cytotoxic form (see Searle et al., *Brit. J. Cancer* 53:377-384, 1986).

Mammalian viruses in general tend to have "immediate early" genes which are necessary for subsequent transcriptional activation from other viral promoter elements. RNA sequences of this nature are excellent candidates for activating alphavirus vectors intracellular signals (or "identifying agents") of viral infection. Thus, conditionally lethal genes expressed from alphavirus cell-specific vectors responsive to these viral "immediate early" gene products could specifically kill cells infected with any particular virus. Additionally, since the human and interferon promoter elements are transcriptionally activated in response to infection by a wide variety of nonrelated viruses, the introduction of vectors expressing a conditionally lethal gene product like HSVTK, for example, in response to interferon production could result in the destruction of cells infected with a variety of different viruses.

In another aspect of the present invention, the recombinant alphavirus viral vector carries a vector construct that directs the expression of a gene product capable of activating an otherwise inactive precursor into an active inhibitor of the pathogenic agent. For example, the HSVTK gene product may be used to more effectively metabolize potentially antiviral nucleoside analogues such as AZT or ddC. The HSVTK gene may be expressed under the control of a cell-specific responsive vector and introduced into these cell types. AZT (and other nucleoside antivirals) must be metabolized by cellular mechanisms to the nucleotide triphosphate form in order to specifically inhibit retroviral reverse transcriptase, and thus, HIV replication (Furmam et al., *Proc. Natl. Acad. Sci. USA* 83:8333-8337, 1986). Constitutive expression of HSVTK (a nucleoside and nucleoside kinase with very broad substrate specificity) results in more effective metabolism of these drugs to their biologically active nucleotide triphosphate form. AZT or ddC therapy will thereby be more effective, allowing lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, will be made more efficacious.

Administration of these alphavirus vectors to human T cell and macrophage/monocyte cell lines can increase their resistance to HIV in the presence of AZT and ddC compared to the same cells without retroviral vector treatment. Treatment with AZT would be at lower than normal levels to avoid toxic side effects but still efficiently inhibit the spread of HIV. The course of treatment would be as described for the blocker.

In one embodiment, the recombinant alphavirus vector carries a gene specifying a product which is not in itself toxic but, when processed or modified by a protein such as a protease specific to a viral or other pathogen, is converted into a toxic form. For example, the recombinant alphavirus could carry a gene encoding a proprotein for ricin A chain, which becomes toxic upon processing by the HIV protease. More specifically, a synthetic inactive proprotein form of the toxin ricin or diphtheria A chains could be cleaved to the active form by arranging for the HIV virally encoded protease to recognize and cleave off an appropriate "pro" element.

In another embodiment, the alphavirus construct may express a "reporting product" on the surface of the target cells in response to the presence of an identifying agent in the cells (such as expression of a viral gene). This surface protein can be recognized by a cytotoxic agent, such as antibodies for the reporting protein, or by cytotoxic T cells. In a similar manner, such a system can be used as a detection system (see below) to simply identify those cells having a particular gene which expresses an identifying protein.

Similarly, in another embodiment, a surface protein could be expressed which would itself be therapeutically beneficial. In the particular case of HIV, expression of the human CD4 protein specifically in HIV-infected cells may be beneficial in two ways:

1. Binding of CD4 to HIV env intracellularly could inhibit the formation of viable viral particles, much as soluble CD4 has been shown to do for free virus, but without the problem of systematic clearance and possible immunogenicity, since the protein will remain membrane bound and is structurally identical to endogenous CD4 (to which the patient should be immunologically tolerant).
2. Since the CD4/HIV env complex has been implicated as a cause of cell death, additional expression of CD4 (in the presence of excess HIV-env present in HIV-infected cells) leads to more rapid cell death and thus inhibits viral dissemination. This may be particularly applicable to monocytes and macrophages, which act as a reservoir for virus production as a result of their relative refractility to HIV-induced cytotoxicity (which, in turn, is apparently due to the relative lack of CD4 on their cell surfaces).

In another embodiment, the alphavirus vector codes for a ribozyme which will cleave and inactivate RNA molecules essential for viability of the vector infected cell. By making ribozyme production dependent on a specific RNA sequence corresponding to the pathogenic state, such as HIV tat, toxicity is specific to the pathogenic state.

5. Expression of Markers

The above-described technique of expressing a palliative in a cell in response to a specific RNA sequence can also be modified to enable detection of a particular gene in a cell which expresses an identifying protein (for example, a gene carried by a particular virus), and hence enable detection of cells carrying that virus. In addition, this technique enables the detection of viruses (such as HIV) in a clinical sample of cells carrying an identifying protein associated with the virus.

This modification can be accomplished by providing a genome coding for a product, the presence of which can be readily identified (the "marker product"), in an alphavirus vector which responds to the presence of the identifying protein in the infected cells. For example, HIV, when it infects suitable cells, makes tat and rev. The indicator cells can thus be provided with a genome (such as by infection with an appropriate recombinant alphavirus) which codes for a marker gene, such as the alkaline phosphatase gene, β-galactosidase gene, or the luciferase gene which is expressed by the recombinant alphavirus upon activation by the tat and/or rev RNA transcript. In the case of β-galactosidase or alkaline phosphatase, exposing the cells to substrate analogues results in a color or fluorescence change if the sample is positive for HIV. In the case of luciferase, exposing the sample to luciferin will result in luminescence if the sample is positive for HIV. For intracellular enzymes such as β-galactosidase, the viral titre can be measured directly by counting colored or fluorescent cells, or by making cell extracts and performing a suitable assay. For the membrane bond form of alkaline phosphatase, virus titre can also be measured by performing enzyme assays on the cell surface using a fluorescent substrate. For secreted enzymes, such as an engineered form of alkaline phosphatase, small samples of culture supernatant are assayed for activity, allowing continuous monitoring of a single culture over time. Thus, different forms of this marker system can be used for different purposes. These include counting active virus, or sensitively and simply measuring viral spread in a culture and the inhibition of this spread by various drugs.

Further specificity can be incorporated into the preceding system by testing for the presence of the virus either with or without neutralizing antibodies to that virus. For example, in one portion of the clinical sample being tested, neutralizing antibodies to HIV may be present; whereas in another portion there would be no neutralizing antibodies. If the tests were negative in the system where there were antibodies and positive where there were no antibodies, this would assist in confirming the presence of HIV.

Within an analogous system for an in vitro assay, the presence of a particular gene, such as a viral gene, may be determined in a cell sample. In this case, the cells of the sample are infected with a suitable alphavirus vector which carries the reporter gene which is only expressed in the presence of the appropriate viral RNA transcript. The reporter gene, after entering the sample cells, will express its reporting product (such as β-galactosidase or luciferase) only if the host cell expresses the appropriate viral proteins.

These assays are more rapid and sensitive, since the reporter gene can express a greater amount of reporting product than identifying agent present, which results in an amplification effect.

6. Immune Down-Regulation

As briefly described above, the present invention also provides recombinant alphavirus which carry a vector construct capable of suppressing one or more elements of the immune system in target cells infected with the alphavirus.

Briefly, specific down-regulation of inappropriate or unwanted immune responses, such as in chronic hepatitis or in transplants of heterologous tissue such as bone marrow, can be engineered using immune-suppressive viral gene products which suppress surface expression of transplantation (MHC) antigen. Group C adenoviruses Ad2 and Ad5 possess a 19 kd glycoprotein (gp 19) encoded in the E3 region of the virus. This gp 19 molecule binds to class I MHC molecules in the endoplasmic reticulum of cells, and prevents terminal glycosylation and translocation of class I MHC to the cell surface. For example, prior to bone marrow transplantation, donor bone marrow cells may be infected with gp 19-encoding vector constructs which, upon expression of the gp 19, inhibit the surface expression of MHC class I transplantation antigens. These donor cells may be transplanted with low risk of graft rejection and may require a minimal immunosuppressive regimen for the transplant patient. This may allow an acceptable donor-recipient chimeric state to exist with fewer complications. Similar treatments may be used to treat the range of so-called autoimmune diseases, including lupus erythromiatis, multiple sclerosis, rheumatoid arthritis or chronic hepatitis B infection.

An alternative method involves the use of anti-sense message, ribozyme, or other specific gene expression inhibitor specific for T cell clones which are autoreactive in nature. These block the expression of the T cell receptor of particular unwanted clones responsible for an autoimmune response. The anti-sense, ribozyme, or other gene may be introduced using the viral vector delivery system.

7. Replacement or Augmentation Gene Therapy

One further aspect of the present invention relates to transforming cells of an animal with recombinant alphavirus vectors which serve as gene transfer vehicles to supply genetic sequences capable of expressing a therapeutic protein. Within one embodiment of the present invention, the viral vector construct is designed to express a therapeutic protein capable of preventing, inhibiting, stabilizing or reversing an inherited or noninherited genetic defect in metabolism, immune regulation, hormonal regulation, enzymatic or membrane associated structural function. This embodiment also describes the viral vector capable of transducing individual cells, whereby the therapeutic protein is able to be expressed systemically or locally from a specific cell or tissue, whereby the therapeutic protein is capable of (a) the replacement of an absent or defective cellular protein or enzyme, or (b) supplement production of a defective of low expressed cellular protein or enzyme. Such diseases may include cystic fibrosis, Parkinson's disease, hypercholesterolemia, adenosine deaminase deficiency, β-globin disorders, Hemophilia A & B, Gaucher's disease, diabetes and leukemia.

As an example of the present invention, a recombinant alphavirus viral vector can be used to treat Gaucher disease. Briefly, Gaucher disease is a genetic disorder that is characterized by the deficiency of the enzyme glucocerebrosidase. This type of therapy is an example of a single gene replacement therapy by providing a functional cellular enzyme. This enzyme deficiency leads to the accumulation of glucocerebroside in the lysosomes of all cells in the body. However, the disease phenotype is manifested only in the macrophages, except in the very rare neuronpathic forms of the disease. The disease usually leads to enlargement of the liver and spleen and lesions in the bones. (For a review, see *Science* 256:794, 1992, and *The Metabolic Basis of Inherited Disease,* 6th ed., Scriver et al., vol. 2, p. 1677).

8. Lymphokines and Lymphokine Receptors

As noted above, the present invention provides alphavirus particles which can, among other functions, direct the expression of one or more cytokines or cytokine receptors.

Briefly, in addition to their role as cancer therapeutics, cytokines can have negative effects resulting in certain pathological conditions. For example, most resting T-cells, B cells, large granular lymphocytes and monocytes do not express IL-2R (receptor). In contrast to the lack of IL-2R expression on normal resting cells, IL-2R is expressed by abnormal cells in patients with certain leukemias (ATL, Hairy-cell, Hodgkins, acute and chronic granulocytic), autoimmune diseases, and is associated with allograft rejection. Interestingly, in most of these patients the serum concentration of a soluble form of IL-2R is elevated. Therefore, with certain embodiments of the invention therapy may be effected by increasing the serum concentration of the soluble form of the cytokine receptor. For example, in the case of IL-2R, an alphavirus vector can be engineered to produce both soluble IL-2R and IL-2R, creating a high affinity soluble receptor. In this configuration, serum IL-2 levels would decrease, inhibiting the paracrine loop.

This same strategy may also be effective against autoimmune diseases. In particular, because some autoimmune diseases (e.g., Rheumatoid arthritis, SLE) are also associated with abnormal expression of IL-2, blocking the action of IL-2 by increasing the serum level of receptor may also be utilized in order to treat such autoimmune diseases.

In other cases inhibiting the levels of IL-1 may be beneficial. Briefly, IL-1 consists of two polypeptides, IL-1 and IL-1, each of which has plieotropic effects. IL-1 is primarily synthesized by mononuclear phagocytes, in response to stimulation by microbial products or inflammation. There is a naturally occurring antagonist of the IL-1R, referred to as the IL-1 Receptor antagonist ("IL-1Ra"). This IL-1R antagonist has the same molecular size as mature IL-1 and is structurally related to it. However, binding of IL-1Ra to the IL-1R does not initiate any receptor signaling. Thus, this molecule has a different mechanism of action than a soluble receptor, which complexes with the cytokine and thus prevents interaction with the receptor. IL-1 does not seem to play an important role in normal homeostasis. In animals, antibodies to IL-1 receptors reduce inflammation and anorexia due to endotoxins and other inflammation inducing agents.

In the case of septic shock, IL-1 induces secondary compounds which are potent vasodilators. In animals, exogenously supplied IL-1 decreases mean arterial pressure and induces leukopenia. Neutralizing antibody to IL-1 reduced endotoxin-induced fever in animals. In a study of patients with septic shock who were treated with a constant infusion of IL-1R for three days, the 28 day mortality was 16% compared to 44% in patients who received placebo infusions.

In the case of autoimmune disease, reducing the activity of IL-1 reduces inflammation. Similarly, blocking the activity of IL-1 with recombinant receptors can result in increased allograft survival in animals, again presumably by decreasing inflammation.

These diseases provide further examples where alphavirus vectors may be engineered to produce a soluble receptor or more specifically the IL-1Ra molecule. For example, in patients undergoing septic shock, a single injection of IL-1Ra producing vector particles could replace the current approach requiring a constant infusion of recombinant IL-1R.

Cytokine responses, or more specifically, incorrect cytokine responses may also be involved in the failure to control or resolve infectious diseases. Perhaps the best studied example is non-healing forms of leishmaniasis in mice and humans which have strong, but counterproductive $T_H2$-dominated responses. Similarly, lepromotomatous leprosy is associated with a dominant, but inappropriate $T_H2$ response. In these conditions, alphavirus-based gene therapy may be useful for increasing circulating levels of IFN gamma, as opposed to the site-directed approach proposed for solid tumor therapy. IFN gamma is produced by $T_H$-1 T-cells, and functions as a negative regulator of $T_H$-2 subtype proliferation. IFN gamma also antagonizes many of the IL-4 mediated effects on B-cells, including isotype switching to IgE.

IgE, mast cells and eosinophils are involved in mediating allergic reaction. IL-4 acts on differentiating T-cells to stimulate $T_H$-2 development, while inhibiting $T_H$-1 responses. Thus, alphavirus-based gene therapy may also be accomplished in conjunction with traditional allergy therapeutics. One possibility is to deliver alphavirus-IL4R with small amounts of the offending allergen (i.e., traditional allergy shots). Soluble IL-4R would prevent the activity of IL-4, and thus prevent the induction of a strong $T_H$-2 response.

9. Suicide Vector

One further aspect of the present invention relates to the expression of alphavirus suicide vectors to limit the spread of wild-type alphavirus in the packaging/producer cell lines. Briefly, within one embodiment the alphavirus suicide vector would be comprised of an antisense or ribozyme sequence, specific for the wild-type alphavirus sequence generated from an RNA recombination event between the 3' sequences of the junction region of the vector, and the 5' alphavirus structural sequences of the packaging cell line expression vector. The antisense or ribozyme molecule would only be thermostable in the presence of the specific recombination sequence and would not have any other effect in the alphavirus packaging/producer cell line. Alternatively, a toxic molecule (such as those disclosed below), may also be expressed in the context of a vector that would only express in the presence of wild-type alphavirus.

10. Alphavirus Vectors to Prevent the Spread of Metastatic Tumors

One further aspect of the present invention relates to the use of alphavirus vectors for inhibiting or reducing the invasiveness of malignant neoplasms. Briefly, the extent of malignancy typically relates to vascularization of the tumor. One cause for tumor vascularization is the production of soluble tumor angiogenesis factors (TAF) (Paweletz et al., *Crit. Rev. Oncol. Hematol.* 9:197, 1989) expressed by some tumors. Within one aspect of the present invention, tumor vascularization may be slowed by using alphavirus vectors to express antisense or ribozyme RNA molecules specific for TAF. Alternatively, anti-angiogenesis factors (Moses et al., *Science* 248:1408, 1990; Shapiro et al., *PNAS* 84:2238, 1987) may be expressed either alone or in combination with the above-described ribozymes or antisense sequences in order to slow or inhibit tumor vascularization. Alternatively, alphavirus vectors can also be used to express an antibody specific for the TAF receptors on surrounding tissues.

11. Administration of Alphavirus Particles

Within other aspects of the present invention, methods are provided for administering recombinant alphavirus vectors or particles. Briefly, the final mode of viral vector administration usually relies on the specific therapeutic application, the best mode of increasing vector potency, and the most convenient route of administration. Generally, this embodiment includes recombinant alphavirus vectors which can be designed to be delivered by, for example, (1) direct injection into the blood stream; (2) direct injection into a specific tissue or tumor; (3) oral administration; (4) nasal inhalation; (5) direct application to mucosal tissues; or (6) ex vivo administration of transduced autologous cells into the animal. Thus the therapeutic alphavirus vector can be administered in such a fashion such that the vector can (a) transduce a normal healthy cell and transform the cell into a producer of a therapeutic protein or agent which is secreted systemically or locally, (b) transform an abnormal or defective cell, transforming the cell into a normal functioning phenotype, (c) transform an abnormal cell so that it is destroyed, and/or (d) transduce cells to manipulate the immune response.

I. Modulation of Transcription Factor Activity

In yet another embodiment, alphavirus vectors may be utilized in order to regulate the growth control activity of transcription factors in the infected cell. Briefly, transcription factors directly influence the pattern of gene expression through sequence-specific transactivation or repression (Karin, *New Biologist* 21:126-131, 1990). Thus, it is not surprising that mutated transcription factors represent a family of oncogenes. Alphavirus gene transfer therapy can be used, for example, to return control to tumor cells whose unregulated growth is activated by oncogenic transcription factors, and proteins which promote or inhibit the binding cooperatively in the formation of homo- and heterodimer trans-activating or repressing transcription factor complexes.

One method for reversing cell proliferation would be to inhibit the trans-activating potential of the c-myc/Max heterodimer transcription factor complex. Briefly, the nuclear oncogene c-myc is expressed by proliferating cells and can be activated by several distinct mechanisms, including retroviral insertion, amplification, and chromosomal translocation. The Max protein is expressed in quiescent cells and, independently of c-myc, either alone or in conjunction with an unidentified factor, functions to repress expression of the same genes activated by the myc/Max heterodimer (Cole, *Cell* 65:715-716, 1991).

Inhibition of c-myc or c-myc/Max proliferation of tumor cells may be accomplished by the overexpression of Max in target cells controlled by alphavirus vectors. The Max protein is only 160 amino acids (corresponding to 480 nucleotide RNA length) and is easily incorporated into an alphavirus vector either independently, or in combination with other genes and/or antisense/ribozyme moieties targeted to factors which release growth control of the cell.

Modulation of homo/hetero-complex association is another approach to control transcription factor activated gene expression. For example, transport from the cytoplasm to the nucleus of the trans-activating transcription factor NF-B is prevented while in a heterodimer complex with the inhibitor protein IB. Upon induction by a variety of agents, including certain cytokines, IB becomes phosphorylated and NF-B is released and transported to the nucleus, where it can exert its sequence-specific trans-activating function (Baeuerle and Baltimore, *Science* 242:540-546, 1988). The dissociation of the NF-B/IB complex can be prevented by masking with an antibody the phosphorylation site of IB. This approach would effectively inhibit the trans-activation activity of the NF-IB transcription factor by preventing its transport to the nucleus. Expression of the IB phosphorylation site specific antibody or protein in target cells may be accomplished with an alphavirus gene transfer vector. An approach similar to the one described here could be used to prevent the formation of the trans-activating transcription heterodimer factor AP-1 (Turner and Tijan, *Science* 243:1689-1694, 1989), by inhibiting the association between the jun and fos proteins.

J. Pharmaceutical Compositions

As noted above, the present invention also provides pharmaceutical compositions comprising a recombinant Sindbis particle or virus, or Sindbis vector construct, in combination with a pharmaceutically acceptable carrier, diluent, or recipient.

Briefly, infectious recombinant virus (also referred to above as particles) may be preserved either in crude or purified forms. In order to produce virus in a crude form, virus-producing cells may first be cultivated in a bioreactor, wherein viral particles are released from the cells into the culture media. Virus may then be preserved in crude form by first adding a sufficient amount of a formulation buffer to the culture media containing the recombinant virus to form an aqueous suspension. Within certain preferred embodiments, the formulation buffer is an aqueous solution that contains a saccharide, a high molecular weight structural additive, and a buffering component in water. The aqueous solution may also contain one or more amino acids.

The recombinant virus can also be preserved in a purified form. More specifically, prior to the addition of the formulation buffer, the crude recombinant virus described above may be clarified by passing it through a filter and then concentrated, such as by a cross flow concentrating system (Filtron Technology Corp., Nortborough, Mass.). Within one embodiment, DNase is added to the concentrate to digest exogenous DNA. The digest is then diafiltrated in order to remove excess media components and to establish the recombinant virus in a more desirable buffered solution. The diafiltrate is then passed over a Sephadex S-500 gel column and a purified recombinant virus is eluted. A sufficient amount of formulation buffer is then added to this eluate in order to reach a desired final concentration of the constituents and to minimally dilute the recombinant virus. The aqueous suspension may then be stored, preferably at −70° C., or immediately dried. As above, the formulation buffer may be an aqueous solution that contains a saccharide, a high molecular weight structural additive, and a buffering component in water. The aqueous solution may also contain one or more amino acids.

Crude recombinant virus may also be purified by ion exchange column chromatography. Briefly, crude recombinant virus may be clarified by first passing it through a filter, followed by loading the filtrate onto a column containing a highly sulfonated cellulose matrix. The recombinant virus may then be eluted from the column in purified form by using a high salt buffer, and the high salt buffer exchanged for a more desirable buffer by passing the eluate over a molecular exclusion column. A sufficient amount of formulation buffer is then added, as discussed above, to the purified recombinant virus and the aqueous suspension is either dried immediately or stored, preferably at −70° C.

The aqueous suspension in crude or purified form can be dried by lyophilization or evaporation at ambient temperature. Briefly, lyophilization involves the steps of cooling the aqueous suspension below the gas transition temperature or below the eutectic point temperature of the aqueous suspension, and removing water from the cooled suspension by sublimation to form a lyophilized virus. Within one embodiment, aliquots of the formulated recombinant virus are placed into an Edwards Refrigerated Chamber (3 shelf RC3S unit) attached to a freeze dryer (Supermodulyo 12K). A multistep freeze drying procedure as described by Phillips et al. (*Cryobiology* 18:414, 1981) is used to lyophilize the formulated recombinant virus, preferably from a temperature of −40° C. to −45° C. The resulting composition contains less than 10% water by weight of the lyophilized virus. Once lyophilized, the recombinant virus is stable and may be stored at −20° C. to 25° C., as discussed in more detail below.

Within the evaporative method, water is removed from the aqueous suspension at ambient temperature by evaporation. Within one embodiment, water is removed through spray-drying (EP 520,748). Within the spray-drying process, the aqueous suspension is delivered into a flow of preheated gas, usually air, whereupon water rapidly evaporates from droplets of the suspension. Spray-drying apparatus are available from a number of manufacturers (e.g., Drytec, Ltd., Tonbridge, England; Lab-Plant, Ltd., Huddersfield, England). Once dehydrated, the recombinant virus is stable and may be stored at −20° C. to 25° C. Within the methods described herein, the resulting moisture content of the dried or lyophilized virus may be determined through use of a Karl-Fischer apparatus (EM Science Aquastar V1B volumetric titrator, Cherry Hill, N.J.), or through a gravimetric method.

The aqueous solutions used for formulation, as previously described, are preferably composed of a saccharide, high molecular weight structural additive, a buffering component, and water. The solution may also include one or more amino acids. The combination of these components act to preserve the activity of the recombinant virus upon freezing and lyophilization or drying through evaporation. Although a preferred saccharide is lactose, other saccharides may be used, such as sucrose, mannitol, glucose, trehalose, inositol, fructose, maltose or galactose. In addition, combinations of saccharides can be used, for example, lactose and mannitol, or sucrose and mannitol. A particularly preferred concentration of lactose is 3%-4% by weight. Preferably, the concentration of the saccharide ranges from 1% to 12% by weight.

The high molecular weight structural additive aids in preventing viral aggregation during freezing and provides structural support in the lyophilized or dried state. Within the context of the present invention, structural additives are considered to be of "high molecular weight" if they are greater than 5000 m.w. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight. Preferably, the concentration of the high molecular weight structural additive ranges from 0.1% to 10% by weight.

The amino acids, if present, function to further preserve viral infectivity upon cooling and thawing of the aqueous suspension. In addition, amino acids function to further preserve viral infectivity during sublimation of the cooled aqueous suspension and while in the lyophilized state. A preferred amino acid is arginine, but other amino acids such as lysine, ornithine, serine, glycine, glutamine, asparagine, glutamic acid or aspartic acid can also be used. A particularly preferred arginine concentration is 0.1% by weight. Preferably, the amino acid concentration ranges from 0.1% to 10% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. A particularly preferred pH of the recombinant virus formulation is 7.4, and a preferred buffer is tromethamine.

In addition, it is preferable that the aqueous solution contain a neutral salt which is used to adjust the final formulated recombinant alphavirus to an appropriate iso-osmotic salt concentration. Suitable neutral salts include sodium chloride, potassium chloride or magnesium chloride. A preferred salt is sodium chloride.

Aqueous solutions containing the desired concentration of the components described above may be prepared as concentrated stock solutions.

It will be evident to those skilled in the art, given the disclosure provided herein, that it may be preferable to utilize certain saccharides within the aqueous solution when the lyophilized virus is intended for storage at room temperature. More specifically, it is preferable to utilize disaccharides, such as lactose or trehalose, particularly for storage at room temperature.

The lyophilized or dehydrated viruses of the subject invention may be reconstituted using a variety of substances, but are preferably reconstituted using water. In certain instances, dilute salt solutions which bring the final formulation to iso-tonicity may also be used. In addition, it may be advantageous to use aqueous solutions containing components known to enhance the activity of the reconstituted virus. Such components include cytokines, such as IL-2, polycations, such as protamine sulfate, or other components which enhance the transduction efficiency of the reconstituted virus. Lyophilized or dehydrated recombinant virus may be reconstituted with any convenient volume of water or the reconstituting agents noted above that allow substantial, and preferably total solubilization of the lyophilized or dehydrated sample.

The following examples are offered by way of illustration, and not by way of limitation.

EXAMPLES

Example 1

Cloning of a Sindbis genomic length cDNA

The nature of viruses having an RNA genome of positive polarity is such that, when introduced into a eukaryotic cell which serves as a permissive host, the purified genomic nucleic acid serves as a functional message RNA (mRNA) molecule for translation of the viral replicase proteins. Therefore, this genomic RNA, purified from the virus, can initiate the same infection cycle that is characteristic of infection by the wild-type virus from which the RNA was purified.

For example, Sindbis virus strain AR339 (ATCC #VR-1248, Taylor et al., *Am. J. Trop. Med. Hyg.* 4:844 1955; isolated from the mosquito *Culexus univittatus*) is propagated in baby hamster kidney (BHK-21) cells (ATCC #CCL-10), infected at low multiplicity (0.1 PFU/cell). Alternatively, another HR-derived Sindbis virus strain, obtained from Lee Biomolecular (San Diego, Calif.), also is used and propagated by the same methods. Sindbis virions are precipitated from a clarified lysate at 48 hours post-infection, with 10% (w/v) of polyethylene glycol (PEG-8000) at 0° C., as described previously. Sindbis virions which are contained in the PEG pellet are then lysed with 2% SDS, and the polyadenylated mRNA isolated by chromatography utilizing commercially available oligo-dT columns (Invitrogen, San Diego, Calif.).

Two rounds of first strand cDNA synthesis are performed on the polyA selected mRNA, using an oligonucleotide primer with the sequence shown below:

5'-TATATTCTAGA(dT)$_{25}$-GAAATG-3'     (SEQ. ID NO. 3)

Briefly, this primer contains at its 5' end, a five nucleotide 'buffer sequence' for efficient restriction endonuclease digestion, followed by the Xba I recognition sequence, 25 consecutive dT nucleotides and six nucleotides which are precisely complementary to the extreme Sindbis 3' end. Thus, selection for first round cDNA synthesis occurs at two levels: (1) polyadenylated molecules, a prerequisite for functional mRNA, and (2) selective priming from Sindbis mRNA molecules, in a pool possibly containing multiple mRNA species. Further, the reverse transcription is performed in the presence of 10 mM MeHgOH to mitigate the frequency of artificial stops during reverse transcription.

Primary genomic length Sindbis cDNA is then amplified by PCR in six distinct segments using six pairs of overlapping primers. Briefly, in addition to viral complementary sequences, the Sindbis 5' end forward primer is constructed to contain a 19 nucleotide sequence corresponding to the bacterial SP6 RNA polymerase promoter and the Apa I restriction endonuclease recognition sequence linked to its 5' end. The bacterial SP6 RNA polymerase is poised such that transcription in vitro results in the inclusion of only a single non-viral G ribonucleotide linked to the A ribonucleotide, which corresponds to the authentic Sindbis 5' end. Inclusion of the Apa I recognition sequence facilitates insertion of the PCR amplicon into the plasmid vector (pKS II$^+$, Stratagene, San Diego, Calif.) polylinker sequence. A five nucleotide 'buffer sequence' is also inserted prior to the Apa I recognition sequence in order to permit efficient digestion. The sequence of the SP6-5' Sindbis forward primer and all of the primer pairs necessary to amplify the entire Sindbis genome are shown below. (Note that "nt" and "nts" as utilized hereinafter refer to "nucleotide" and "nucleotides," respectively). The reference sequence (GenBank accession no. SINCG) is from Strauss et al., *Virology* 133:92-110.

| Primer | Location | Seq. ID No. | Sequence | Recognition Sequence (5'->3') |
|---|---|---|---|---|
| SP6-1A | Apa I/SP6/+ SIN nts.1-18 | 4 | TATATGGGCCCGATTTAGGTGAC ACTATAGATTGACGGCGTAGTAC AC | Apa I |
| 1B | 3182-3160 | 5 | CTGGCAACCGGTAAGTACGATAC | Age I |
| 2A | 3144-3164 | 6 | ATACTAGCCACGGCCGGTATC | Age I |
| 2B | 5905-5885 | 7 | TCCTCTTTCGACGTGTCGAGC | Eco RI |

-continued

| Primer | Location | Seq. ID No. | Sequence | Recognition Sequence (5'->3') |
|---|---|---|---|---|
| 3A | 5844-5864 | 8 | ACCTTGGAGCGCAATGTCCTG | Eco RI |
| 7349R | 7349-7328 | 9 | CCTTTTCAGGGGATCCGCCAC | Bam HI |
| 7328F | 7328-7349 | 10 | GTGGCGGATCCCCTGAAAAGG | Bam HI |
| 3B | 9385-9366 | 11 | TGGGCCGTGTGGTCGTCATG | Bcl I |
| 4A | 9336-9356 | 12 | TGGGTCTTCAACTCACCGGAC | Bcl I |
| 10394R | 10394-10372 | 13 | CAATTCGACGTACGCCTCACTC | Bsi WI |
| 10373F | 10373-10394 | 14 | GAGTGAGGCGTACGTCGAATTG | Bsi WI |
| 4B | Xba I/dT$_{25}$/ 11703-11698 | 3 | TATATTCTAGA(dT)$_{25}$-GAAATG | Xba I |

PCR amplification of Sindbis cDNA with the six primer sets shown above is performed in separate reactions, using the THERMALASE™ thermostable DNA polymerase (Amresco Inc., Solon, Ohio) and the buffer containing 1.5 mM MgCl$_2$, provided by the supplier. Additionally, the reactions contain 5% DMSO, and the HOT START WAX™ beads (Perkin-Elmer), using the PCR amplification protocol shown below:

| Temperature (° C.) | Time (Min.) | No. Cycles |
|---|---|---|
| 94 | 2 | 1 |
| 94 | 0.5 | |
| 55 | 0.5 | 35 |
| 72 | 3.5 | |
| 72 | 10 | 10 |

Following amplification, the six reaction products are inserted first into the pCR II vector (Invitrogen), then using the appropriate enzymes shown above, are inserted, stepwise, into the pKS II$^+$ (Stratagene) vector, between the Apa I and Xba I sites. This clone is designated as pVGSP6GEN.

The Sindbis genomic cDNA clone pVGSP6GEN is linearized by digestion with Xba I, which cuts pVGSP6GEN once, immediately adjacent and downstream of the 25 nucleotide long poly dA:dT stretch. The linearized pVGSP6GEN clone is purified with GENECLEAN™ (BIO 101, La Jolla, Calif.), and adjusted to a concentration of 0.5 mg/ml. Transcription of the linearized pVGSP6GEN clone is performed in vitro at 40° C. for 90 minutes according to the following reaction conditions: 2 ul DNA/4.25 ul H$_2$O; 10 ul 2.5 mM NTPs (UTP, ATP, GTP, CTP); 1.25 ul 20 mM Me$^7$G(5')ppp(5')G cap analogue; 1.25 ul 100 mM DTT; 5 ul 5× transcription buffer (Promega, Madison, Wis.); 0.5 ul RNasin (Promega); 0.25 ul 10 mg/ml bovine serum albumin; and 0.5 ul SP6 RNA polymerase (Promega). The in vitro transcription reaction products can be digested with DNase I (Promega) and are purified by sequential phenol/CHCl$_3$ and ether extraction, followed by ethanol precipitation, or alternatively, can be used directly for transfection. The in vitro transcription reaction products or purified RNA are complexed with a commercial cationic lipid compound (for example, LIPOFECTIN™, GIBCO-BRL, Gaithersburg, Md.), and applied to BHK-21 cells maintained in a 60 mM petri dish at 75% confluency. The transfected cells are incubated at 30° C. After 94 hours post-transfection, extensive cytopathologic effects (CPE) are observed. No obvious CPE is observed in plates not receiving RNA transcribed from the Sindbis cDNA clone. Further, 1 ml of supernatant taken from transfected cells, added to fresh monolayers of BHK-21 cells, and incubated at 30° C. or 37° C. results in obvious CPE within 18 hours. This demonstrates that the Sindbis cDNA clone pVGSP6GEN is indeed infectious.

Sequence analysis of pVGSP6GEN, shown in Table 1, reveals multiple sequence differences between the Sindbis genomic clone described herein, and the viral clone sequence provided in Genbank (GenBank Accession No. SINCG). Many sequence differences result in the substitution of non-conservative amino acids changes in the Sindbis proteins. To address which sequence changes are unique to the virus strain used for cloning, as described herein, or are a result of cloning artifact, virion RNA is amplified by RT-PCR as described above, and sequence relating to the nucleotides in question is determined by direct sequencing of the RT-PCR amplicon product, using a commercially available kit (Promega, Madison Wis.), and compared to the corresponding pVGSP6GEN sequence. The results of this study are given in Table 2. Briefly, three non-conservative amino acid changes, Gly→Glu, Asp→Gly, and Tyr→Cys, which are a result of cloning artifact are observed respectively at viral nucleotides 2245, 6193, and 6730. These nucleotide changes resulting in non-conservative amino acid changes all map to the viral non-structural protein (NSP) genes, nt 2245 to NSP 2, and nts 6193 and 6730 to NSP4.

Repair of the NSP 2 and NSP 4 genes is accomplished by RT-PCR, as described above, using virion RNA from a 5 times plaque purified stock. The SP6-1A/1B primer pair described above is used to repair the nt 2245 change. The RT-PCR amplicon product is digested with Eco 47111 and Bgl II, and the 882 by fragment is purified by 1% agarose/TBE gel electrophoresis, and exchanged into the corresponding region of the pVGSP6GEN clone, prepared by digestion with Eco 47E1 and Bgl II, and treatment with CIAP. The 3A/7349R primer pair described above is used to repair the nt 6193 and nt 6730 changes. The RT-PCR amplicon product is digested with Eco RI and Hpa I, and the 1,050 by fragment is purified by 1% agarose/TBE gel electrophoresis, and exchanged into the corresponding region of the pVGSP6GEN clone. This clone is designated pVGSP6GENrep. Transfection of BHK cells with in vitro transcribed RNA from pVGSP6GENrep DNA, linearized by digestion with Xba I as described above, results in extensive CPE within 18 hours post-transfection.

TABLE 1

SINDBIS GENOMIC CLONE DIFFERENCES BETWEEN PVGSP6GEN AND GENBANK SEQUENCES

| SIN nt # | Change | Codon Change | Location in Codon | amino acid change |
|---|---|---|---|---|
| Noncoding Region: | | | | |
| 45 | T→C | N.A. | N.A. | N.A. |
| Non-structural Proteins: | | | | |
| 353 | C→T | UAU→UAC | 3' | Tyr→Tyr |
| 1095 | A→C | AUA→CUA | 1' | Ile→Leu |
| 1412 | T→C | UUU→UUC | 3' | Phe→Phe |
| 2032 | A→G | GAG→GGG | 2' | Glu→Gly |
| 2245 | G→A | GGG→GAG | 2' | Gly→Glu |
| 2258 | A→C | UCA→UCC | 3' | Ser→Ser |
| 2873 | A→G | CAA→CAG | 3' | Gln→Gln |
| 2992 | C→T | CCC→CUC | 2' | Pro→Leu |
| 3544 | T→C | GUC→GCC | 2 | Val→Leu |
| 3579 | A→G | AAA→GAA | 1' | Leu→Glu |
| 3822 | A→G | ACC→GCC | 1' | Thr→Ala |
| 3851 | T→C | CUU→CUC | 3' | Leu→Leu |
| 5351 | A→T | CAA→CAU | 3' | Gln→His |
| 5466 | G→A | GGU→AGU | 1' | Gly→Ser |
| 5495 | T→C | AUU→AUC | 3' | Ile→Ile |
| 5543 | A→T | ACA→ACU | 3' | Thr→Thr |
| 5614 | T→C | GUA→GCA | 2' | Val→Ala |
| 6193 | A→G | GAC→GGC | 2' | Asp→Gly |
| 6564 | G→A | GCA→ACA | 1' | Ala→Thr |
| 6730 | A→G | UAC→UGC | 2' | Tyr→Cys |
| Structural Proteins: | | | | |
| 8637 | A→G | AUU→GUU | 1' | Ile→Val |
| 8698 | T→A | GUA→GAA | 2' | Val→Glu |
| 9108 | AAG del | AAG→del | 1'-3' | Glu→del |
| 9144 | A→G | AGA→GGA | 1' | Arg→Gly |
| 9420 | A→G | AGU→GGU | 1' | Ser→Gly |
| 9983 | T→G | GCU→GCG | 3' | Ala→Ala |
| 10469 | T→A | AUU→AUA | 3' | Ile→Ile |
| 10664 | T→C | UUU→UUC | 3' | Phe→Phe |
| 10773 | T→G | UCA→GCA | 1' | Ser→Ala |

TABLE 2

SINDBIS GENOMIC CLONE ARTIFACT ANALYSIS

| SIN nt # | Amino Acid change | pVGSP6GEN Unique | Cloning Artifact |
|---|---|---|---|
| Nonstructural Proteins: | | | |
| 2032 | Glu→Gly | +* | |
| 2245 | Gly→Glu | | + |
| 2258 | Ser→Ser | +* | |
| 2873 | Gln→Gln | + | |
| 2992 | Pro→Leu | + | |
| 3544 | Val→Leu | | + |
| 3579 | Leu→Glu | + | |
| 3822 | Thr→Ala | | + |
| 3851 | Leu→Leu | | + |
| 5351 | Gln→His | + | |
| 5466 | Gly→Ser | | + |
| 5495 | Ile→Ile | | + |
| 5543 | Thr→Thr | | + |
| 6193 | Asp→Gly | | + |
| 6730 | Tyr→Cys | | + |
| Structural Proteins: | | | |
| 8637 | Ile→Val | + | |
| 8698 | Val→Glu | + | |
| 9108 | Glu→del | + | |
| 9144 | Arg→Gly | + | |

*Mixture: Both Genbank and pVGSP6GEN Sindbis strains present at this nucleotide.

Example 2

Generation of DNA Vectors which Initiate Alphavirus Infection: Eukaryotic Layered Vector Initiation Systems As noted above, the present invention provides eukaryotic layered vector initiation systems which generally comprise a promoter which is capable of initiating the 5' synthesis of RNA from cDNA, a construct which is capable of autonomous or autocatalytic replication in a cell, the construct also being capable of expressing a heterologous nucleic acid sequence, and a 3' sequence which controls transcription termination. Within one embodiment, such constructs may be constructed of the following ordered elements: a 5' eukaryotic promoter capable of initiating the synthesis of viral RNA at the authentic alphavirus 5' end, a 5' sequence which is capable of initiating transcription of an alphavirus, a nucleotide sequence encoding alphavirus non-structural proteins, a viral junction region, a heterologous sequence, an alphavirus RNA polymerase recognition sequence, and a 3' transcription termination/polyadenylation signal sequence. Such alphavirus cDNA expression vectors may also include intervening sequences (introns), which are spliced from the pre-RNA in the nucleus prior to transport to the cytoplasm, and which may improve the overall efficiency of the system, in terms of molecules of functional mRNA transported to the cytoplasm/nuclear DNA template. The intron splicing signals are located, for example, between Sindbis and heterologous gene regions as described in Example 3.

Construction of a eukaryotic layered vector initiation system utilizing the Sindbis clone pVGSP6GENrep and mammalian RNA polymerase II promoters is accomplished as follows. Briefly, plasmid pVGSP6GENrep is digested with Bgl II and Xba I, and the reaction products are electrophoresed on a 0.8% agarose/TBE gel. The resulting 9,438 by fragment is excised, purified with GENECLEAN™, and ligated into the 4,475 bp vector fragment resulting from treatment of pcDNA3 (Invitrogen) with Bgl II, Xba I, and CIAP. This construction is designated as pcDNASINbgl/xba.

The U3 region of the long terminal repeat (LTR) from Moloney murine leukemia virus (Mo-MLV) is positioned at the 5' viral end such that the first transcribed nucleotide is a single G residue, which is capped in vivo, followed by the Sindbis 5' end. Juxtaposition of the Mo-MLV LTR and the Sindbis 5' end is accomplished by overlapping PCR as described below. Amplification of the Mo-MLV LTR in the first primary PCR reaction is accomplished in a reaction containing the BAG vector (Price et al., *PNAS* 84:156-160, 1987) and the following primer pair:

```
Forward primer: BAGBgl2F1 (buffer sequence/Bgl II
recognition sequence/Mo-MLV LTR nts 1-22):
                                       (SEQ. ID NO. 15)
5'-TATATAGATCTAATGAAAGACCCCACCTGTAGG Reverse primer: BAGwt441R2 (SIN nts 5-1/Mo-MLV LTR
nts 441-406):
                                       (SEQ. ID NO. 16)
5'-TCAATCCCCGAGTGAGGGGTTGTGGGCTCTTTTATTGAGC
```

PCR amplification of the Mo-MLV LTR with the primer pair shown above is performed using the THERMALASE™ thermostable DNA polymerase and the buffer containing 1.5 mM MgCl$_2$, provided by the supplier. Additionally, the reaction contains 5% DMSO, and the HOT START WAX™ beads, using the PCR amplification protocol shown below:

| Temperature (° C.) | Time (Min.) | No. Cycles |
|---|---|---|
| 94 | 2 | 1 |
| 94 | 0.5 | |
| 55 | 0.5 | 35 |
| 72 | 0.5 | |
| 72 | 10 | 1 |

Amplification of the Sindbis 5' end in the second primary PCR reaction is accomplished in a reaction containing the pVGSP6GENrep clone and the following primer pair

```
Forward primer: (Mo-MLV LTR nts 421-441/SIN
nts 1-16):
                                       (SEQ. ID NO. 17)
5'-CCACAACCCCTCACTCGGGGATTGACGGCGTAGTAC Reverse primer: (SIN nts 3182-3160):
                                       (SEQ. ID NO. 18)
5'-CTGGCAACCGGTAAGTACGATAC
```

PCR amplification of the Mo-MLV LTR is accomplished with the primer pair and amplification reaction conditions described above, utilizing the PCR amplification protocol shown below:

| Temperature (° C.) | Time (Min.) | No. Cycles |
|---|---|---|
| 94 | 2 | 1 |
| 94 | 0.5 | |
| 55 | 0.5 | 35 |
| 72 | 3.0 | |
| 72 | 10 | 1 |

The 457 by and 3202 by products from the primary PCR reactions are purified with GENECLEAN™, and combined in a secondary PCR reaction with the following primer pair.

```
Forward primer: BAGBgl2F1 (buffer sequence/Bgl II
recognition sequence/Mo-MLV LTR nts 1-22):
                                       (SEQ. ID NO. 15)
5'-TATATAGATCTAATGAAAGACCCCACCTGTAGG Reverse primer: (SIN nts 2300-2278):
                                       (SEQ. ID NO. 19)
5'-GGTAACAAGATCTCGTGCCGTG
```

PCR amplification of the primer PCR amplicon products is accomplished utilizing the primer pair and amplification reaction conditions shown above, and using the following PCR amplification protocol:

| Temperature (° C.) | Time (Min.) | No. Cycles |
|---|---|---|
| 94 | 2 | 1 |
| 94 | 0.5 | |
| 55 | 0.5 | 35 |
| 72 | 3.0 | |
| 72 | 10 | 1 |

The 25 3' terminal bases of the first primary PCR amplicon product overlaps with the 25 5' terminal bases of the second primary PCR amplicon product; the resultant 2,752 by overlapping secondary PCR amplicon product is purified by 0.8% agarose/TBE electrophoresis, digested with Bgl II, and the 2,734 by product is ligated into pcDNASINbgl/xba treated with Bgl II and CIAP. The resulting construction is 16,656 bps and is designated pVGELVIS. The sequence of pVGELVIS is given in FIG. 3 (SEQ. ID NO. 1). Sindbis nucleotides are contained within bases 1-11,700 of the sequence.

pVGELVIS plasmid DNA is complexed with LIPOFECTANLINE™ (GIBCO-BRL, Gaithersburg, Md.) according to the conditions suggested by the supplier (ca. 5 ug DNA/8 ug lipid reagent) and added to 35 mm wells containing BHK-21 cells at approximately 75% confluency. Cytopathic effects (CPE), characteristic of wild type Sindbis virus infection are observed within 48 hours post-infection. Addition of 1 ml of transfection supernatant to fresh BHK-21 monolayers results in CPE within 16 hrs. This data demonstrates the correct juxtaposition of viral cDNA and RNA polymerase II expression cassette signals in the pVGELVIS construct, resulting in the de novo initiation of an RNA virus from a DNA expression module.

In order to determine the relative efficiency of the pVGELVIS plasmid DNA to initiate infection characteristic of wild type Sindbis virus after transfection into BHK cells, an infectious centers assay is performed. Briefly, 5 ug of pVGELVIS plasmid DNA is transfected into BHK-21 cells in 35 mm wells as described above, and at 1.5 hours post transfection the cells are trypsinized and serially diluted 10.000-fold, over 10-fold increments, into $5 \times 10^5$ untreated BHK cells. This transfected and untreated BHK cell mixture is then added to 35 mm wells. The cells are allowed to attach to the plate, and subsequently overlayed with media containing 1.0% Noble Agar. At 48 hrs post transfection, plaques due to cell lysis (as a result of Sindbis virus replication) are visualized either directly or after overlaying with a second layer containing Neutral Red Stain. This experiment reveals that the efficiency of the pVGELVIS plasmid in generating wild type Sindbis virus after transfection onto BHK cells is approximately $1 \times 10^4$ PFU/ug of plasmid DNA.

Example 3

Preparation of RNA and DNA Alphavirus Vectors

A. Construction of the Sindbis Basic Vector

A first step in the construction of the Sindbis Basic Vector is the generation of two plasmid subclones containing separate elements from the viral 5' and 3' ends. These elements may then be utilized in order to subsequently assemble a basic gene transfer vector.

Briefly, the first plasmid subclone is constructed to contain the 40 terminal nucleotides of the viral 3' end and a 25 base pair stretch of consecutive dA:dT nucleotides. In particular, the following oligonucleotide pairs are first synthesized:

```
Forward Primer: SIN11664F: (buffer sequence/Not I
site/SIN nts 11664-11698):
                                    (SEQ. ID NO. 20)
5'-TATATATATATGCGGCCGCTTTCTTTTATTAATCAACAAAA-
TTTTGTTTTTAA Reverse Primer: SINSac11700R (buffer sequence/Sac
I site dT25/SIN nts 11700-11692):
                                    (SEQ. ID NO. 21)
5'-TATATGAGCTCTTTTTTTTTTTTTTTTTTTTTTTGAAATGTT
AAAA
```

The above oligonucleotides are then mixed together at equal molar concentrations in the presence of 10 mM $MgCl_2$, heated to 100° C. for 5 minutes and cooled slowly to room temperature. The partially double-stranded molecule is then filled in using Klenow DNA polymerase and 50 uM dNTPs. The resultant 89 bp molecule is then digested with Not I and Sac I, purified on a 2% NuSieve/1% of agarose gel, and ligated into pKS II+ plasmid (Stratagene, La Jolla, Calif.), prepared by digestion with Not I and Sac I and treatment with CIAP, at a 10:1 molar excess of insert:vector ratio. This construction is designated pKSII3'SIN.

The second plasmid subclone is constructed to contain the first 5' 7,643 nucleotides of Sindbis, and a bacteriophage RNA polymerase promoter is positioned at the viral 5' end such that only a single non-viral nucleotide is added to the authentic viral 5' end after in vitro transcription. Briefly, the 3' end of this clone is derived by a standard three temperature PCR amplification with a reverse primer having the sequence shown below.

```
Reverse Primer: SINXho7643R (buffer sequence/Xho I
site/SIN nts 7643-7621):
                                    (SEQ. ID NO. 22)
5'TATATCTCGAGGGTGGTGTTGTAGTATTAGTCAG
```

The reverse primer maps to viral nucleotides 7643-7621 and is 41 by downstream from the junction core element 3' end. Additionally, viral nucleotide 7643 is 4 nucleotides upstream from the structural protein gene translation initiation codon. The first five 5' nucleotides in this primer are included to serve as a 'buffer sequence' for the efficient digestion of the PCR amplicon products, and are followed by 6 nucleotides comprising the Xho I recognition sequence.

The forward primer in this reaction is primer 2A (described in Example 1), having the following sequence:

```
ATACTAGCCACGGCCGGTATC          (SEQ. ID NO. 6)
```

The 4510 by amplicon product, resulting from the PCR amplification shown above with pVGSP6GENrep plasmid (described in Example 1) as template, is digested with the enzymes Sfi I and Xho I. The resultant 2526 by fragment is gel purified. Sindbis cDNA clone pVGSP6GENrep is also digested with Apa I and Sfi I, and the resultant 5144 by fragment which includes the SP6 RNA polymerase promoter at its 5' end is gel purified. The 5144 by fragment is ligated together with the 2526 by fragment from above, along with Apa I and the Xho I digested CIAP treated pKS II+ plasmid. A clone is isolated having the Sindbis nucleotides 1-7643 including the RNA polymerase promoter at its 5' end contained in the pKSII+ plasmid vector. This construction is designated pKSII5'SIN.

Assembly of the complete basic vector is accomplished by digesting pKSII5'SIN with Xho I and Sac I, treating with CIAP, and gel purifying of a large 10,533 by fragment. The 10,533 by fragment is then ligated together with a 168 by small fragment resulting from digestion of pKSII3'SIN with Xho I and Sac I. This resultant construction is designated pKSSINBV (also known as SINDBIS basic vector, see FIG. 4).

B. Construction of Sindbis Luciferase Vector

The firefly luciferase reporter gene is inserted into the Sindbis Basic Vector in order to demonstrate the expression of a heterologous gene in cells transfected with RNA that is transcribed in vitro from the Sindbis vector clone, and to demonstrate the overall functionality of the Sindbis basic vector.

Construction of the Sindbis luciferase vector is performed by assembling together components of 3 independent plasmids: pKSII3'SIN, and pGL2-basic vector. The pGL2-basic vector plasmid (Promega, Madison, Wis.) contains the entire firefly luciferase gene. Briefly, the luciferase gene is first inserted into the pKSII3'SIN plasmid. This is accomplished by digesting pGL2 with Bam HI and Hind III, and gel purifying a 2689 by containing fragment. This fragment is ligated with a gel purified 3008 by large fragment resulting from digestion of pKSII3'SIN with Bam HI and Hind III and treatment with CIAP. The resultant construction is designated pKSII3'SIN-luc.

Final assembly of a Sindbis luciferase vector is accomplished by digesting pKSII5'SIN with Xho I and Sac I, treating with CIAP, and gel purifying the large 10,533 by fragment. The pKS 5'SIN 10,533 by fragment is ligated together with the 2854 by small fragment resulting from digestion of pKSII3'SIN-luc with Xho I and Sac I. This construction contains the entire Sindbis nonstructural gene coding region and 3' viral elements necessary for genome replication, as well as the firefly luciferase gene positioned between these two viral 5' and 3' elements. This vector is designated pKSSINBV-luc (also known as SINDBIS-luciferase) and is shown schematically in FIG. 4.

C. Expression of Luciferase in Transfected and Infected BHK-21 Cells

In order to test the functionality of the Sindbis Basic Vector, the expression of luciferase in cells transfected with RNA transcribed in vitro from Sac I-linearized pKSSINBV-luc, as described in Example 1, is tested.

In addition, a complementary packaging vector, which is deleted of most of the non structural gene region, is constructed by digestion of pVGSP6GENrep with Bsp EI and re-ligation under dilute conditions. This construction, designated pVGSP6GENdlBsp (also known as "dl Bsp EI") is deleted of nonstructural gene sequences between bases 422-7,054, and is shown schematically in FIG. 5. Transcription in vitro of Xba I-linearized pVGSP6GENdlBsp is as described in Example 1. Transfections and co-transfections are performed by complexing in vitro transcription products with LIPOFECTIN™ and applying to BHK-21 cells. The expression of luciferase in transfected cells is tested 18 hours after transfection. Additionally, 1 ml of the transfection supernatant is used to infect a confluent monolayer of BHK-21 cells and the expression of luciferase is tested at 24 hours post-infection.

Figure 6:
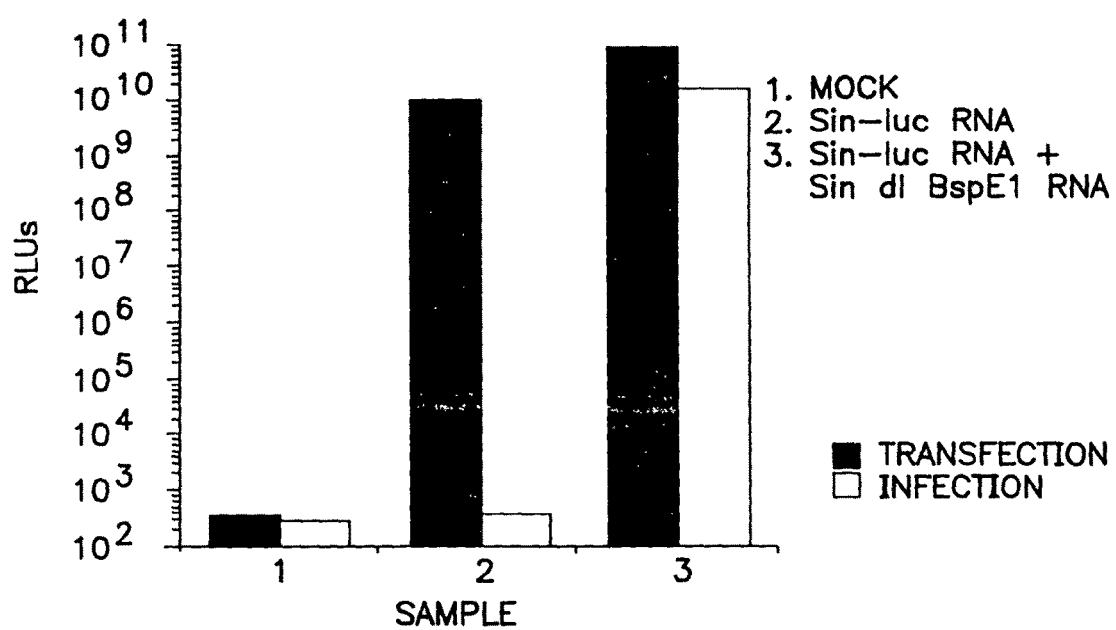
FIG. 6 is a graph which illustrates expression and rescue of a Sindbis luciferase Vector.

The results of this experiment shown in FIG. 6, demonstrate clearly abundant reporter gene expression follows transfection of BHK-21 cells with in vitro transcribed RNA from pKSSINBV-luc, and transfer (e.g., packaging) of the expression activity when cells are co-transfected with in vitro transcribed RNA from pVGSP6GENdlBsp.

D. Construction of Altered Junction Region Sindbis Vectors

Figure 7:
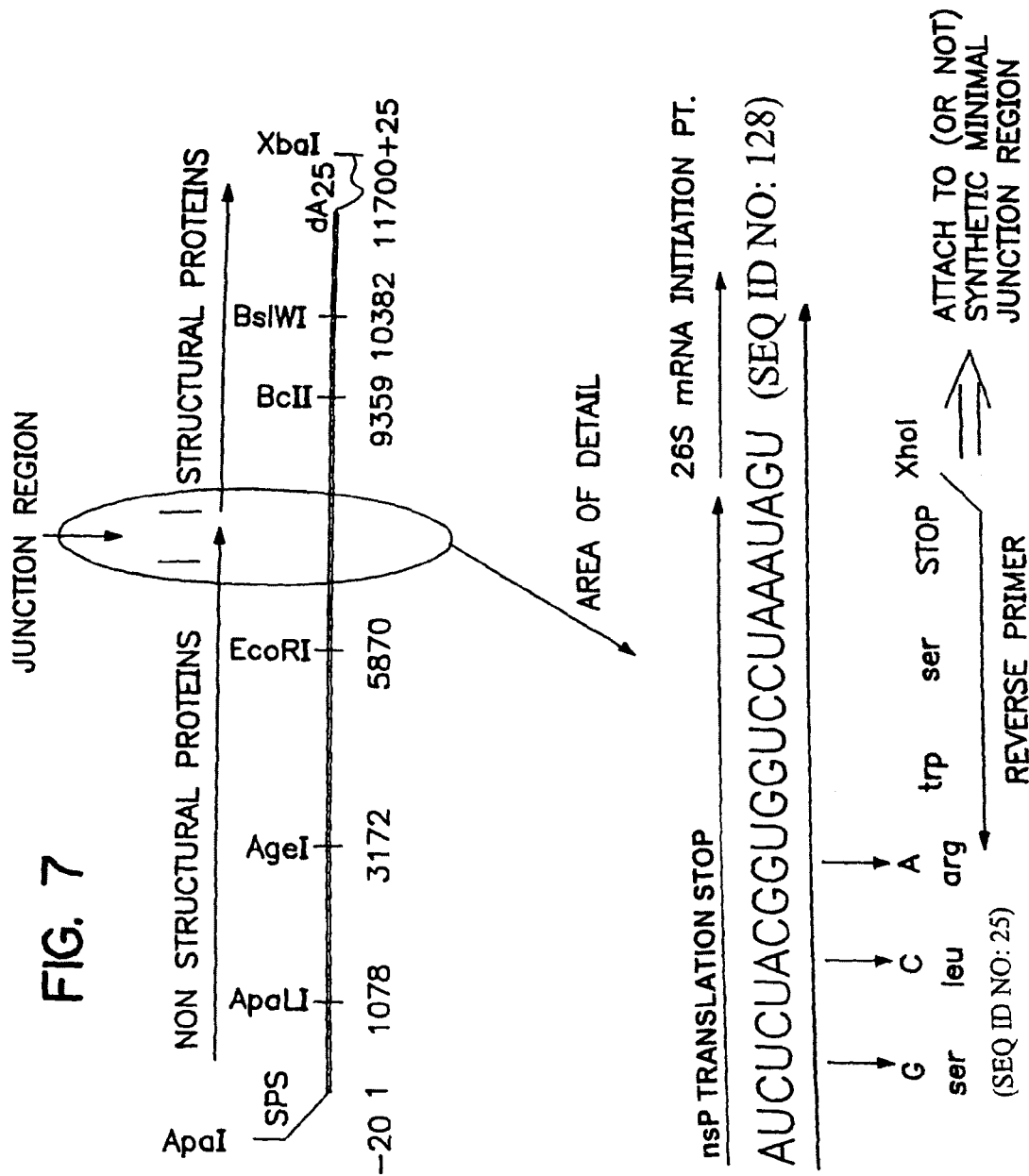
FIG. 7 is an illustration of one method for modifying a Sindbis junction region. (SEQ ID NO:128). Exemplary modifications to the junction are depicted with arrows beneath particular nucleotides (SEQ ID NO:129).

In order to inactivate the Sindbis viral junction region, nucleotides within the NSP4 carboxy terminus and junction region overlap are changed, and the vector nucleotides corresponding to Sindbis are terminated prior to the subgenomic initiation point at Sindbis nt 7598. This construction is shown schematically in FIG. 7.

Briefly, a fragment is PCR amplified from the pKSSINBV clone under nonstringent reaction cycle conditions utilizing a reverse primer having the following sequence:

```
                                       (SEQ. ID NO. 23)
TATATGGGCCCTTAAGACCATCGGAGCGATGCTTTATTTCCCC
```

The underlined bases in the reverse primer relate to nucleotide changes which can be made in the junction region without affecting the coded amino acid (see below). All of the nucleotide changes are transversions.

```
3' end of NSP 4 (viral nts 7580-7597):
TCT CTA CGG TGG TCC TAA      (SEQ. ID NO. 24)

ser leu arg trp ser stop     (SEQ. ID NO. 25)
    G   C   A       T
(resulting nt changes from reverse primer)
```

The reverse primer is complementary to Sindbis nts 7597-7566 (except at nucleotides, as shown, where junction region changes were made), and includes at its 5' end the 6 nucleotide Apa I recognition sequence following a 5' terminal TATAT tail 'buffer sequence' for efficient enzyme digestion. The forward primer in this reaction is primer 2A (described in Example 1), having the following sequence:

```
5'-ATACTAGCCACGGCCGGTATC      (SEQ. ID NO. 6)
```

The 4,464 by amplicon resulting from a PCR reaction with pKSSINBV template and using the primer pair described above is digested with Sfi I and Apa I and the gel purified 2,480 by fragment is ligated together with the gel purified 5,142 by fragment resulting from the digestion of pKSSINBV with Apa I and Sfi I, and with the gel purified 2,961 by fragment resulting from the digestion of pKSII+ with Apa I and from the treatment with CIAP. This construction, comprised of Sindbis nucleotides 1-7597, including the changes in the junction region described above, and including the bacterial SP6 promoter attached to Sindbis nt 1 is referred to as pKS5'SINdlJR.

Final construction of the inactivated junction region vector is accomplished by ligation of the 7,622 by large Sindbis fragment resulting from digestion of pKS5'SINdlJR with Apa I, with the 3,038 by fragment resulting from digestion of pKSII3'SIN with Apa I and treatment with CIAP. The positive orientation of the 5' Sindbis element, relative to the 3' Sindbis element, is confirmed by restriction endonuclease analysis. This construction is referred to as pKSSINBVdlJR.

Initiation and synthesis of subgenomic mRNA cannot occur from the pKSSINBVdlJR vector. In order to prove this supposition, comparative RNase protection assays using the pKSSINBV and pKSSINBVdlJR vectors are performed. Briefly, a $^{32}$P-end labeled RNA probe complementary in part to the junction region, including the subgenomic RNA initiation point at viral nt 7,598 is used to hybridize with the viral RNA resulting from the transfection of BHK-21 cells with the pKSSINBV and pKSSINBVdlJR vectors. The RNase protection assay demonstrates that cells transfected with pKSSINBV have two fragments, of genomic and subgenomic specificity, while cells transfected with pKSSINBVdlJR have only a single fragment of genomic specificity. These results prove that the junction region in the pKSSINBVdlJR vector is indeed inactivated.

In order to test translation of genomic RNA from the region corresponding to the subgenomic RNA message, the luciferase reporter gene is inserted into the inactivated junction region vector pKSSINBVdlJR described above. This construction is accomplished by digesting the pKSSINBVdlJR with Xho I and Sac I, treating with CIAP, and gel purifying the resulting 10,197 by fragment. The pKSSINBVdlJR fragment is ligated together with the 2854 by small fragment resulting from digestion of pKSII3'SIN-luc with Xho I and Sac I. This construction contains the entire Sindbis nonstructural gene coding region terminating in an inactivated junction region at Sindbis nt 7597, and 3' viral elements necessary for genome replication; the firefly luciferase gene is placed between these two viral 5' and 3' elements. This vector is known as pKSSINBVdlJR-luc.

The expression of the reporter gene from the pKSSINBVdlJR-luc vector is tested in transfected BHK-21 cells. Translation of functional luciferase protein is determined by the luciferin luminescent assay, using a luminometer for detection. The sensitivity in this assay is $1\times10^{-20}$ moles of luciferase. Given that the molecular weight of luciferase is 62,000 daltons, this limit of detection transforms to 6,020 molecules. Thus, in a typical experiment if only 0.6% of the $1\times10^6$ cells contained in a 60 mM petri dish are transfected with the pKSSINBVdlJR-luc vector, and if these transfected cells express only a single functional molecule of luciferase, the enzymatic activity is detected by the assay used. It is important to demonstrate in this experiment that the junction region of the pKSSINBVdlJR-luc vector is inactivated. This is accomplished by an RNase protection assay, comparing the viral RNA's synthesized in cells transfected with the pKSSINBVdlJR-luc and the pKSSINBV-luc vectors, using the probe described above.

The minimal −19→+5 junction region core oligonucleotide pair, comprised of Sindbis nts 7579-7602, is synthesized in vitro, and flanked with Apa I and Xho I recognition sequences as shown:

oligonucleotide 1:
(SEQ. ID NO. 26)
5'-CATCTCTACGGTGGTCCTAAATAGTC oligonucleotide 2:
(SEQ. ID NO. 27)
5'-TCGAGACTATTTAGGACCACCGTAGAGATGGGCC The oligonucleotides above are mixed together in the presence of 10 mM $Mg^{2+}$, heated to 100° C. for 5 minutes and cooled slowly to room temperature. The annealed oligonucleotides are ligated at a 25:1 molar ratio of insert to the pKSS-INBVdlJR vector, prepared accordingly: complete digestion with Xho I, followed by digestion with Apa I under partial conditions, resulting in one Apa I induced cleavage per molecule (of two cleavages possible), gel purification of the 10,655 by fragment, and treatment with CIAP. This vector containing the entire nonstructural protein coding region which terminates in an inactivated junction region core, attached to a synthetic junction region core and followed by 3' viral elements required for replication, and contained in the pKSII+ plasmid, is known pKSSINdlJRsjrc.

In order to regulate the level of subgenomic mRNA synthesis, further modifications of the tandemly inserted synthetic junction region core in plasmid pKSSINdlJRsjrc are performed. These modifications of the junction region core may be accomplished by at least two approaches: nucleotide changes within the junction region core; or extension at the 5' and 3' junction region core termini of flanking Sindbis nucleotides, according to the authentic viral sequence. The minimal junction region core, spanning viral nts 7579-7602 is shown below:

5'-ATCTCTACGGTGGTCCTAAATAGT (SEQ. ID NO. 2)

By comparing genomic sequence between eight alphaviruses, it has been shown previously that there is sequence diversity within the junction region core. Shown below, for particular junction region locations, is the Sindbis nucleotide followed by the corresponding nucleotide found in other alphaviruses:

| Nucleotide Number | Sindbis | Permissive Change |
|---|---|---|
| 7579 | A | C |
| 7580 | U | C |
| 7581 | C | U |
| 7583 | C | G |
| 7589 | U | C |
| 7590 | G | U |
| 7591 | G | A |
| 7592 | U | A |
| 7600 | A | U or G |
| 7602 | U | G or A |

Junction region changes at Sindbis nts 7579, 7580, 7581, 7583, 7589, 7590, 7591, 7592, result in potential amino acid coding changes within all 5 codons of the carboxy terminus of NSP 4 which overlap in the junction region. These changes observed in the junction region between alphaviruses at the level of NSP 4 coding potential and at the level of junction region cis activity may represent either, or both, permissive changes in NSP 4 and the junction region which do not affect functionality, or on the other hand, simply different viruses. In any event, the junction region changes presented herein regard the tandemly inserted junction region core, from which no NSP protein synthesis occurs. Discussed above, translation of the entire NSP region occurs from the pKSS-INBVdlJR construct. Junction region changes at Sindbis nts 7600 and 7602 are downstream of the NSP 4 termination codon and upstream of the structural proteins initiation codon.

Locations of nucleotide differences within the junction region core observed between the several alphavirus strains are referred to here as permissive changes. Locations of nucleotides within the junction region core corresponding to conserved sequences between the several alphavirus strains are referred to here as nonpermissive changes.

To decrease the level of subgenomic mRNA initiation from the synthetic junction region core, changes are made separately within nucleotides corresponding to permissive changes, and within nucleotides corresponding to nonpermissive changes. Junction region nucleotides corresponding to permissive changes are given in the table above. Fourteen junction region nucleotides for which no changes are observed among the eight alphaviruses sequenced (Semliki Forest virus, Middleburg virus, Ross River virus, O'Nyong Nyong virus, Eastern Equine Encephalitis virus, Western Equine Encephalitis virus, and Venezuelan Equine Encephalitis virus) are given below:

| Nucleotide Number: |
|---|
| 7582 |
| 7584 |
| 7585 |
| 7586 |
| 7587 |
| 7588 |
| 7593 |
| 7594 |
| 7595 |
| 7596 |
| 7597 |
| 7598 |
| 7599 |
| 7601 |

Changes within the junction region observed among alphaviruses may reflect a specific interaction between a given alphaviral RNA polymerase and its cognate junction region. Thus, changes among the "permissive" nucleotides may result in as marked a decrease in the subgenomic mRNA synthesis levels as changes among the "nonpermissive" nucleotides of the junction region. On the other hand, these may indeed be sites of permissive change within the junction region core.

The single authentic nonpermissive change within the junction region core is likely Sindbis nt 7598, corresponding to the subgenomic mRNA initiation point. Changes of this nucleotide in the tandemly inserted junction region core of plasmid pKSSINdlJRsjrc are not described here.

Substitution of the permissive nucleotides in toto in the synthetic minimal −19→+5 junction region core, is accomplished with the following oligonucleotide pair, synthesized in vitro, and flanked with Apa I and Xho I recognition sequences as shown:

oligonucleotide 1:
(SEQ. ID NO. 28)
5'-CCCTTGTACGGCTAACCTAAAGGAC oligonucleotide 2:
(SEQ. ID NO. 29)
5'-TCGAGTCCTTTAGGTTAGCCGTACAAGGGGCC The oligonucleotides above are mixed together in the presence of 10 mM Mg, heated to 100° C. for 5 minutes and cooled slowly to room temperature. The annealed oligonucleotides are ligated at a 25:1 molar ratio of insert to the pKSS-INBVdlJR vector, prepared accordingly: complete digestion with Xho I, followed by digestion with Apa I under partial conditions, resulting in one Apa I induced cleavage per molecule (of two cleavages possible), gel purification of the 10,655 by fragment, and treatment with CIAP. This vector is known as pKSSINdlJRsjrPc.

Each of the 13 (nt 7598 not changed) nonpermissive nucleotides in the junction region core are changed individually, using the following rules, resulting in the most drastic transversional substitution:

A→C
T→G
G→T
C→A

For example, nt 7582 is changed from T→G, using the following oligonucleotide pair, synthesized in vitro, and flanked with Apa I and Xho I recognition sequences as shown:

oligonucleotide 1:
(SEQ. ID NO. 30)
5'-CATCGCTACGGTGGTCCTAAATAGTC oligonucleotide 2:
(SEQ. ID NO. 31)
5'-TCGAGACTATTTAGGACCACCGTAGCGATGGGCC (Nucleotides effecting transversion in nonpermissive junction region sites shown in boldface type)

The oligonucleotides above are mixed together in the presence of 10 mM Mg$^{2+}$, heated to 100° C. for 5 minutes and cooled slowly to room temperature. The annealed oligonucleotides are ligated at a 25:1 molar ratio of insert to the pKSS-INBVdlJR vector, prepared accordingly: complete digestion with Xho I, followed by digestion with Apa I under partial conditions, resulting in one Apa I induced cleavage per molecule (of two cleavages possible), gel purification of the 10,655 by fragment, and treatment with CIAP. This vector is known pKSSINdlJRsjrNP7582.

Using the transversion change rules shown above, changes in each of the 12 remaining nonpermissive sites in the junction region core are made with 12 separate oligonucleotide pairs, flanked with Apa I and Xho I recognition sites, as described above. These vectors are known as:

pKSSINdlJRsjrNP7584
pKSSINdlJRsjrNP7585
pKSSINdlJRsjrNP7586
pKSSINdlJRsjrNP7587
pKSSINdlJRsjrNP7588
pKSSINdlJRsjrNP7593
pKSSINdlJRsjrNP7594
pKSSINdlJRsjrNP7595
pKSSINdlJRsjrNP7596
pKSSINdlJRsjrNP7597
pKSSINdlJRsjrNP7599
pKSSINdlJRsjrNP7601

In order to test the relative levels of subgenomic mRNA synthesis, the luciferase reporter gene is inserted into the modified tandem junction region vectors. This construction is accomplished by digesting with Xho 1 and Sac I and treating with CIAP the tandemly inserted synthetic junction region core vectors and gel purifying the resulting approximate 10,200 by fragment. The treated vector fragment is then ligated together with the 2854 by small fragment resulting from digestion of pKSII3'SIN-luc with Xho I and Sac I. These constructions contain the entire Sindbis nonstructural gene coding region terminating in an inactivated junction region at Sindbis nt 7597, the tandemly inserted synthetic junction region core (modified or unmodified), the firefly luciferase gene, and 3' viral elements necessary for genome replication. The names of these vectors are as follows:

| Sindbis-luciferase vector | Tandemly Inserted Junction Region Modification |
|---|---|
| pKSSINdlJRsjrc-luc | not modified |
| pKSSINdlJRsjrPc-luc | permissive changes |
| pKSSINdlJRsjrNP7582-luc | nonpermissive change |
| pKSSINdlJRsjrNP7584-luc | " |
| pKSSINdlJRsjrNP7585-luc | " |
| pKSSINdlJRsjrNP7586-luc | " |
| pKSSINdlJRsjrNP7587-luc | " |
| pKSSINdlJRsjrNP7588-luc | " |
| pKSSINdlJRsjrNP7593-luc | " |
| pKSSINdlJRsjrNP7594-luc | " |
| pKSSINdlJRsjrNP7595-luc | " |
| pKSSINdlJRsjrNP7596-luc | " |
| pKSSINdlJRsjrNP7597-luc | " |
| pKSSINdlJRsjrNP7599-luc | " |
| pKSSINdlJRsjrNP7601-luc | " |

Assuming that the translation efficiencies are equivalent in all of the luciferase vectors shown immediately above, the relative levels of subgenomic synthesis are determined by comparing the levels of luciferase production at 16 hours post-transfection of BHK-21 cells. The relative levels of subgenomic transcription are determined by comparing luciferase production by the vectors pKSSINBV-luc and pKSSINdlJRsjrc-luc with all of the modified junction region luciferase vectors shown above.

Vectors containing the tandemly inserted synthetic junction region core (pKSSINdlJRsjrc, and derivatives thereof) should have a lower level of subgenomic mRNA expression, relative to the pKSSINBV construct. Therefore, in certain embodiments, it may be necessary to increase the level of subgenomic mRNA expression observed from the pKSSINdlJRsjrc vector. This may be accomplished by extension at the 5' and 3' synthetic junction region core termini with 11 additional flanking Sindbis nucleotides, according to the authentic viral sequence.

The synthetic oligonucleotide pair shown below is synthesized in vitro, and contains 46 Sindbis nts, including all 24 nts (shown in boldface type) of the minimal junction region core. The Sindbis nts are flanked with the Apa I and Xho I recognition sequences as shown:

oligonucleotide 1:
(SEQ. ID NO. 32)
5'-CGGAAATAAAGCATCTCTACGGTGGTCCTAAATAGTCAGCATAGTAC
C oligonucleotide 2:
(SEQ. ID NO. 33)
5'-TCGAGGTACTATGCTGACTATTTAGGACCACCGTAGAGATGCTTTA
TTTCCGGGCC The oligonucleotides above are mixed together in the presence of 10 mM Mg, heated to 100° C. for 5 minutes and cooled slowly to room temperature. The annealed oligonucleotides are ligated at a 25:1 molar ratio of insert to the pKSS-INBVdlJR vector, prepared accordingly: complete digestion with Xho I, followed by digestion with Apa I under partial conditions, resulting in one Apa I induced cleavage per molecule (of two cleavages possible), gel purification of the 10,655 by fragment, and treatment with CIAP. This vector containing the entire nonstructural protein coding region which terminates in an inactivated junction region core, attached to an extended synthetic junction region, and followed by 3' viral elements required for replication, and contained in the pKSII+plasmid, is known pKSSINdlJRsexjr.

In order to test the relative levels of subgenomic mRNA synthesis, the luciferase reporter gene is inserted into the extended tandem junction region pKSSINdlJRsexjr vector. This construction is accomplished by digesting the pKSS-INdlJRsexjr plasmid with Xho I and Sac I, treating with CIAP, and gel purifying the resulting approximate 10,200 by fragment. The thus-treated vector fragment is ligated together with the 2854 by small fragment resulting from digestion of pKSII3'SIN-luc with Xho I and Sac I. This construction contains the entire Sindbis nonstructural gene coding region terminating in an inactivated junction region at Sindbis nt 7597, the tandemly inserted extended synthetic junction region, the firefly luciferase gene, and 3' viral elements necessary for genome replication. The name of this vector is pKSSINdlJR-sexjr-luc.

The relative levels of subgenomic transcription are determined by comparing luciferase production by the pKSSINdl-JRsexjr-luc vector with the pKSSINBV-luc and pKSSINdl-JRsjrc-luc vectors.

E. Construction of Plasmid DNA Alphavirus Expression Vectors

Figure 8:
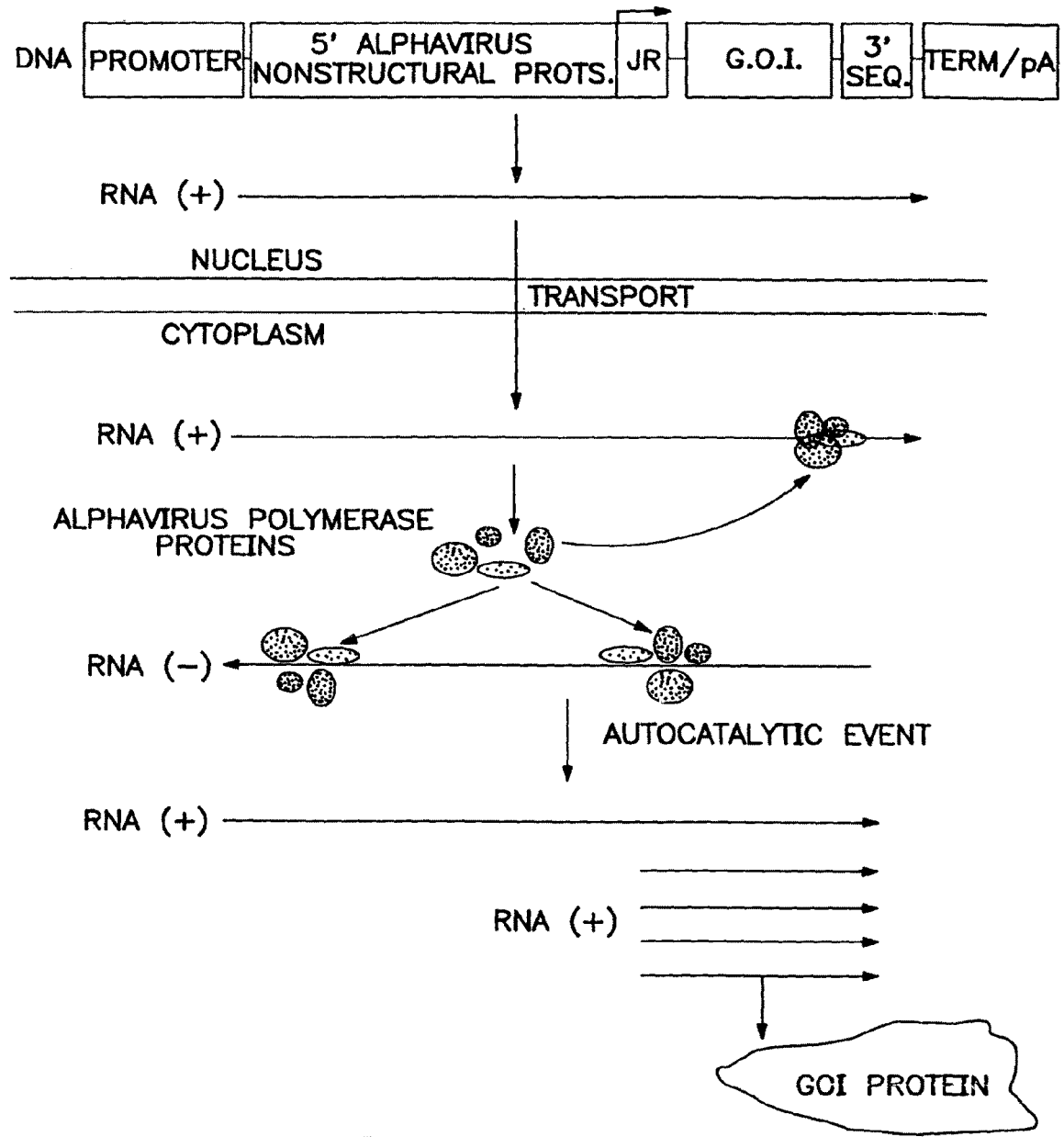
FIG. 8 is a schematic illustration of a representative embodiment of a Eukaryotic Layered Vector Initiation System.

The SINDBIS basic vector and SINDBIS-luciferase constructs described in sections A and B of Example 3, above, are inserted into the pVGELVIS vector configurations described previously in Example 2 such that expression of the heterologous gene from Sindbis vectors occurs after direct introduction of the plasmid DNA into cells. As described in Example 2, the ability to transfect alphavirus-based vector plasmid DNA directly onto cells resulting in expression levels of heterologous genes typical of transfection of RNA-based alphavirus vectors, without a primary step consisting of in vitro transcription of linearized template vector DNA, enhances greatly the utility and efficiency of certain embodiments of the alphavirus-based expression vector system. FIG. 8 is a schematic representation of one mechanism of expression of heterologous genes from a plasmid DNA alphavirus expression (ELVIS) vectors. Primary transcription in the nucleus and transport of the vector RNA to the cytoplasm leads to the synthesis of alphavirus nonstructural proteins which catalyze the expansion of heterologous gene mRNA via an antigenome intermediate which in turn serves as the template for production of genomic and subgenomic mRNA. The ELVIS vectors may be introduced into the target cells directly by physical means as a DNA molecule, as a complex with various liposome formulations, or as a DNA ligand complex including the alphavirus DNA vector molecule, a polycation compound such as polylysine, a receptor specific ligand, and, optionally, a psoralen inactivated virus such as Sendai or Adenovirus.

The first step of constructing one representative plasmid DNA Sindbis expression vector consists of digesting pKSS-INBV with Sac I, blunting with T4 polymerase, digesting with Sfi I, isolating the 2,689 by fragment, and ligating into the pVGELVIS 10,053 by vector fragment prepared by digestion with XbaI, blunting with T4 polymerase, digesting with Sfi I, treatment with CIAP, and 1% agarose/TBE gel electrophoresis. This construction is known as pVGELVIS-SINBV.

In order to insert the luciferase gene into the pVGELVIS-SINBV vector, the SV40 intron and transcription termination sequences at the 3'-end of luciferase must be removed so that when the pre-RNA, transcribed from the plasmid DNA luciferase vector after transfection into cells, is processed the 3'-end of the reporter gene is not separated from the Sindbis vector 3'-end. The Sindbis 5'- and 3'-ends contained within the pVGELVIS-SINBV vector are required in cis for the autocatalytic replication activity of the vector. The Sindbis vector 3'-end is required for initiation of synthesis of the antigenomic strand, which is the template for the subgenomic RNA encoding the heterologous or reporter protein.

The SV40 RNA processing signals positioned at the 3'-end of the luciferase gene are removed from the SIN-BV-luc construction described in section B above. The modified luciferase fragment is then placed in the pVGELVIS-SINBV construction described above via unique restriction sites. The alteration of the luciferase gene is accomplished with the primer pair shown below:

Forward primer 7328F (SIN nts 7328-7349):
(SEQ. ID NO. 10)
5'-GTGGCGGATCCCCTGAAAAGG Reverse primer LucStop (buffer sequence/Not I. Xba I recognition sequences/pGL-2 nts 1725-1703):
(SEQ. ID NO. 34)
5'-TATATGCGGCCGCTCTAGATTACAATTTGGACTTTCCGCCC The primers shown above are used in a PCR reaction with a three temperature cycling program using a 3 minute extension period. The amplification products are purified with GENECLEAN™, digested with Xho I and Xba I, purified again with GENECLEAN™, and the 2,037 by fragment is ligated into the 13,799 by fragment of pVGELVIS-SINBV resulting from digestion with Xho I and Xba I, and treatment with CIAP. This construction is known as pVGELVIS-SINBV-lnc (abbreviated as ELVIS-luc).

Figure 9:
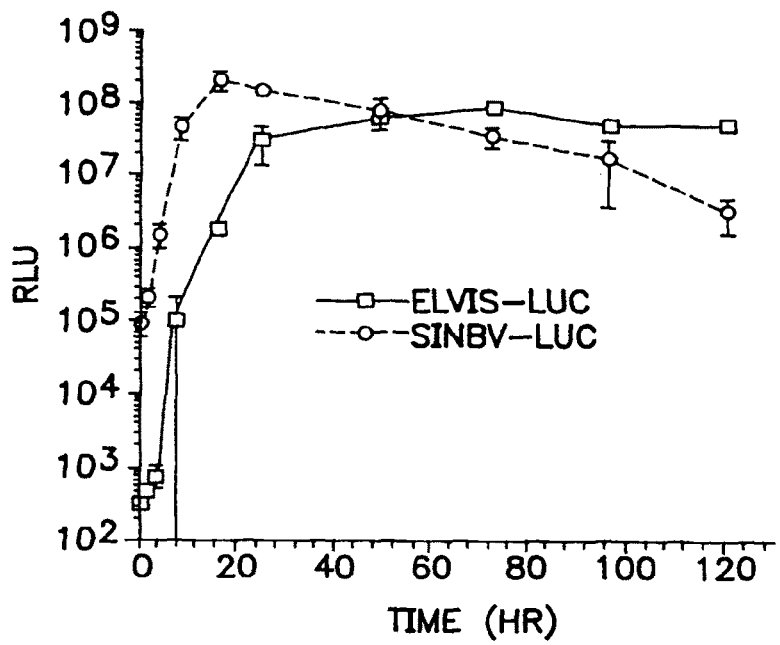
FIG. 9 is a graph which shows a time course for luciferase expression from ELVIS-LUC and SINBV-LUC vectors.

The expression of luciferase in BHK-21 cells transfected with pVGELVIS-SINBV-luc DNA is measured in order to demonstrate that the Sindbis physical gene transfer vector is functional. Briefly, 5 ug of pVGELVIS-SINBV-luc DNA or 5 ug of in vitro transcribed RNA from linearized SINBV-luc template as described in section B, above, are complexed with 10 ul of LIPOFECTAMINE™ or LIPOFECTIN™, respectively, and transfected into 5×10$^5$ BHK-21 cells contained in 35 mM petri plates. The luciferase activity is determined from each of three samples at 2, 4, 8, 16, 20, 28, 48, 72, 96, and 120 hrs. post transfection. The results of this study, given in FIG. 9, demonstrate that the maximal level of reporter gene expression from the pVGELVIS-SINBV-luc vector is similar to that observed in cells transfected with in vitro transcribed RNA from linearized SINBV-luc template. However, the luciferase activity expressed from the pVGELVIS-SINBV-luc vector is at maximal levels at later time points compared to that observed with the SINBV-luc RNA vector, and continues at high levels while the activity from the RNA vector begins to diminish.

The following experiment is performed in order to demonstrate the level of enhancement of heterologous gene expression provided by the ELVIS vector system compared to the same RNA polymerase II promoter linked directly to the luciferase gene reporter. Briefly, the Sindbis NSPs are first deleted from the pVGELVIS-SINBV-luc vector in order to demonstrate the requirement for the viral enzymatic proteins for high levels of reporter gene expression. This is accomplished by digestion of pVGELVIS-SINBV-luc DNA with Bsp EI, purification with GENECLEAN, and ligation under dilute conditions. This construction is deleted of nonstructural gene sequences between bases 422-7,054 and is analogous to the pVGSP6GENdlBsp construction described in Example 3, section C above and shown schematically in FIG. 5. The construction described here is known as pVGELVIS-SINBVdlBsp-luc (abbreviated as dlNSP ELVIS-luc). To link the luciferase gene directly to the MoMuLV LTR, the reporter is first inserted into the pcDNA3 vector (Invitrogen, San Diego, Calif.) between the Bam HI and Hind III sites. The luciferase fragment is derived from pGL2 plasmid exactly as described in Example 3 section B, above, and inserted into the 5428× bp fragment of pcDNA3 prepared by digestion with Hind III and Bam HI, treatment with CIAP, and purification on a 1% agarose/TBE gel. This construction is known as pcDNA3-luc. The U3 region of the MoMuLV LTR is amplified from the BAG vector using the PCR primers shown below as described in Example 2.

```
Forward primer: BAGBgl2F1 (buffer sequence/Bgl
II recognition sequence/Mo-MLV LTR nts 1-22):
                                    (SEQ. ID NO. 15)
5'-TATATAGATCTAATGAAAGACCCCACCTGTAGG Reverse primer: BAGwt441R2 (SIN nts 5-1/Mo-MLV
LTR nts 441-406):
                                    (SEQ. ID NO. 16)
5'-TCAATCCCCGAGTGAGGGGTTGTGGGCTCTTTTATTGAGC
```

The amplification products are purified with GENECLEAN and the ends are first blunted with T4 DNA polymerase, then digested with Bgl II, purified with GENECLEAN™ and ligated into the pcDNA3-luc plasmid prepared by digestion with Hind III, blunting with the Klenow enzyme and 50 uM dNTPs, digestion with Bgl II, and purification by 1% agarose/TBE gel electrophoresis. This construction is known as LTR-luc.

Figure 10:
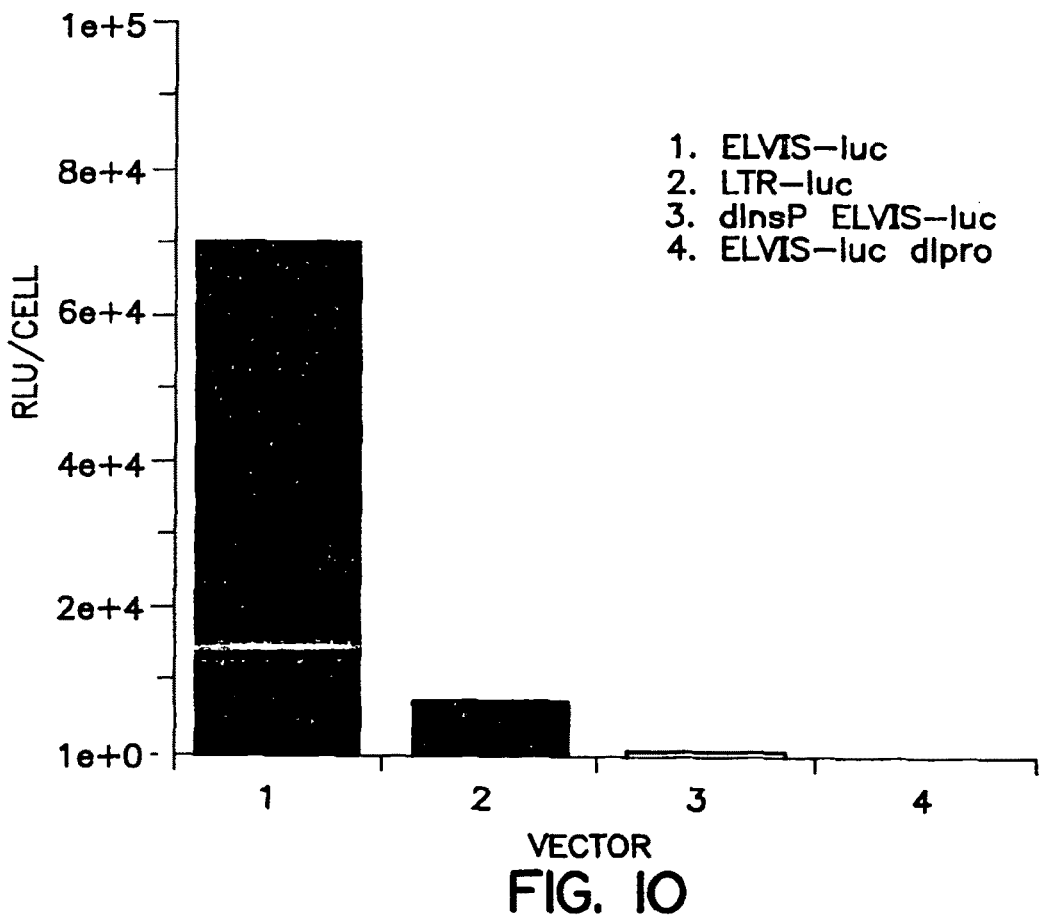
FIG. 10 is a bar graph which depicts the level of ELVIS vector reporter gene expression compared to several different vector constructs.
Figure 11:
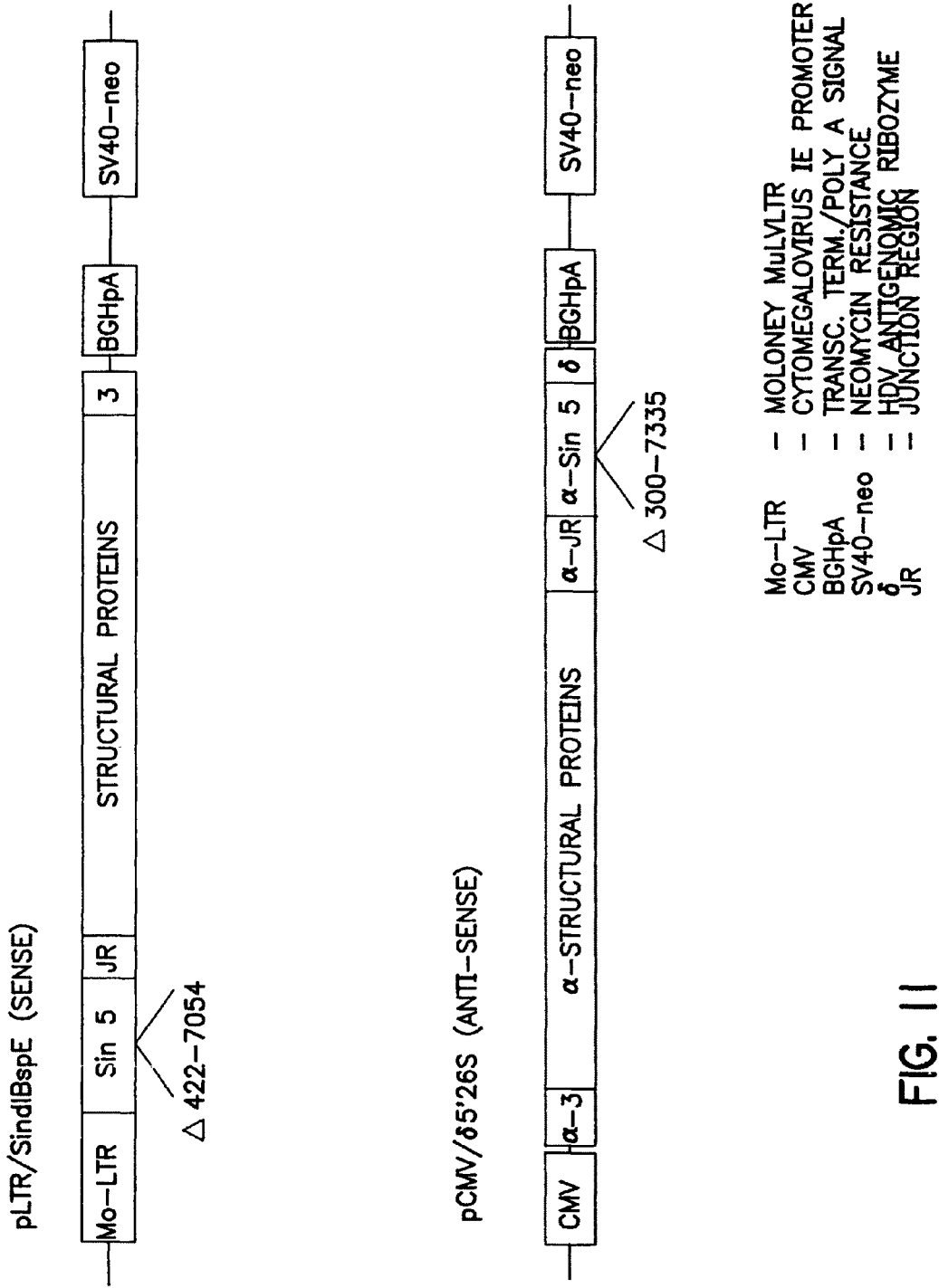
FIG. 11 is a schematic illustration of Sindbis Packaging Expression Cassettes.
Figure 12:
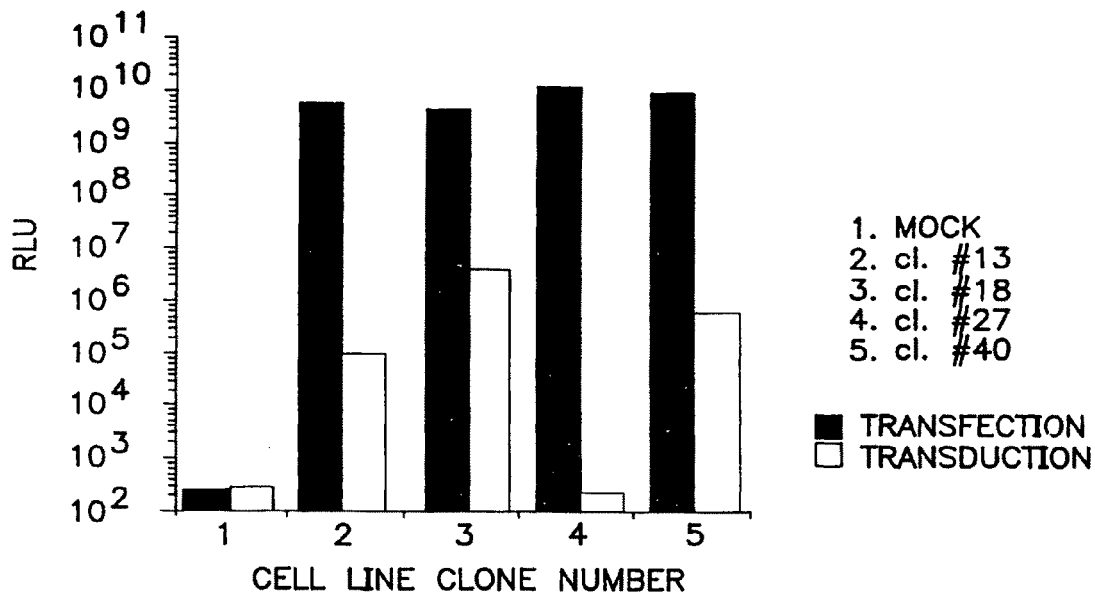
FIG. 12 is a bar graph which shows SIN-luc vector packaging by representative packaging cell lines.
Figure 13:
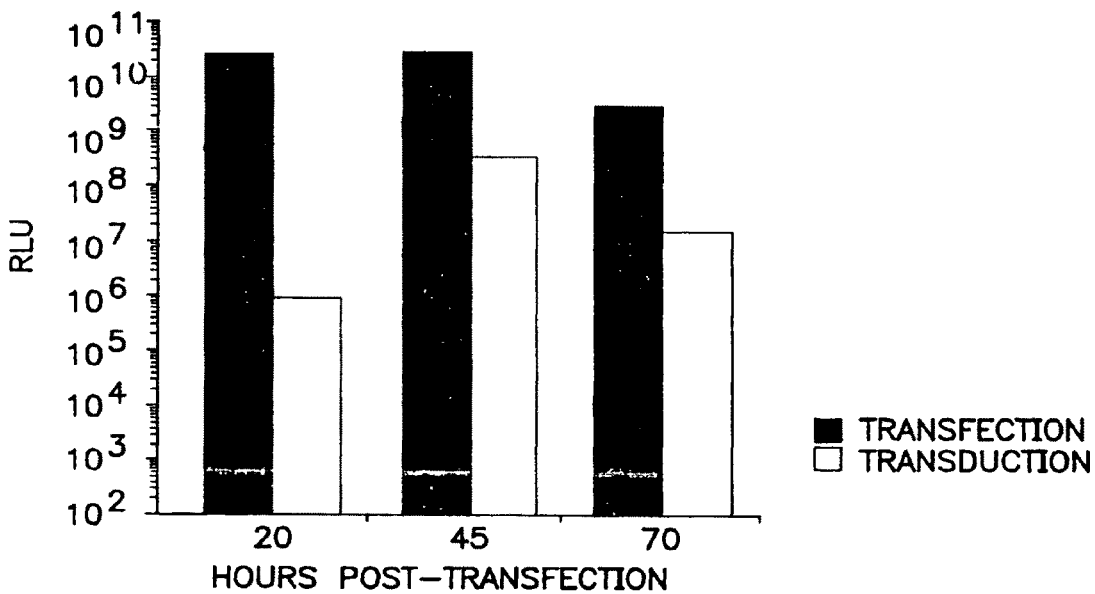
FIG. 13 is a bar graph which shows SIN-luc vector packaging by PCL clone #18 over time.

The plasmids ELVIS-luc, dlNSP ELVIS-luc, LTR-luc, and ELVIS-luc dlpro are each complexed with 10 ul of LIPOFECTAMINE™ and transfected into $5 \times 10^5$ BHK-21 cells contained in 35 mM petri plates. The luciferase activity is determined from each of three samples at 48 hrs. post-transfection. The results of this study, given in FIG. 10, demonstrate that the level of heterologous gene expression enhancement provided by the ELVIS system, compared to the same promoter linked directly to the heterologous gene is at least 10-fold. The comparatively low level of luciferase expression in cells transfected with the dlNSP ELVIS-luc construction demonstrates that the expression enhancement is a direct result of functional Sindbis NSPs. The autocatalytic amplification of the reporter gene mRNA as depicted in FIG. 8 provides a significant advantage in terms of levels of gene expression, compared to primary transcription from simple promoter-heterologous gene constructions. Thus, as shown schematically in FIG. 8, after transfection of the ELVIS vector primary transcription in the nucleus and transport of the vector RNA to the cytoplasm leads to the synthesis of Sindbis NSPs which catalyze the expansion of heterologous gene mRNA via an antigenome intermediate which in turn serves as the template for production of genomic and subgenomic mRNA.

Figure 23:
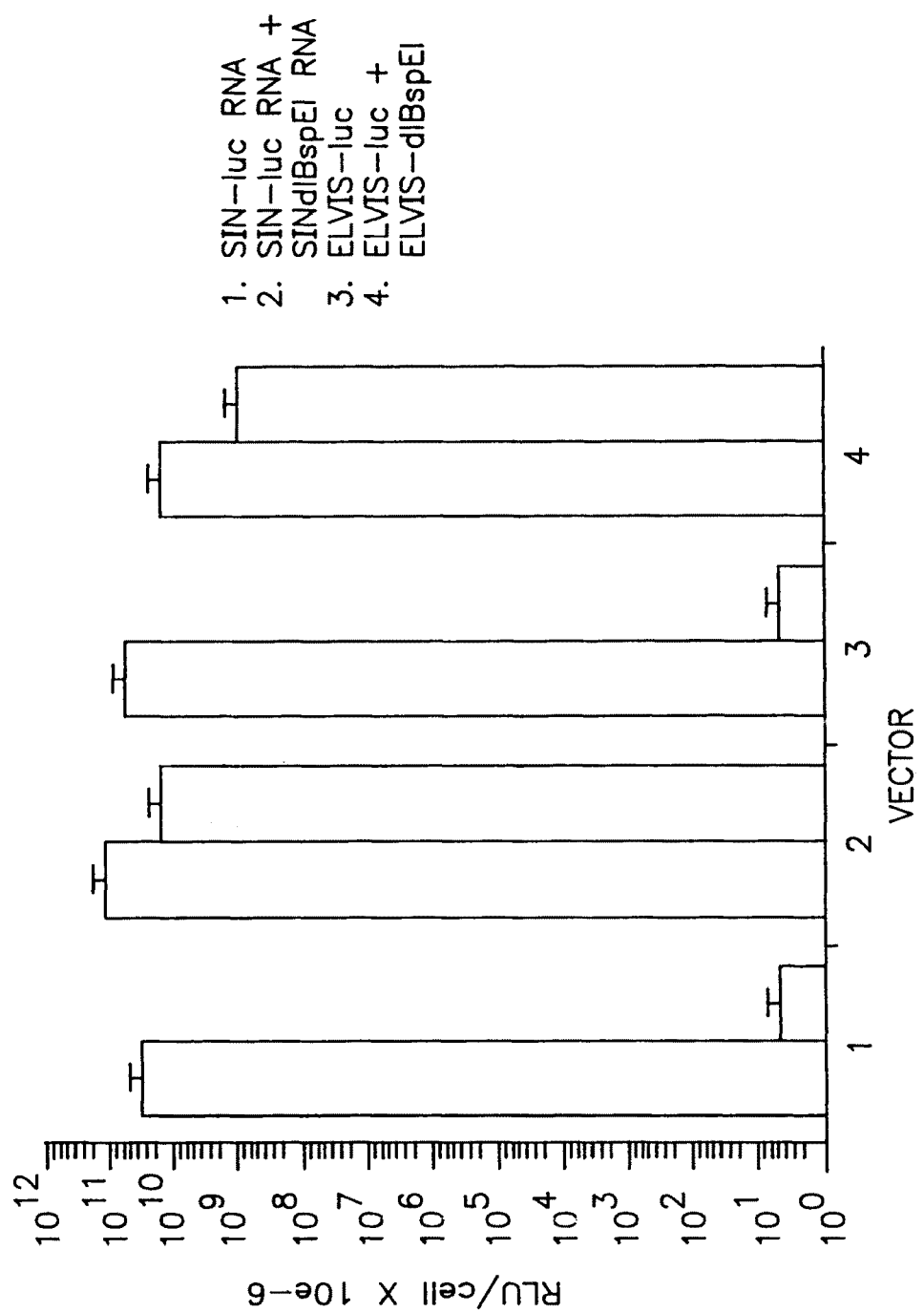
FIG. 23 is a bar graph which demonstrates the level of luciferase or β-galactosidase expression in BHK cells transfected with ELVIS expression vectors, co-transfected with ELVIS expression and helper vectors, or transduced with packaged ELVIS expression vectors.

An experiment is performed to demonstrate the expression and rescue of RNA- and plasmid DNA (ELVIS)-based Sindbis expression vectors. For the RNA vectors, $5 \times 10^5$ BHK-21 cells contained in 35 mM petri plates are transfected with SIN-luc RNA, or co-transfected with SIN-luc RNA and SINdlBspEI RNA, complexed with LIPOFECTIN™. For the ELVIS vectors, $5 \times 10^5$ BHK-21 cells contained in 35 mM petri plates are transfected with ELVIS-luc, or co-transfected with ELVIS-luc and pVGELVISdlBspEI, whose construction is described in Example 7, complexed with LIPOFECTAMINE™. The results of this study, shown in FIG. 23 demonstrate clearly that the level of expression after transfection and transduction is similar between BHK cells co-transfected with RNA or ELVIS vectors. Thus, the ELVIS vectors are used not only as plasmid DNA expression vectors, but additionally expression and helper vector ELVIS constructs can be cotransfected into cells to generate recombinant vector particles.

F. Construction of Modified DNA-Based Alphavirus Expression Vectors

The overall efficiency of the ELVIS vector, as determined by level of heterologous gene expression, is enhanced by several modifications to the pVGELVIS-SINBV-luc vector. These modifications include alternate RNA polymerase II promoters and transcription termination signals, the addition of intron sequences and ribozyme processing signals in the vector construct, and substitution with a smaller plasmid vector backbone. The construction of these modified ELVIS vectors is detailed below.

The modified ELVIS vector is assembled on the plasmid vector pBGS131 (ATCC #37443) which is a kanamycin resistant analogue of pUC 9 (Spratt et al., Gene 41:337-342, 1986). Propagation of pBGS131 is in LB medium with 10 ug/ml kanamycin.

The transcription termination signals from the SV40 early region or Bovine growth hormone are inserted between the Sac I and Eco RI sites of pBGS131. The SV40 nts between viral nts 2643 to 2563 containing the early region transcription termination sequences are isolated by PCR amplification using the primer pair shown below and the pBR322/SV40 plasmid (ATCC #45019) as template.

```
Forward primer SSVTT 2643 (buffer sequence/Sac I
site/SV40 nts 2643-2613):
                                    (SEQ. ID NO. 35)
5'-TATATATGAGCTCTTACAAATAAAGCAATAGCATCACAAATTTC Reverse primer RSVTT2563R (buffer sequence/Eco RI
site/SV40 nts 2563-2588):
                                    (SEQ. ID NO. 36)
5'-TATATGAATTCGTTTGGACAAACCACAACTAGAATG
```

The primers shown above are used in a PCR reaction with a three temperature cycling program as described throughout this example, using a 30 second extension period. The amplification products are purified with GENECLEAN™, digested with Sac I and Eco RI, purified again with GENECLEAN™, and the 90 by fragment is ligated into the 3,655 by fragment of pBGS131 resulting from digestion with Sac I and Eco RI, and treatment with CIAP. This construction is known as pBGS131-3'SV40TT The Bovine growth hormone transcription termination sequences are isolated by PCR amplification using the primer pair shown below and the pcDNA3 plasmid (Invitrogen) as template.

```
Forward primer BGHTTF (buffer sequence/Sac I
site/pCDNA3 nts 1132-1161):
                                   (SEQ. ID NO. 37)
5'-TATATATGAGCTCTAATAAAATGAGGAAATTGCATCGCATTGTC Reverse primer BGHTTR (buffer sequence/Eco RI
site/pCDNA3 nts 1180-1154):
                                   (SEQ. ID NO. 38)
5'-TATATGAATTCATAGAATGACACCTACTCAGACAATGCGATGC
```

The primers shown above are used in a PCR reaction with a three temperature cycling program, using a 30 sec. extension period. The amplification products are purified with GENECLEAN™, digested with Sac I and Eco RI, purified again with GENECLEAN™, and the 58 by fragment is ligated into the 3,655 by fragment of pBGS131 resulting from digestion with Sac I and Eco RI, and treatment with CIAP. This construction is known as pBGS131-3'BGHTT.

In additional modifications to the ELVIS vector, the transcription termination sequences are fused directly to the 3'-end Sindbis sequences, resulting in deletion of the polyadenylate tract; or alternatively the antigenomic ribozyme sequence of hepatitis delta virus (HDV) is inserted between the 3'-polyadenylate tract of the ELVIS vector and the transcription termination signals.

The HDV ribozyme-containing construct is generated with PCR techniques and overlapping oligonucleotide primers which contain the minimal 84 nucleotide antigenomic ribozyme sequence (Perotta and Been, *Nature* 350:434-6, 1991). In addition to the HDV sequence, the primers contain flanking Sac I recognition sites for insertion at the 3' end of the ELVIS vector. The HDV ribozyme sequence is generated with the three overlapping primers shown below.

```
Forward primer SHDV1F (Buffer sequence/Sac I
site/HDV RBZ seq.):
                                   (SEQ. ID NO. 39)
5'-TATATGAGCTCGGGTCGGCATGGCATCTCCACCTCCTCGCGGTCCG Nested primer HDV17-68:
                                   (SEQ. ID NO. 40)
5'-TCCACCTCCTCGCGGTCCGACCTGGGCATCCGAAGGAGGACGCAC
GTCCACT-3'

Reverse primer SHDV84R (Buffer sequence/Sac I
site/HDV RBZ seq.):
                                   (SEQ. ID NO. 41)
5'-TATATGAGCTCCTCCCTTAGCCATCCGAGTGGACGTGCGTCCTCCT
TC
```

The primers shown above are used in a PCR reaction with a three temperature cycling program as described throughout this example, using a 30 sec. extension period. The amplification products are purified with GENECLEAN™, digested with Sac I, purified again with GENECLEAN™, and the 94 by fragment subsequently is ligated into plasmid vectors pBGS131-3'SV40TT or pBGS131-3'BGHTT that are digested with Sac I under limiting conditions that linearize (cut 1 of 2 sites) and are treated with CIAP. These constructions are known as pBGS131/HDV/3'SV40TT and pBGS131/HDV/3'BGHTT. Insertion of the HDV ribozyme in both the correct orientation and in the correct Sac I site is determined by sequencing. In addition, longer or shorter HDV ribozyme sequences, or any other catalytic ribozyme sequence, may be readily substituted given the disclosure provided herein.

In the second vector 3'-end configuration, the SV40 or BGH transcription termination signals are fused directly to the 3'-end of the ELVIS vector corresponding to Sindbis nt 11,700 and the polyadenylate tract is deleted. This construction is accomplished according to the steps outlined above in Example 3, sections A and B for the assembly of the pKSSINBV and pKSSINBV-luc vectors. However, in this application the vector 3'-end primer does not contain a 25 polyadenylate tract. The 3'-end of the vector is synthesized with the primer pair shown below:

```
Forward Primer: SIN11664F: (buffer sequence/Not I
site/SIN nts 11664-11698):
                                   (SEQ. ID NO. 42)
5'-TATATGCGGCCGCTTTCTTTTATTAATCAACAAAATTTTGTTTTTAA Reverse Primer: SSIN11700R (buffer sequence/Sac I
site/SIN nts 11700-11655:
                                   (SEQ. ID NO. 43)
5'-TATATGAGCTCGAAATGTTAAAAACAAAATTTTGTTG
```

The primers shown above are used in a PCR reaction with a three temperature cycling program as described throughout this example, using a 30 sec. extension period. Assembly of the pKSSINBV and pKSSINBV-luc vectors is precisely as shown in Example 3, sections A and B. These constructions are known as pKSSINBVdlA and pKSSINBVdlA-luc.

The ELVIS expression vectors are assembled further onto the various 3' end processing plasmid constructions described above. The Sindbis vectors containing a polyadenylate tract are combined with the plasmid constructions containing the HDV ribozyme sequence and the SV40 or BGH transcription termination signals. This construction corresponds to the insertion of pKSSINBV and pKSSINBV-luc vector sequences into the pBGS131/HDV/3'SV40TT and pBGS131/HDV/3'BGHTT plasmids. Alternatively, the Sindbis vectors terminating precisely at the viral 3' end corresponding to viral nt 11,700 are linked directly to the SV40 or BGH transcription termination signals. This construction corresponds to the insertion of pKSSINBVdlA and pKSSINBVdlA-luc vector sequences into the pBGS131/HDV/3'SV40TT and pBGS131/HDV/3'BGHTT plasmids.

The Sindbis vectors pKSSINBV and pKSSINBV-luc are digested with Sac I and Bgl II, and the 5,522 by (pKSSINBV) or 8211 by (pKSSINBV-luc) fragments are purified by 1% agarose/TBE gel electrophoresis and inserted into the linearized pBGS131/HDV/3'SV40TT and pBGS131/HDV/3'BGHTT plasmids prepared by digestion with Sac I and Bgl II and treatment with CIAP. These constructions are known as:

pBGS131/dlproSINBV-luc/HDV/3'SV40TT
pBGS131/dlproSINBV-luc/HDV/3'BGHTT
pBGS131/dlproSINBV/HDV/3'SV40TT
pBGS131/dlproSINBV/HDV/3'BGHTT Using the same strategy described above, the Sindbis vectors pKSSINBVdlA and pKSSINBVdlA-luc are digested with Sac I and Bgl II, and the 5,497 by (pKSSINBVdlA) or 8186 by (pKSSINBVdlA-luc) fragments are purified by 1% agarose/TBE gel electrophoresis and inserted into the linearized pBGS131/3'SV40TT and pBGS131/3'BGHTT plasmids prepared by digestion with Sac I and Bgl II and treatment with CIAP. These constructions are known as:

pBGS131/dlproSINBV-luc/3'SV40TT
pBGS131/dlproSINBV-luc/3'BGHTT
pBGS131/dlproSINBV/3'SV40TT
pBGS131/dlproSINBV/3'BGHTT The addition of an RNA polymerase II promoter and Sindbis nucleotides 1-2289 is the last step required to complete the construction of the modified ELVIS expression vectors of the eight constructions shown below:

pBGS131/dlproSINBV-luc/HDV/3'SV40TT
pBGS131/dlproSINBV-luc/HDV/3'BGHTT
pBGS131/dlproSINBV/HDV/3'SV40TT
pBGS131/dlproSINBV/HDV/3'BGHTT
pBGS131/dlproSINBV-luc/3'SV40TT
pBGS131/dlproSINBV-luc/3'BGHTT
pBGS131/dlproSINBV/3'SV40TT
pBGS131/dlproSINBV/3'BGHTT These eight constructions contain a unique Bgl II restriction site, corresponding to Sindbis nt 2289. The RNA polymerase II promoter and Sindbis nucleotides 1-2289 are inserted into these constructions by the overlapping PCR technique described for the pVGELVIS construction in Example 2. In order to insert the RNA polymerase II promoter and the 2289 Sindbis nts, the eight constructions shown above are digested with Bgl II and treated with CIAP.

The U3 region of the long terminal repeat (LTR) from Moloney murine leukemia virus (Mo-MLV) is positioned at the 5' viral end such that the first transcribed nucleotide is a single G residue, which is capped in vivo, followed by the Sindbis 5' end. Amplification of the Mo-MLV LTR in the first primary PCR reaction is accomplished in a reaction containing the BAG vector (Price et al., *PNAS* 84:156-160, 1987) and the following primer pair:

```
Forward primer: BAGBgl2F1 (buffer sequence/Bgl II
recognition sequence/Mo-MLV LTR nts 1-22):
                                       (SEQ. ID NO. 15)
5'-TATATAGATCTAATGAAAGACCCCACCTGTAGG Reverse primer: BAGwt441R2 (SIN nts 5-1/Mo-MLV LTR
nts 441-406):
                                       (SEQ. ID NO. 16)
5'-TCAATCCCCGAGTGAGGGGTTGTGGGCTCTTTTATTGAGC
```

The primers shown above are used in a PCR reaction with a three temperature cycling program using a 30 second extension period.

Amplification of the Sindbis 5' end in the second primary PCR reaction is accomplished in a reaction containing the pVGSP6GENrep clone and the following primer pair:

```
Forward primer: (Mo-MLV LTR nts 421-441/
SIN nts 1-16):
                                       (SEQ. ID NO. 17)
5'-CCACAACCCCTCACTCGGGGATTGACGGCGTAGTAC Reverse primer: (SIN nts 3182-3160):
                                       (SEQ. ID NO. 18)
5'-CTGGCAACCGGTAAGTACGATAC
```

The primers shown above are used in a PCR reaction with a three temperature cycling program using a 3 minute extension period.

The 457 by and 3202 by products from the primary PCR reactions are purified with GENECLEAN™, and used together in a PCR reaction with the following primer pair.

```
Forward primer: BAGBgl2F1 (buffer sequence/Bgl II
recognition sequence/Mo-MLV LTR nts 1-22):
                                       (SEQ. ID NO. 15)
5'-TATATAGATCTAATGAAAGACCCCACCTGTAGG Reverse primer: (SIN nts 2300-2278):
                                       (SEQ. ID NO. 19)
5'-GGTAACAAGATCTCGTGCCGTG
```

The primers shown above are used in a PCR reaction with a three temperature cycling program using a 3 minute extension period. The 25 3'-terminal bases of the first primary PCR amplicon product overlap with the 25 5'-terminal bases of the second primary PCR amplicon product the resultant 2,752 by overlapping secondary PCR amplicon product is purified by 1% agarose/TBE electrophoresis, digested with Bgl II, and the 2,734 by product is ligated into the eight ELVIS constructions described above. These constructions are named as shown below:

MpLTRELVIS-luc/D/S
MpLTRELVIS-luc/D/B
MpLTRELVIS/D/S
MpLTRELVIS/D/B
MpLTRELVIS-luc/S
MpLTRELVIS-luc/B
MpLTRELVIS/S
MpLTRELVIS/B Using the same overlapping PCR approach, the CMV promoter is positioned at the 5' viral end such that transcription initiation results in the addition of a single non-viral nucleotide at the Sindbis 5' end. Amplification of the CMV promoter in the first primary PCR reaction is accomplished in a reaction containing the pcDNA3 plasmid and the following primer pain

```
Forward primer: pCBgl233F (buffer sequence/Bgl II
recognition sequence/CMV promoter nts 1-22):
                                       (SEQ. ID NO. 44)
5'-TATATATAGATCTTTGACATTGATTATTGACTAG Reverse primer: SNCMV1142R (SIN nts 8-1/CMV
pro nts 1142-1108):
                                       (SEQ. ID NO. 45)
5'-CCGTCAATACGGTTCACTAAACGAGCTCTGCTTATATAGACC
```

The primers shown above are used in a PCR reaction with a three temperature cycling program using a 1 minute extension period.

Amplification of the Sindbis 5' end in the second primary PCR reaction is accomplished in a reaction containing the pVGSP6GENrep clone and the following primer pair

```
Forward primer: CMVSIN1F (CMV pro nts 1124-1142/
SIN nts 1-20):
                                       (SEQ. ID NO. 46)
5'-GCTCGTTTAGTGAACCGTATTGACGGCGTAGTACACAC Reverse primer: (SIN nts 3182-3160):
                                       (SEQ. ID NO. 18)
5'-CTGGCAACCGGTAAGTACGATAC
```

The primers shown above are used in a PCR reaction with a three temperature cycling program using a 3 minute extension period.

The 600 by and 3200 by products from the primary PCR reactions are purified with GENECLEAN™, and used together in a PCR reaction with the following primer pair.

Forward primer: pCBg1233F (buffer sequence/Bgl II
recognition sequence/CMV promoter nts 1-22):
(SEQ. ID NO. 44)
5'-TATATATAGATCTTTGACATTGATTATTGACTAG Reverse primer: (SIN nts 2300-2278):
(SEQ. ID NO. 19)
5'-GGTAACAAGATCTCGTGCCGTG The primers shown above are used in a PCR reaction with a three temperature cycling program using a 3 minute extension period.

The 26 3' terminal bases of the first primary PCR amplicon product overlaps with the 26 5' terminal bases of the second primary PCR amplicon product the resultant 2,875 by overlapping secondary PCR amplicon product is purified by 1% agarose/TBE electrophoresis, digested with Bgl II, and ligated into the four ELVIS constructions described above. These constructions are named as shown below:

MpCMVELVIS-luc/D/S
MpCMVELVIS-luc/D/B
MpCMVELVIS/D/S
MpCMVELVIS/D/B
MpCMVELVIS-luc/S
MpCMVELVIS-luc/B
MpCMVELVIS/S
MpCMVELVIS/B Using the same overlapping PCR approach, the SV40 early region promoter is positioned at the 5' viral end such that the major cap site of transcription initiation results in the addition of a single non-viral nucleotide at the Sindbis 5' end. Amplification of the SV40 promoter in the first primary PCR reaction is accomplished in a reaction containing the pBR322/SV40 plasmid (ATCC #45019) and the following primer pair.

Forward primer: B2SVpr250F (buffer sequence/Bgl II
recognition sequence/SV40 nts 250-231):
(SEQ. ID NO. 47)
5'-TATATATAGATCTGGTGTGGAAAGTCCCCAGGC Reverse primer: SINSV5235R (SIN nts 13-1/SV40 nts
5235-10):
(SEQ. ID NO. 48)
5'-CTACGCCGTCAATGCCGAGGCGGCCTCGGCC The primers shown above are used in a PCR reaction with a three temperature cycling program using a 30 second extension period.

Amplification of the Sindbis 5' end in the second primary PCR reaction is accomplished in a reaction containing the pVGSP6GENrep clone and the following primer pair:

Forward primer: SVSIN1F (SV40 nts 3-5235/SIN nts
1-25):
(SEQ. ID NO. 49)
5'-GGCCGCCTCGGCATTGACGGCGTAGTACACACTATTG Reverse primer: (SIN nts 3182-3160):
(SEQ. ID NO. 18)
5'-CTGGCAACCGGTAAGTACGATAC The primers shown above are used in a PCR reaction with a three temperature cycling program using a 3 minute extension period.

The 280 by and 3,194 by products from the primary PCR reactions are purified with GENECLEAN™, and used together in a PCR reaction with the following primer pair.

Forward primer: B2SVpr250F (buffer sequence/Bgl II
recognition sequence/SV40 nts 250-231):
(SEQ. ID NO. 47)
5'-TATATATAGATCTGGTGTGGAAAGTCCCCAGGC Reverse primer: (SIN nts 2300-2278):
(SEQ. ID NO. 19)
5'-GGTAACAAGATCTCGTGCCGTG The primers shown above are used in a PCR reaction with a three temperature cycling program using a 3 minute extension period.

The 25 3' terminal bases of the first primary PCR amplicon product overlaps with the 25 5' terminal bases of the second primary PCR amplicon product; the resultant 2,543 by overlapping secondary PCR amplicon product is purified by 1% agarose/TBE electrophoresis, digested with Bgl II, and ligated into the four ELVIS constructions described above. These constructions are named as shown below:

MpSV40ELVIS-luc/D/S
MpSV40ELVIS-luc/D/B
MpSV40ELVIS/D/S
MpSV40ELVIS/D/B
MpSV40ELVIS-luc/S
MpSV40ELVIS-luc/B
MpSV40ELVIS/S
MpSV40ELVIS/B The luciferase expression levels, after transfection of BHK-21 cells, are determined with each of the reporter gene containing complete modified ELVIS constructions detailed above, in order to determine the optimal desired configuration. The heterologous gene is inserted into the multiple cloning site of the ELVIS vector, as described for the insertion of the luciferase gene in Example 3, section B.

In order to increase the efficiency of the ELVIS system, in terms of functional vector RNA transported to the cytoplasm per nuclear DNA template, the SV40 small t antigen intron can be inserted into the ELVIS expression vectors. Insertion of the SV40 small t antigen intron sequences into the Xho I site immediately downstream of the 5' Sindbis sequences is accomplished by limited digestion (cut 1 of 2 sites); or, alternatively at the unique Not I site immediately upstream of the 3' Sindbis sequences.

For insertion into the Xho I site of the ELVIS vectors, amplification of the SV40 small t antigen intron sequences is accomplished in a reaction containing the pBR322/SV40 plasmid (ATCC #45019) and the following primer pair.

Forward primer: XSVSD4647F (buffer sequence/Xho I
recognition sequence/SV40 nts 4647-4675):
(SEQ. ID NO. 50)
5'-TATATATCTCGAGAAGCTCTAAGGTAAATATAAAATTTACC Reverse primer: XSVSA4562R (buffer sequence/Xho I
recognition sequence/SV40 nts 4562-4537):
(SEQ. ID NO. 51)
5'-TATATATCTCGAGAGGTTGGAATCTAAAATACACAAAC The primers shown above are used in a PCR reaction with a three temperature cycling program using a 30 second extension period. The amplification products are purified with GENECLEAN™, digested with Xho I, re-purified with GENECLEANT™ and inserted into Xho I linearized (by limited digest) and CIAP treated complete modified ELVIS vectors described above. Insertion of the SV40 small t antigen intron in the correct orientation in the ELVIS vector is determined by sequencing.

For insertion into the Not I site of the ELVIS vectors, amplification of the SV40 small t antigen intron sequences is accomplished in a reaction containing the pBR322/SV40 plasmid and the following primer pair:

```
Forward primer: NSVSD4647F (buffer sequence/Not I
recognition sequence/SV40 nts 4647-4675):
                                    (SEQ. ID NO. 52)
5'-TATATATGCGGCCGCAAGCTCTAAGGTAAATATAAAATTTACC Reverse primer: XSVSA4562R (buffer sequence/Not I
recognition sequence/SV40 nts 4562-4537):
                                    (SEQ. ID NO. 53)
5'-TATATATGCGGCCGCAGGTTGGAATCTAAAATACACAAAC
```

The primers shown above are used in a PCR reaction with a three temperature cycling program using a 30 second extension period. The amplification products are purified with GENECLEANT™, digested with Not I, re-purified with GENECLEAN™ and inserted into Not I linearized and CIAP treated complete modified ELVIS vectors described above. Insertion of the SV40 small t antigen intron in the correct orientation in the ELVIS vector is determined by sequencing. Alternatively, the SV40 small t antigen may be inserted at other sites within the ELVIS vector, which do not impair function of the vector, using the disclosure provided herein.

The luciferase expression levels, after transfection of BHK-21 cells with the SV40 small t antigen intron containing ELVIS vectors, are assayed in order to determine the optimal desired configuration. The heterologous gene is inserted into the multiple cloning site of the ELVIS vector, as described for the insertion of the luciferase gene in Example 3, section B.

A linker sequence is inserted into the pKSSINBV and into the pVGELVIS-SINBV constructs to facilitate the insertion of heterologous sequences. The linker is constructed using two complementary 35 nt oligonucleotides that form a duplex with Xho I and Xba I compatible sticky ends when hybridized.

```
SINBVLinkF:
                                    (SEQ. ID NO. 54)
5'TCGAGCACGTGGCGCGCCTGATCACGCGTAGGCCT SINBVLinkR:
                                    (SEQ. ID NO. 55)
5'CTAGAGGCCTACGCGTGATCAGGCGCGCCACGTGC
```

The oligonucleotides are phosphorylated with T4 polynucleotide kinase, heated to 90° C., and slow cooled to allow hybridization to occur. The hybrid is then ligated to the 10.6 kb fragment of pKSSINBV-Luc obtained after digestion with XhoI and XbaI, followed by treatment with alkaline phosphatase and agarose gel purification. The resulting construct contains Xho I, Pml I, Asc I, Bcl I, Mlu I, Stu I, Xba I, and Not I as unique sites between the Sindbis junction region and the Sindbis 3' end. This construct is known as pKSSINBV-Linker.

This linker also is cloned into the pVGELVIS-SINBV constructs. The linker is inserted by digestion of pVGELVIS-SINBV-luc with Sfi I and Not I. The 10.1 kb fragment is agarose gel purified, and this fragment was ligated to the gel purified 2.6 kb fragment from a Sfi I/Not I digest of pKSSINBV-Linker. The resulting construct contains Xho I, Pml I, Asc I, Mlu I, and Not I as unique sites between the Sindbis junction region and the Sindbis 3' end. This construct is known as pVGELVIS-SINBV-Linker.

Figure 22A:
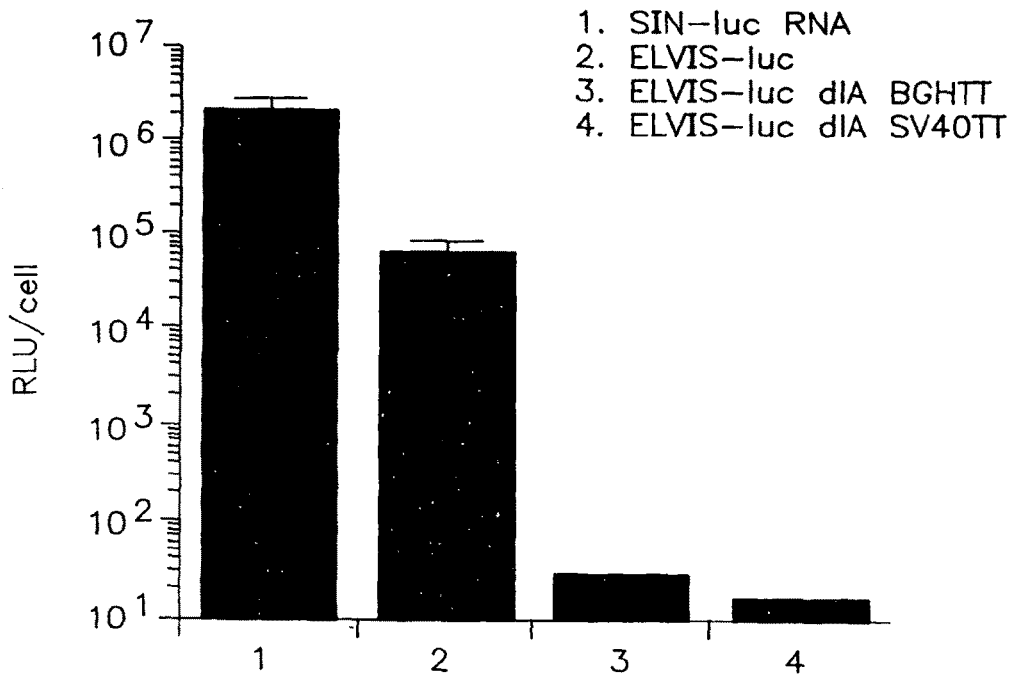
FIG. 22 is a bar graph which demonstrates the level of expression of luciferase in BHK cells transfected with ELVIS-LUC vector, and various modifications thereof.
Figure 22B:
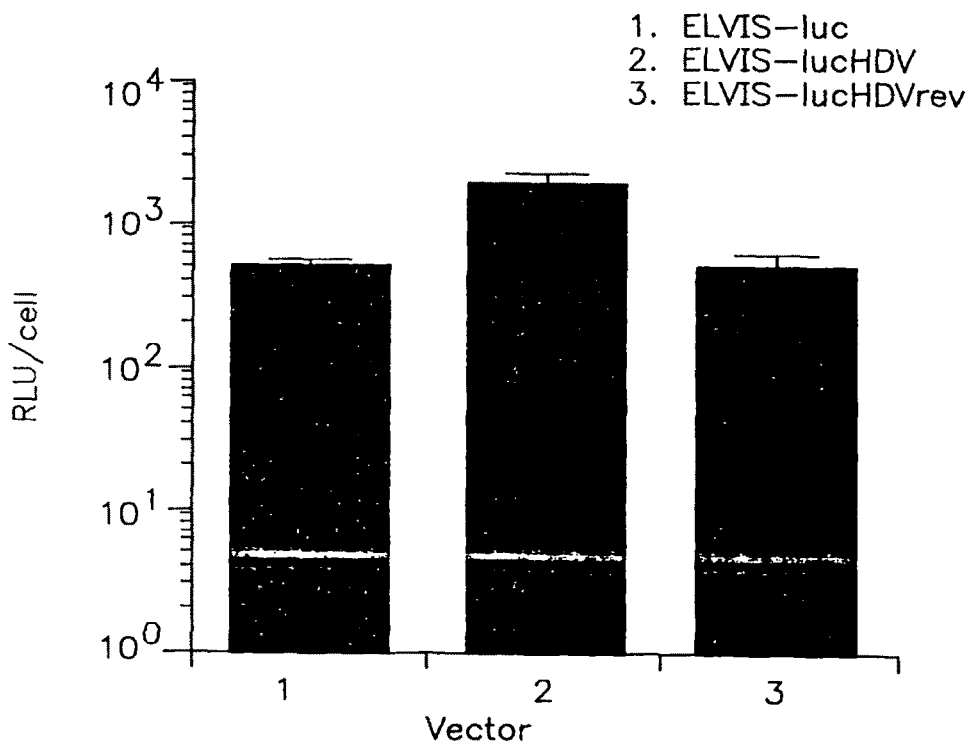

Additional experiments are performed to compare the relative expression activities of Sindbis RNA and DNA reporter vectors in transfected BHK cells (FIG. 22). Luciferase expression is approximately 30-fold higher in cells tranfected with in vitro transcribed SIN-luc RNA, compared to the level in cells transfected with ELVIS-luc plasmid DNA (FIG. 22A). The data also demonstrate that direct linkage between the Sindbis virus 3'-end and two different transcription termination/polyadenylation signals, resulting in deletion of the synthetic A25 tract, decreased the activity of the DNA vector by more than three orders of magnitude (FIG. 22A). However, measurable expression of luciferase is detected, suggesting that these 3' end modified Sindbis DNA vectors do function in transfected cells at some low level. Additionally, the insertion of a HDV ribozyme processing sequence, downstream of the $A_{25}$ tract, increases activity of the DNA vector 3-4 fold over the ELVIS-luc vector or an analogous construct with the HDV ribozyme inserted in a reverse orientation (FIG. 22B).

Figure 24:
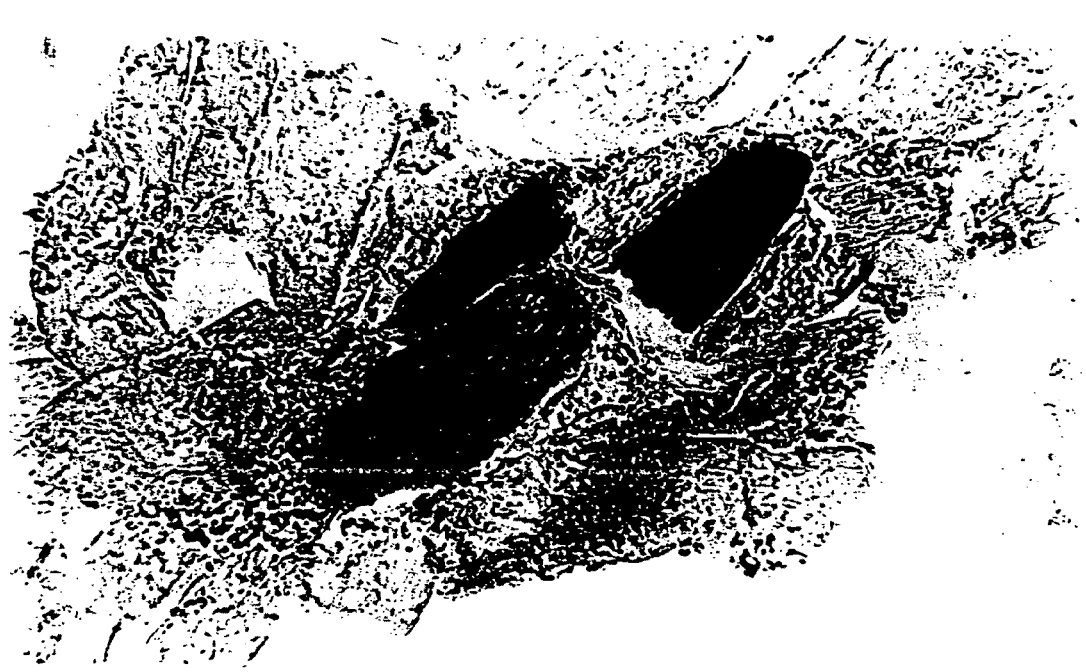
FIG. 24 depicts a photomicrograph of a ELVIS-β-gal injected rat muscle at three days post inoculation. A transverse cryosection from gastronemius muscle injected with 50 µg of ELVIS-β-gal contained in PBS is shown. Four blue stained transverse fibers are evident.

Based on the decreased expression levels observed when the synthetic A25 tract is deleted, additional constructs related to MpELVIS/S and MpELVIS/B are then made exactly as outlined in the above example utilizing the Sindbis sequences from the pKSSINBV and pKSSINBV-luc vectors to include the $A_{25}$ tract. These constructions are named as shown below:

MpLTRELVIS-luc/A/S
MpLTRELVIS-luc/A/B
MpLTRELVIS/A/S
MpLTRELVIS/A/B
MpCMVELVIS-luc/A/S
MpCMVELVIS-luc/A/B
MpCMVELVIS/A/S
MpCMVELVIS/A/B
MpSV40ELVIS-luc/A/S
MpSV40ELVIS-luc/A/B
MpSV40ELVIS/A/S
MpSV40ELVIS/A/B G. Reporter Gene Expression in Rodents Inoculated Intramuscularly with ELVIS Vectors Using techniques described above, the lacZ gene encoding the β-galactosidase reporter protein was cut from the plasmid pSV-β-galactosidase (PROMEGA CORP, Madison, Wis.) and substituted into the ELVIS-luc plasmid DNA vector in place of luciferase. To examine in vivo gene expression from ELVIS vectors, Balb/c mice and rats are injected intramuscularly (i.m.) with ELVIS-β-gal or ELVIS-luc plasmid DNA vectors. FIG. 24 demonstrates the in vivo expression of β-galactocidase in muscle tissue taken from a rat and stained with X-gal at three days post i.m. injection. Mice injected with ELVIS-β-gal also demonstrate positively staining blue muscle fibers. Luciferase expression levels from muscle which were between 75- and 300-fold higher than control levels were detected in ¾ Balb/c mice at two days post i.m. inoculation with ELVIS-luc plasmid. In other experiments, C3H/HeN mice were injected i.m. with ELVIS vectors expressing either the hepatitis B virus core (HBV-core) or hepatitis B virus e (HBV-e) proteins. Using ELISA detection systems, both HBV-core- and HBV-e-specific IgG antibodies were detected in serum samples collected from the mice 10 days following the second injection with the vectors. These experiments demonstrate that Sindbis-derived DNA vectors are able to express foreign genes in vivo, in rat and mouse muscle.

H. Adaptation of Alphavirus Expression Vectors

The following description details how to identify alphaviral vectors according to the invention adapted to grow in cells of a particular eukaryotic species. Specifically, adaptation of Sindbis virus variants adapted to grow in human cells is disclosed. As those in the art will appreciate, the following procedure can be employed to adapt other alphaviral vectors to particular eukaryotic species.

To adapt Sindbis viral vectors derived from BHK-21 cells to human cells, Sindbis viral vectors produced in accordance with this invention are propagated by serial passage in HT1080 (ATCC acc. no. CCL 121) and DM150 (a human cell line established from a primary melanoma tumor) cell lines in order to select variants which are able to establish high titer productive infections in human cells. Isolation of Sindbis variants adapted to human cells is accomplished by the following method: HT1080 and DM150 cells propogated in DMEM with 10% fetal calf serum (FCS) are infected at a multiplicity of infection of 5 with the virus contained in a small volume to facilitate infection. At one hour post infection, the inoculum is removed, the monolayer washed several times with DMEM, and the media replenished. The viral supernatant is harvested at 7 hours post infection, clarified by centrifugation, and divided into three aliquots. Two aliquots are frozen and the other aliquot is split and used to infect fresh HT1080 and DM150 monolayers. This process is repeated at least 10 times or as sufficient to generate variants which replicate efficiently in human cells. After each serial passage, plaque assays are performed in BHK cells or the homologous cell line in which the virus was propagated to determine an increase in virus titer in human cell lines. Sindbis variants adapted to human cells which contain the highest level of virus produced during serial HT1080 or DM150 cell line passage are then isolated from supernatants by three rounds of plaque purification. The phenotype of the plaque purified human variant is verified by determining its growth properties in human cell lines.

In an alternative approach, variants which are able to establish high titer productive infections in human cells are isolated by plaque morphology. Human cell lines, for example HT1080 and DM150, are infected at low multiplicity of infection with Sindbis virus grown in BHK-21 cells and overlaid with agar. At 24-30 hours post infection, large plaques, indicative of variants able to propagate efficiently in human cells, are picked. The variants are then purified by two additional serial rounds of plaque purification. The phenotype of candidate Sindbis variants can then be determined by comparing growth properties on human and BHK-21 cells with BHK-21 cell-propagated Sindbis virus.

Another similar approach enables the production of Sindbis variants which establish high titer persistent, i.e., noncytotoxic, infection of human cells. Specifically, human cells are infected with a Sindbis virus preparation containing a high percentage of defective interfering (DI) particles isolated by undiluted serial passage in HT1080 or DM150 cells. Cells which survive infection with this DI contaminated Sindbis stock are allowed to proliferate. Virus is isolated from the supernatant and purified by multiple rounds of plaque purification in BHK-21 or human cells. The desired phenotype of the Sindbis variant is verified by determining its ability to establish persistent noncytotoxic persistent infection in human cell lines.

Following identification of one or more Sindbis variants having the desired phenotype, purified viral RNA from the Sindbis variant is cloned and characterized in order to identify the nonstructural and structural genes and noncoding region changes which contribute to the observed phenotype. Sindbis variant genomic cDNA cloning is accomplished by RT-PCR, as detailed in Example 1 and the phenotype of the molecularly cloned virus strains is verified.

Viral genetic determinants can be mapped by identifying at what level Sindbis infection of human cells is inhibited, i.e., at the stage of adsorption, entry, replication, or assembly. The 5'-end, junction region, and nonstructural and noncoding region genetic determinants responsible for human variant phenotypes can be mapped by exchanging defined regions from pKSSINBV-luc, supra, with corresponding regions from the variant cDNA to produce various "test" SIN-luc vectors. After packaging by co-transfection, the level of luciferase expression in DM150, HT1080, and BHK cells infected with either pKSSINBV-luc or the "test" SIN-luc vector is compared. Exchanging defined regions between vectors may be accomplished by exploiting convenient restriction endonuclease recognition sites, for example (Viagene SIN-BV numbering): Afl II (4573), Age I (3172, 6922), Avr II (4281), Bgl II (2289), Bpu1102I (5602, 6266), BsaBI (2479) BstBI (4706, 6450), Eco47III (1407), Hpa I (6920), Mun I (42, 2785), Nru I (2324), Nsi I (2006, 6462), PflMI (4374), Sfi I (5122), and XhoI (7645). Precise nucleotide identification of genetic determinants resulting in the human variant phenotype can be accomplished by sequencing.

The 3'-end nonstructural and coding region genetic determinants responsible for the variant phenotype may be mapped by exchanging defined regions with the dl-BspEI cotransfection packaging vector. After packaging by co-transfection, the level of luciferase expression in DM150, HT1080, and BHK cells infected with pKSSINBV-luc packaged with the dl-BspEI cotransfection packaging vector or with the "test" dl-BspEI cotransfection packaging vector is compared. Exchanging defined regions between vectors may be accomplished by exploiting convenient restriction endonuclease recognition sites, for example (Viagene genomic Sindbis numbering): AatII (8000), Afl II (7969, 8836), AvaI (9414), BclI (9356), Bpu1102I (8911), BsiWI (10379), BspMII (7054), Bsu36I (8892), EcoNI (10048, 10923), EcoRI (9077), KasI (10036, 11308), NruI (8329), PflMI (9554), PmlI (8070), SalI (9589, 11085), SmaI (9416), SplI (10379), StuI (8572), and (9414). Precise nucleotide identification of genetic determinants resulting in the human variant phenotype can be accomplished by sequencing.

I. Recombinant Protein Expression

The eukaryotic layered vector initiation systems of the invention can be used to direct the expression of one or more recombinant proteins in transformed or transfected eukaryotic host cells. A representative example of a recombinant protein which may be expressed using a eukaryotic layered vector initiation system is insulin.

The gene encoding human insulin was identified in 1980 by Bell, et al. [*Nature*, vol. 284, pp. 26-32]. The entire coding region for human preproinsulin (hppi) can be cloned from a variety of sources, e.g., a human pancreatic cDNA library [Clontech, Palo Alto, Calif., catalog no. HL1163a] using standard PCR techniques. Primers for amplifying the coding region flank the 5' and 3' ends of the gene. The 5' primer includes an XhoI site and the 3' primer includes a NotI recognition sequence. After PCR amplification, the reaction products are purified using GENECLEAN™, followed by XhoI and NotI digestion. The DNA is then gel purified and ligated into XhoI/NotI cleaved, CIAP-treated pVGELVIS-SINBV, infra, to make pELVS-hppi.

Alternatively, the hppI amplicon is inserted into Xho I/Not I cleaved, CIAP-treated SIN-BV, infra, to make pSIN-BV-hppI. RNA from Sac I-linearized pSIN-BV-hppI plasmid is synthesized in vitro as described in Example 3. Production of SIN-BV-hppI recombinant vector particles is accomplished by transfection of LIPOFECTIN™-complex SIN-BV-hppI RNA into the Sindbis vector packaging cell lines as described in Example 7. Generation of vector particles having expression vectors derived from Sindbis variants which establish high titer persistent noncytotoxic infection of human cells is accomplished by the same procedure.

pELVS-hppi is then introduced (e.g., by electroporation or by complexing with lipofectamine) into a suitable eukaryotic host cell, preferably an undifferentiated cell, for instance, F9 cells, infra. The transformed cells are then grown in the presence of G418 under suitable nutrient conditions (i.e., an appropriate medium, such as DMEM, including any required supplements, at 37° C.). The cells can be grown in a variety of formats, including in roller bottles, cell hotels, and bioreactors. Recombinant protein production is initiated by adding retinoic acid or another suitable inducing agent to the medium. At 12 to 48 hours post-vector induction, the optimal level of insulin is expressed into the medium and is recovered according to techniques known in the art. The insulin is recovered from the cell supernatants up to 18 hrs from the time in which the vector establishes a cytotoxic infection. Recovery of insulin from cells infected with expression vectors derived from Sindbis human cell variants may be harvested over a period extending to 3-5 days post induction. Insulin so produced is recovered according to techniques known in the art. The isolated recombinant protein may then be formulated in any of a number of pharmaceutical compositions suitable for human administration.

J. Lyophilized Eukaryotic Layered Vector Initiation System Vaccines

One aspect of the invention concerns the use of eukaryotic layered vector initiation systems according to the invention as vaccines to immunize a human patient's or non-human animal's immune system against a particular disease. Such vaccines can be employed either prophylatically or therapeutically to prevent or treat disease. Diseases which may be treated with such vaccines include those caused by various pathogenic agents, such as procaryotic or eukaryotic microorganisms or viruses, or cancer.

For example, each of the vector constructs described herein and containing the heterologous sequence of a suitable antigen is readily lyophilized for long term stability. Upon rehydration in an appropriate diluent, administration is performed and subsequent expression occurs. Additional alphavirus vector constructs not disclosed in the present invention, including those described in the literature (see Hahn et al., *Proc Natl Acad Sci USA* 89: 2679-2683, 1992) are readily convertible to a eukaryotic layered vector initiation system format by those skilled in the art and using the knowledge provided herein. Conversion of transient alphavirus vector systems to the format of a eukaryotic layered vector initiation system thus modify the duration of heterologous sequence expression to that of a more permanent and stable expression system. Advantages of this permanent and stable system include longer term expression, allowing greater prophylatic and therapeutic effects in both medical and veterinary applications.

K. Eukaryotic Layered Vector Initiation Systems for Plant Applications

Given the disclosures provided herein, the adaptation of eukaryotic vector initiation system technologies to plant application is readily performed by those skilled in the art. For illustration purposes, any of several positive-stranded plant viruses (for example, potato virus X (PVX, Huisman et al., *J. Gen. Virol.* 69:1789-1798, 1988), tobacco mosaic virus (TMV, Goelet et al., *Proc. Natl. Acad. Sci. USA* 79:5818-5822, 1982), and tobacco etch virus (TEV, Allison et al., *Virology* 154:9-20, 1986), see also, specifications) may be converted to a cDNA form using PCR and specific oligonucleotide primers, chosen from published sequences, as described in Example 1. After assembly of a full-length genomic clone linked to a bacteriophage RNA polymerase promoter, and determination of infectivity of in vitro synthesized transcripts, the cDNA is exchanged into a vector containing an RNA polymerase II promoter and transcription termination/polyadenylation sequence, as described in Example 2. For plant applications, such promoter and termination sequences are chosen from the appropriate plant systems (e.g., CaMV $^{35}$S promoter (Guilley et al., *Cell* 30:763-773, 1982), and nopaline synthase promoter and transcription termination sequence (Sanders et al., *Nucleic Acids Res.* 15:1543-1558). Vector constructs derived from these infectious genomic cDNA clones is subsequently accomplished using any of the approaches described in the present invention (e.g., use of subgenomic promoters, replacement of structural protein genes, use of IRES sequences). Specific applications of such plant eukaryotic layered vector initiation systems may include, but are not limited to, the expression of host-derived resistance sequences, pathogen-derived resistance sequences (e.g., protein-encoding, nonprotein-encoding, and defective interfering sequences), and growth promoting sequences, by the creation of transgenic plants harboring such systems.

L. Transgenic Animal Applications

In accordance with the non-parenteral administration the present invention, the gene delivery vehicles, particularly those comprised of unencapsidated nucleic acid, may be complexed with a polycationic molecule to provide polycation-assisted non-parenteral administration. Such a method of gene delivery facilitates delivery of a gene via mediation by a physical particle comprised of multiple components that augment the efficiency and specificity of the gene transfer. In particular, polycationic molecules, such as polylysine and histone, have been shown to neutralize the negative charges on a nucleic acid molecule and to condense the molecule into a compact form. This form of molecule is transferred with high efficiency in cells, apparently through the endocytic pathway. The uptake in expression of the nucleic acid molecule in the host cell results after a series of steps, as follows: (1) attachment to cell surface; (2) cell entry via endocytosis or other mechanisms; (3) cytoplasmic compartment entry following endosome release; (4) nuclear transport; and (5) expression of the nucleic acid molecule carried by the gene delivery vehicle. In a further preferred embodiment, multilayer technologies are applied to the polycation-nucleic acid molecule complex to facilitate completion of one or more of these steps. For example, a ligand such as asialoglycoprotein, transferrin, and immunoglobulin may be added to the complex to facilitate binding of the cell complex to the cell surface, an endosomal disruption component (e.g., a viral protein, a fusogenic peptide such as the n-terminus of the influenza virus hemaglutinin or an inactivated virus) is added to facilitate the release of DNA from the endosome, or a nuclear protein (or a peptide containing a nuclear localization signal) is added to facilitate the transport of the DNA into the nucleus. In a further preferred embodiment, the composition comprising the complex includes inactivated adenovirus particles (Curiel, D. T., et al., *PNAS* 88: 8850-8854, 1991; Cristiano, R. J., *PNAS* 90: 2122-2126 1993; Cotten, M., et al., *PNAS* 89: 60946098 1992; Lozier, J. N., et al., *Human Gene Therapy* 5: 313-322, 1994; Curiel, D. T., et al., *Human Gene Therapy* 3: 147-154, 1992; Plank, C. et al., *Bioconjugate Chem.* 3: 533-539, 1992; Wagner, E. et al., *PNAS* 88: 4255-4259, 1991). The assorted components comprising the multilayer complex may be varied as desired, so that the specificity of the complex for a given tissue, or the gene expressed from the gene delivery vehicle, may be varied to better suit a particular disease or condition.

As noted above, various methods may be utilized to administer gene delivery vehicles of the present invention, including nucleic acids which encode the immunogenic portion(s) discussed above, to warm-blooded animals such as humans, directly. Suitable methods include, for example, various physical methods such as direct DNA injection (Acsadi et al., *Nature* 352:815-818, 1991), and microprojectile bombardment (Williams et al., *PNAS* 88:2726-2730, 1991).

Within an in vivo context, the gene delivery vehicle can be injected into the interstitial space of tissues including muscle, brain, liver, skin, spleen or blood (see, WO 90/11092). Administration may also be accomplished by intravenous injection or direct catheter infusion into the cavities of the body (see, WO 93/00051), discussed in more detail below.

It is generally preferred that administration of the gene delivery vehicles at multiple sites be via at least two injections. In this regard, suitable modes of administration include intramuscular, intradermal and subcutaneous injections with at least one of the injections preferably being intramuscular. In particularly preferred embodiments, two or more of the injections are intramuscular. However, although administration via injections is preferred, it will be evident that the gene delivery vehicles may be administered through multiple topical or separate ocular administrations. Further, a number of additional routes are suitable for use within the present invention when combined with one or more of the routes noted above, including intraperitoneal, intracranial, oral, rectal, nasal, vaginal and sublingual administration. Methods of formulating and administering the gene delivery vehicles at multiple sites through such routes would be evident to those skilled in the art and are described in U.S. Ser. No. 08/366,788, filed Dec. 30, 1994 and U.S. Ser. No. 08/367,071, filed Dec. 30, 1994, incorporated herein by reference in their entireties.

M. Veterinary Applications

From the description provided herein, those skilled in the art will appreciate that the alphavirus vector constructs, recombinant alphavirus particles, and eukaryotic layered vector initiation systems provided by the present invention can also be readily utilized in non-human animal (e.g., veterinary) applications. Such applications may include prophylactics (e.g., vaccines), immunotherapeutics, and palliatives. Within such aspects, compositions and methods are provided for administering an alphavirus vector construct, recombinant alphavirus particle, or eukaryotic layered vector initiation system which is capable of preventing, inhibiting, stabilizing or reversing infectious diseases in non-human animals.

Specifically, within one aspect of the present invention, compositions and methods are provided for stimulating an immune response (either humoral or cell-mediated) to a pathogenic agent, such that the pathogenic agent is either killed or inhibited. Representative examples of pathogenic agents of veterinary importance include bacteria, fungi, parasites and viruses.

More specifically, sequences which encode immunoreactive polypeptides of the pathogenic agents may, in certain embodiments, be chosen from a group that includes the Bunyaviridae (e.g., Rift Valley Fever virus (Giorgi et al., *Virology* 180:738-753, 1991; Collett et al., *Virology* 144:228-245, 1985)), Paramyxoviridae (e.g., Newcastle disease virus (Millar et al., *J. Gen. Virol.* 69:613-620, 1988; Chambers et al., *Nucl. Acid. Res.* 14:9051-9061, 1986; Schaper et al., *Virology* 165:291-295, 1988), and canine distemper virus (Curran et al., *J. Gen. Virol.* 72:443-447, 1991; Barrett et al., *Virus Res.* 8:373-386, 1987; Bellini et al., *J. Virol.* 58:408-416, 1986)), Togaviridae (e.g., WEE virus (Weaver et al., *Virology* 197:375-390, 1993), EEE virus (Chang et al., *J. Gen. Virol.* 68:2129-2142, 1987), and VEE virus (Kinney et al., *Virology* 152:400-413, 1986)), Rhabdoviridae (e.g., vesicular stomatitis virus (Gill et al., *Virology* 150:308-312, 1986; Gallione et al., *J. Virol.* 46:162-169, 1983; Banerjee et al., *Virology* 137:432-438, 1984), and rabies virus (Tordo et al., *Nucl. Acid. Res.* 14:2671-2683, 1986; Hiramatsu et al., *Virus Genes* 7:83-88, 1993; Kieny et al., *Nature* 312:163-166, 1984)), Coronaviridae (e.g., transmissable gastroenteritis virus (Britton et al., *Molec. Micro.* 2:89-99, 1988; Godet et al., *Virology* 188:166-175, 1992; Jackwood et al., *Adv. Exp. Med. and Biol.* 342:43-48, 1993), and feline infectious peritonitis virus (Reed et al., *Adv. Exp. Med. and Biol.* 342:17-21, 1993)), Reoviridae (e.g., porcine rotavirus (Burke et al., *J. Gen. Virol.* 75:2205-2212, 1994; Nishikawa et al., *Nucl. Acid. Res.* 16:11847, 1988)), Orthomyxoviridae (e.g. equine influenza (Gibson et al., *Virus Res.* 22:93-106, 1992; Dale et al., *Virology* 155:460-468, 1986)), Picornaviridae (e.g., FMD virus (Graham et al., *Virology* 176:524-530, 1990; Brown et al., *Gene* 75:225-233, 1989; Fross et al., *Nucl. Acid. Res.* 12:6587-6601, 1984)), and Herpesviridae (e.g., equine herpesvirus (Crabb et al., *J. Gen. Virol.* 72:2075-2082)).

In other embodiments, the sequences which encode immunoreactive polypeptides of the pathogenic agents may be chosen from a group that includes the agents of coccidiosis (e.g., *Eimeria Acervulina, E. tenella, E. maxima* (Talebi et al., *Infect. Immun.* 62:4202-4207, 1994; Pasamotites et al., *Mol. Biochem. Parasit.* 57:171-174, 1993; Tomley et al., *Mol. Biochem. Parasit.* 49:277-288, 1991; Castle et al., *J. of Parasit.* 77:384-390, 1991; Jenkins et al., *Exp. Parasit.* 70:353-362, 1990)), anaplasmosis (e.g., *Anaplasma marginale* (McGuire et al., *Vaccine* 12:465-471, 1994; Palmer et al., *Infect. Immun.* 62:3808-3816, 1994; Oberle et al., *Gene* 136:291-294, 1993; Barbet et al., *Infect. Immun.* 59:971-976, 1991; Barbet et al., *Infect. Immun.* 55:2428-2435; 1987)), babesiosis (e.g., *Babesia bovis* (Suarez et al., *Infect. Immun.* 61:3511-3517, 1993; Hines et al., *Mol. Biochem. Parasit.* 55:85-94, 1992; Jamer et al., *Mol. Biochem. Parasit.* 55:75-83, 1992; Suarez et al., *Mol. Biochem. Parasit.* 46:45-52, 1991)), theileriosis (e.g. *Theileria parva* (Nene et al., *Mol. Biochem. Parasit.* 51:17-27, 1992; Iams et al., *Mol. Biochem. Parasit.* 39:47-60, 1990)), malaria (e.g. *Plasmodium falciparum* (Haeseleer et al., *Mol. Biochem. Parasit.* 57:117-126, 1993)), salmonellosis (*Salmonella typhimurium* and *S. dublin*), bovine and ovine mastitis (*Staphylococcus aureus*), bovine tuberculosis (*Mycobacterium bovis*), pseudotuberculosis (*Yersinia pseudotuberculosis*), coccidioidomycosis (*Coccidioides immitis*), cryptococcosis (*Cryptococcus neoformans*), anthrax (*Bacillus anthracis*), brucellosis (*Brucella abortus* and *B. suis*), and leptospirosis (*Leptospira interrogans* and *L. biflexa*).

To illustrate this aspect in more detail, methods used in constructing recombinant alphavirus vectors and eukaryotic layered vector initiation systems containing these sequences for veterinary application are described for two of the above pathogenic agents (one viral and one parasitic). The construction of additional alphavirus vectors and eukaryotic; layered vector initiation systems is readily accomplished by those skilled in the art, based on the following methodologies and using sequences from other related or non-related pathogenic agents. In the case of foot-and-mouth disease virus (FMDV), a cassette comprising each of the four P1 capsid proteins (1A, 1B, 1C, 1D) and the 3C protease responsible for their post-translational cleavage is obtained as plasmids MR1 or MR2 from Graham et al. (Virology 176:524-530, 1990). Plasmid MR1 or MR2 is digested with the enzymes HindIII and DraI to remove the FMDV P1 cassette, followed by fill-in of the HindIII terminus with Klenow, and purification from a 1% agarose gel using GENECLEAN™. Plasmid vectors pKSSINBV and pVGELVIS-SINBV (see Example 3) are digested with XhoI and the termini also made blunt using Klenow, followed by treatment with CIAP and purification from a 1% agarose gel using GENECLEAN™. The purified fragments are subsequently ligated to generate the alphavirus vector construct pKSSIN-FMDV and eukaryotic layered vector initiation system plasmid pVGELVIS-FMDV. The purified FMDV sequences are also readily inserted into any of the other vector constructs described in this invention (see Example 3). Packaging of the FMDV-containing alphavirus vector construct pKSSIN-FMDV can be accomplished as described in Example 7.

For construction of a recombinant alphavirus vector construct or eukaryotic layered vector initiation system comprising sequences from a pathogenic agent of anaplasmosis, the major surface protein 2 (MSP-2) of *A. marginale* is obtained by PCR amplification from plasmid pCKR11.2 (Palmer et al., *Infect. Immun.* 62:3808-3816, 1994) using the following oligonucleotide pair, each containing a flanking XhoI site:

```
forward primer (AM-MSP-2F):
                                 (SEQ. ID NO. 115)
5'-TATATCTCGAGACCACCATGAGTGCTGTAAGTAATAGGAAGC reverse primer (AM-MSP-2R):
                                 (SEQ. ID NO. 116)
5'-TATATCTCGAGCTAGAAGGCAAACCTAACACCCAAC
```

A standard three temperature cycling protocol is performed as described previously using THERMALASE™ thermostable polymerase, the oligonucleotide pair, and plasmid pCKR11.2 as template. Following amplification, the MSP-2 amplicon is purified using GENECLEAN™, digested with XhoI, and re-purified with GENECLEAN™. Plasmid vectors pKSSINBV and pVGELVIS-SINBV (see Example 3) also are digested with XhoI, followed by treatment with CIAP and subsequent ligation to the MSP-2 fragment to generate the alphavirus vector construct pKSSIN-MSP2 and eukaryotic layered vector initiation system plasmid pVGELVIS-MSP2. The purified MSP-2 sequences are also readily inserted into any of the other vector constructs described elsewhere in this specification (e.g., Example 3). Packaging of the MSP-2-containing alphavirus vector construct pKSSIN-MSP2 can be accomplished as described in Example 7.

Example 4

A. Insertion of Adenovirus Early Region E3 Gene into Sindbis Vectors

In order to inhibit the host CTL response directed against viral specific proteins expressed in vector infected cells, in applications where repeated administration of the therapeutic is desired, the Adenovirus type 2 (Ad 2) E3/19K gene ATCC No. VR-846 is cloned into the pKSSINdlJRsjrc plasmid, immediately downstream from the junction region core. Briefly, Ad 2 is propagated in a permissive cell line, for example HeLa or Vero cells, and after evidence of cytopathologic effects, virions are purified from the cell lysate, and the Ad 2 DNA is purified from the virus.

The Ad 2 DNA E3/19K gene, including the amino terminal signal sequence, followed by the intraluminal domain and carboxy terminal cytoplasmic tail which allows the E3 19K protein to embed itself in the endoplasmic reticulum, is located between viral nucleotides 28,812 and 29,288. Isolation of the Ad 2 E3 19K gene from the viral genomic DNA is accomplished by PCR amplification, with the primer pair shown below:

```
Ad 2 E3 Forward primer (Ad 2 nucleotides
28,812-28,835):
                                 (SEQ. ID NO. 56)
5'-TAT ATC TCC AGA TGA GGT ACA TGA TTT TAG GCT
TG-3'

Ad 2 E3 Reverse primer (Ad 2 nucleotides
29,241-29,213):
                                 (SEQ. ID NO. 57)
5'-TAT ATA TCG ATT CAA GGC ATT TTC TTT TCA TCA ATA
AAA C
```

In addition to the Ad 2 complementary sequences, both primers contain a five nucleotide 'buffer sequence' at their 5' ends for efficient enzyme digestion of the PCR amplicon products. This sequence in the forward primer is followed by the Xho I recognition site, and in the reverse primer this sequence is followed by the Cla I recognition site. Thus, in the 5' to 3' direction, the E3/19K gene is flanked by Xho I and Cla I recognition sites. Amplification of the E3/19K gene from Ad 2 DNA is accomplished with the following PCR cycle protocol:

| Temperature (° C.) | Time (Min.) | No. Cycles |
| --- | --- | --- |
| 94 | 2 | 1 |
| 94 | 0.5 | |
| 55 | 0.17 | 5 |
| 72 | 3.5 | |
| 94 | 0.5 | 30 |
| 70 | 3.5 | |
| 72 | 10 | 10 |

Following amplification, the 451 by amplicon is purified on a 1.5% agarose gel, and digested with the Xho I and Cla I enzymes. pKSSINdlJRsjrc plasmid is partially digested with ClaI. Plasmid that has been digested only once is isolated by gel electrophoresis then digested with XhoI. The large fragment is isolated by gel electrophoresis and ligated to the digested PCR amplicon. This clone is designated pKSSINdl-JRsjrcAdE3. Using the same cloning strategy, the Ad 2 E3/19K gene may be inserted into any of the modified synthetic junction region vectors or ELVIS vectors described in Example 3.

B. Insertion of the Human Cytomegalovirus H301 Gene into Sindbis Vectors

In order to inhibit the host CTL directed response against viral specific proteins expressed in vector infected cells in applications where repeated administration of the therapeutic is desired, the human cytomegalovirus (HCMV) H301 gene is cloned into the pKSSINdlJRsjrc plasmid, immediately downstream from the junction region core.

Briefly, HCMV strain AD169 (ATCC No. VR-538), is propagated in a permissive cell line, for example primary human foreskin fibroblasts (HFF) (GIBCO/BRL, Gaithersburg, Md.), and after evidence of cytopathologic effects, virions are purified from the cell lysate. Subsequently, HCMV DNA is purified from the virons.

The HCMV H301 gene is located between viral nucleotides 23,637 and 24,742. Isolation of the HCMV H301 gene from the viral genomic DNA is accomplished by PCR amplification, with the primer pair shown below:

HCMV H301 Forward primer (buffer sequence/Xho I
site/HCMV nucleotides 23,637-23,660):
                                     (SEQ. ID NO. 58)
5'-TAT ATC TCC AGA TGA TGA CAA TGT GGT GTC TGA
CG-3'

HCMV H301 Reverse primer (buffer sequence/Cla I
site/HCMV nucleotides 24,744-24,722):
                                     (SEQ. ID NO. 59)
5'-TAT ATA TCG ATT CAT GAC GAC CGG ACC TTG CG-3'

In addition to the HCMV H301 gene complementary sequences, both primers contain a five nucleotide 'buffer sequence' at their 5' ends for efficient enzyme digestion of the PCR amplicon products. This sequence in the forward primer is followed by the Xho I recognition site, and in the reverse primer this sequence is followed by the Cla I recognition site. Thus, in the 5' to 3' direction, the HCMV H301 gene is flanked by Xho I and Cla I recognition sites. Amplification of the HCMV 11301 gene from HCMV DNA is accomplished with the following PCR cycle protocol:

| Temperature (° C.) | Time (Min.) | No. Cycles |
|---|---|---|
| 94 | 2 | 1 |
| 94 | 0.5 | |
| 55 | 0.17 | 5 |
| 72 | 3.5 | |
| 94 | 0.5 | 30 |
| 70 | 3.5 | |
| 72 | 10 | 10 |

Following amplification, the 1,129 by amplicon product is purified on a 1.0% agarose gel, and subsequently digested with the Xho I and Cla I enzymes and ligated into the CIAP treated pKSSINdlJRsjrc plasmid, previously digested with Xho I and Cla I as described above. This clone is designated pKSSINdlJRsjrCH301. Using the same cloning strategy, the HCMV H301 gene is inserted into all of the modified synthetic junction region vectors and all of the ELVIS vectors described in Example 3.

Example 5
Expression of Multiple Heterologous Genes from Sindbis Vectors

The plasmid pBS-ECAT (Jang et al., *J. Virol* 63:1651, 1989) includes the 5' nontranslated region of Encephalomyocarditis virus (EMCV) from nts 260-848 of the viral genome, which contains the internal ribosome entry site (IRES). EMCV nucleotides 260-827 are amplified from pBS-ECAT by PCR, using the following primer pain EMCV IRES Forward primer A (For insertion next to
disabled junction region in vector pKSSINBVdlJR at
Apa I site):
                                     (SEQ. ID NO. 60)
5'-TAT ATG GGC CCC CCC CCC CCC AAC G-3'

EMCV IRES Forward primer B (For insertion between
heterologous genes terminating with Cla I sites
and initiating with Nco I sites):
                                     (SEQ. ID NO. 61)
5'-TAT ATA TCG ATC CCC CCC CCC CCA ACG-3'

EMCV IRES Reverse Primer (To be used with either
primers A or B):
                                     (SEQ. ID NO. 62)
5'-TAT ATC CAT GGC TTA CAA TCG TGG TTT TCA AAG
G-3'

The amplicon resulting from amplification with the forward primer A and the reverse primer is flanked by Apa I and Nco I recognition sites, inside a 5 by 'buffer sequence'.

The amplicon resulting from amplification with the forward primer B and the reverse primer is flanked by Cla I and Nco I recognition sites, inside a 5 by 'buffer sequence'.

Amplification of the EMCV IRES sequence from the pBS-ECAT plasmid is accomplished with the following PCR cycle protocol:

| Temperature (° C.) | Time (Min.) | No. Cycles |
|---|---|---|
| 94 | 2 | 1 |
| 94 | 0.5 | |
| 55 | 0.17 | 5 |
| 72 | 3.5 | |
| 94 | 0.5 | 30 |
| 70 | 3.5 | |
| 72 | 10 | 1 |

In a similar manner, the ATG corresponding to the start codon of the heterologous gene to be inserted immediately downstream of the EMCV IRES insert is modified to contain an NcoI site (CCATGG) while the 3' end is modified to contain a ClaI site.

For insertion into the pKSSINBVdlJR vector, the 589 by ECMV-IRES amplicon is digested with ApaI and NcoI, purified on a 1% agarose gel. The heterologous gene amplicon is digested with NcoI and ClaI and purified in a similar manner. Both fragments are ligated into the CIAP treated vector digested with Apa I and ClaI as described in example 4.

For insertion into the pKSSINBV or pKSSINBVdlJRsjrc vectors between heterologous genes, the 589 by amplicon is digested with Cla I and Nco I, purified on a 1% agarose gel, and ligated into the bicistronic heterologous gene vector digested with Cla I and Nco I and treated with CIAP. In a bicistronic heterologous gene configuration, the 3' end of the upstream heterologous gene is modified to terminate in a Cla I recognition site. The ATG corresponding to the start codon of the second downstream heterologous gene to be inserted immediately downstream of the EMCV IRES insert is modified to contain an Nco I site (CCATGG). Thus, from 5' to 3', the order of components is: pKSSINBV or pKSSINBVdlJRsjrc-gene #1-Cla/Nco EMCV IRES gene #2-3' SIN. Insertion into all of the modified junction region vectors described in Example 2 and all of the ELVIS vectors described in Example 3 follows the strategy given here for the pKSSINBV or pKSSINBVdlJRsjrc vectors.

The pKSSINBVdlJR vector containing a bicistronic heterologous configuration is constructed with each of the EMCV IRES amplicons described above. The first EMCV IRES amplicon is flanked by Apa I and Nco I sites and is inserted immediately downstream of the disabled junction region at the Apa I site, as described above. This EMCV IRES sequence is followed by the first heterologous gene, which terminates in a Cla I recognition site. The first heterologous gene is followed by the second EMCV IRES sequence, using the amplicon flanked by Cla I and Nco I recognition sites. The second heterologous gene follows the second EMCV IRES sequence. Thus, from 5' to 3', the order of components is: SINBVdlJR-Apa/Nco EMCV IRES gene #1-Cla/Nco EMCV IRES gene #2-3' SIN.

The plasmid pP2-5' (Pelletier et al., *Mol. Cell. Biol.* 8:1103, 1988) includes the 5' nontranslated region of the poliovirus P2/Lansing strain from nucleotides 1-1,872 of the viral genome, which contains the polio IRES. Poliovirus nucleotides 320-631 are amplified from pP2-5' by PCR, using the following primer pair.

```
Polio IRES Forward primer A (For insertion next to
disabled junction region in vector pKSSINBVdlJR
at Apa I site):
                                    (SEQ. ID NO. 63)
5'-TAT ATG GGC CCT CGA TGA GTC TGG ACG TTC CTC-3'

Polio IRES Forward primer B (For insertion between
heterologous genes terminating with Cla I sites
and initiating with Nco I sites):
                                    (SEQ. ID NO. 64)
5'-TAT ATA TCG ATT CGA TGA GTC TGG ACG TTC CTC-3'

Polio IRES Reverse Primer (To be used with either
primers A or B):
                                    (SEQ. ID NO. 65)
5'-TAT ATC CAT GGA TCC AAT TTG CTT TAT GAT AAC AAT
C-3'
```

The amplicon resulting from PCR with the Polio IRES forward primer A/reverse primer pair shown above is flanked by Apa I and Nco I recognition sites, inside a 5 by 'buffer sequence'. The amplicon resulting from PCR with the Polio IRES forward primer B/reverse primer pair is shown above is flanked by Cla I and Nco I recognition sites, inside a 5 by 'buffer sequence'. Amplification of the polio IRES sequence from the pP2-5' plasmid is accomplished with the PCR protocol shown in Example 5. In a similar manner, the ATG corresponding to the start codon of the heterologous gene to be inserted immediately downstream of the Polio IRES insert is modified to contain an NcoI site (CCATGG) while the 3' end is modified to contain a ClaI site.

For insertion into the pKSSINBVdlJR vector, the 333 by Polio-IRES amplicon is digested with Apa I and Nco I and purified on a 1.5% agarose gel. The heterologous gene amplicon is digested with NcoI and ClaI and purified in a similar manner. Both fragments are ligated into the CIAP treated vector digested with Apa I and ClaI as described in example 4.

For insertion into the pKSSINBV or pKSSINBVdlJRsjrc vectors between heterologous genes, the 333 by amplicon is digested with Cla I and Nco I, purified on a 1.5% agarose gel, and ligated into the bicistronic heterologous gene vector digested with Cla I and Nco I and treated with CIAP. In a biscistronic heterologous gene configuration, the 3' end of the upstream heterologous gene is modified to terminate in a Cla I recognition site. The ATG corresponding to the start codon of the second downstream heterologous gene to be inserted immediately downstream of the polio IRES insert is modified to contain an Nco I site (CCATGG). Thus, from 5' to 3', the order of components is: pKSSINBV or pKSSINBVdlJRsjrc-gene #1-Cla/Nco polio IRES gene #2-3' SIN. Insertion into all of the modified junction region vectors and all of the ELVIS vectors described in Example 3 follows the strategy given here for the pKSSINBV or pKSSINBVdlJRsjrc vectors.

The pKSSINBVdlJR vector containing a bicistronic heterologous configuration is constructed with each of the polio IRES amplicons described above. The first polio IRES amplicon is flanked by Apa I and Nco I sites and is inserted immediately downstream of the disabled junction region at the Apa I site, as described above. This polio IRES sequence is followed by the first heterologous gene, which terminates in a Cla I recognition site. The first heterologous gene is followed by the second polio IRES sequence, using the amplicon flanked by Cla I and Nco I recognition sites. The second heterologous gene follows the second polio IRES sequence. Thus, from 5' to 3', the order of components is: SINBVdlJR Apa/Nco polio IRES gene #1-Cla/Nco EMCV IRES gene #2-3' SIN.

The 220 by BiP cDNA, corresponding to the 5' leader region of the human immunoglobulin heavy-chain binding protein mRNA, is amplified from a plasmid containing the 5' noncoding region of the BiP gene, pGEM5ZBiP5' (provided by P. Sarnow, University of Colorado Health Sciences Center), using PCR. The sequence corresponding to BiP cDNA was determined originally in the bacteriophage lambda hu28-1 clone of the human GRP78 gene (Ting and Lee, *DNA* 7:275-286, 1988). The forward primer to be used in the PCR reaction varies, depending on the Sindbis vector into which the BiP cDNA is inserted. The reverse primer for the PCR reaction is the same for all Sindbis vectors. Amplification of the BiP cDNA sequence from pGEM5ZBiP5' from the plasmid for insertion into the Sindbis vector pKSSINBVdlJR, immediately downstream of the disabled junction region, is accomplished by amplification with the following forward primer:

```
                                    (SEQ. ID NO. 66)
5'-TAT ATG GGC CCG GTC GAC GCC GGC CAA GAC-3'
```

In addition to the BiP cDNA complementary sequences, beginning at nucleotide 12, the primer contains a five nucleotide 'buffer sequence' at its 5' end for efficient enzyme digestion of the PCR amplicon products. This sequence is followed by the Apa I recognition site.

Amplification of the BiP cDNA sequence from the pGEM5ZBiP5' plasmid for insertion into the Sindbis vectors pKSSINBV, or pKSSINBVdlJRsjrc, is accomplished by amplification with the following forward primer shown below. For these vectors, the BiP cDNA is inserted between two heterologous genes, which are placed in the region corresponding to the Sindbis structural genes.

```
                                    (SEQ. ID NO. 67)
5'-TAT ATA TCG ATG GTC GAC GCC GGC CAA GAC-3'
```

In addition to the BiP cDNA complementary sequences, beginning at nucleotide 12, the primer contains a five nucleotide 'buffer sequence' at its 5' end for efficient enzyme digestion of the PCR amplicon products. This sequence is followed by the Cla I recognition site.

The reverse primer for amplification of the BiP cDNA sequence from the pGEM5ZBiP5' plasmid for insertion into the Sindbis vectors pKSSINBVdlJR, pKSSINBV, or pKSSINBVdlJRsjrc, is:

```
                                    (SEQ. ID NO. 68)
5'-TAT ATC CAT GGT GCC AGC CAG TTG GGC AGC AG-3'
```

In addition to the BiP cDNA complementary sequences, beginning at nucleotide 12, the reverse primer contains a five nucleotide 'buffer sequence' at its 5' end for efficient enzyme digestion of the PCR amplicon products. This sequence is followed by the Nco I recognition site. Amplification of the BiP cDNA from the pGEM5ZBiP5' is accomplished with PCR protocol that are described above. In a similar manner, the ATG corresponding to the start codon of the heterologous gene to be inserted immediately downstream of the BiP IRES insert is modified to contain an NcoI site (CCATGG) while the 3' end is modified to contain a ClaI site.

For insertion into the pKSSINBVdlJR vector, the 242 by BiP IRES amplicon is digested with Apa I and Nco I and purified on a 2% agarose gel The heterologous gene amplicon is digested with NcoI and ClaI and purified in a similar manner. Both fragments are ligated into the CIAP treated vector digested with Apa I and ClaI as described in example 4.

For insertion into the pKSSINBV or pKSSINBVdlJRsjrc vectors between heterologous genes, the 242 by BiP IRES amplicon is digested with Cla I and Nco I, purified on a 2% agarose gel, and ligated into the bicistronic heterologous gene vector digested with Cla I and Nco I and treated with CIAP. In a biscistronic heterologous gene configuration, the 3' end of the upstream heterologous gene is modified to terminate in a Cla recognition site. The ATG corresponding to the start codon of the second downstream heterologous gene to be inserted immediately downstream of the BiP cDNA insert is modified to contain an Nco I site (CCATGG). Thus, from 5' to 3', the order of components is: pKSSINBV or pKSSINBVdl-JRsjrc-gene #1-Cla/Nco BiP-gene #2-3' SIN. Insertion into all of the modified junction region vectors described in Example 2, and into all of the ELVIS vectors described in example 3, follows the strategy given here for the pKSSINBV or pKSSINBVdlJRsjrc vectors.

The pKSSINBVdlJR vector containing a bicistronic heterologous configuration is constructed with each of the BiP cDNA amplicons described above. The first BiP cDNA amplicon is flanked by Apa I and Nco I sites and is inserted immediately downstream of the disabled junction region at the Apa I site, as described above. This BiP sequence is followed by the first heterologous gene, which terminates in a Cla I recognition site. The first heterologous gene is followed by the second BiP cDNA sequence, using the amplicon flanked by Cla I and Nco I recognition sites. The second heterologous gene follows the second BiP sequence. Thus, from 5' to 3', the order of components is: SINBVdlJR-Apa/Nco BiP-gene #1-Cla/Nco BiP-gene #2-3' SIN.

Sequences which promote ribosomal readthrough are placed immediately downstream of the disabled junction region in the pKSSINBVdlJR vector, which allows ribosomal scanning in genomic mRNA from non-structural gene termination to the heterologous genes. The heterologous proteins are expressed from genomic length mRNA by ribosomal scanning. This extends the life of the infected target cell because no subgenomic transcription occurs in cells infected with this vector. Further, these same ribosomal scanning sequences are placed between heterologous genes contained in polycistronic subgenomic mRNAs. The ribosomal spanning sequence to be used in the pKSDINBVdlJR vector and between heterologous genes in the polycistronic mRNA region is:

(SEQ. ID NO. 69)
5'-TTA ATT AAC GGC CGC CAC CAT GG-3'

The boldfaced codons refer to the ochre stop codon and AUG start codon, respectively. The bases underlined surrounding the stop codon refer to the Pac I recognition site and the bases underlined surrounding the start codon refer to the Nco I recognition site. The intercistronic distance of 15 by between the start and stop codons allows efficient ribosomal readthrough, as shown previously (Levine et al., *Gene* 108: 167-174, 1991). The sequences surrounding the ATG start codon from bases −9 to +1 conform to the Kozak consensus sequence for efficient translational initiation (Kozak, *Cell* 44:283-292, 1986). Where possible, the 3' terminal nucleotide corresponding to the carboxy terminal amino acid is changed to T, by site-directed mutagenesis. Also, the 5' terminal nucleotide corresponding to the amino terminal amino acid in the downstream cistron is changed to G, by site-directed mutagenesis.

Insertion of the intercistronic sequence between heterologous genes, or downstream of the disabled junction region in vector pKSDINBVdlJR, modified as described above, is accomplished by insertion of the double-stranded oligonucleotide pair shown below, into compatible Pac I/NcoI ends:

```
Read through sense Oligonucleotide:
5'-TAA CGG CCG CCA C-3'          (SEQ. ID NO. 70)

Read through antisense Oligonucleotide:
5'-CCA TGG TGG CGG CCG TTA AT-3'   (SEQ. ID NO. 71)
```

The oligonucleotides above are mixed in equal molar quantities in the presence of 10 mM $MgCl_2$, heated at 95° C. for 5 min, then allowed to cool slowly to room temperature, yielding the desired intercistronic sequence flanked by Pac I and Nco I sites. The intercistronic sequence is then ligated into the appropriate vector containing Pac I and Nco I compatible sites.

Another aspect of the present invention to enable expression of multiple heterologous genes in eukaryotic layered vector initiation systems is based on the use of alternate splicing signals. In this configuration, a splice donor sequence is inserted immediately downstream of the junction region promoter, followed by one or more heterologous genes, each of which is preceded by a splice acceptor sequence. As such, multiple splice acceptor/heterologous gene inserts may be arrayed 3' to one another. This creates a system whereby multiple heterologous genes are expressed from a single eukaryotic layered vector initiation system transcript, which is processed alternately at each splice acceptor site to give rise to individual autocatalytic RNAs encoding an individual heterologous gene. In such a system, levels of expression for each heterologous gene is controlled independently by altering the nucleotide sequence of the splice acceptor site. In addition, multiple splice donor/acceptor sites may be engineered into the system. Finally, tissue specific splice donor/acceptor sequences may be utilized in such a system to control the expression in specific tissues.

Example 6

Expression of Multiple Heterologous Genes by Copackaging

The ability to copackage multiple RNA molecules in the same alphavirus vector particle can be useful for the expression of multiple heterologous gene products from a single alphavirus vector particle. In addition, this concept can also be adapted in order to allow very large genes to be carried on RNA molecules separate from the alphavirus vector RNA containing the nonstructural genes, thus avoiding the need to package very long vector RNA molecules.

In order to accomplish such copackaging, all RNA fragments must contain a 5' sequence which is capable of initiating transcription of an alphavirus RNA, an alphavirus RNA polymerase recognition sequence for minus-strand synthesis, and at least one copy of the RNA packaging sequence. At least one of the RNA fragments also must contain sequences which code for the alphavirus non-structural proteins. Within preferred embodiments of the invention, one or more of the RNA fragments to be copackaged also will contain a viral junction region followed by a heterologous gene.

A. Construction of Copackaged Expression Cassettes for Expression of Multiple Heterologous Genes In order to demonstrate the feasibility of copackaging to allow for the expression of multiple heterologous genes, two vector constructs are created. The first construct consists of a 5' sequence that is capable of initiating transcription of Sindbis virus RNA, Sindbis RNA sequences required for packaging, sequences encoding the synthesis of nonstructural proteins 1-4, a Sindbis junction region, the luciferase gene, and Sindbis 3' sequences required for synthesis of the minus strand RNA. The second construct consists of a 5' sequence that is capable of initiating transcription of a Sindbis virus, Sindbis sequences required for packaging, a Sindbis Junction region, Sequences encoding the LacZ gene, and Sindbis 3' sequences required for synthesis of the minus strand RNA. RNA transcripts of these constructs transfected into a packaging cell line are copackaged to produce a vector particle capable of transferring expression of both luciferase and β-galactosidase into the same eukaryotic cell.

The β-galactosidase reporter gene is inserted into the Sindbis Basic Vector (pKSSINBV) followed by deletion of a portion of the Sindbis non-structural proteins from the vector. RNA from this construct is cotransfected with RNA from Sindbis Luciferase Vector (pKSSINBV-luc) and is copackaged by one of the methods described in Example 7. Infection of fresh BHK-21 cells with vector particles containing the copackaged RNA expression cassettes should result in the expression of both luciferase and β-galactosidase in the same cell.

B. Construction of a β-Galactosidase Expression Cassette pKSSINBV-Linker is digested with the enzyme Sac I, which cleaves immediately after the Sindbis 3'-end and poly A sequence. The digested fragment is treated with alkaline phosphatase and purified using Geneclean. Two 12 mer oligonucleotides,

```
5' GGTTTAAACAGGAGCT 3'    (SEQ. ID NO. 72)

5' CCTGTTTAAACCAGCT 3'    (SEQ ID NO. 73)
``` which form the Pme I site with SacI compatible ends when hybridized, were phosphorylated and ligated into the SacI digested vector. This construct is known as pKSSINBV-Linker-PmeI. The Pme I recognition site is substituted for the Sac I site in order to create a site for linearization of the plasmid prior to SP6 transcription. The lacZ gene contains several Sac I sites. pKSSINBV-Linker-PmeI is digested with Pml I and Bcl I followed by purification with GENECLEAN. The lacZ gene is obtained by digestion of pSV β-galactosidase vector DNA (Promega Corp., Madison, Wis.) with the enzyme HindIII. The digest is blunt-ended with Klenow DNA polymerase and dNTPs. The Klenow is heat killed and the plasmid is further digested with Bam HI and Xmn I. Xmn I reduces the size of the remaining vector fragment to simplify gel purification of the lacZ fragment. The 3.7 kbp lacZ fragment is purified from a 1% agarose gel and ligated into the Pml I/Bcl I digested pKSSINBV-Linker-PmeI fragment. This construct is known as pKSSINBV-lacZ. pKSSINBV-lacZ is digested with Bsp EI and religated under dilute conditions. This results in the removal of the Sindbis nonstructural proteins between nt#422-7054. This Sindbis construct is known as pKSSINBVdlNSP-lacZ.

pKSSINBVdlNSP-lacZ and pKSSINBV-luc are linearized with Pme I and Sac I, respectively, and SP6 transcripts are prepared as described in Example 3. These RNA transcripts are cotransfected into packaging cells that express the Sindbis structural proteins by one of the mechanisms described in Example 7. Each RNA transcript contains a 5' sequence that is capable of initiating transcription of a Sindbis virus, RNA sequences required for packaging, a Sindbis junction region, a reporter gene, and Sindbis 3' sequences required for synthesis of the minus strand RNA. The pKSSINBV-luc transcript also contains the Sindbis non-structural proteins. In cotransfected cells, both RNA transcripts are replicated and some viral particles will contain both RNA transcripts copackaged into the same particle. Infection of fresh cells with the copackaged RNA particles will result in cell that express both luciferase and β-galactosidase.

C. Copackaging of Multiple Expression Cassettes to Increase Packaging Capacity

Large genes such as Factor VIII can benefit from copackaging. Briefly, insertion of the cDNA coding for Factor VIII into the Sindbis Basic Vector (pKSSINBV) results in an RNA transcript approaching 16 kb in length. Because of the increased length, this RNA cannot be replicated or packaged efficiently. Using approaches described above, the Sindbis nonstructural proteins and the Factor VIII gene could be divided onto separate RNA molecules of approximately 8 kb and 9 kb in length, and copackaged into the same particles.

D. Construction of a Factor VIII Expression Cassette

The pKSSINBV-Linker-PmeI construct is digested with the enzyme Bsp EI and religated under dilute conditions. This results in the removal of Sindbis nonstructural proteins between nt#422-7054. This construct is known as pKSSINBVdlNSP-Linker-PmeI. The pKSSINBVdlNSP-Linker-PmeI construct is digested with the enzymes Pml I and Stu I and purified by using Geneclean. The source of Factor VIII cDNA is clone pSP64-VIII, an ATCC clone under the accession number 39812 having a cDNA encoding the full-length human protein. pSP64-VIII is digested with Sal I, the ends are blunted with T4 DNA polymerase and 50 uM of each dNTP, and the ca. 7700 bp. fragment is electrophoresed on a 0.7% agarose/TBE gel and purified with Geneclean. The 7.7 kb fragment encoding Factor VIII is purified in a 0.7% agarose gel and subsequently ligated to the Pml I/Stu I digested pKSSINBVdlNSP-Linker-PmeI fragment. This construct is known as pKSSINBVdlNSP-Factor VIII.

pKSSINBVdlNSP-Factor VIII and pKSSINBV constructs are linearized with Pme I and Sac I, respectively. SP6 transcripts are prepared as described in Example 3. These RNA transcripts are cotransfected into packaging cells that express the Sindbis structural proteins by one of the mechanisms described in Example 7. Both RNA transcripts contain a 5' sequence that is capable of initiating transcription of Sindbis RNA, sequences required for RNA packaging, a Sindbis Junction region, and the Sindbis 3' sequences required for synthesis of the minus strand RNA. In addition, the pKSSINBV transcript contains the Sindbis nonstructural protein genes, and the pKSSINBVdlNSP-Factor VIII construct contains the Factor VIII gene, but not the Sindbis nonstructural protein genes. In cotransfected cells, both RNA transcripts are replicated and some viral particles will contain both RNA transcripts copackaged into the same vector particle. Infection of fresh BHK-21 cells with the copackaged RNA will result in Factor VIII expression only if both RNA molecules are present in the same cell.

E. Construction of an Aura Virus Copackaging Vector

To develop Aura virus expression systems analagous to those described for Sindbis, standard techniques known in the art (e.g., Sambrook et al., *Molecular Cloning: A Laboratory Manual*, Cold Spring Harbor Laboratory Press, 1989), as well as specific approaches described herein, will be utilized for constructions. Virus, obtained from the ATCC, is propagated on cultured cells, its virion RNA extracted, and cDNA spanning the entire genome synthesized and cloned using conventional techniques. This cDNA is then used to construct gene transfer vector systems similar in principal to those described above, including, but not limited to, a replicon capable of carrying the heterologous gene(s), packaging cell lines that express the structural protein genes, and unique to this system, a separate packaging-competent subgenomic vector capable of carrying the additional heterologous gene(s). Since Aura virus subgenomic RNA contains a packaging signal, preliminary experiments are performed to identify this sequence, in order to prevent its inactivation during replacements with heterologous the gene(s). After identification of the packaging sequence, the individual elements of this Aura-based system are generated.

A basic replicon vector is constructed to contain the following minimum elements: Aura 5' sequences necessary for replication, nonstructural protein coding regions, a modified or unmodified junction region for subgenomic mRNA synthesis, a restriction enzyme site for insertion of heterologous gene(s), one or more copies of the packaging signal, and 3' Aura sequences necessary for replication, including a polyadenylate sequence. An upstream bacteriophage RNA polymerase promoter will be utilized for in vitro transcription of replicon RNA; alternatively, a eukaryotic RNA polymerase promoter will be utilized for transcription directly from cDNA.

A packaging-competent subgenomic vector is also constructed to contain the following minimum elements: a modified or unmodified junction region, a restriction enzyme site for insertion of heterologous gene(s), one or more copies of the packaging signal, and 3' Aura sequences necessary for replication/minus-strand synthesis, including a polyadenylate sequence. The subgenomic vector may, in some cases, be constructed with the Aura 5' replication sequences positioned upstream of the junction region, such that the vector will function as an amplicon. Transcription of subgenomic vector RNA can be accomplished in vitro using a bacteriophage RNA polymerase promoter, or cDNA in vivo using a eukaryotic RNA polymerase promoter. Further, the initial transcript may be of the sense-configuration or of the antisense-configuration.

Packaging cell lines are also constructed as described previously for Sindbis vectors, such that mRNA for one or more of the structural proteins will be transcribed from the junction region and be inducible by the Aura replicon. In other cases, one or more of the structural proteins can be expressed under the control of an inducible or constitutive eukaryotic promoter. In each case, specific inactivating mutations are made in any packaging sequences present in the structural protein genes, in order to prevent encapsidation of these sequences with the replicon. These mutations should be silent changes, usually at the third position of the codon, which do not affect the amino acid encoded.

The ability to package multiple heterologous genes can be exploited for many therapeutic applications, which include, but are not limited to, expression of multiple cytokines, multiple CTL epitopes, combinations of cytokines and CTL epitopes to enhance immune presentation, multiple subunits of a therapeutic protein, combinations of therapeutic proteins and antisense RNAs, etc. In addition to its utility for the expression of multiple heterologous genes, the packaging of subgenomic mRNAs into virions also enables this vector system for the transfer of extremely long heterologous sequences. Furthermore, this multipartite approach is useful in the development of producer cell lines, wherein replicase proteins and structural proteins are being stably expressed, and any heterologous gene contained within a subgenomic vector could then be readily introduced as a stable integrant.

Example 7

Construction of Alphavirus Packaging Cell Lines

A. Selection of Parent Cell Lines for Alphavirus Packaging Cell Line Development 1. Persistently or Chronically Infectable Cells An important criteria in selecting potential parent cell lines for the creation of alphavirus packaging cell lines, is the choice of cell lines that exhibit little or no cytopathological effects, prior to the appropriate production of alphavirus vector particles. This criteria is essential for the development of an alphavirus vector producer cell line which can be propagated for long periods of time and used as a stable source of vector. It is known that alphavirus infection of most mammalian cells results in cytopathology and lysis of the cell. However, the derivation of packaging cells from various insect cell lines may circumvent this problem. For example, insect cell lines, such as *Aedes albopictus, Aedes aegypti, Spodoptera frugiperda*, and *Drosophila melanogaster* cells, may be utilized to construct packaging cell lines. For example, in one embodiment, alphavirus packaging cell lines are provided using an configuration uses an insect parent cell line, such as the *Aedes albopictus*, containing a stably transfected expression cassette vector which allows for expression of alphavirus structural proteins under the control of inducible or non-inducible promoters active in these cell types, and co-expressing a selectable marker.

Recently, a Sindbis virus-induced protein of cellular origin, which has been associated with the down-regulation of Sindbis virus production in some infected *Aedes albopictus* cells, has been identified and purified (*Virology* 194:44). The protein is a small hydrophobic peptide of approximately 3200 Da., which can induce an antiviral state and inhibit both 49S and 26S viral RNA synthesis. Cells treated with the antiviral peptide usually demonstrate quiescent arrest of cellular division for 96 hours in uninfected cells, and then normal growth rates are restored. Cells that have been exposed to this peptide prior to infection are unable to replicate Sindbis virus and appear to maintain this phenotype by constitutively producing the antiviral protein through 10 months of continuous passage.

It is recognized that this cellular response to Sindbis replication in *Aedes albopictus* cells might decrease the efficiency of a recombinant alphavirus vector producing system in those cells. To improve the efficiency of alphavirus vector production, two methods have been devised to inactivate the virus-induced cellular antiviral protein, thus preventing any reduction of vector particle titers. The first method entails purification of this cellular protein described above, and determination of a portion of the primary amino acid sequence using established techniques known in the art. The resulting amino acid sequence is then used to derive possible corresponding genomic sequences, enabling one to design a degenerate PCR primer pair which can be used to amplify the specific cellular sequence. This amplified sequence is then cloned using standard techniques known in the art, to obtain a discreet region of the gene encoding this inhibitory protein. Determination of the nucleotide sequence of this clone then enables one to design a vector which will integrate specifically within this Sindbis inhibitory gene by homologous recombination, and "knock out" its capacity to express a functional protein. Cell clones which contain the knock out sequence are identified by insertion of a selectable marker into the discreet cloned region of the inhibitory protein, prior to transfecting cells with the vector.

A second method for disabling this Sindbis virus inhibitory protein involves the treatment of *Aedes albopictus*-derived packaging cells with a mutagen, for example, BUDR (5-bromodeoxyuridine). The mutagenized packaging cell line population is then transfected or transduced with a Sindbis vector, which is able to express the neomycin resistance marker. Under high concentrations of the G418 drug, only those cells producing large amounts of Sindbis vector, and thus unable to express the Sindbis inhibitory gene, will be able to survive. After selection, resistant colonies are pooled, dilution cloned, and tested for high titer Sindbis production.

2. Modification of Cells to Decrease Susceptibility to Alphavirus Expression:

Suppression of Apoptosis and Cytopathology

Packaging cell lines may also be modified by overexpressing the bcl-2 gene product in potential parent cell lines, such as canine D-17 and Cf2; human HT1080 and 293; quail QT-6; baby hamster kidney BHK-21; mouse neuroblastoma N18; and rat prostatic adenocarcinoma AT-3. The conversion of these cells to a persistently infectable state allows for their use as alphavirus packaging and producer cell lines, similar to those of retrovector producer lines.

In order to construct such packaging cells, a bcl-2 expression vector is constructed by using standard recombinant DNA techniques in order to insert the 910 base pair Eco RI cDNA fragment derived from the plasmid p84 (*Nature* 336: 259) into any commercially available expression vector containing a constitutive promoter and encoding a selectable marker, for example, pcDNA3 (Invitrogen, San Diego, Calif.). Careful consideration must be taken to avoid any type of homology between alphavirus nucleic acid sequences and other transduced vectors. This precaution should be taken in order to prevent recombination events which may lead to undesirable packaging of selectable markers or the bcl-2 oncogene in recombinant Sindbis particles. This is an important point, since the alphavirus vector system described herein is designed for use as a biological therapeutic. Once the bcl-2 expression vector is constructed, the parent cell line (i.e., BHK-21 cells) is transfected using any standard technique and selected after 24 hours using the appropriate marker. Resistant colonies are pooled, followed by dilution cloning, and then individual clones are propagated and screened for bcl-2 expression. Once expression is verified, persistent Sindbis infection is tested, followed by its use as a parent cell line for alphavirus packaging cell line development.

Other gene products, in addition to the bcl-2 oncogene, which suppress apoptosis may likewise be expressed in an alphavirus packaging or producer cell line. Three viral genes which are particularly preferred include: the adenovirus MB gene encoding the 19-kD protein (Rao et al., *PNAS* 89:7742-7746, 1992), the herpes simplex virus type 1 $\gamma$34.5 gene (Chou and Roizman, *PNAS* 89:3266-3270, 1992), and the AcMNPV baculovirus p35 gene (Clem et al., *Science* 254:1388-1390, 1991). These individual genes may be inserted into any commercially available plasmid expression vectors, under the control of appropriate constitutive eukaryotic transcriptional promoters, and also containing a selectable marker, using standard techniques. The expression vector constructs are subsequently transfected into cell lines as described above, and the appropriate selection is applied. Selection for stable integration of these genes and constitutive expression their products should allow for more extended vector production in cell lines found to be susceptible to alphavirus-induced apoptotic events. In addition, it is feasible that each gene product inhibits apoptosis by its own unique mechanism. Therefore, the genes may also be introduced into packaging or producer cell lines in various combinations in order to obtain a stronger suppressive effect. Finally, other gene products having similar effects on apoptosis can also be readily incorporated into packaging cell lines as they are identified.

In the derivation of alphavirus vector packaging and producer cell lines, many approaches are outlined to control the expression of viral genes, such that producer cell lines stably transformed with both vector and vector packaging cassettes, can be derived. These approaches include inducible and/or cellular differentiation sensitive promoters, antisense structural genes, heterologous control systems, and mosquito or other cells in which viral persistent infections are established. Regardless of the final configuration for the alphavirus vector producer cell line, the ability to establish persistent infection, or at least delay cell death as a result of viral gene expression, may be enhanced by inhibiting apoptosis. For example, the DNA tumor viruses, including adenovirus, HPV, SV40, and mouse polyomavirus (Py), transform cells in part, by binding to, and inactivating, the retinoblastoma (Rb) gene product p105 and its closely related gene product, p107, and other gene products involved in the control of the cell cycle including cyclin A, $p33^{cdk2}$ and $p34^{cdc2}$. All of these viruses, except for Py, encode gene products which bind to and inactivate p53. Uniquely, Py encodes middle T antigen (mT) which binds to and activates the membrane tyrosine kinase, src, and also phosphatidylinositol-3-kinase, which is required for the full transformation potential of this virus (Talmage et al., *Cell* 59:55-65, 1989). The binding to and inactivation of the Rb and p53 recessive oncogene products prevents cells transformed by these DNA tumor viruses from entering the apoptotic pathway. It is known that p53 is able to halt the division of cells, in part by inhibiting the expression of proteins associated with cellular proliferation, including c-fos, hsc70, and bcl-2 (Miyashita et al., *Cancer Research* 54:3131-3135, 1994).

In order to extend the duration of alphavirus vector production, or to promote a persistently infectable state, packaging and producer cells are transformed with viral genomic DNA from Py or SV40. In particular, SV40 and Py transformed cell lines are established, and the kinetics and level of Sindbis production and cytopathology after viral infection determined. If apoptic events characteristic of Sindbis proliferation in hamster cells are diminished, each prototype alphavirus packaging and producer cell line subsequently is transformed with Py or SV40, in order to increase the yield of packaged vector from these cells.

3. Modification of Cells to Decrease Susceptibility to Alphavirus Expression:

Production of Activation-Dependent Vector Particles

The Sindbis E2 glycoprotein is synthesized as a precursor, PE2. This PE2 precursor along with the second viral glycoprotein, E1, associate in the endoplasmic reticulum and are processed and transported to the infected cell membrane as a heterodimer for virion incorporation. At some point during this processing, PE2 is cleaved into E3 and the mature virion glycoprotein E2. E3 is the 64 amino-terminal residues of PE2 and is lost in the extracellular void during maturation. The larger cleavage product, E2, is associated with E1 and anchored in what becomes the viral envelope. Host cell protease(s) is responsible for processing of the PE2 precursor, cleaving at a site that immediately follows a highly conserved canonical four amino acid (aa) residue motif, basic-X-basic-basic aa's. A mutant cell line derived from the CHO-K1 strain, designated RPE.40 (Watson et al., *J. Virol* 65:2332-

2339, 1991), is defective in the production of Sindbis virus strain AR339, through its inability to process the PE2 precursor into the E3 and mature E2 forms. The envelopes of Sindbis virions produced in the RPE.40 cell line therefore contain a PE2/E1 heterodimer. RPE.40 cells are at least 100-fold more resistant to Sindbis virus infection than the parental CHO-K1 cells, suggesting an inefficiency in the ability of PE2 containing virions to infect these cells. The defective virions produced by the RPE.40 cell line can be converted into a fully infectious form by treatment with trypsin.

In packaging and producer cell lines, any wild-type alphavirus that is produced by recombination between vector and structural protein gene RNAs will re-infect cells and be rapidly amplified; thus, significantly contaminating and decreasing the titer of packaged vector preparations. Packaging and producer cells developed from the RPE.40 line are an alternative to other cell lines permissive for alphavirus infection due to the inefficient amplification of any wild-type virus generated during vector production and packaging. Thus, vector preparations are not significantly contaminated with wild-type virus. Furthermore, the benefits of this system are extended to other packaging and producer cell lines by developing "knock-out" mutants in their analogous cellular protease(s), using techniques known in the art.

4. Hopping Cell Line Development

Alphavirus hopping cell lines, as discussed previously, are used transiently to produce infectious RNA vector particles which have been pseudotyped for a different cellular receptor tropism. Once the hopping cell line produces vector particles, it is no longer required because only the infectious culture supernatants are needed to transduce the original alphavirus packaging cell lines discussed above. Therefore, the hopping cell line need not exhibit persistent infection by alphavirus in order to transiently produce vector particles. In this instance, the parent cell line can be either an insect cell line that exhibits persistent infection, or a mammalian cell line which is likely to lyse within 24-72 hours after a productive alphavirus infection. The only criteria is that the cell lines are able to express either VSV-G protein, with or without the appropriate alphavirus structural proteins, or retroviral gag-pol and env protein without affecting cell growth prior to introduction of the alphavirus RNA vector. Therefore, the alphavirus hopping cell line can be any of the aforementioned parent cell lines able to support either alphavirus or retroviral replication, without the additional cell modifications discussed previously, such as bcl-2 oncogene expression.

The generation of VSV-G pseudotyped alphavirus vector particles can be accomplished by at least three alternative approaches, two of which are dependent on the stable integration of a VSV-G expression cassette into cells. VSV-G protein is known to be highly cytotoxic when expressed in cells. Therefore, synthesis of this protein by the expression cassette is controlled by an inducible promoter. Specifically, a DNA fragment containing the VSV-G protein gene is isolated from plasmid pLGRNL (Emi et al., J. Virol. 65:1202-1207, 1991) by digestion with Bam HI, the termini made blunt using Klenow fragment enzyme and dNTPs, and the 1.7 kb fragment purified from a 1% agarose gel. Plasmid vector pVGELVIS-SINBV-linker (from Example 3), is digested with the enzyme Bsp EI to remove Sindbis nonstructural protein coding sequences nts. 422-7054, and the remaining vector is re-ligated to itself to generate plasmid pVGELVIS-dlNSP-BV-linker. This plasmid is then digested with Xho I and the termini made blunt using Klenow fragment enzyme and dNTPs. The previously purified VSV-G fragment is subsequently ligated with this vector DNA, and resulting clones are screened for proper VSV-G insert orientation. This pVGELVIS-based VSV-G expression construct, in which VSV-G synthesis is controlled by a Sindbis replicon-inducible junction region, is designated pVGELVISdl-G.

Alternatively, a similar Sindbis replicon-inducible VSV-G expression cassette may be generated in the antisense configuration. In particular, plasmid vector pKSSINBV-linker (described in Example 3) is digested with the enzymes Apa I and Bam HI to most of the Sindbis nonstructural protein coding region, and the resulting 3309 by vector fragment is purified from a 1% agarose gel. In addition, plasmid pd5'-26s (described in section B.3., this example) also is digested with the enzymes Apa I and Bam HI. The resulting 400 bp fragment which contains the HDV ribozyme/Sindbis 5'-end fusion is purified from a 1% agarose gel and subsequently ligated with the purified pKSSINBV-linker vector fragment to generate a plasmid designated pd5'-BVlinker. Plasmid pd5'-BVlinker is subsequently digested with Xho I, the termini made blunt using Klenow fragment enzyme and dNTPs, and ligated with the previously purified VSV-G fragment. The resulting construct, containing the expression cassette elements HDV antigenomic ribozyme/Sindbis 5'-end 299 nts./Sindbis junction region/VSV-G protein gene/Sindbis 3'-end untranslated region, is designated as plasmid pd5'-BV-G. Insertion of this VSV-G gene cassette into the pcDNA3 vector is as follows. Plasmid pd5'-BV-G is digested with the enzymes Pme I and Apa I, and the termini are made blunt by the addition of T4 DNA polymerase and dNTPs. The entire 2.5 kb VSV-G protein gene cassette is purified in a 1% agarose gel. Plasmid pcDNA3 is digested with the enzymes HindIII and Apa I and the termini are made blunt by the addition of T4 DNA polymerase and dNTPs, and the 5342 by vector is purified in a 1% agarose gel. The two purified, blunt-end DNA fragments are subsequently ligated, and the resulting VSV-G protein gene expression cassette vector is known as plasmid pCMV/d5'VSV-G. Further modifications of the VSV-G expression cassettes pVGELVISdl-G and pCMV/d5'VSV-G to substitute other selectable markers, for example hygromycin resistance or E. coli gpt, for the current neomycin resistance, or other promoter elements, for example Drosophilia metallothionein or hsp 70, for the current CMV, MuLV, and SV40 promoters, may be readily accomplished given the disclosure provided herein.

In a first VSV-G/alphavirus hopping cell line configuration, VSV-G expression cassette plasmid DNA (pVGELVISdl-G or pCMV/d5'VSV-G, or modified versions thereof) is transfected into the appropriate cell type (for example, BHK-21 cells) and selection for G418 resistance is applied using media containing 400 g/ml of G418 as described elsewhere in this example. G418-resistant cells are cloned by limiting dilution and the individual cell lines expanded for screening. VSV-G expressing cell lines are detected by transfection with any nonstructural protein gene-containing RNA vector (see Example 3) to induce the VSV-G expression cassette, followed by immunofluorescence using polyclonal rabbit anti-VSV antibody as described (Rose and Bergmann, Cell 34:513-524, 1983). The stably transfected VSV-G expressing cell line, in some cases, is subsequently transfected with plasmid expression cassette(s) which express one or more Sindbis structural proteins (described elsewhere in this example). For the production of VSV-G pseudotyped alphavirus particles, the appropriate vector RNA is transfected into the VSV-G hopping cell line, and vector particle-containing supernatants are recovered at least 24 hours post-transfection.

In a second VSV-G/alphavirus hopping cell line configuration, VSV-G expression cassette DNA (pVGELVISdl-G or pCMV/d5'VSV-G, or modified versions thereof) is transfected into previously derived alphavirus packaging cell lines (described elsewhere in this example) and the appropriate selection is applied as described previously. The selected cells are cloned by limiting dilution and the individual cell lines expanded for screening. VSV-G expressing cell lines are detected by transfection with any nonstructural protein gene-containing RNA vector (see Example 3) to induce the VSV-G expression cassette, followed by immunofluorescence using polyclonal rabbit anti-VSV antibody as described (Rose and Bergmann, *Cell* 34:513-524, 1983). For the production of VSV-G pseudotyped alphavirus particles, the appropriate vector RNA is transfected into the VSV-G hopping cell line, and vector particle-containing supernatants are recovered at least 24 hours post-transfection.

In a third VSV-G/alphavirus hopping cell line configuration, VSV-G expression cassette DNA is co-transfected with the appropriate vector RNA into previously derived alphavirus packaging cell lines (described elsewhere in this example). Supernatants containing pseudotyped vector particles are recovered at least 24 hours post-transfection.

For the pseudotyping of alphavirus vectors in retroviral packaging cell lines, any cell line referenced in the literature, which expresses retroviral gag-pol and env sequences, may be used to package alphavirus RNA vector that has been engineered to contain a retroviral packaging sequence. The retrovirus psi packaging sequence is inserted between the inactivated junction region and a synthetic junction region tandem repeat, such that only genomic-length vector, and not subgenomic RNA, is packaged by the retroviral envelope proteins. Retroviral-based particles containing alphavirus vector RNA are produced by transfecting in vitro transcribed alphavirus vector RNA using procedures that have been described previously. Supernatants with pseudotyped retroviral particles containing alphavirus RNA vector are harvested at 24 hours post-transfection, and these supernatants are then used to transduce an alphavirus packaging cell line.

5. Identification of Parent Cell Lines which Produce Alphavirus Resistant to Inactivation by Human Complement Successful intravenous administration of recombinant alphavirus particles requires that the vector is resistant to inactivation in serum. It is well known to those skilled in the art that Sindbis grown on BHK cells is sensitive to inactivation, in terms of effective virus titer. In order to identify parent cell lines which produce Sindbis particles which are resistant to inactivation by human complement, the level of serum inactivation of Sindbis virus grown on multiple cell types is tested. The cell types tested are derived from many species, including human, for example, 293 or HT1080 (ATCC No. CCL 121).

As a source of human complement, approximately 70 mls of blood are collected from patients into serum separating tubes (Becton Dickinson, Los Angeles, Calif.). The blood is allowed to clot for one half hour at room temperature. After clotting the serum is centrifuged at 2000 g for 10 minutes at 4° C. The serum is collected and placed into a 15 ml conical tube (Corning, Corning, N.Y.) and placed on ice. Approximately, 1.1 ml aliquots of the serum are placed in 2 ml cryovials, frozen in a dry ice/ethanol bath and stored at −70° C. for subsequent serum inactivation assays. Complement inactivated controls are prepared by heat inactivation of control aliquots for 30 minutes at 56° C.

To test Sindbis for serum inactivation, two vials containing 1.1 ml of 100% non-heat inactivated human serum are used for various virus preparations. One vial of serum is quick thawed at 37° C. The serum is then heated to 56° C. for 30 minutes to heat inactivate complement present in the serum. Following inactivation the serum is placed on ice. The second vial is quick thawed at 37° C. After thawing the serum is placed on ice.

Approximately, 1.0 ml of the non-heat inactivated serum, medium, and heat-inactivated serum are placed in separate 1.5 ml tubes (Fisher Scientific, Pittsburgh, Pa.) and mixed with $10^5$ Plaque Forming units (PFU) of Sindbis virus and incubated at 37° C. for 1 hour. After incubation the tubes are placed on ice.

In order to identify the parent cell line host from which an alphavirus is resistant to human serum inactivation, the non-heat inactivated serum, medium, and heat-inactivated serum virus preparations are titered by plaque assay on BHK cells. Equivalent virus titers regardless of incubation with non-heat inactivated serum, medium, or heat-inactivated serum, are indicative of parent cell line hosts from which Sindbis virus is resistant to human complement inactivation.

B. Structural Protein Expression Constructs

1. Inducible and Constitutive Structural Protein Vector Expression Cassettes

The development of alphavirus packaging cell lines is dependent on the ability to synthesize high intracellular levels of the necessary structural proteins: capsid, pE2 and/or E2, and E1. Unfortunately, high level expression of these proteins, in particular, the envelope glycoproteins E2 and E1, may lead to concomitant cytopathology and eventual cell death. Therefore structural protein expression cassettes have been designed with inducible regulatory elements which control the levels of gene expression, in addition to others which maintain constitutive levels of expression.

In a first configuration, expression of the alphavirus structural proteins is under control of the RSV LTR, in conjunction with the inducible lac operon sequences. This is achieved by insertion of alphavirus cDNA corresponding to the viral structural protein genes into the pOP13 and pOPRSV1 vectors (Stratagene). These vectors, used separately, are co-transfected with the p3'SS vector (Stratagene), which expresses the lac repressor "i" protein. In the absence of inducer, for example, Isopropyl-B-D-thiogalactopyranoside (IPTG), the basal, or constitutive, level of expression of a luciferase reporter gene has been reported to be 10-20 copies per cell. Addition of IPTG, results in a conformational change of the repressor protein, which results in decreased affinity of the lac i protein for lac-operator sequences, permitting high level expression of the heterologous gene. Induction levels in the presence of IPTG of 95-fold have been reported for heterologous genes contained in the pOP13 vector.

Specifically, the Sindbis structural protein gene (SP) cDNA is inserted into the pOP13 and pOPRSV1 vectors as follows. The SP coding region is amplified in toto with a primer pair whose 5' ends map, respectively, to the authentic AUG translational start and UGA translational stop sites, including the surrounding nucleotides corresponding to the Kozak consensus sequence for efficient translational initiation at Sindbis nt 7638. The forward primer is complementary to Sindbis nts 7638-7661, and the reverse primer is complementary to Sindbis nts 11,384-11,364. PCR amplification of Sindbis cDNA corresponding to the structural protein genes is accomplished by a standard three-temperature cycling protocol, using the following oligonucleotide pair.

Forward primer (7638F):

(SEQ. ID NO. 74)
5'-TATATGCGGCCGCACCACCACCATGAATAGAGGATTCTTTAACATG
C-3'

Reverse primer (11384R):

(SEQ. ID NO. 75)
5'-TATATGCGGCCGCTCATCTTCGTGTGCTAGTCAG-3'

In addition to their respective complementarities to the indicated Sindbis nts, a 5 nucleotide "buffer sequence" followed by the Not I recognition sequence is attached to the 5' ends of each primer. Following PCR amplification, the 3,763 by fragment is purified in a 1% agarose gel, then subsequently digested with the Not I enzyme. The resulting 3,749 by fragment is then ligated, separately, into the pOP13 and pOPRSV1 vectors, which are digested with Not I and treated with calf intestine alkaline phosphatase. These expression cassette vectors, which contain the entire coding capacity of the Sindbis structural proteins are known as pOP13-SINSP and pOPRSV1-SINSP.

Variations of the lac operon-Sindbis structural protein gene expression cassettes also can be constructed using other viral, cellular or insect-based promoters. Using common molecular biology techniques known in the art, the lac operon and the RSV LTR promoter, or just the RSV LTR promoter, sequences can be switched out of the Stratagene pOP13 and pOPRSV1 vectors and replaced by other promoter sequences, such as the cytomegalovirus major immediate promoter (pOPCMV-SINSP); the adenovirus major late promoter (pOPAMLP-SINSP); the SV40 promoter (pOPSV-SINSP): or insect promoter sequences, which include the *Drosophila* metallothionein inducible promoter (pMET-SINSP), *Drosophila* actin 5C distal promoter (pOPA5C-SINSP), heat shock promoters HSP65 or HSP70 (pHSP-SINSP), or the baculovirus polyhedrin promoter (pPHED-SINSP).

2. Modification of Cassettes to Increase Protein Expression Levels

Alphavirus structural protein expression can be increased if the level of mRNA transcripts is increased. Increasing the level of mRNA transcripts can be accomplished by modifying the expression cassette such that alphavirus nonstructural proteins recognize these transcripts, and in turn, replicate the message to higher levels. This modification is performed by adding the wild-type minimal junction region core (nucleotides 7579 to 7602) to the extreme 5'-end of the Sindbis structural protein coding region, prior to the first authentic ATG start site for translation and inverting the expression cassette in the vector, so as to produce antisense structural protein gene transcripts. This can be accomplished by following the same PCR amplification technique described above for placing the Sindbis structural protein cDNA into the pOP13 and pOPRSV1 expression vectors. The only modification to this procedure is the replacement of the 7638F forward primer with a similar primer that includes junction region core nucleotides 7579-7602 between the Not I restriction enzyme site and the first ATG of the coding region as follows:

Forward primer (JUN7638F):

(SEQ. ID NO. 76)
5'-TATATGCGGCCGCATCTCTACGGTGGTCCTAAATAGTACCACCACC-
ATGAATAGAGGATTC-3'

Following PCR amplification, the resulting 3,787 by fragment is purified in a 1% agarose gel, then subsequently digested with the Not I enzyme. The resulting 3,773 by fragment is then ligated, separately, into the pOP13 and pOPRSV1 vectors which are digested with Not I and treated with calf intestine alkaline phosphatase. The resulting expression cassette vectors are known as pOP13-JUNSINSP and pOPRSVI-JUNSINSP. However, it must be stated that the introduction of junction region sequences into the structural protein expression cassettes will introduce sequences which may possibly lead to undesirable recombination events, leading to the generation of wild-type virus.

3. Inducible Expression of Structural Proteins Via Alphavirus Vector

Because of potential cytotoxic effects from structural protein expression, the establishment of inducible packaging cell lines which express even modest basal levels of these proteins may not always be preferred. Therefore, packaging cell line expression cassettes are constructed which contain regulatory elements for the high level induction of structural protein synthesis via nonstructural proteins supplied in trans by the alphavirus vector, but with no basal level of synthesis until appropriately stimulated.

In this configuration, a structural protein gene cassette is constructed, whereby transcription of the structural protein genes occurs from an adjacent alphavirus junction region sequence. The primary features of this cassette are: an RNA polymerase II promoter positioned immediately adjacent to alphavirus nucleotide 1, such that transcription initiation begins with authentic alphavirus nucleotide 1, the 5'-end alphavirus sequences required for transcriptase recognition, the alphavirus junction region sequence for expression of the structural protein gene mRNA, the alphavirus structural protein gene sequences, the 3'-end alphavirus sequences required for replication, and a transcription termination/polyadenylation sequence. Because of an upstream open-reading frame which ends in translation termination codons prior to the AUG start site of the structural protein genes, expression of the alphavirus structural proteins can occur only after the synthesis of minus-strand RNA by vector-supplied nonstructural proteins, followed by the subsequent transcription of a structural protein gene mRNA from the junction region. Therefore, the inducibility of this system is dependent entirely on the presence of nonstructural proteins, supplied by the alphavirus vector itself, introduced as either RNA transcribed in vitro, or cDNA positioned downstream of an appropriate promoter element. In addition, the 5'- and 3'-end alphavirus sequences allow for this RNA transcript of the structural protein gene cassette to be amplified by the same vector-supplied nonstructural proteins (see FIG. 11).

Specifically, the construction of a positive-sense, vector-inducible Sindbis packaging cassette is accomplished as follows. Briefly, the pVGELVIS vector described previously is digested with the enzyme Bsp EI to remove nucleotides 422 to 7054, including most of the nonstructural gene coding sequences, and the remaining 9925 by fragment is purified in a 0.8% agarose gel, and subsequently re-ligated to itself to generate the construct (mown as pLTR/SindlBspE (FIG. 11). This deletion leaves the 5'-end authentic translation start codon at nts 60-62 intact, and creates in-frame downstream UAA and UGA stop codons at nts 7130-7132 and 7190-7192 (original numbering), respectively, thus preventing translation of the downstream structural protein gene open-reading frame. The pLTR/SindlBspE packaging cassette construct is subsequently transfected into BHK cells (ATCC #CCL 10) and transfectants are selected using the G418 drug at 400 ug/ml and cloned by limiting dilution. After expansion of the transfected clonal lines, screening for packaging activity is performed by transfection of Sindbis-luciferase (Sin-luc) vector RNA as described previously. The data shown in FIG. 12 demonstrate that transfection of Sin-luc vector RNA into several of these clonal LTR/SindlBspE packaging cells results in the production of infectious Sindbis particles containing the Sin-luc RNA, as the recovered supernatants are shown to transfer Sin-luc vector RNA to fresh monolayers of BHK cells.

A similar packaging construct can also be made using the pVG-ELVISd clone (described previously) as initial material for creation of the Bsp EI deletion. In this clone, the Sindbis 3'-end sequence is followed by a catalytic ribozyme sequence to allow more precise processing of the primary transcript adjacent to the 3'-end sequences of Sindbis. In addition, a wide variety of variations of these packaging cassette constructions can be made given the disclosure provided herein, including for example, the substitution of other RNA polymerase promoters for the current MuLV LTR, the addition of 1 or more nucleotides between the RNA polymerase promoter and the first Sindbis nucleotide, the substitution of other ribozyme processing sequences, or the substitution of a non-Sindbis-encoded open reading frame upstream of the structural protein gene sequences, which may or may not retain the 5'-end Sindbis sequences required for transcriptase recognition. Furthermore, these constructs can be transfected into other cell lines, as discussed previously In another vector-inducible packaging configuration, expression cassettes contain a cDNA copy of the alphavirus structural protein gene sequences flanked by their natural junction and 3'-untranslated regions, and are inserted into an expression vector in an orientation, such that primary transcription from the promoter produces antisense structural protein gene RNA molecules. Additionally, these constructs contain, adjacent to the junction region, alphavirus 5'-end sequences necessary for recognition by the viral transcriptase, and a catalytic ribozyme sequence positioned immediately adjacent to alphavirus nucleotide 1 of the 5'-end sequence. As such, this ribozyme cleaves the primary RNA transcript precisely after the first alphavirus nucleotide. In this antisense orientation, the structural protein genes cannot be translated, and are dependent entirely on the presence of alphavirus virus nonstructural proteins for transcription into positive-strand mRNA, prior to their expression. These nonstructural proteins again are provided by the alphavirus vector itself. In addition, because this configuration contains the precise alphavirus genome 5'- and 3'-end sequences, the structural protein gene transcripts undergo amplification by utilizing the same nonstructural proteins provided by the alphavirus vector.

Specifically, the Sindbis structural protein gene cDNA is removed from the genomic clone pVGSP6GEN and inserted into the pcDNA3 (Invitrogen Corp., San Diego, Calif.) expression vector as follows. First, plasmid pVGSP6GEN is digested with the enzymes Apa I and Bam HI to remove all Sindbis sequences through nucleotide 7335, including the genes encoding nonstructural proteins 1, 2, 3, and most of 4. The remaining 7285 by vector fragment, which contains the Sindbis structural protein genes, is purified in a 0.8% agarose gel, and subsequently ligated with a polylinker sequence, called SinMCS, that is obtained by annealing two synthetic oligonucleotides. The oligonucleotides, SinMCSI and SinMCSII, contain the recognition sites for Cla I, Bgl II, and Spe I, and have Apa I and Bam HI ends after annealing. Their sequences are as follows:

```
SinMCSI:
                                        (SEQ. ID NO. 77)
5'-CTCATCGATCAGATCTGACTAGTTG-3'

SinMCSII:
                                        (SEQ. ID NO. 78)
5'-GATCCAACTAGTCAGATCTGATCGATGAGGGCC-3'
```

The resulting construct, known as pMCS-26s, is then modified to contain the 5'-end 299 nucleotides of Sindbis, fused to an 84 nucleotide ribozyme sequence from the antigenomic strand of hepatitis delta virus (HDV) (*Nature* 350: 434), using overlapping PCR amplification. Two primer pairs are used initially in separate reactions, followed by their overlapping synthesis in a second round of PCR. In reaction #1, the forward primer (HDV49-XC) is complementary to HDV genome nucleotides 823-859, and the reverse primer (HDV17-68) is complementary to HDV genome nucleotides 839-887, with sequences as follows:

```
Forward primer (HDV49-XC):
                                        (SEQ. ID NO. 79)
5'-ACTTATCGATGGTTCTAGACTCCCTTAGCCATCCGAGTGGACGTG-
CGTCCTCCTTC-3'

Reverse primer (HDV17-68):
                                        (SEQ. ID NO. 80)
5'-TCCACCTCCTCGCGGTCCGACCTGGGCATCCGAAGGAGGACGCAC-
GTCCACT-3'
```

In addition to their respective complementarities, primer HDV49-XC contains flanking Xba I and Cla I recognition sequences at the 5'-end. PCR amplification of HDV sequences is accomplished by a standard three-temperature cycling protocol with these primers and Vent polymerase. In reaction #2, the forward primer (SIN-HDV), which joins precisely the HDV and Sindbis sequences, is complementary to nucleotides 1-21 of Sindbis, and genomic nucleotides 871-903 of HDV, and overlaps the sequence of primer HDV17-68 (from above) by 20 nucleotides, and the reverse primer (SIN276-SPE) is complementary to Sindbis nucleotides 299-276, with sequences as follows:

```
Forward primer (SIN-HDV):
                                        (SEQ. ID NO. 81)
5'-TCGGACCGCGAGGAGGTGGAGATGCCATGCCGACCCATTGACGGC-
GTAGTACACACT-3'

Reverse primer (SIN276-SPE):
                                        (SEQ. ID NO. 82)
5'-CTGGACTAGTTAATACTGGTGCTCGGAAAACATTCT-3'
```

In addition to their respective complementarities, primer SIN276-SPE contains a flanking UAA translation termination codon and SpeI recognition sequence at its 5' end. PCR amplification of the fragment containing Sindbis 5'-end sequences fused to HDV ribozyme sequences is accomplished by a standard three-temperature cycling protocol, using Vent polymerase, these primers, and pVGSP6GEN plasmid as template. After the first round of PCR amplification, ½0th of the total amounts from each of reaction #1 and reaction #2 is combined and used as template in a second round of PCR amplification with additional input of primers HDV49-XC and SIN276-SPE and a standard three-temperature cycling protocol. Following the second round of PCR, the 414 by amplicon is purified with the MERMAID KIT (Bio101, La Jolla, Calif.), and digested with the enzymes ClaI and SpeI. The digested amplicon is purified in a 1% agarose gel, and subsequently ligated into plasmid pMCS-26s, which also is digested with ClaI and SpeI and purified in a 1% agarose gel. The resulting construct, containing the expression cassette elements HDV antigenomic ribozyme/Sindbis 5'-end 299 nts/Sindbis junction region/Sindbis structural protein genes/Sindbis 3'-end untranslated region, is known as pd5'26s.

Insertion of the structural protein gene cassette from pd5'26s into the pcDNA3 vector is performed as follows. Plasmid pd5'26s is digested with the enzyme Xba I and the 3'-recessed ends are made blunt by the addition of Klenow enzyme and dNTPs. The entire 4798 by structural protein gene cassette is purified in a 1% agarose gel. Plasmid pcDNA3 is digested with the enzymes HindIII and Apa I and the ends are made blunt by the addition of T4 DNA polymerase enzyme and dNTPs, and the 5342 by vector is purified in a 1% agarose gel. The two purified, blunt-end DNA fragments are subsequently ligated, and the resulting structural protein gene expression cassette vector is known as pCMV-d5'26s (see FIG. 11). Transfection of this DNA into cells and selection for G418 resistance is performed as previously described.

Modifications of the CMV promoter/antisense-Sindbis structural protein vector also can be constructed using other viral, cellular, or insect-based promoters. Using common molecular biology techniques know in the art, the CMV promoter can be switched out of the Invitrogen pcDNA3 vector and replaced by promoters such as those listed previously. Other variation of this antisense packaging cassette may include, but are not limited to: the addition of 1 or more nucleotides between the first Sindbis nucleotide and the catalytic ribozyme, the use of longer or shorter HDV or other catalytic ribozyme sequences for transcript processing, the substitution of a precise transcription termination signal for the catalytic ribozyme sequence, or the antisense expression of structural protein gene cassettes using any downstream sequence recognized by an RNA polymerase which results in transcription of a structural protein gene mRNA.

Further, it should be noted that each of the vector-inducible constructs described contains sequences homologous to the Sindbis vector itself. Therefore, the potential exists for the generation of wild-type virus by recombination between the two RNA molecules. Additional modifications may be made to eliminate this possibility as described below.

4. Separation of Structural Protein Genes to Prevent Recombination

Packaging cell lines may also be generated which segregate the integration and expression of the structural protein genes, allowing for their transcription as non-overlapping, independent RNA molecules. For example, the expression of capsid protein independently of glycoproteins E2 and E1, or each of the three proteins independent of each other, eliminates the possibility of recombination with vector RNA and subsequent generation of contaminating wild-type virus.

Specifically, capsid protein is expressed independently from an inducible expression vector, such that sequences which might result in recombination with vector RNA are eliminated. As an example, the capsid protein gene is amplified from plasmid pVGSP6GEN with a primer pair complementary to nucleotides 7632-7655 (forward primer) and 8415-8439 (reverse primer), with sequences as follows:

```
Forward primer (Sin7632F):
                                        (SEQ. ID NO. 83)
5'-GTCAAGCTTGCTAGCTACAACACCACCACCATGAATAGAG-3'

Reverse primer (Sin8439R):
                                        (SEQ. ID NO. 84)
5'-CAGTCTCGAGTTACTACCACTCTTCTGTCCCTTCCGGGGT-3'
```

In addition to their respective complementarities, the forward primer contains Nhe I and HindIII recognition sequences at its 5'-end, and the reverse primer contains both UAG and UAA translation stop codons and a Xho I recognition sequence at its 5'-end. Amplification is accomplished using a standard three-temperature cycling protocol, and the resulting amplicon is digested with the enzymes Nhe I and Xho I, and purified in a 1% agarose gel. Expression plasmid pMAM (Clontech), which contains a dexamethasone-inducible MMTV LTR promoter sequence, is digested with the enzymes Nhe I and Xho I and the plasmid DNA purified in a 1% agarose gel. The capsid protein gene fragment is ligated into the pMAM vector, and the resulting construct is known as pMAM/C. Plasmid pMAM/C is transfected into the appropriate cell line (for example BHK-21) as described previously and selection for stable transfectants is accomplished by using HAT (hypoxanthine, aminopterin, thymidine) media, supplemented with dialyzed fetal calf serum, mycophenolic acid and xanthine, as described by Mulligan and Berg (*PNAS* 78:2072-2076, 1981). HAT-selected cell lines expressing capsid protein are identified following induction with $10^{-6}$ M dexamethasone by lysing the cells with Lammeli sample buffer, separating the proteins using 12% SDS-PAGE, blotting onto nitrocellulose membrane, and detecting by western blot using polyclonal rabbit anti-Sindbis antibody. FIG. 21 shows expression of capsid protein in such cells, along with wild-type BHK-21 cells as a negative control, and Sindbis virus-infected BHK-21 cells as a positive control.

Alternatively, capsid protein is expressed using the lac-inducible vectors (Stratagene) described previously. The Sindbis capsid protein gene is amplified by PCR using primers Sin7632F and Sin8439R (described previously), and ligated with TA vector DNA (Stratagene). The resulting plasmid, designated TA/SinC, is digested with Eco RI, the termini are made blunt by the addition of Klenow fragment enzyme and dNTPs, and the capsid protein gene purified from a 1% agarose gel. Plasmid vectors pOP13 and pORSV1 are digested with Not I, their termini made blunt by the addition of Klenow fragment enzyme and dNTPs, and subsequently treated with calf intestinal alkaline phosphatase. The capsid protein gene is ligated with both pOP13 and pORSV1 vector DNA to generate the expression constructs designated pOP13CAP and pORSV1CAP, respectively. Each plasmid is co-transfected with p3'SS into the appropriate cell line as described previously, and selection for stable transfectants is accomplished using G418 and hygromycin selection. Cell lines expressing capsid protein are identified following IPTG induction by immunofluorescence using polyclonal rabbit anti-Sindbis antibody.

The glycoprotein genes, E1 and E2, are expressed together using one of the inducible systems previously described. For example, the Sindbis E1 and E2 genes are amplified from plasmid pVGSP6GEN using a primer pair complementary to Sindbis nucleotides 8440-8459 (forward primer) and Sindbis nts 11,384-11,364 (reverse primer). PCR amplification is performed using a standard three-temperature cycling protocol and the following oligonucleotide pair.

Reverse primer (11384R):
(SEQ. ID NO. 75)
5'-TATATGCGGCCGCTCATCTTCGTGTGCTAGTCAG-3'

Forward primer (8440F):
(SEQ. ID NO. 85)
5'-TATATGCGGCCGCACCACCATGTCCGCAGCACCACTGGTCACG-3'

In addition to their respective complementarities, the forward primer contains an "in-frame" AUG translation initiation codon, and both primers contain a NotI recognition sequence at their 5'-ends. Following PCR amplification, the amplicon is digested with the Non enzyme and purified in a 1% agarose gel. The resulting fragment is then ligated separately into the pOP13 and pOPRSV1 vectors (Stratagene), digested with Not I and treated with calf intestinal alkaline phosphatase, as described previously. These glycoprotein expression vectors are used to transfect cells that have been previously transfected with a capsid protein expression construct, and stable glycoprotein gene transfectants are identified by selection for G418 and hygromycin resistance.

Alternatively, the E1 and E2 glycoproteins are expressed under the control of the replicon-inducible junction region promoter, described previously. The ELVIS expression plasmid pVGELVIS0SINBV-linker (Example 3) is digested with the enzyme Not I, and treated with calf intestinal alkaline phosphatase. PCR amplified Sindbis E1 and E2 glycoprotein genes digested with Not I (previous paragraph) are then ligated to the ELVIS vector to generate a construct designated pVGELVIS-E1/E2. Plasmid pVGELVIS-E1/E2 subsequently is digested with the enzyme Bsp EI, removing most of the nonstructural protein gene coding region, and the remaining E1- and E2-containing vector DNA is re-ligated to itself, creating an inducible expression cassette identified as pVGELVdl-E1/E2. This glycoprotein expression vector is used to transfect cells that have been previously transfected with a capsid protein expression construct, and stable glycoprotein gene transfectants are identified by selection for G418 resistance. For both the capsid and envelope glycoprotein expression cassettes, additional mammalian or non-mammalian (including insect)-derived promoters, which may or may not be inducible, are readily substituted for those described above, using standard techniques known in the art.

5. Assembling the Components to Create the Alphavirus Packaging Cell Line

For example purposes, the BHK-21 cell line and replicon-inducible packaging expression cassette are used to demonstrate assembly of the components. However, other possible parent cell lines can be used to create alphavirus packaging cell lines and have been discussed previously. Briefly, BHK-21 cells (CCL 10) are grown at 37° C. in 5% $CO_2$ in Dulbecco's modified Eagle's Media (DMEM), 2 mM L-glutamine, and 10% fetal bovine serum (optimal media). Approximately $5\times10^5$ BHK-21 cells, grown in a 35 mM petri dish, are transfected with 5 ug pLTR/SindIBspE using 5 ul of the Transfectam (Promega) cationic lipid reagent, in serum-free media conditions, as suggested by the supplier. However any method of transfection is rapidly substituted, i.e., by electroporation, calcium phosphate precipitation, or by using any of the readily available cationic liposome formulations and procedures commonly known in the art. At 24 hours post-transfection, the cells are trypsinized and reseeded in 100 mm dishes in 10 ml of optimal media, as described above, supplemented with 400 ug/ml of G418 (Gibco/BRL) and selected over a period of 5 to 7 days. Colonies displaying resistance to the G418 drug are then pooled, dilution cloned, and propagated. Individual clones are screened for high levels of Sindbis structural protein expression and functional packaging after transfection with Sindbis-luciferase vector RNA transcribed in vitro from Sad linearized plasmid pKSSINBV-luc (see Example 3). Specifically, clonally-derived pLTR/SindlBspE transfected BHK-21 cells (referred to as LTR/SindlBspE or BK-Bsp cells) grown in 60 mm petri dishes are transfected with 2 ug of Sindbis-luciferase vector RNA and overlayed with 3 ml of optimal Media (see above). At 20 hours post-transfection, the supernatants are removed, and clarified by centrifugation for 30 min. at 3000 rpm in a Sorvall RT6000B tabletop centrifuge. In addition, the transfected cell monolayer is lysed in reporter lysis buffer (Promega) as described by the manufacturer, and assayed for luciferase expression as described previously.

The transfer of luciferase activity (and thus functional packaging) is tested by using 1 ml of the above supernatants to infect fresh monolayers of BHK-21 cells in 60 mm dishes. At 20 hours post-infection, the cell monolayers are lysed as described above, and tested for luciferase expression. As shown in FIG. 12, three clones (#13, 18, and 4-0) produce packaged Sindbis-luciferase vector and are the first examples of alphavirus packaging cell lines. In addition, transfected clone #18 cells are tested for increased vector packaging over a timecourse following transfection. Supernatants from transfected clone #18 cells are harvested at 20, 45, and 70 hours post-transfection, as described above, and used to infect fresh monolayers of BHK-21 cells. FIG. 13 shows that Sindbis-luciferase vector packaging increases significantly at 45 hours post-transfection, as compared to 20 hours post-transfection. Expression also can be tested by western blot analysis using polyclonal rabbit anti-Sindbis antibodies (available in the literature).

C. Inducible Vector and Structural Protein Expression for Alphavirus Producer Cell Lines 1. Use of Viral Promoters The challenge of developing an alphavirus vector producer cell line lies in the question of whether a virus, whose infection of mammalian cells results almost exclusively in productive lytic cell death, can be modified to establish persistent infection in these same cells. One approach is to generate alphavirus vector producer lines from mosquito cells, where viral persistence often results after infection. However, the titer of infectious virus produced in persistently infected mosquito cells is only about $1\times10^4$ PFU/ml, at least five orders of magnitude less than that observed after lytic infection of BHK cells by Sindbis.

Several strategies are described for inducible alphavirus vector producer cell lines, containing both vector and viral structural gene cassettes, such that productive cytolytic infection occurs only after the correct stimulus. Because these approaches operate on a "feed forward" level, any leakiness in the system will result in initiation of the alphavirus replication cycle and probable cell death. Therefore, tightly regulated control mechanisms are necessary for such a system.

The hallmark of development is the differentiation state-dependent pattern of gene expression. Briefly, gene expression patterns differ widely between undifferentiated and terminally differentiated states. Thus, a cell whose differentiation state can be controlled is likely an ideal host in which to derive an alphavirus vector producer cell line. In such a configuration, the vector expression cassette and, in some instances, structural components are coupled to terminal differentiation state-inducible promoters, according to the strategy described for ELVIS, and used to transform stably an undifferentiated host cell. Terminal differentiation of the host producer cell after induction with the appropriate stimuli coincidentally results in induction of the alphavirus replication cycle and production of packaged vector. Other strategies described herein, including antisense structural genes and heterologous viral expression systems, are readily coupled with cellular differentiation state-dependent promoters described below.

In this approach, four examples are described, using either a viral or cellular promoter which are active in only terminally differentiated cells.

It has been shown that mouse Polyomavirus (Py), SV40, and Moloney murine leukemia virus (M-MuLV), all are able to infect and enter undifferentiated mouse embryonal carcinoma (EC) cells, but the expression of their genes (and heterologous genes) and establishment of productive infection is blocked (Swartzendruber and Lehman, *J. Cell. Physiol.* 85:179-188, 1975; Peries et al., *J. Natl. Cancer Inst.* 59:463-465, 1977). These viral growth properties also have been demonstrated in two cell lines, PCC4 and F9, which are derived from the malignant stem cells of mouse teratorcarcinomas. The block to viral propagation occurs at the level of transcription and replication, and maps to the enhancers, contained within the viral non-coding control regions (Linney et al., *Nature* 308:470-472, 1984; Fujimura et al., *Cell* 23:809-814, 1981; Katinka and Yaniv, *Cell* 20:393-399, 1980). When M-MuLV infects undifferentiated EC cells, the viral DNA integrates into the genome. However, as stated above, expression of viral genes or of heterologous genes is blocked. This block of viral expression is released upon terminal differentiation of EC cells by addition of retinoic acid to the growth medium.

To test the RNA expression properties of the pVGELVIS construct in EC cells, plasmid DNA is complexed with LIPO-FECTAMINE (GIBCO-BRL, Gaithersburg, Md.) according to the conditions suggested by the supplier (ca. 5 g DNA/8 g lipid reagent) and added to 35 mm wells containing undifferentiated PCC4 or F9 cells (Fujimura et al., 1981, *Cell* 23:809-814) at approximately 75% confluency. The development of cytopathic effects (CPE), and the level of Sindbis productive infection, quantitated by plaque assay of media supernatant, is determined at regular intervals over 5 days in undifferentiated and differentiated transfected PCC4 or F9 cells. Differentiation of F9 and PCC4 cells is accomplished by addition of retinoic acid (Sigma Chemical Co., St. Louis, Mo.), at a final concentration of 1 M.

It has been proposed that the hierarchy of relative expression of heterologous genes observed in undifferentiated EC cells infected with M-MuLV vectors may be in part insertional dependent (Linney et al., 1987, *J. Virol.* 61:3248-3253). Thus, undifferentiated EC cells transfected with pVGELVIS may likely produce different results, in terms of transcription of the Sindbis genomic cDNA and, in turn, initiation of the viral life cycle. In this event, following G418 selection of pVGELVIS transfected undifferentiated EC cells, remaining cells are cloned and expanded. The cell clones are then tested for the production of Sindbis virus after differentiation by addition of retinoic acid (Sigma Chemical Co., St. Louis, Mo.), at a final concentration of 1 M.

To isolate vector packaging cell lines, whose production of structural proteins in the presence of Sindbis NSP is cell differentiation state dependent, undifferentiated F9 or PCC4 cells are transfected with pLTR/SINdlBspE and G418 selected as described above. Differentiation state-sensitive clones are then selected by infection at high multiplicity with packaged SIN-luc vector. Clones which are resistant to cell lysis or do not produce packaged SIN-luc vector particles, are candidate vector packaging clones. These candidate clones are tested for SIN-luc vector particle production following terminal differentiation with retinoic acid, as described.

The murine wild type polyomavirus (Py) is unable to replicate in the teratocarcinoma cell lines PCC4 or F9. This block of replication in undifferentiated cells occurs at the level of transcription of early region (i.e., T antigen) genes, and is released by induction of terminal differentiation with vitamin A. Py mutants which are able to establish productive infection in undifferentiated PCC4 and F9 cells map to the viral enhancer region. The genesis of an embryonic tissue specific transcriptional enhancer element has resulted in these mutants. In order to exploit this property of inhibition of Py replication in undifferentiated teratocarcinoma cell lines, the viral regulatory non-coding region, including the enhancer, is coupled to the genomic cDNA of Sindbis virus, according to the ELVIS strategy. The precise transcriptional start site of the Py early region has been determined (see Tooze, DNA Tumor Viruses). The PCC4 and F9 cell lines are stably transformed with the Py-Sindbis vectors. In this model Sindbis productive infection occurs after addition of retinoic acid to the culture medium and induction of terminal differentiation.

The Py non-coding region from bases 5021-152, which includes the sequences corresponding to the viral enhancers, 21 by repeats, replication origin, CAAT and TATA boxes, and the early mRNA transcription 5' cap site, is positioned at the 5' viral end such that n vivo, only a single capped C residue is added to the Sindbis 5' end. Juxtaposition of the Py non-coding region and the Sindbis 5' end is accomplished by overlapping PCR as described in the following detail. Amplification of the Py non-coding region in the first primary PCR reaction is accomplished in a reaction containing the pBR322/Py, strain A2 plasmid (ATCC number 45017-p53.A6.6 (pPy-1)) and the following primer pair:

```
Forward primer: Pybgl5021F (buffer sequence/Bgl II
recognition sequence/Py nts 5021-5043):
                                        (SEQ. ID NO. 86)
5'-TATATAGATCTCTTGATCAGCTTCAGAAGATGGC Reverse primer: SINPy152R (SIN nts 5-1/Py nts
152-134):
                                        (SEQ. ID NO. 87)
5'-TCAATGGCGGGAAGAGGCGGTTGG
```

PCR amplification of the Py non-coding region with the primer pair shown above is performed using the Thermalase thermostable DNA polymerase (Ameresco Inc., Solon, Ohio) and the buffer containing 1.5 mM $MgCl_2$, provided by the supplier. Additionally, the reaction contains 5% DMSO, and the Hot Start Wax beads (Perkin-Elmer), using the following PCR amplification protocol shown below:

| Temperature (° C.) | Time (Min.) | No. Cycles |
|---|---|---|
| 94 | 2 | 1 |
| 94 | 0.5 | |
| 55 | 0.5 | 35 |
| 72 | 0.5 | |
| 72 | 10 | 1 |

Amplification of the Sindbis 5' end in the second primary PCR reaction is accomplished in a reaction containing the pVGSP6GEN clone and the following primer pair:

```
Forward primer: (Py nts 138-152/SIN nts 1-16):
                                              (SEQ. ID NO. 88)
5'-CCGCCTCTTCCCGCCATTGACGGCGTAGTAC Reverse primer: (SIN nts 3182-3160):
                                              (SEQ. ID NO. 18)
5'-CTGGCAACCGGTAAGTACGATAC
```

PCR amplification of Sindbis 5' end region with the primer pair shown above is with the reaction conditions described above, using the following PCR amplification protocol shown below:

| Temperature (° C.) | Time (Min.) | No. Cycles |
|---|---|---|
| 94 | 2 | 1 |
| 94 | 0.5 | |
| 55 | 0.5 | 35 |
| 72 | 3.0 | |
| 72 | 10 | 1 |

The 442 by and 3202 by products from the primary PCR reactions are purified with GENECLEAN (BIO 101), and used together in a PCR reaction with the following primer pain

```
Forward primer: Pybg15021F (buffer sequence/Bgl II
recognition sequence/Py nts 5021-5043):
                                              (SEQ. ID NO. 89)
5'-TATATAGATCTCTTGATCAGCTTCAGAAGATGGC Reverse primer: (SIN nts 2300-2278):
                                              (SEQ. ID NO. 19)
5'-GGTAACAAGATCTCGTGCCGTG
```

PCR amplification of the of the primer PCR amplicon products with the primer pair shown above is with the reaction conditions described above, using the following PCR amplification protocol shown below:

| Temperature (° C.) | Time (Min.) | No. Cycles |
|---|---|---|
| 94 | 2 | 1 |
| 94 | 0.5 | |
| 55 | 0.5 | 35 |
| 72 | 3.0 | |
| 72 | 10 | 1 |

The 20 3' terminal bases of the first primary PCR amplicon product overlaps with the 20 5' terminal bases of the second primary PCR amplicon product; the resultant 2,742 by overlapping secondary PCR amplicon product is purified by 0.8% agarose/TBE electrophoresis, digested with Bgl II, and the 2,734 by product is ligated into pcDNASINbgl/xba (see Example 3) treated with Bgl II and CIAP. The resulting construction is 16,641 bps and is known as ELVIS-PySIN. In order to construct a structural protein expression vector similar to pLTR/SindlBsp for the derivation of vector packaging cell lines, the ELVIS-PySIN construction is digested to completion with Bsp EI, and religated under dilute conditions, in order to accomplish deletion of the nonstructural proteins between bases 422-7054. This construction is known as ELVIS-PySINdlBspE.

ELVIS-PySIN plasmid DNA is complexed with LIPOFECTAMINE (GIBCO-BRL, Gaithersburg, Md.) according to the conditions suggested by the supplier (ca. 5 g DNA/8 g lipid reagent) and added to 35 mm wells containing undifferentiated PCC4 or F9 cells at approximately 75% confluency. The development of cytopathic effects (CPE), and the level of Sindbis productive infection, quantitated by plaque assay of media supernatant, is determined at regular intervals of 5 days in undifferentiated and differentiated PCC4 or F9 cells. Differentiation of F9 and PCC4 cells is accomplished by addition of retinoic acid (Sigma Chemical Co., St. Louis, Mo.), at a final concentration of 1 mM.

If the undifferentiated EC cells demonstrate a heterologous response to transfection with ELVIS-PySIN, remaining cells not lysed by Sindbis virus propagation following G418 selection of pVGELVIS transfected undifferentiated EC cells are cloned and expanded. The cell clones are then tested for the production of Sindbis virus after differentiation, by addition of retinoic acid (Sigma Chemical Co., St. Louis, Mo.), at a final concentration of 1 mM.

Isolation of vector packaging cell lines stably transfected with ELVIS-PySINdlBspE, having a cell differentiation state dependent pattern of expression of structural proteins in the presence of Sindbis NSP, is accomplished as described above for the pLTR/SindlBspE plasmid.

Figure 14:
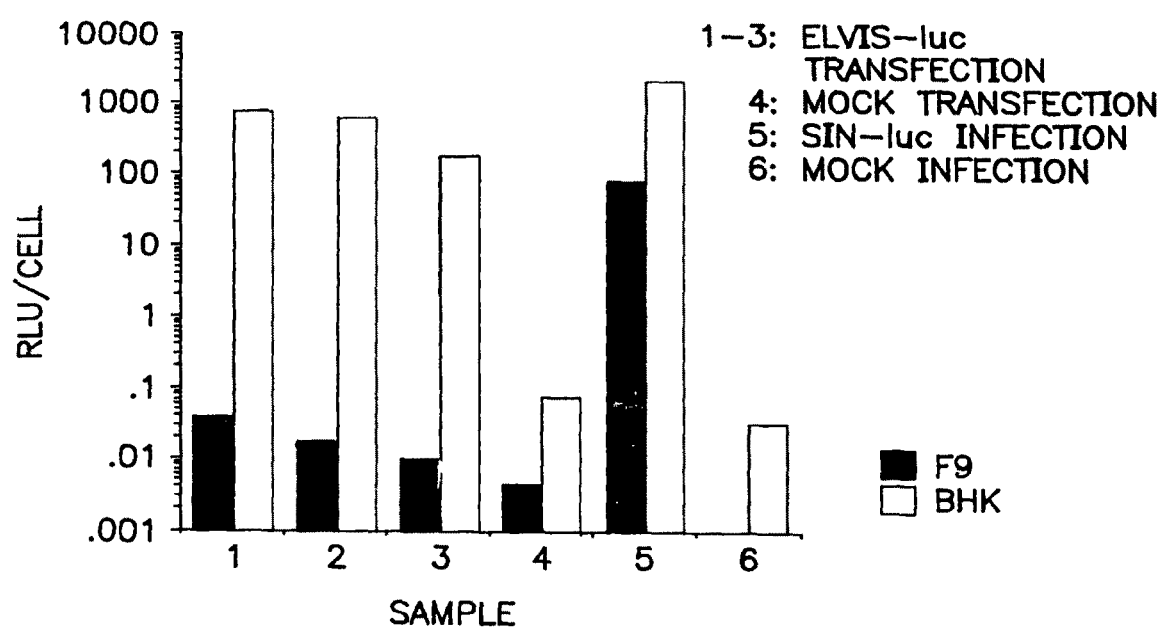
FIG. 14 is a bar graph which depicts the level of expression by several different luciferase vectors in BHK cells and undifferentiated F9 cells.
Figure 15:
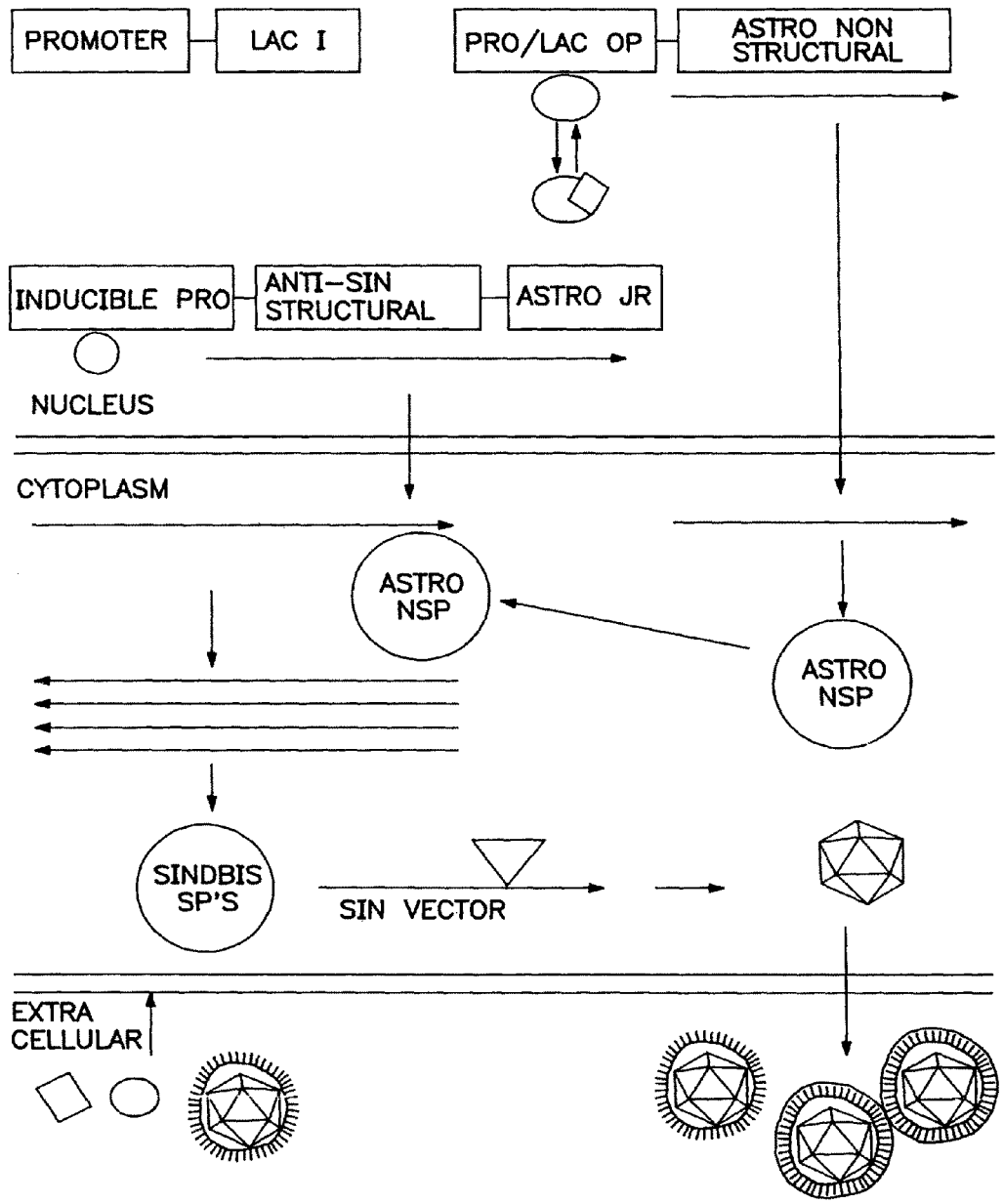
FIG. 15 is a schematic illustration of how Astroviruses or other heterologous viruses may be used to express Sindbis structural proteins.

In order to demonstrate the feasibility of an inducible Sindbis vector producer cell line, the reporter gene expression from the ELVIS-luc vector, whose construction is described in Example 3, section E, after transfection of BHK and undifferentiated F9 cells is determined. In addition, both cell types are infected with packaged SIN-luc vector, whose production is described in Example 3 section C. This later experimental group serves as a control that expression restriction (if any) lies at the level of transcription rather than a receptor difference on unique cell types. The results of this study, shown in FIG. 14, demonstrate that the expression of luciferase is inhibited in undifferentiated F9 cells. The level of luciferase expression in BHK cells transfected with ELVIS-luc and BHK and undifferentiated F9 cells infected with packaged SIN-luc vector is similar. Thus, in ELVIS-luc transfected undifferentiated F9 cells, transcription from the LTR and subsequent luciferase expression via the Sindbis vector autocatalytic pathway is inhibited. This study demonstrates that packaging cell lines can be developed where synthesis of Sindbis vector or Sindbis vector packaging is inducible and controlled by the differentiation state of the cell.

2. Use of Cellular Promoters.

The third example of this strategy uses the β-globin locus control region. The 0-globin multigene cluster contains five developmentally regulated genes. In the early stages of human development, the embryonic yolk sac is the hematopoietic tissue and expresses the ε-globin gene. This is followed by a switch to the γ-globin gene in the fetal liver and the δ- and β-globin genes in adult bone marrow (Collins and Weissman, 1984, *Prog. Nucleic Acid Res. Mol. Biol.* 31:315).

At least two mouse erythroleukemia lines, MEL and Friend, serve as models for terminal differentiation dependent expression of β-globin. Expression of β-globin is observed in these lines only after induction of terminal differentiation by addition of 2% DMSO to the growth medium.

The entire β-globin locus is regulated by the locus control region (LCR). Within the LCR is the dominant control region (DCR) residing within the DNase I hypersensitive region, which is 5' of the coding region The DCR contains five DNase I hypersensitive (HS1-HS5) sites. The DCR directs high level site of integration independent, copy number dependent expression on a linked human βglobin gene in transgenic mice and stably transfected mouse erythroleukemia (MEL) cells (Grosveld et al., 1993, *CSHSQB* 58:7-12). In a recent study (Ellis et al., 1993, *EMBO* 12:127-134), concatamers of a synthetic core coinciding to sequences within HS2 were shown to function as a locus control region.

In order to accomplish the differentiation state dependent expression of alphavirus vectors, the viral genomic cDNA is juxtaposed with a promoter containing a tandem synthetic core corresponding to the LCR HS2 site. Alternatively, the desired alphavirus vector construct can be inserted downstream of the LCR in the endogenous-globin gene by homologous recombination. In such a strategy, the β-globin transcription initiation site after terminal differentiation would be first determined, in order that the alphavirus vector could be placed precisely at the start site.

Initiation of a lytic viral life cycle is controlled by the differentiation state of the host cell is applicable to other systems, where the control of viral induced cytopathology is desired.

Yet another approach to regulating alphavirus gene expression through a differentiation state sensitive promoter is the use of the retinoic acid receptor a (RARA) and acute promyelomonocytic leukemia cells (APL). APL cells are clonal myeloid precursors characterized by high growth rate and differentiation arrest. A non-random chromosomal translocation breakpoint, t(15; 17)(q22; 21), occurs in almost all patients with APL. The RARA gene has been localized to chromosome 17q21. Analysis of APL mRNA from patients has shown that most APL breakpoints occur within the second intron of the RARA gene and result in abnormal fusion transcripts. Co-transfection assays with RARA and PML-RARA fusion cDNAs have demonstrated that the resulting fusion proteins can antagonize wild-type RARA in the presence of retinoic acid. These studies implicate PML-RARA fusion protein in the molecular pathogenesis of APL. Importantly, a significant number of patients achieve complete remission after all-trans retinoic acid treatment (ATRA). High concentration of ATRA may overcome the RARA deficiency leading to high levels of RA in the nucleus. Differentiation of the APL cells can then be achieved through activation of RARA responsive genes. RA can induce differentiation of a number of cell lines, including the human leukemia line HL-60.

The retinoic acid receptor is a member of a nuclear receptor superfamily that includes the thyroid and steroid hormone receptors. Four different forms of the human RAR have been identified, and the corresponding cDNAs cloned and characterized. In order to accomplish the differentiation state dependent expression of Sindbis vectors, viral genomic cDNA is juxtaposed with the RARA DNA binding site, creating ELVIS-RARASIN. As with the strategy proposed for ELVIS-PySIN expression in undifferentiated EC cells, differentiation sensitive ELVIS-RARASIN expressing cells are isolated.

3. Insertion of Vector Constructs into Differentiation State Controlled Inducible Promoters.

Generation of clones whose expression of heterologous genes from Sindbis vectors positioned in the ELVIS configuration as described in Example 3 is differentiation state dependent, is accomplished as described above for the pVGELVIS, pLTR/SindlBspE plasmids. Generation of clones whose production of vector particles is differentiation state dependent, is accomplished by transfecting the isolated differentiation dependent vector packaging clones described above with ELVIS heterologous gene expression vectors. Clones having the desired phenotype or vector production after retinoic acid induced differentiation are isolated as described above.

D. Structural Protein Expression from a Heterologous Astrovirus Junction Region.

Among the critical properties of a vector packaging system are a cell line which expresses the structural components necessary to generate an infectious particle, without the creation of wild-type virus through recombination between vector and structural gene components. These two desired properties of the packaging cell line are accomplished in the retrovirus based systems through the constitutive expression of the gag/pol and env genes on individual heterologous RNA polymerase II expression cassettes.

Another important aspect of vector packaging cell lines is to derive a system which mimics as closely as possible the normal replication strategy of the wild type virus. This issue is important in terms of the observed titer level of packaged recombinant vector. Synthesis of the viral structural proteins during alphavirus infection is accomplished after transcription of high levels of subgenomic mRNA from the junction region promoter, followed by efficient translation into the structural proteins. The junction region promoter is functional only in the antisense orientation and synthesis of the antigenomic RNA occurs after translation of the nonstructural proteins, thus delaying the expression of the structural proteins. It follows that, with regard to alphavirus, it would be desirable to construct a packaging cell line in which synthesis of the structural proteins is initiated from the junction region promoter, which in turn is activated by nonstructural proteins expressed from the recombinant vector molecule.

It is known that a relatively high frequency of recombination occurs between RNA genomic molecules occurs during infection with Sindbis virus via a copy choice mechanism (*PNAS* 88:3253-3257, 1991). Recombination between vector and junction region/structural gene cassettes would result in the generation of wild-type Sindbis virus, perhaps at a level of 1 wild-type virus per million of packaged vector particles (*Liljestrom Bio Technology* 9:1356-1361, 1991). One way to mitigate the generation of wild-type virus is to separate the structural genes onto separate expression cassettes, an approach which has been discussed previously in Example 7.

An additional approach to diminish the level of wild-type virus production in alphavirus vector packaging cell lines is to express the structural proteins under the control of Astrovirus genetic elements. A schematic for this configuration is depicted in FIG. 15. Similar to alphaviruses, the expression of Astrovirus structural proteins incorporates a junction region strategy, in which high levels of structural proteins are synthesized from a subgenomic message. The Astrovirus expression cassette may consist of one of the two following ordered elements: (1) inducible promoter/Astrovirus 5' end/Astrovirus junction region/alphavirus structural gene/Astrovirus 3' end, or (2) antisense Astrovirus 3' end/antisense alphavirus structural gene/antisense Astrovirus junction region/antisense Astrovirus 5' end/Hepatitis Delta virus ribozyme, or other configurations described in Example 7. In both configurations, the expression unit is amplified by the Astrovirus nonstructural proteins through the same mechanism that occurs during viral replication. Since multiple rounds of subgenomic mRNA synthesis initiated from the junction region occur from each expression unit, amplification of the expression unit by the Astrovirus nonstructural proteins results in the production of very high levels of alphavirus structural proteins. The second configuration of the alphavirus structural protein expression cassette described above may function better than the first, because the primary transcript of the toxic alphavirus structural gene is antisense. Although expression of the structural genes in the first configuration should not occur until synthesis of the negative strand followed by synthesis of the positive subgenomic RNA from the junction region, the antisense nature of the primary transcript in the second configuration represents an additional level of control to prevent cytotoxic protein expression.

It is likely that no wild-type virus would be generated in a packaging cell line in which the alphavirus virus structural proteins are synthesized individually from Astrovirus junction region expression cassettes. Recombination between the nonstructural protein region of the vector and an Astrovirus structural protein expression cassette would result in a molecule in which Astrovirus cis elements were coupled with alphavirus genes, a nonviable combination. Correct coupling of alphavirus cis and trans elements would require two precise recombination events between the vector and the Astrovirus expression cassette, between the Astrovirus junction-region and structural gene ATG, and between the structural gene termination codon and the Astrovirus 3' end. In order to generate wild type virus, this dual recombination event would have to occur three times on the same molecule (six total events), to incorporate the three separated alphavirus structural genes.

In order to diminish any possible toxicity of the Astrovirus proteins, synthesis of the Astrovirus expression cassettes may also be controlled by inducible promoters. One possibility is to use the lac operon, according to the "lac-switch" system described previously in Example 7 (Stratagene). The constitutive level of expression of the lac operon controlled gene in the absence of the gratuitous inducer IPTG is about 10 copies of RNA per cell. The inducible promoter corresponding to the Astrovirus/alphavirus structural gene expression cassette may be the lac operon or other suitable promoters which have very low level of constitutive expression. Construction of packaging cell lines of these configurations, in which the control of alphavirus proteins is directed by a heterologous virus should result in the generation of high titer wild-type virus free packaged vector particles.

Example 8

Alternative Viral Vector Packaging Techniques

Various alternative systems can be used to produce recombinant alphavirus particles carrying the vector construct. Each of these systems takes advantage of the fact that baculovirus, and the mammalian viruses vaccinia and adenovirus, among others, have been adapted recently to make large amounts of any given protein for which the gene has been cloned. (Smith et al., *Mol. Cell. Biol.* 3:12, 1983; Piccini et al., *Meth. Enzymology* 153:545, 1987; and Mansour et al., *Proc. Natl. Acad. Sci. USA* 82:1359, 1985). These and other viral vectors are used to produce proteins in tissue culture cells by insertion of appropriate genes into the viral vector and can be readily adapted to make alphavirus vector particles.

For example, adenovirus vectors are derived from nuclear replicating viruses and can be modified so they are defective. Heterologous genes are inserted into these vectors either by in vitro construction (Ballay et al., *EMBO J.* 4:3861, 1985) or by recombination in cells (Thummel et al., *J. Mol. Appl. Genetics* 1:435, 1982), and used to express proteins in mammalian cells. One preferred method is to construct plasmids using the adenovirus major late promoter (MLP) driving: (1) alphavirus structural proteins; and (2) an alphavirus vector construct. The alphavirus vector in this configuration still contains a modified junction region, and would allow the transcribed RNA vector to be self-replicating, as in previously described configurations.

These plasmids are then used to make adenovirus genomes in vitro (Ballay et al., *EMBO. J.* 4:3861, 1985). The recombinant adenoviral genomes, which are replication defective, are separately transfected into 293 cells (ATCC #CRL 1573, a human cell line making adenovirus E1A protein), to yield pure stocks of defective adenovirus vectors expressing either alphavirus structural proteins or alphavirus vectors. Since the titres of such vectors are typically $10^7$-$10^{11}$/ml, these stocks are then used to infect tissue culture cells simultaneously at high multiplicity of infection, resulting in the production of alphavirus proteins and vector genomes at high levels. Since the adenovirus vectors are defective, little or no direct cell lysis will occur and vectors are harvested from the cell supernatants. Similar approaches are readily carried out using recombinant vaccinia virus vectors constructed by inserting the alphavirus sequences into the shuttle plasmid pK (Bergmann et al., *Eur. J. Immunol.* 23:2777, 1993) for in vivo recombination into the vaccinia WR strain.

Other viral vectors, such as those derived from unrelated vectors (e.g., RSV, MMTV or HIV), also may be used in the same manner to generate packaged vectors from primary cells. In one embodiment, these adenoviral vectors are used in conjunction with primary cells, giving rise to recombinant alphavirus particles.

An alternative expression system also has been described in which chimeric HIV/poliovirus genomes result in the generation of chimeric minireplicons (*J. Virol.* 65:2875, 1991) capable of expressing fusion proteins. These chimeric poliovirus minireplicons, in which HIV-1 gag-pol sequences were substituted for the VP2 and VP3 capsid genes of the P1 capsid of poliovirus, were later demonstrated to be encapsidated and produce infectious particles by using a recombinant vaccinia virus (VV-P1) that expresses the substituted poliovirus capsid precursor P1 proteins defective in the chimeric minireplicon (*J. Virol.* 67:3712. 1993). For use in accordance with this invention, the alphavirus vector genome is substituted for the P1 capsid sequences and used as a means for providing polio-pseudotyped alphavirus vectors after transfecting in vitro transcribed alphavirus vector RNA transcripts into the cell line. Conversely, alphavirus structural proteins also may be substituted for the VP2 and VP3 proteins, subsequently providing an alternative packaging cell line system for alphavirus based vectors.

In an alternative system, several components are used, including: (1) alphavirus structural proteins made in the baculovirus system using techniques described by Smith et al. (supra) (or in other protein production systems, such as yeast or *E. coli*); (2) viral vector RNA made in the known T7, SP6 or other in vitro RNA-generating system (Flamant et al., *J. Virol.* 62:1827, 1988); (3) tRNA transcribed in vitro or purified from yeast or mammalian tissue culture cells; (4) liposomes (with embedded envelope glycoproteins); and (5) cell extract or purified necessary components when identified (typically from mouse cells) to provide RNA processing, and any or other necessary cell-derived functions.

Within this procedure, components (1), (2) and (3), from above, are mixed, and then envelope glycoprotein associated alphavirus proteins, cell extract and pre-liposome mix (lipid in a suitable solvent) are added. In an alteration of the procedure, the alphavirus envelope glycoproteins are embedded in the liposomes prior to addition to the mixture of (1), (2), and (3). The resulting mixture is then treated (e.g., by sonication, temperature manipulation, or rotary dialysis) to allow envelopment of the viral nucleocapsid particles with lipid plus embedded alphavirus envelope glycoprotein in a manner similar to that for liposome encapsidation of pharmaceuticals (Gould-Fogerite et al., *Anal. Biochem.* 148:15, 1985). This or

Example 9

Cell Line or Tissue Specific Alphavirus Vectors—"Hybrid Envelopes"

The tissue and cell-type specificity of alphaviruses is determined primarily by the virus-encoded envelope proteins, E1 and E2. These virion structural proteins are transmembrane glycoproteins embedded in a host cell-derived lipid envelope that is obtained when the viral particle buds from the surface of the infected cell. The envelope surrounds an icosahedral nucleocapsid, comprised of genomic RNA complexed with multiple, highly ordered copies of a single capsid protein. The E1 and E2 envelope glycoproteins are complexed as heterodimers which have been reported to assemble into trimeric structures, forming the characteristic "spikes" on the virion surface. In addition, the cytoplasmic tails of these proteins interact with the nucleocapsids, initiating the assembly of new viral particles (*Virology* 193:424, 1993). Properties ascribed to the individual glycoproteins of Sindbis virus include receptor binding by glycoprotein E2 (*Virology* 181: 694, 1991) and glycoprotein E1-mediated fusion of the virion envelope and the endosomal membrane, resulting in delivery of the nucleocapsid particle into the cytoplasm (*New Aspects of Positive-Stranded RNA Virus*, pp. 166-172, 1990).

The present invention recognizes that by disrupting glycoprotein activity (in particular, but not limited to that of E2) and co-expressing an intact heterologous glycoprotein, or by creating hybrid envelope gene products (i.e., specifically, an alphavirus envelope glycoprotein having its natural cytoplasmic domain and membrane-spanning domain, with its exogenous binding domain replaced by the corresponding domain(s) from a different envelope glycoprotein, or by replacing the E2 and/or E1 glycoproteins with those of other alphaviruses or their derivatives which differ from that of the vector in their tissue tropism, the host range specificity may be altered without disrupting the cytoplasmic functions required for virion assembly. Alternatively, by replacing one or more of the alphavirus structural proteins with the structural protein(s) of another virus and introducing the corresponding viral packaging sequence into the alphavirus vector construct, assembly of recombinant alphavirus vector constructs into particles of other virus types can be achieved. Thus, recombinant alphavirus particles can be produced which have an increased affinity for pre-selected target cells, depending on the tropism of the protein molecule(s) or domain(s) introduced.

In one embodiment, substitution of the analagous envelope glycoproteins E1 and/or E2 from other alphaviruses or their variants is performed to alter tissue tropism. For example, Venezuelan equine encephalitis virus (VEE) is an alphavirus which exhibits tropism for cells of lymphoid origin, unlike its Sindbis virus counterpart. Therefore, Sindbis-derived vector constructs packaged in a cell line expressing the VEE structural proteins display the same lymphotropic properties as the parental VEE virus from which the packaging cell structural protein gene cassette was obtained.

Specifically, the Trinidad donkey strain of VEE virus (ATCC #VR-69) is propagated in BHK-21 cells, and virion RNA is extracted using procedures similar to those described in Example 1. The entire structural protein coding region is amplified with a primer pair whose 5'-ends map, respectively, to the authentic AUG translational start site, including the surrounding Kozak consensus sequence, and UGA translational stop site. The forward primer is complementary to VEE nucleotides 7553-7579, and the reverse primer is complementary to VEE nucleotides 11206-11186 (sequence from Kinney et al., *Virology* 170:19-30, 1989). PCR amplification of VEE cDNA corresponding to the structural protein genes is accomplished using a two-step reverse transcriptase-PCR protocol as described above, the VEE genome RNA as template, and the following oligonucleotide pair.

```
Forward primer (VEE 7553F):
                                      (SEQ. ID NO. 90)
5'-TATATATATGCGGCCGCACCGCCAAGATGTTCCCGTTCCAGCCA-3'

Reverse primer (VEE 11206R):
                                      (SEQ. ID NO. 91)
5'-TATATATATGCGGCCGCTCAATTATGTTTCTGGTTGGT-3'
```

In addition to their respective complementarities to the indicated VEE nucleotides, each primer includes a Not I recognition sequence at their 5' ends. Following PCR amplification, the 3800 by fragment is purified in a 1% agarose gel and digested with the enzyme Not I. The resulting fragment is then ligated separately into the pOP13 and pOPRSVI vectors (Stratagene) described previously, which are digested with Not I and treated with calf intestinal alkaline phosphatase. These resulting vectors, which contain the entire VEE structural protein coding sequence, are known as pOP13-VEESP and pOPRSV1-VEESP. The use of these clones in the development of VEE-based packaging cell lines follows that described for Sindbis packaging lines. Alternatively, the PCR amplified VEE structural protein gene fragment digested with NotI is ligated into the replicon inducible ELVIS cassette described in Example 7. Plasmid pVGELVISBV-linker is digested with Bsp E1 to remove most nonstructural protein coding sequences, and the vector is then re-ligated with itself to generate the construct pVGELVISdI-linker. Subsequently, this plasmid is digested with NotI, treated with calf intestinal alkaline phosphatase, and ligated with the NotI digested VEE fragment to generate the expression cassette pVGELVdIVEE. Plasmid DNA of this construct is transfected into the appropriate cell line and selection for G418 resistance is performed as described in Example 7. In addition, variations of the vector-inducible or lac operon-VEE structural protein gene expression vectors may be constructed using other systems described herein. Additionally, other variations may be constructed which combine the capsid protein gene of one alphavirus (for example, Sindbis) with the envelope glycoprotein genes of another alphavirus (for example, VEE) in a split gene approach, as described in Example 7. Furthermore, variants of VEE, and other alphaviruses and their variants differing in tissue tropism, are useful when following this approach.

In another embodiment, a RNA packaging signal derived from another virus is inserted into the alphavirus vector to allow packaging by the structural proteins of that corresponding virus. For example, the 137 nt. packaging signal from hepatitis B virus, located between nts. 3134 and 88 and spanning the precore/core junction (Junker-Niepmann et al. *EMBO J.* 9:3389, 1990), is amplified from an HBV template using two oligonucleotide primers. PCR is performed using a standard three temperature cycling protocol, plasmid pHBV1.1 (Junker-Niepmann et al. *EMBO J.* 9:3389, 1990) as the template, and the following oligonucleotide pair, each of which contain 20 nucleotides complementary to the HBV sequence and flanking ApaI recognition sequences:

```
Forward primer (HBVpkgF):
                                (SEQ ID NO: 117)
5'-TATATGGGCCCTACATGTCCCACTGTTCAAG-3'

Reverse primer (HBVpkgR):
                                (SEQ ID NO: 118)
5'-TATATGGGCCCGTACGGAAGGAAAGAAGTCA-3'
```

Following amplification, the PCR amplicon is digested with ApaI and purified from a 1.5% agarose gel using MERMAID™ (Bio101). Sindbis vector plasmid pKSSINdlJRsjrc (Example 3) also is digested with ApaI, under limited conditions to cleave at only one of its two sites, followed by treatment with CIAP, purification from a 1% agarose gel, and ligation with the above-synthesized HBV amplicon, to produce a construct designated pKSSINhbvJR. Other alphavirus vectors (see Example 3) are readily modified in a similar manner. Cell lines which express the HBV core, preS/S, and P proteins necessary for packaging of the RNA sequence are derived by modification of helper plasmid pCH3143 (Junker-Niepmann et al., EMBO J. 9:3389, 1990) to include a selectable marker. An expression cassette containing the neomycin resistance marker is obtained by digestion of plasmid pBK-RSV (Stratagene) with Mst II and blunt-ending with Klenow fragment. The selectable marker is then ligated into any one of several unique sites within pCH3143 that have been digested and their termini made blunt. The resulting construct is transfected into a desired cell line, for example, mouse hepatoma line Hepal-6 (ATCC #CRL1830), and selected using the drug G418, as described in Example 7. Introduction of the pKSSINhbvJR vector, or related RNA- or DNA-based alphavirus vectors, results in the production of packaged vector particles with the same hepatotropism as HBV.

Similarly, the packaging signal from a coronavirus can be incorporated into the alphavirus vector. For example, the 190 nt packaging signal from mouse hepatitis virus (MH'V), comprising nts 2899 to 3089 (Fosrmire et al., *J. Virol* 66:3522, 1992), is amplified in a standard three cycle PCR protocol using THERMALASE™ polymerase, DIssF plasmid MP51-2 (Fosmire et al., *J. Virol* 66:3522, 1992) as the template, and the following oligonucleotides, which contain flanking ApaI recognition sites:

```
Forward primer (MHVpkgF):
                                        (SEQ ID NO: 119)
5'-TATATGGGCCCATTTTGGTITTGCTATGCGTA-3'

Reverse primer (MHVpkgF):
                                        (SEQ ID NO: 125)
5'-TATATGGGCCCATCGAGGTGAGAAAGAGGAC-3'
```

Following amplification, the PCR amplicon is digested with ApaI, purified from a 1.5% agarose gel using MERMAID™, and ligated into pKSSINdlJRsjrc, prepared as described for HBV. The resulting construct is designated pKSSINmhvJR. Other alphavirus vectors (see Example 3) are readily modified in a similar manner. Packaging of vectors modified with this MHV sequence is accomplished by using expression cassettes which produce each of the required coronavirus structural proteins: nucleocapsid (N protein; Armstrong et al., *NAR* 11:883, 1983); membrane (M protein, Armstrong et al., *Nature* 308:751, 1984); and spike (S protein, Luytjes et al., *Virology* 161:479, 1987). Preferably, these proteins are inserted into the vector-inducible pVGELVSdl-linker plasmid (described previously in this example) and selected for with the 0418 drug following transfection into the appropriate cell type. Other expression methodologies (see Example 7) may also be readily utilized. Additional coronaviruses, for example, human coronaviruses OC43 (ATCC #VR-759) and 229E (ATCC #VR-740), can be readily used in place of MHV to produce packaged recombinant alphavirus particles which show tropism for cells in the respiratory tract.

Similarly, the packaging signal from a retrovirus can be incorporated into an alphavirus vector construct. For example, the 351 nt extended packaging signal (Ψ+) from Mo-MLV, corresponding to nts 212 to 563 (Mann et al., *Cell* 33:153, 1983), is amplified in a standard three cycle PCR protocol as described above, using plasmid pMLV-K (Miller, *J. Virol.* 49:214, 1984) as template and the following oligonucleotides, each of which contain a flanking ApaI recognition site:

```
Forward primer (MLVpkgF):
                                        (SEQ ID NO: 126)
5'-TATATGGGCCCTGTATCTGGCGGACCCGTGG-3'

Reverse primer (MLVpkgR):
                                        (SEQ ID NO: 127)
5'-TATATGGGCCCGCAGACAAGACGCGCGGCGC-3'
```

Following amplification, the PCR amplicon is digested with ApaI, purified from a 1.5% agarose gel using GENECLEAN™, and ligated into plasmid pKSSINdlJRsjrc, prepared as described above. The resulting construct is designated pKSSINmlvJR. Other alphavirus vectors (see Example 3) are readily modified in a similar manner. The generation of a retroviral-derived producer cell line for packaging and production of the above alphavirus vector constructs is accomplished by transfecting an appropriate packaging cell line, for example amphotropic line DA (WO 92/05266), and selecting for resistance to the drug G418, as described previously.

In each case, the packaging sequences from HBV, coronavirus, retrovirus, or any other virus, also may be incorporated into alphavirus vectors at locations other than those outlined above, provided the location is not present in the subgenomic transcript. For example, the next most preferable site of insertion is the carboxy-terminal region of nonstructural protein 3, which has been shown to be highly variable in both length and sequence among all alphaviruses for which sequence information is available. Further, these applications are not limited by the ability to derive the corresponding packaging cell lines, as the necessary structural proteins also may be expressed using any of the alternative approaches described in Example 8.

In yet another embodiment, a heterologous glycoprotein or cellular ligand is expressed in the lipid bilayer of a packaging cell line for producing enveloped recombinant alphavirus particles. This approach is similar to that described in Example 8 for the production of VSV-G pseudo-typed alphavirus vectors, except that in this configuration, the E2 receptor-binding function is inactivated by insertion, deletion, or site-specific mutagenesis. As an example, receptor binding function of E2 can be inactivated by techniques known in the art to restrict vector particle tropism to that which is supplied by the heterologous glycoprotein or cellular ligand. In addition to the example of VSV-G pseudo-typing, other viral glycoproteins which target specific cellular receptors (such as the retroviral HIV gp120 protein for CD4 cell targeting) are utilized when expressed from standard vectors stably transfected into alphavirus packaging cell lines.

In another configuration, chimeric glycoproteins are prepared which allow for targeting of alphavirus vector constructs into particular cell lines in vitro or tissue types in vivo.

To construct such a chimeric glycoprotein, specific oligonucleotides encoding the ligand binding domain of the desired receptor, plus homologous alphavirus sequences (which include a unique specific restriction endonuclease site), are used to amplify an insert sequence that can be substituted into an alphavirus structural protein expression cassette. Alternatively, limited Bal-31 digestions from a convenient restriction enzyme site are performed in order to digest back to a permissive insertion site, followed by blunt end ligation of a fragment encoding a small receptor binding domain, an entire viral glycoprotein, or cell surface ligand. As an example, peptides corresponding to the principal neutralizing domain of the HIV gp120 envelope protein (*Virology* 185:820, 1991) can be used to disrupt normal E2 tropism and provide CD4 cell targeting.

While inclusion of the HIV gp120 neutralizing domain illustrates one example of a hybrid or chimeric envelope protein, the possibilities are not limited to viral glycoproteins. For example, the receptor binding portion of human interleukin-2 can be combined with the envelope protein(s) of an alphavirus to target vectors to cells with IL-2 receptors. Furthermore, the foregoing technique can be used to create a recombinant alphavirus particles with envelope proteins that recognize Fc portions of antibodies. Monoclonal antibodies which recognize only preselected target cells are then bound to such Fc receptor-bearing alphavirus vector particles, such that the vector particles bind to and infect only those preselected target cells (for example, tumor cells). Alternatively, a hybrid envelope with the binding domain of avidin is used to target cells that have been coated with biotinylated antibodies or other ligands. The patient is first flooded with antibodies, and then allowed time to clear unbound and nonspecifically-bound antibody before administering the vector. The high affinity ($10^{-15}$) of the avidin binding site for biotin will allow accurate and efficient targeting to the original tissue identified by the monoclonal "image". Additional targeting approaches are known in the art and can readily be adopted for use in the practice of the present invention. For example, see U.S. Ser. No. 08/242,407.

Example 10

Lactose Formulation of a Recombinant Alphavirus Vector

Crude recombinant alphavirus particles are obtained from a Celligan bioreactor (New Brunswick, N.J.) containing packaging cells transfected or transduced with the alphavirus vector construct, and bound to the beads of the bioreactor matrix. The cells release the packaged recombinant alphavirus particles into growth media that is passed over the cells in a continuous flow process. The media exiting the bioreactor is collected and passed initially through a 0.8 micron filter, then through a 0.65 micron filter to clarify the crude recombinant alphavirus particles. The filtrate is concentrated utilizing a cross flow concentrating system (Filtron, Boston, Mass.). Approximately 50 units of DNase (Intergen, New York, N.Y.) per nil of concentrate is added to digest exogenous DNA. The digest is diafiltrated using the same cross flow system to 150 mM NaCl, 25 mM tromethamine, pH 7.2. The diafiltrate is loaded onto a Sephadex S-500 gel column (Pharmacia, Piscataway, N.J.), equilibrated in 50 mM NaCl, 25 mM tromethamine, pH 7.4. The purified recombinant alphavirus particles are eluted from the Sephadex S-500 gel column in 50 mM NaCl, 25 mM tromethamine, pH 7.4.

The formulation buffer containing lactose is prepared as a 2× concentrated stock solution. The formulation buffer contains 25 mM tromethamine, 70 mM NaCl, 2 mg/ml arginine, 10 mg/ml human serum albumin (HSA), and 100 mg/ml lactose in a final volume of 100 mls at a pH 7.4.

The purified recombinant alphavirus particles are formulated by adding one part 2× lactose formulation buffer to one part S-500 purified recombinant alphavirus particle preparation. The formulated recombinant alphavirus particles can be stored at −70° C. to −80° C. or dried.

The formulated alphavirus particles are lyophilized in an Edwards Refrigerated Chamber (3 Shelf RC3S unit) attached to a Supermodulyo 12K freeze dryer (Edwards High Vacuum, Tonawanda, N.Y.). When the freeze drying cycle is completed, the vials are stoppered under a vacuum following a slight nitrogen gas bleeding. Upon removal, vials are crimped with aluminum seals. The lyophilized recombinant alphavirus particles are reconstituted with 1.0 ml water or other physiologically acceptable diluent.

Example 11

Administration of Recombinant Alphavirus Particles

A therapeutic alphavirus vector used for the treatment of Gaucher disease (see Example 17) may be administered by transducing autologous CD34$^+$ cells in an ex vivo protocol or by direct injection of the vector into the patient's bone marrow. In order to achieve the longest therapeutic expression of GC from the recombinant multivalent vector, the best mode of administration is to transduce long lived cell precursors of the clinically affected cell type, for example monocytes or macrophages. By transducing the earliest precursors of the effected cell type, the cell precursors are able to self renew and repopulate the peripheral blood with maturing GC positive cells. The earliest pluripotent hematopoietic stem cell studied to date are the CD34$^+$ cells which make up 1%-4% of a healthy bone marrow population or 0.1% in the peripheral blood population. Being able to transduce CD34$^+$ cells is important in sustaining long term expression not only for the monocyte/macrophage lineage but any hematopoietic cell targeted for a therapeutic protein. Two approaches for transducing CD34$^+$ cells include an ex vivo and an in vivo protocol. The in vivo protocol focuses on transducing an indiscriminate population of bone marrow cells by direct injection of the vector into the bone marrow of patients. The ex vivo protocol focuses on isolating CD34$^+$ positive stem cells, from the patient's bone marrow, or an infant patient's umbilical cord blood, transducing the cells with vector, then subsequently injecting the autologous cells back into the patient. Both approaches are feasible, but the ex vivo protocol enables the vector to be used most efficiently by transducing a specific cultured population of CD34$^+$ cells. Details of an ex vivo method are provided in the following section.

Ex Vivo Administration of a Multivalent GC Sindbis Vector

CD34$^+$ cells are collected from the patient's bone marrow by a syringe evacuation performed by a physician familiar with the technique. Alternatively, CD34$^+$ cells may also be obtained from an infant's umbilical cord blood if the patient is diagnosed before birth. Generally, if the bone marrow is the source of the CD34$^+$ cells, 20 bone marrow aspirations are obtained by puncturing femoral shafts or from the posterior iliac crest under local or general anesthesia. Bone marrow aspirations are then pooled, suspended in Hepes-Buffered Hanks' balanced salt solution containing heparin at 100 units per ml and deoxyribonuclease I at 100 ug/ml and then subjected to a Ficoll gradient separation. The buffy coated marrow cells are then collected and washed according to Cell-Pro's CEPRATE® LC (CellPro, Bothell, Wash.) (CD34

Separation system (see U.S. Pat. Nos. 5,215,927; 5,225,353; 5,262,334; 5,215,926 and PCT/US91/07646). The washed buffy coated cells are then stained sequentially with anti-CD34 monoclonal antibody, washed then stained with biotinylated secondary antibody supplied with CEPRATE® system. The cell mixture is then loaded onto the CEPRATE® avidin column. The biotin-labeled cells are adsorbed onto the column while unlabeled cells passed through. The column is then rinsed according to the CEPRATE® system directions and CD34+ cells eluted by agitation of the column by manually squeezing the gel bed. Once the CD34+ cells are purified, the purified stem cells are counted and plated at a concentration of $1 \times 10^5$ cells/ml in Iscove's modified Dulbecco's medium (IMDM; Irvine Scientific, Santa Ana, Calif.) containing 20% pooled non-heat inactivated human AB serum (hAB serum).

After purification, several methods of transducing purified stem cells may be performed. One approach involves immediate transduction of the purified stem cell population with recombinant alphavirus particles contained in culture supernatants derived from vector packaging or producing cells. A second approach involves co-cultivation of an irradiated monolayer of vector producing cells with the purified population of nonadherent CD34+ cells. A third approach involves a similar co-cultivation approach, however, the purified CD34+ cells are prestimulated with various cytokines and cultured 48 hours prior to the co-cultivation with the irradiated vector producing cells. Since alphavirus vectors are able to infect nonreplicating cells, prestimulation of these cells may not be required, however prestimulation of these cultures causing proliferation will provide increased cell populations for reinfusion into the patient.

Prestimulation of the CD34+ cells is performed by incubating the cells with a combination of cytokines and growth factors which include IL-1, IL-3, IL-6 and mast cell growth factor (MGF). Prestimulation is performed by culturing $1-2 \times 10^5$ CD34+ cells/ml of medium in T25 tissue culture flasks containing bone marrow stimulation medium for 48 hours. The bone marrow stimulation medium consists of IMDM containing 30% non-heat inactivated hAB serum, 2 mM L-glutamine, 0.1 mM 2-mercaptoethanol, 1 M hydrocortisone, and 1% deionized bovine serum albumin. All reagents used in the bone marrow cultures should be screened for their ability to support maximal numbers of granulocyte, erythrocyte, macrophage, megakaryocyte, colony-forming units from normal marrow. Purified recombinant human cytokines and growth factors (Immunex Corp., Seattle, Wash.) for prestimulation should be used at the following concentrations: *E. coli*-derived IL-1 (100 U/ml), yeast-derived IL-3 (5 ng/ml), IL-6 (50 U/ml), and MGF (50 ng/ml) (Anderson et al., *Cell Growth Differ.* 2:373, 1991).

After prestimulation of the CD34+ cells, they are then infected by co-cultivation with the irradiated Sindbis producer cell line (expressing the GC therapeutic vector) in the continued presence of the stimulation medium. The Sindbis vector producing cell line is first trypsinized, irradiated (10,000 Rads) and replaced at $1-2 \times 10^5$ cells/ml of bone marrow stimulation medium. The following day, $1-2 \times 10^5$ prestimulated CD34+ cells/ml is added to the Sindbis vector producing cell line monolayer. Co-cultivation of the cells is performed for 48 hours. After co-cultivation, the CD34+ cells are collected from the adherent Sindbis vector producing cell monolayer by vigorous washing with medium and plated for 2 hours to allow adherence of any dislodged vector producing cells. The CD34+ cells are collected and expanded for an additional 72 hours. The cells are then harvested and frozen in liquid nitrogen using a cryo-protectant in aliquots of $1 \times 10^7$ cells per vial. Once the treated CD34+ cells have been tested for the absence of adventitious agents, frozen transformed CD34+ cells may be thawed, plated to a concentration of $1 \times 10^5$ cells/ml and cultured for an additional 48 hours in bone marrow stimulation medium. Transformed cells are collected, washed twice and resuspended in normal saline. The number of transduced cells used to infuse back into the patient per infusion is projected to be at a minimum of $1-10 \times 10^7$ cells per patient per injection site requiring up to four injection sites. Infusion may be performed directly back into the patient's bone marrow or directly into the peripheral blood stream. Patients receiving autologous transduced bone marrow cells may be either partially or whole body irradiated, to deplete existing bone marrow populations. Treatment may be assessed at various time points post infusion to determine GC activity and for length of expression in differentiated cell types. If at some point during the course of follow-up procedures expression decreases or is nonexistent, transduced autologous cells may be reinjected into the patient.

Example 12

Determination of Vector Units in a Preparation by Infection of a Reporter Protein Expressing Cell Line Under the Control of the Sindbis Junction Region Determination of Vector Units in a Preparation by Infection of a β-Galactosidase Expressing Reporter Cell Line In order to administer the proper therapeutic dose of vector to individuals, it is desirable to derive a method by which the vector infectious units contained in a preparation can be determined easily. This is accomplished by the generation of a cell line which expresses β-galactosidase or another reporter gene only when functional Sindbis nonstructural proteins are present in the cell. The cell line can be infected with increasing dilutions of a Sindbis vector preparation such that individual cells are not infected with more than one vector particle, allowing the titer, or vector units, to be determined. Thus, the cell line is an assay of functional particles present in a vector preparation.

A. Generation of a Cell Line which Expresses Functional β-Galactosidase Protein Under the Control of Sindbis Nonstructural Proteins In one configuration, a eukaryotic expression cassette is constructed which contains a 5'-end sequence capable of initiating transcription of Sindbis RNA, a Sindbis junction region, a reporter gene, and a 3'-end Sindbis RNA polymerase recognition sequence for minus-strand synthesis. This cassette is positioned in an antisense orientation, adjacent to a eukaryotic transcriptional promoter. Additionally, these constructs also may contain a catalytic ribozyme sequence immediately adjacent to Sindbis nucleotide 1 of the 5'-end sequence which will result in cleavage of the primary RNA transcript precisely after this Sindbis nucleotide. In this antisense orientation, the reporter gene cannot be translated and is dependent entirely on the presence of Sindbis nonstructural proteins for transcription into positive stranded mRNA prior to reporter gene expression. These non-structural proteins will be provided by the Sindbis vector preparation being titered. In addition, this configuration, if designed to contain the precise Sindbis genome 5'- and 3'-end sequences, will allow for the reporter gene transcripts to undergo amplification by utilizing the same nonstructural proteins provided by the Sindbis vector.

An example of this antisense titering construction is as follows. Briefly, the plasmid pKSSINBV-lacZ (described in Example 6) is digested with the enzymes Apa I and Bam HI. This results in the removal of the Sindbis 5' and Sindbis nonstructural protein sequences. The 7 kbp fragment is purified on a 0.7% agarose gel. This fragment is ligated to a fragment obtained by digestion of pd5'26s (described in Example 7) with ApaI and BamHI followed by gel purification of the 0.4 kbp fragment containing the HDV ribozyme and 5' Sindbis sequences. The resulting construct is known as pKSd5'BV-lacZ. pKSd5'BV-lacZ is digested with Apa I and Pme I followed by purification of the 7.4 kbp fragment on a 0.7% agarose gel. This fragment contains the HDV ribozyme, Sindbis 5' end, junction region, LacZ gene, and Sindbis 3' end sequences. This fragment is ligated in the antisense orientation into pcDNA3 (Promega Corp., Madison, Wis.) by digestion of pcDNA3 with Apa I and EcoRV followed by GENECLEANT™ purification. The resulting construct, containing a CMV promoter which transcribes an antisense reporter cassette RNA of the configuration Sindbis 3'-end sequence/LacZ gene/junction region/Sindbis 5'-end sequence/HDV ribozyme, is known as pSINjra-gal.

BHKSINjra-gal cells are derived by transfection of $5\times10^5$ BHK-21 cells, grown in a 60 mm petri dish, with 5 ug of the pSINjra-gal vector complexed with the polycation reagent Transfectam™ (Promega, Madison, Wis.). At 24 hour post-transfection, the media is supplemented with 400 ug/ml of G418 (GibcoBRL, Gaithersburg, Md.). After all non-transfected cells have died and G418 resistant colonies have begun dividing, the cells are removed from the plate by trypsinization, pooled, then cloned by limiting dilution. Several clones are tested for the production of functional β-galactosidase by infection with a known titer of a wild-type stock of Sindbis virus. Production of functional β-galactosidase in candidate BHKSINjra-gal clones is determined 6 hours post-infection by first fixing PBS-rinsed cells with a solution containing 2% formaldehyde (37% stock solution)/0.2% glutaraldehyde, then staining the cells with a solution containing 0.5 mM potassium ferricyanide/0.5 mM potassium ferrocyanide/2 mM $MgCl_2$/1 mg/ml X.gal. Blue cells are clearly visible within 3 hours. Provided that the Sindbis virus stock does not contain a high level of defective interfering (DI) particles, the virus titer as determined by plaque assay on BHK-21 cells should be similar to the titer observed by X-gal staining on BHKSINjra-gal cells.

The titer of various alphavirus vector preparations, in vector units, produced from packaging cell lines such as those described in Example 7, is determined by infection of confluent monolayers of BHKSINjra-gal cells with several dilutions of vector. The titer of the vector preparation is determined at 6 hour post-infection by visualization of cells producing β-galactosidase protein, as described above. Since the alphavirus vectors described do not contain the viral region corresponding to the structural genes, it is not possible to determine the titer of a vector preparation by plaque assay in BHK-21 cells.

Alternatively, a titering cell line is produced by using a different reporter cassette configuration, which consists of a eukaryotic promoter/5'-end Sindbis sequence recognized by the viral transcriptase/Sindbis junction region/reporter gene/Sindbis RNA polymerase recognition sequence for minus-strand synthesis, and is expressed in a sense-orientation. This reporter expression cassette requires synthesis, by vector-supplied Sindbis nonstructural proteins, into an antisense RNA molecule, prior to transcription of the subgenomic message encoding the reporter gene.

Specifically, the sense-orientation packaging construct is created as follows. Plasmid pVGELVIS is digested with the enzyme Apa I, which cleaves at nucleotide 11737, just downstream of the Sindbis 3'-end. The Apa I-digested DNA is blunt-ended by the addition of T4 DNA polymerase and dNTPs and incubation at 16° C. for 10 minutes. After heat inactivation of the polymerase, the DNA fragment is digested with the enzyme Sfi I, and the 10041 by fragment is purified in a 1% agarose gel. Plasmid pSKSINBV-lacZ is digested with the enzymes Pme I and Sfi I. The 6.4 kbp fragment is purified in a 1% agarose gel. The 6.4 kbp pSKSINBV-lacZ fragment then is ligated into the purified pVGELVIS fragment to create the plasmid pELVIS-gal. This plasmid contains the complete Sindbis nonstructural proteins, Sindbis junction region, LacZ gene and Sindbis 3'-end replicase recognition sequence under the control of the MuLV LTR promoter. Plasmid pELVIS-gal is digested with Bsp EI, purified by GENECLEAN (Bio 101 Corp., San Diego, Calif.) and religated to itself. Bsp EI removes the Sindbis nonstructural protein gene sequences between nts 422-7054. The re-ligated construct contains a 5' sequence that is capable of initiating transcription of Sindbis RNA, Sindbis junction region, sequences encoding the LacZ gene, and Sindbis 3'-end sequences required for synthesis of the minus-strand RNA, all downstream, and under the transcriptional control of a MuLV-LTR promoter. This construct is known as pELVIS-dINSP-gal.

Plasmid pELVISdINSP-gal is transfected into BHK-21 cells and tested as described previously. The BHK pELVIS-dINSP-gal cells produces an RNA transcript with a 5'-end sequence that is recognized by the Sindbis transcriptase, a Sindbis junction region, sequences encoding the LacZ gene, and Sindbis 3'-end sequences required for synthesis of the minus-strand RNA. β-galactosidase expression from the primary transcript is prevented because of an upstream open-reading frame and stop codons created by the Bsp EI deletion. The addition of Sindbis nonstructural proteins, provided by the Sindbis vector being titered, results in transcription of active LacZ transcripts from the Sindbis junction region, after initial synthesis of an antisense intermediate. Furthermore, this configuration, if designed to contain the precise Sindbis genome 5'- and 3'-end sequences, allows the reporter gene transcripts to undergo amplification by utilizing the same nonstructural proteins provided by the Sindbis vector.

In another configuration, a titering cell line is produced using an expression cassette containing an antisense reporter gene followed by the 3'-end alphavirus replicase recognition sequences, positioned in the sense-orientation. This construct, under the control of a eukaryotic promoter, produces an RNA transcript that is recognized and transcribed by alphavirus nonstructural proteins provided by the vector to be titered. The alphavirus nonstructural proteins recognize sequences in the primary reporter transcript, and in turn, synthesize a sense reporter transcript. This construct does not benefit from amplification of the reporter gene transcript, but should still provide sufficient transcripts to allow for vector titering.

Construction of this type of titering cassette is as follows. Briefly, pSV-β-galactosidase vector (Promega Corp., Madison, Wis.) is digested with the enzyme Hind III and blunt-ended as described above. The plasmid is further digested with the enzymes Bam HI and Xmn I to remove the LacZ gene, and reduce the size of the remaining fragment. The 3737 nt fragment, containing the LacZ gene, is purified in a 1% agarose gel and ligated into pcDNA3 (Invitrogen, San Diego, Calif.) that has been digested with the enzymes Bam HI and Eco RV. The new plasmid construct is known as pcDNAaLacZ. This plasmid is digested with the enzyme Apa I, blunt-ended as above, and further digested with the enzyme Xho I. Plasmid pSKSINBV (described previously) is digested with Sac I, blunt-ended as before, and then digested with Xho I. The resulting 146 nt fragment containing the Sindbis 3' replicase recognition sequence is purified in a 1.2% agarose gel, ligated into the digested pcDNAaLacZ vector. The re-ligated construct contains an antisense LacZ gene and a 3' Sindbis replicase protein recognition sequence downstream from a CMV promoter. The resulting construct is known as pcDNAaLacZ-3'Sin. The construct is transfected into BHK cells and utilized as described previously.

B. Generation of a Cell Line which Expresses Functional Luciferase Protein Under the Control of Sindbis Nonstructural Proteins.

An alternate reporter for a titering construct based upon the sense configuration of the reporter gene and requiring the nonstructural proteins for expression utility is luciferase. Again, the non-structural proteins are supplied in trans by the Sindbis vector preparation being titered. To generate this construct, pELVIS-luc is digested with Eco 47 III and Hpa I. These digests remove nucleotides 1407-6920 from within the non-structural coding region. After heat inactivation of the enzymes, the digested vector is religated under dilute conditions. This construct is known as pELVISdlE-Hluc. The construct is transfected into BHK cells and utilized as described previously.

Example 13

Generation of Vector Constructs which Express HBV Antigens for the Induction of an Immune Response A. Isolation of HBV E/Core Sequence A 1.8 Kb fragment containing the entire precore/core coding region of hepatitis B is obtained from plasmid pAM6 (ATCC No 45020) following Bam HI digestion and gel purification, and ligated into the Bam HI site of KS II+(Stratagene, La Jolla, Calif.). This plasmid is designated KS II+ HBpc/c. Xho I linkers are added to the Stu I site of precore/core in KS II+ HBpc/c (at nucleotide sequence 1,704), followed by cleavage with Hinc II (at nucleotide sequence 2,592). The resulting 877 base pair Xho I-Hinc II precore/core fragment is cloned into the Xho I/Hinc II site of SK II+. This plasmid is designated SK+ HBe.

B. Preparation of Sequences Utilizing PCR

1. Site-Directed Mutagenesis of HBV E/Core Sequence Utilizing PCR

The precore/core gene in plasmid KS II+ HB pc/c is sequenced to determine if the precore/core coding region is correct. This sequence was found to have a single base-pair deletion which causes a frame shift at codon 79 that results in two consecutive in-frame TAG stop codons at codons 84 and 85. This deletion is corrected by PCR overlap extension (Ho et al., Gene 77:51, 1989) of the precore/core coding region in plasmid SK+ HBe. Four oligonucleotide primers are used for the 3 PCR reactions performed to correct the deletion.

The first reaction utilizes two primers. The sense primer sequence corresponds to the nucleotide sequence 1,805 to 1,827 of the adw strain and contains two Xho I restriction sites at the 5' end. The nucleotide sequence numbering is obtained from Genbank (Intelligenics, Inc., Mountain View, Calif.).

(SEQ. ID NO. 92)
5' CTC GAG CTC GAG GCA CCA GCA CCA TGC AAC TTT TT-3'

The second primer sequence corresponds to the anti-sense nucleotide sequence 2,158 to 2,130 of the adw strain of hepatitis B virus, and includes codons 79, 84 and 85.

(SEQ. ID NO. 93)
5'-CTA CTA GAT CCC TAG ATG CTG GAT CTT CC-3'

The second reaction also utilizes two primers. The sense primer corresponds to nucleotide sequence 2,130 to 2,158 of the adw strain, and includes codons 79, 84 and 85.

(SEQ. ID NO. 94)
5'-GGA AGA TCC AGC ATC TAG GGA TCT AGT AG-3'

The second primer corresponds to the anti-sense nucleotide sequence from SK+ plasmid polylinker and contains a Cla I site 135 by downstream of the stop codon of the HBV precore/core coding region.

(SEQ. ID NO. 95)
5'-GGG CGA TAT CAA GCT TAT CGA TAC CG-3'

The third reaction also utilizes two primers. The sense primer corresponds to nucleotide sequence 5 to 27 of the adw strain, and contains two Xho I restriction sites at the 5' end.

(SEQ. ID NO. 92)
5'-CTC GAG CTC GAG GCA CCA GCA CCA TGC AAC TTT TT

The second primer sequence corresponds to the anti-sense nucleotide sequence from the SK+ plasmid polylinker and contains a Cla I site 135 by downstream of the stop codon of the HBV precore/core coding region.

(SEQ. ID NO. 96)
5'-GGG CGA TAT CAA GCT TAT CGA TAC CG-3'

The first PCR reaction corrects the deletion in the antisense strand and the second reaction corrects the deletion in the sense strands. PCR reactions one and two correct the mutation from CC to CCA which occurs in codon 79 and a base pair substitution from TCA to TCT in codon 81. Primer 1 contains two consecutive Xho I sites 10 by upstream of the ATG codon of HBV e coding region and primer 4 contains a Cla I site 135 by downstream of the stop codon of HBV precore/core coding region. The products of the first and second PCR reactions are extended in a third PCR reaction to generate one complete HBV precore/core coding region with the correct sequence.

The PCR reactions are performed using the following cycling conditions: The sample is initially heated to 94° C. for 2 minutes. This step, called the melting step, separates the double-stranded DNA into single strands for synthesis. The sample is then heated at 56° C. for 30 seconds. This step, called the annealing step, permits the primers to anneal to the single stranded DNA produced in the first step. The sample is then heated at 72° C. for 30 seconds. This step, called the extension step, synthesizes the complementary strand of the single stranded DNA produced in the first step. A second melting step is performed at 94° C. for 30 seconds, followed by an annealing step at 56° C. for 30 seconds which is followed by an extension step at 72° C. for 30 seconds. This procedure is then repeated for 35 cycles resulting in the amplification of the desired DNA product.

Figure 4:
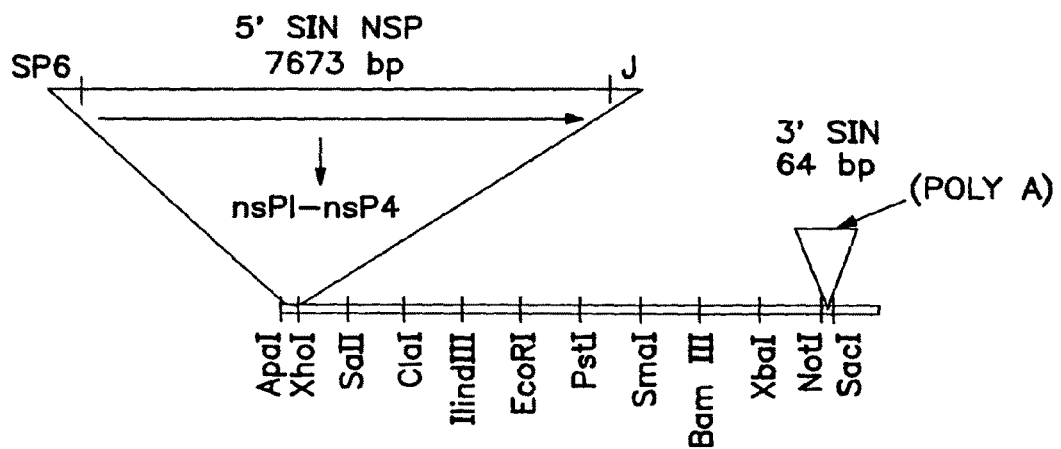
FIG. 4 is a schematic illustration of a Sindbis Basic Vector and a Sindbis-luciferase Vector.
Figure 4:
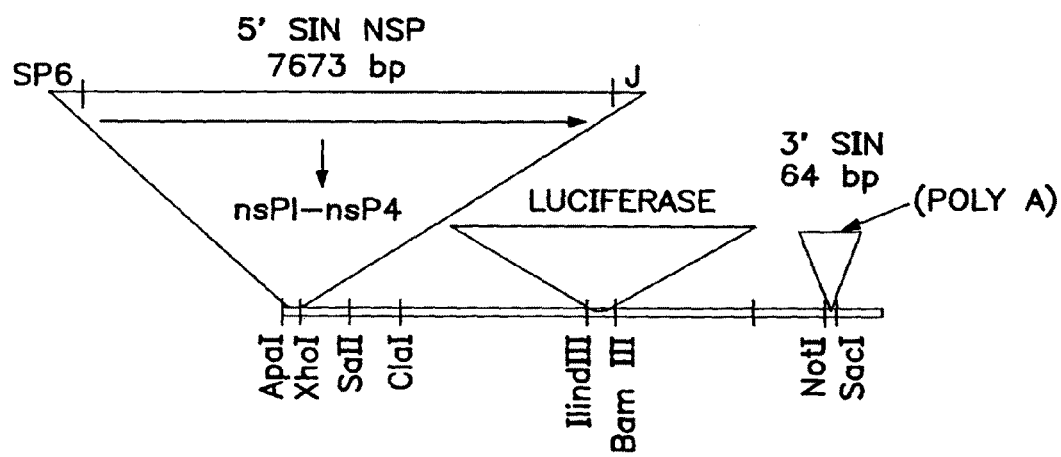

The PCR reaction product is purified by 1.5% agarose gel electrophoresis and transferred onto NA 45 paper (Schleicher and Schuell, Keene, N.H.). The desired 787 by DNA fragment is eluted from the NA 45 paper by incubating for 30 minutes at 65° C. in 400 l high salt buffer (1.5 M NaCl, 20 mM Tris, pH 8.0, and 0.1 mM EDTA). Following elution, 500 µl of phenol:chloroform:isoamyl alcohol (25:24:1) is added to the solution. The mixture is vortexed and then centrifuged 14,000 rpm for 5 minutes in a Brinkmann Eppendorf centrifuge (5415 L). The aqueous phase, containing the desired DNA fragment, is transferred to a fresh 1.5 ml microfuge tube and 1.0 ml of 100% EtOH is added. This solution is incubated on dry ice for 5 minutes, and then centrifuged for 20 minutes at 10,000 rpm. The supernatant is decanted, and the pellet is rinsed with 500 l of 70% EtOH. The pellet is dried by centrifugation at 10,000 rpm under vacuum, in a Savant Speed-Vac concentrator, and then resuspended in 10 l deionized $H_2O$. One microliter of the PCR product is analyzed by 1.5% agarose gel electrophoresis. The 787 Xho I-Cla I precore/core PCR amplified fragment is cloned into the Xho I-Cla I site of SK+ plasmid. This plasmid is designated SK+HBe-c. *E. coli* (DH5 alpha, Bethesda Research Labs, Gaithersburg, Md.) is transformed with the SK+HBe-c plasmid and propagated to generate plasmid DNA. The plasmid is then isolated and purified, essentially as described by Birnboim et al. (*Nuc. Acid Res.* 7:1513, 1979; see also *Molecular Cloning: A Laboratory Manual*, Sambrook et al. (eds.), Cold Spring Harbor Press, 1989). The SK+HBe-c plasmid is analyzed to confirm the sequence of the precore/core gene (FIG. 4).

2. Isolation of HBV Core Sequence

The single base pair deletion in plasmid SK+ HBe is corrected by PCR overlap extension as described above in Example 13B. Briefly, four oligonucleotide primers are used for the PCR reactions performed to correct the mutation.

The first reaction utilizes two primers. The sense primer corresponds to the nucleotide sequence for the T-7 promoter of SK+HBe plasmid.

5'-AAT ACG ACT CAC TAT AGG G-3'    (SEQ. ID NO. 97)

The second primer corresponds to the anti-sense sequence 2,158 to 2,130 of the adw strain, and includes codons 79, 84 and 85.

(SEQ. ID NO. 98)
5'-CTA CTA GAT CCC TAG ATG CTG GAT CTT CC-3'

The second reaction utilizes two primers. The anti-sense primer corresponds to the nucleotide sequence for the T-3 promoter present in SK+HBe plasmid.

5'-3': ATT AAC CCT CAC TAA AG (SEQ. ID NO. 99)

The second primer corresponds to the sense nucleotide sequence 2,130 to 2,158 of the adw strain, and includes codons 79, 84 and 85.

(SEQ. ID NO. 100)
5'-GGA AGA TCC AGC ATC TAG GGA TCT AGT AG-3'

The third reaction utilizes two primers. The anti-sense primer corresponds to the nucleotide sequence for the T-3 promoter present in SK+HBe plasmid.

5'-ATT AAC CCT CAC TAA AG-3'    (SEQ. ID NO. 101)

The second primer corresponds to the sense sequence of the T-7 promoter present in the SK+HBe plasmid.

5'-AAT ACG ACT CAC TAT AGG G-3'    (SEQ. ID NO. 102)

The PCR product from the third reaction yields the correct sequence for HEY precore/core coding region.

To isolate HBV core coding region, a primer is designed to introduce the Xho I restriction site upstream of the ATG start codon of the core coding region, and eliminate the 29 amino acid leader sequence of the HBV precore coding region. In a fourth reaction, the HBV core coding region is produced using the PCR product from the third reaction and the following two primers.

The sense primer corresponds to the nucleotide sequence 1,885 to 1,905 of the adw strain and contains two Xho I sites at the 5' end.

(SEQ. ID NO. 103)
5'-CCT CGA GCT CGA GCT TGG GTG GCT TTG GGG CAT G-3'

The second primer corresponds to the anti-sense nucleotide sequence for the T-3 promoter present in the SK+ HBe plasmid. The approximately 600 by PCR product from the fourth PCR reaction contains the HBV core coding region and novel Xho I restriction sites at the 5' end and Cla I restriction sites at the 3' end that was present in the multicloning site of SK+ HBe plasmid.

5'-ATT ACC CCT CAC TAA AG-3'    (SEQ. ID NO. 104)

Following the fourth PCR reaction, the solution is transferred into a fresh 1.5 ml microfuge tube. Fifty microliters of 3 M sodium acetate is added to this solution followed by 500 µl of chloroform:isoamyl alcohol (24:1). The mixture is vortexed and then centrifuged at 14,000 rpm for 5 minutes. The aqueous phase is transferred to a fresh microfuge tube and 1.0 ml 100% EtOH is added. This solution is incubated at −20° C. for 4.5 hours, and then centrifuged at 10,000 rpm for 20 minutes. The supernatant is decanted, and the pellet rinsed with 500 µl of 70% EtOH. The pellet is dried by centrifugation at 10,000 rpm under vacuum and then resuspended in 10 µl deionized $H_2O$. One microliter of the PCR product is analyzed by 1.5% agarose gel electrophoresis. The approximately 600 by Xho I-Cla I HBV core PCR fragment is cloned into the Xho I-Cla I site of SK+ plasmid. This plasmid is designated SK+ HBc.

3. Isolation of HBV X Antigen

A 642 by Nco 1-Taq I fragment containing the hepatitis B virus X open reading frame is obtained from the pAM6 plasmid (adw) (ATCC 45020), blunted by Klenow fragment, and ligated into the Hinc II site of SK+ (Stratagene, La Jolla, Calif.). *E. coli* (DH5, Bethesda Research Laboratories, Gaithersburg, Md.) is transformed with the ligation reaction and propagated.

Since this fragment can be inserted in either orientation, clones are selected that have the sense orientation with respect to the Xho I and Cla I sites in the SK+ multicloning site. More specifically, miniprep DNAs are digested with the diagnostic restriction enzyme, Bam HI. Inserts in the correct orientation yield two fragments of 3.0 Kb and 0.6 Kb in size. Inserts in the incorrect orientation yield two fragments of 3.6 Kb and 0.74 Kb. A clone in the correct orientation is selected and designated SK-X Ag.

4. Construction of Sindbis Vectors Expressing HBVe, HBV Core and HBV X

Construction of a Sindbis vector expressing the HBVe sequence is accomplished by digesting the SK$^+$HB e-c plasmid with Xho I and Xba I to release the cDNA fragment encoding HBVe-c sequences. The fragment is then isolated by agarose gel electrophoresis, purified by GENECLEAN™, and inserted into pKSSINBV (see Example 3), prepared by digestion with Xho I and Xba I, and treated with CIAP. This vector is designated pKSSIN-HBe. Similar vectors may also be made from other Sindbis vectors described in Example 3, such as, for example, pKSSINdlJRsjrc, pKSSINdlJRsjrPC, pKSSENIdlJRsjrNP(7582-7601) and pKSSINdlJRsexjr.

Construction of a Sindbis vector expressing the HBV core sequence is accomplished by digestion of plasmid SK+HBc (described above) with Xho I and Xba I. The HBc fragment is isolated by agarose gel electrophoresis, purified by GENECLEAN™ and ligated into pKSSINBV at the Xho I and Xba I sites. This Sindbis-HBc vector is designated pKSSIN-HBc.

Construction of a Sindbis vector expressing the HBV-X antigen sequence is accomplished by digesting the plasmid SK-X Ag with Xho I and Xba I to release a cDNA fragment encoding HBV-X sequences. The fragment is isolated by agarose gel electrophoresis, purified using GENECLEAN™, and inserted into pKSSINBV, pre-treated with Xho I and Xba I enzymes. This Sindbis-HBx vector is designated pKSIN-HBx.

The above Sindbis HBV expressing vectors may also be modified to coexpress a selectable drug resistance marker dependent on the requirements of the experiment or treatment of the vector infected cells. In particular, any of the above Sindbis HBV expression vectors described may also be designed to coexpress G418 resistance. This is accomplished by incorporating an internal ribosomal entry site (Example 5) followed by the bacterial neomycin phosphotransferase gene placed 3' of the HBV coding sequences and 5' of the terminal 3' end of the vector using the multiple cloning site of the vector. These G418 resistant vector constructs can be used for selecting vector infected cells for the generation of HBV specific CTL targets in the following sections.

D. Expression in Infected Cells with Sindbis Vectors

1. ELISA

Cell lysates from cells infected by any of the HBV expressing vectors are made by washing $1.0 \times 10^7$ cultured cells with PBS, resuspending the cells to a total volume of 600 μl in PBS, and sonicating for two 5-second periods at a setting of 30 in a Branson sonicator, Model 350 (Fisher, Pittsburgh, Pa.) or by freeze thawing three times. Lysates are clarified by centrifugation at 10,000 rpm for 5 minutes.

Core antigen and precore antigen in cell lysates and secreted e antigen in culture supernatant are assayed using the Abbott HBe, rDNA EIA kit (Abbott Laboratories Diagnostic Division, Chicago, Ill.). Another sensitive EIA assay for precore antigen in cell lysates and secreted e antigen in culture supernatant is performed using the Incstar ETI-EB kit (Incstar Corporation, Stillwater, Minn.). A standard curve is generated from dilutions of recombinant hepatitis B core and e antigen obtained from Biogen (Geneva, Switzerland).

Figure 16A:
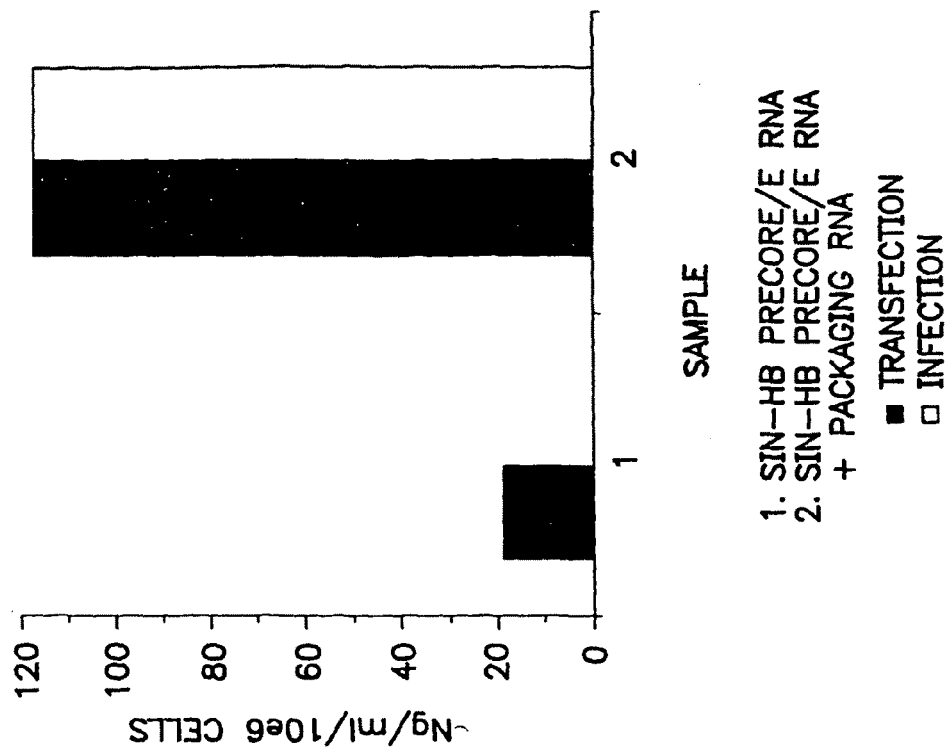
FIG. 16A is a bar graph which shows Sindbis BV-HBe expression and packaging in BHK cells (lysate).
Figure 16B:
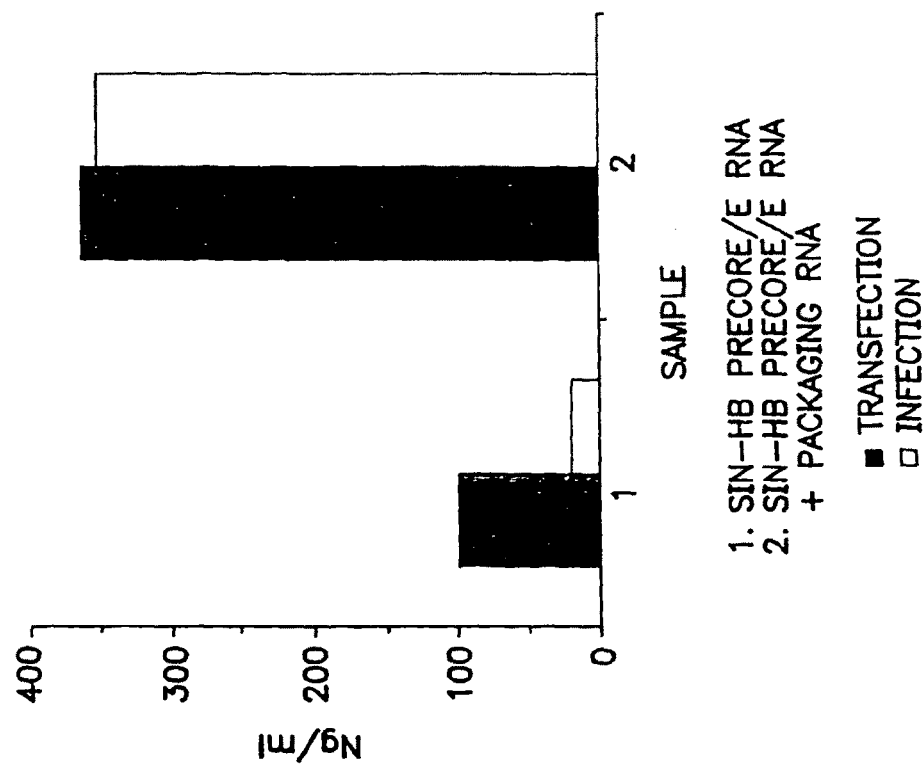
FIG. 16B is a bar graph which shows Sindbis BV-HBe expression and packaging in BHK cells (supernatant).

As shown in FIG. 16, using these procedures approximately 100-200 ng/ml HBV e antigen is expressed in the cell lysates and 300-400 ng/ml HBV e antigen is secreted from BHK cells infected with the Sin BV HB e vector.

Figure 17:
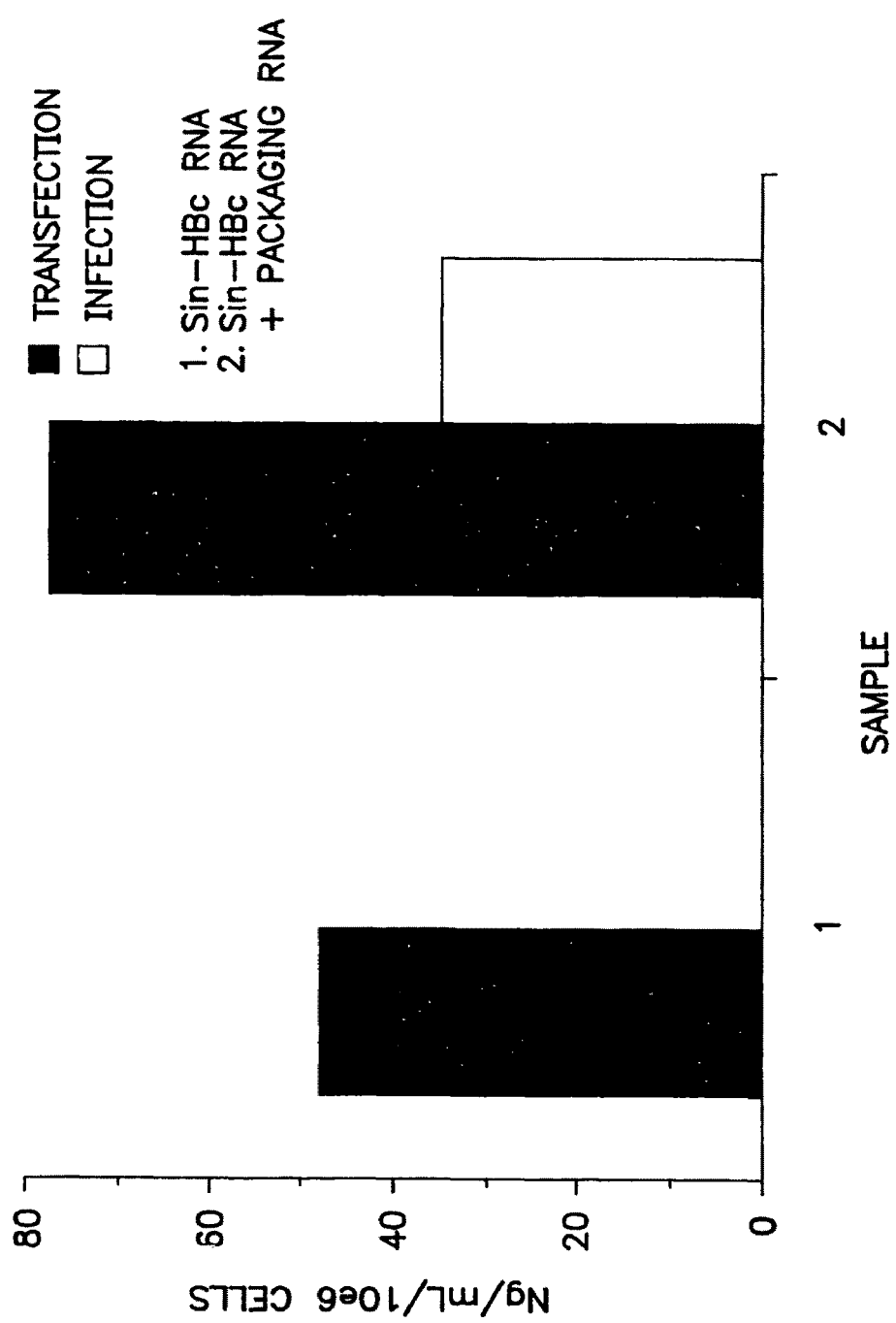
FIG. 17 is a bar graph which shows Sindbis BV-HB core expression and packaging in BHK cells.
Figure 18:
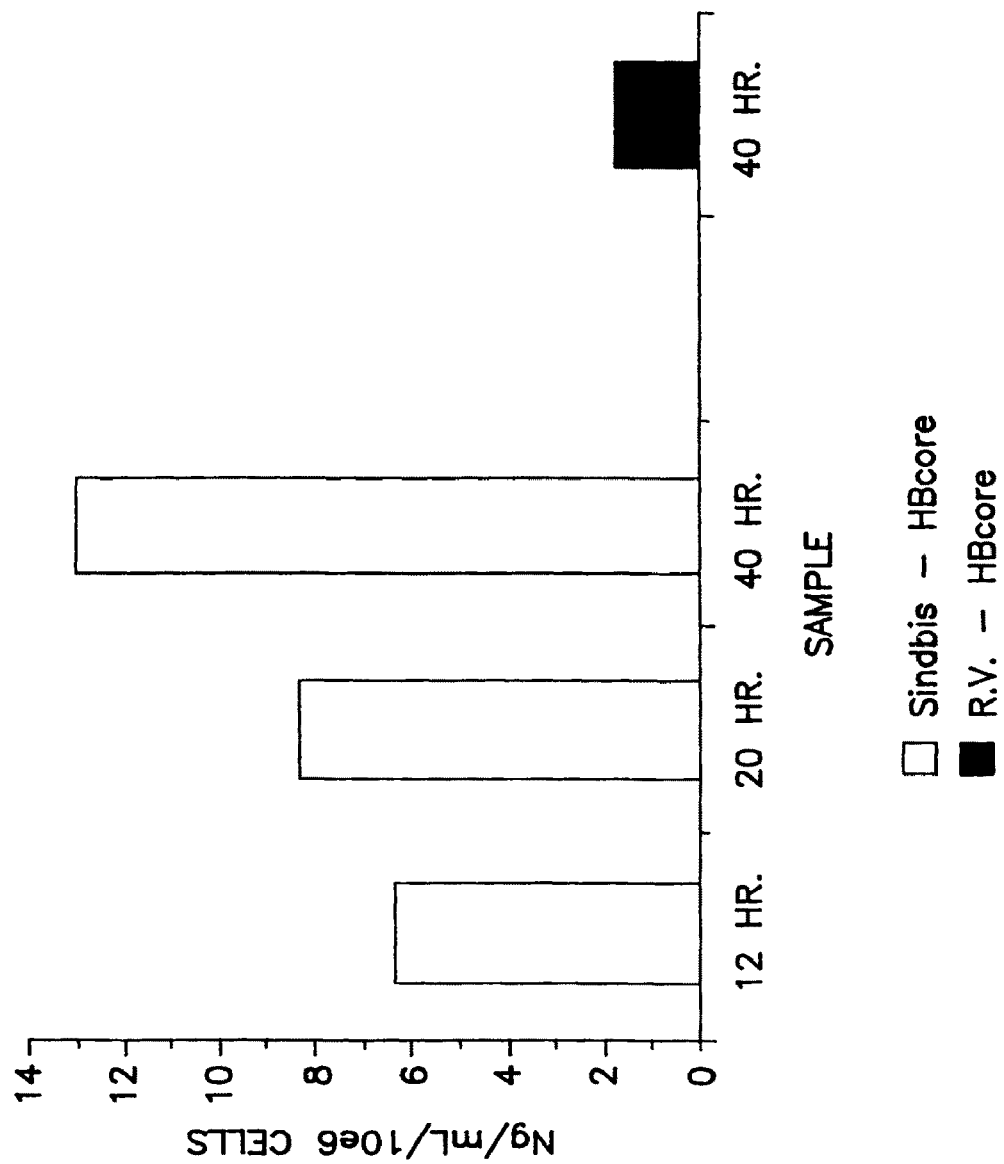
FIG. 18 is a bar graph which shows a comparison of HB core expressed from Sindbis and RETROVECTORST™.
Figure 19:
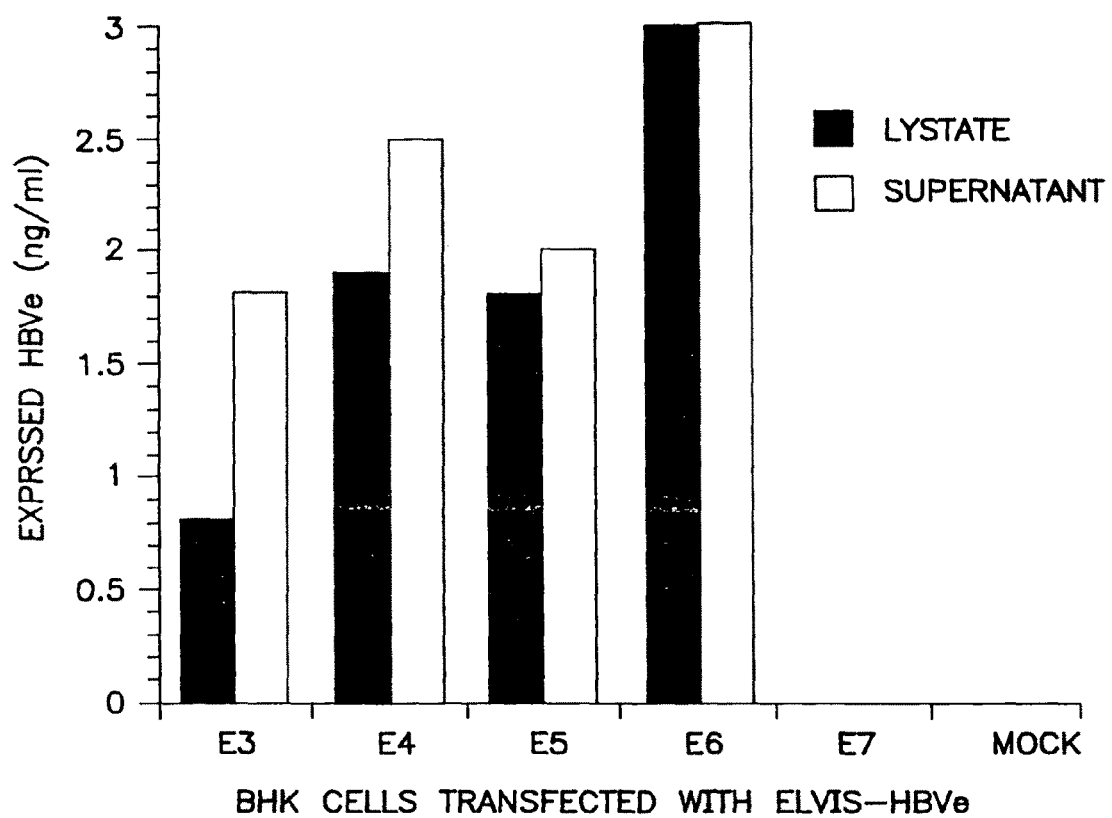
FIG. 19 is a bar graph which shows ELVIS-HBe vector expression in BHK cells.

As shown in FIG. 17, using these procedures, approximately 40 ng/ml HBV core antigen is expressed in the cell lysates from $10^6$ BHK cells infected with the Sin BV HBcore. Mouse fibroblast cells infected with the recombinant HBcore Sindbis vector express 6-7 fold higher HBV core protein levels than the recombinant HBcore retroviral vector transduced cells (WO 93/15207). As shown in FIG. 18, using these procedures, approximately 12-14 ng/ml HBV core antigen is expressed in the cell lysates from $10^6$ L-M(TK-) cells infected with the SinBVHBcore vector as compared to the approximately 2 ng/ml HBV core antigen expressed from recombinant HBcore retroviral vector transducer cells.

2. Immunoprecipitation/Western Blot

Characterization, the precore/core and e antigens expressed by vector infected cells is performed by immunoprecipitation followed by Western blot analysis. Specifically, 0.5-1.0 ml of cell lysate in PBS or culture supernatant is mixed with polyclonal rabbit anti-hepatitis B core antigen (DAKO Corporation, Carpinteria, Calif.) bound to protein G-Sepharose (Pharmacia LKB, Uppsala, Sweden) and incubated overnight at 4° C. Samples are washed twice in 20 mM Tris-HCl, pH 8.0, 100 mM NaCl, 10 mM EDTA and boiled in sample loading buffer with 0.5% 2-mercaptoethanol. Proteins are resolved by SDS polyacrylamide gel electrophoresis, and then transferred to Immobilon (Millipore Corp., Bedford, Me.) and probed with the DAKO polyclonal rabbit anti-hepatitis B core antigen, followed by $^{125}$I-protein A.

E. Testing Immune Response

1. Cytotoxicity Assays.

(a) Inbred Mice

Six- to eight-week-old female C3H/He mice (Charles River, Mass.) are injected twice intraperitoneally (i.p.) at 1 week intervals with $1 \times 10^6$ of Sindbis HBe or HBCore vector. Animals are sacrificed 7 or 14 days later and the splenocytes ($3 \times 10^6$/ml) cultured in vitro with their respective irradiated (10,000 rads) retroviral vector transduced cells ($6 \times 10^4$/ml) (WO 93/15207) in T-25 flasks (Corning, Corning, N.Y.). Culture medium consists of RPMI 1640, 5% heat-inactivated fetal bovine serum, 1 mM sodium pyruvate, 50 ug/ml gentamycin and $10^{-5}$M 2-mercaptoethanol (Sigma, St. Louis, Mo.). Effector cells are harvested 4-7 days later and tested using various effector:target cell ratios in 96 well microtiter plates (Corning, Corning, N.Y.) in a standard chromium release assay. Targets are the retroviral vector transduced L-M(TK$^-$) cells (ATCC No. CCL 1.3) whereas the non-transduced syngeneic cell lines are used as negative controls. CTL targets may also be generated by infecting syngeneic cells with the Sindbis HBe or HBcore vector coexpressing the G418 resistance marker. Infected cells are then selected using 800 g/ml G418 for two weeks. Specifically, Na$_2$$^{51}$CrO$_4$-labeled (Amersham, Arlington Heights, Ill.)(100 uCi, 1 hour at 37° C.) target cells ($1 \times 10^4$ cells/well) are mixed with effector cells at various effector to target cell ratios in a final volume of 200 μl. Following incubation, 100 ul of culture medium is removed and analyzed in a Beckman gamma spectrometer (Beckman, Dallas, Tex.). Spontaneous release (SR) is determined as CPM from targets plus medium and maximum release (MR) is determined as CPM from targets plus 1M HCl. Percent target cell lysis is calculated as: [(Effector cell+ target CPM)−(SR)/(MR)−(SR)]×100. Spontaneous release values of targets are typically 10%-20% of the MR.

For certain CTL assays, the effectors may be in vitro stimulated multiple times, for example, on day 8-12 after the primary in vitro stimulation. More specifically, $10^7$ effector cells are mixed with $6 \times 10^5$ irradiated (10,000 rads) stimulator cells, and 2×10⁷ irradiated (3,000 rads) "filler" cells (prepared as described below) in 10 ml of "complete" RPMI medium. (RPMI containing: 5% heat inactivated Fetal Bovine Serum. two mM L-glutamine, 1 mM sodium pyruvate, 1× non essential amino acids, and 5×10⁻⁵ M 2-mercaptoethanol). Stimulator cells for in vitro stimulation of effector cells are generated from irradiated retroviral vector transduced (10,000 rads) L-M (TK-) cells. "Filler" cells are prepared from naive syngeneic mouse spleen cells resuspended in RPMI, irradiated with 3,000 rads at room temperature. Splenocytes are washed with RPMI, centrifuged at 3,000 rpm for 5 minutes at room temperature, and the pellet is resuspended in RPMI. The resuspended cells are treated with 1.0 ml tris-ammonium chloride (100 ml of 0.17 M tris base, pH 7.65, plus 900 ml of 0.155 M $NH_4Cl$; final solution is adjusted to a pH of 7.2) at 37° C. for 3-5 minutes. The secondary in vitro restimulation is then cultured for 5-7 days before testing in a CTL assay. Any subsequent restimulations are cultured as described above with the addition of 2-10 U of recombinant human IL-2 (200 U/ml, catalog #799068, Boehringer Mannheim, W. Germany).

Using these procedures, it can be shown that CTLs to HBV e antigen can be induced.

(b) HLA A2.1 Transgenic Mice

Six- to eight-week-old female HLA A2.1 transgenic mice (V. Engelhard, Charlottesville, Va.) are injected twice intraperitoneally (i.p.) at one week intervals with 1.0×10⁶ pfu of Sindbis vector expressing HBe or HBcore. Animals are sacrificed 7 days later and the splenocytes (3×10⁶/ml) cultured in vitro with irradiated (10,000 rads) retroviral vector transduced Jurkat A2/K$^b$ cells (WO 93/15207), or with peptide coated Jurkat A2/K$^b$ cells (6×10⁴/ml) in flasks (T-25, Corning, Corning, N.Y.). The remainder of the chromium release assay is performed as described in Example 13E 1.a, where the targets are transduced and non-transduced EL4 A2/K$^b$ (WO 93/15207) and Jurkat A2/K$^b$ cells. Non-transduced cell lines are utilized as negative controls. The targets may also be peptide coated EL4 A2/K$^b$ cells.

(c) Transduction of Human Cells with Vector Construct

Lymphoblastoid cell lines (LCL) are established for each patient by infecting (transforming) their B-cells with fresh Epstein-Barr virus (EBV) taken from the supernatant of a 3-week-old culture of B95-8, EBV transformed marmoset leukocytes (ATCC CRL 1612). Three weeks after EBV-transformation, the LCL are infected with Sindbis vector expressing HBV core or e antigen and G418 resistance. Vector infection of LCL is accomplished by infecting LCL cells with packaged alphavirus vector particles produced from the appropriaste cell line The culture medium consists of RPMI 1640, 20% heat inactivated fetal bovine serum (Hyclone, Logan, Utah), 5.0 mM sodium pyruvate and 5.0 mM non-essential amino acids. Infected LCL cells are selected by adding 800 μg/ml G418. The Jurkat A2/K$^b$ cells (L. Sherman, Scripps Institute, San Diego, Calif.) are infected essentially as described for the infection of LCL cells.

(d) Human CTL Assays

Human PBMC are separated by Ficoll (Sigma, St. Louis, Mo.) gradient centrifugation. Specifically, cells are centrifuged at 3,000 rpm at room temperature for 5 minutes. The PBMCs are restimulated in vitro with their autologous retroviral vector transduced (WO 93/15207) LCL or HLA-matched cells at an effector:target ratio of 10:1 for 10 days. Culture medium consists of RPMI 1640 with prescreened lots of 5% heat-inactivated fetal bovine serum, 1 mM sodium pyruvate and 50 μg/ml gentamycin. The resulting stimulated CTL effectors are tested for CAL activity using Sindbis vector infected autologous LCL or HLA-matched cells as targets in the standard chromium release assay, Example 13 1.a. Since most patients have immunity to EBV, the non-transduced EBV-transformed B-cells (LCL) used as negative controls, will also be recognized as targets by EBV-specific CTL along with the transduced LCL. In order to reduce the high background due to killing of labeled target cells by EBV-specific CTL, it is necessary to add unlabeled non-transduced LCL to labeled target cells at a ratio of 50:1.

2. Detection of Humoral Immune Response

Humoral immune responses in mice specific for HBV core and e antigens are detected by ELISA. The ELISA protocol utilizes 100 μg/well of recombinant HBV core and recombinant HBV e antigen (Biogen, Geneva, Switzerland) to coat 96-well plates. Sera from mice immunized with vector expressing HBV core or HBV e antigen are then serially diluted in the antigen-coated welts and incubated for 1 to 2 hours at room temperature. After incubation, a mixture of rabbit anti-mouse IgG1, IgG2a, IgG2b, and IgG3 with equivalent titers is added to the wells. Horseradish peroxidase ("HRP")-conjugated goat anti-rabbit anti-serum is added to each well and the samples are incubated for 1 to 2 hours at room temperature. After incubation, reactivity is visualized by adding the appropriate substrate. Color will develop in wells that contain IgG antibodies specific for HBV core or HBV e antigen.

3. T Cell Proliferation

Antigen induced T-helper activity resulting from two or three injections of Sindbis vector expressing HBV core or e antigen, is measured in vitro. Specifically, splenocytes from immunized mice are restimulated in vitro at a predetermined ratio with cells expressing HBV core or e antigen or with cells not expressing HBV core or e antigen as a negative control. After five days at 37° C. and 5% $CO_2$ in RPMI 1640 culture medium containing 5% FBS, 1.0 mM sodium pyruvate and 10⁻⁵ 2-mercaptoethanol, the supernatant is tested for IL-2 activity. IL-2 is secreted specifically by T-helper cells stimulated by HBV core or e antigen, and its activity is measured using the CTL clone, CTLL-2 (ATCC TIB 214). Briefly, the CTLL-2 clone is dependent on IL-2 for growth and will not proliferate in the absence of IL-2. CTLL-2 cells are added to serial dilutions of supernatant test samples in a 96-well plate and incubated at 37° C. and 5%, $CO_2$ for 3 days. Subsequently, 0.5 μCi ³H-thymidine is added to the CTLL-2 cells. 0.5Ci ³H-thymidine is incorporated only if the CTLL-2 cells proliferate. After an overnight incubation, cells are harvested using a PHD cell harvester (Cambridge Technology Inc., Watertown, Mass.) and counted in a Beckman beta counter. The amount of IL-2 in a sample is determined from a standard curve generated from a recombinant IL-2 standard obtained from Boehringer Mannheim (Indianapolis, Ind.).

F. Administration Protocols

1. Mice (a) Direct Vector Administration

The mouse system may also be used to evaluate the induction of humoral and cell-mediated immune responses with direct administration of Sindbis vector encoding HBV core or e antigen. Briefly, six- to eight-week-old female C3H/He mice are injected intramuscularly (i.m.) with 0.1 ml of reconstituted (with sterile deionized, distilled water) or intraperitoneally (ip) with 1.0 ml of lyophilized HBV core or HBV e expressing Sindbis vector. Two injections are given one week apart. Seven days after the second injection, the animals are sacrificed. Chromium release CTL assays are then performed essentially as described in Example 13E 1.a.

2. Chimpanzee Administration Protocol

The data generated in the mouse system described above is used to determine the protocol of administration of vector in chimpanzees chronically infected with hepatitis B virus. Based on the induction of HBV-specific CTLs in mice, the subjects in chimpanzee trials will receive four doses of vector encoding core or e antigen at 7 day intervals given in two successively escalating dosage groups. Control subjects will receive a placebo comprised of formulation media. The dosage will be either $10^7$ or $10^8$ pfu given in four 1.0 ml injections i.m. on each injection day. Blood samples will be drawn on days 0, 14, 28, 42, 56, 70, and 84 in order to measure serum alanine aminotransferase (ALT) levels, the presence of hepatitis B e antigen, the presence of antibodies directed against the hepatitis B e antigen, serum HBV DNA levels and to assess safety and tolerability of the treatment. The hepatitis B e antigen and antibodies to HB e antigen is detected by Abbott HB e rDNA EIA kit (Abbott Laboratories Diagnostic Division, Chicago, Ill.) and the serum HBV DNA levels is determined by the Chiron bDNA assay. Efficacy of the induction of CTLs against hepatitis B core or e antigen can be determined as in Example 13E 1.c.

Based on the safety and efficacy results from the chimpanzee studies, the dosage and inoculation schedule is determined for administration of the vector to subjects in human trials. These subjects are monitored for serum ALT levels, presence of HBV e antigen, the presence of antibodies directed against the HBV e antigen and serum HBV DNA levels essentially as described above. Induction of human CTLs against hepatitis B core or e antigen is determined as in Example 13E 1.c, G. Generation of ELVIS Vector Constructs which Express HBV Antigens for the Induction of an Immune Response 1. Construction of ELVIS Actors Expressing HBVe-C. HBV Core and HBV X Construction of an ELVIS vector expressing the HBV e antigen is accomplished by digesting the SK$^+$ HB e-c plasmid with Xho I and Not I to release the cDNA fragment encoding HBVe-c sequences. The fragment is then isolated by agarose gel electrophoresis, purified using GENECLEAN™, and inserted into pVGELVIS-SINBV-linker vector, previously prepared by digestion with Xho I and Not I. This construct is designated pVGELVIS-HBe.

The HBcore PCR product described previously is digested with Xho I and Cla I, isolated by agarose gel electrophoresis, purified using GENECLEAN™, and ligated into SK+II (Bluescript, Stratagene, Calif.) digested with Xho I and Cla I. This construct is designated SK+HBcore. Construction of the ELVIS vector expressing the HBV core sequence is accomplished by digesting the SK$^+$HBcore plasmid with Xho I and Not I to release the cDNA fragment encoding HBVcore sequences. The fragment is then isolated by agarose gel electrophoresis, purified using GENECLEAN™, and inserted into pVGELVIS-SINBV-linker vector, prepared by digestion with Xho I and Not I. This construct is designated pVGELVIS-HBcore.

Construction of the ELVIS vector expressing the HBV-X antigen sequence is accomplished by digesting the plasmid SK-X Ag with Xho I and Not I to release the cDNA fragment encoding HBV-X sequences. The fragment is then isolated by agarose gel electrophoresis, purified using GENECLEAN, and inserted into the pVGELVIS-SINBV-linker vector, prepared by digestion with Xho I and Not I. This construct is designated pVGELVIS-HBX.

Any of the above three constructs can be used for selecting vector infected cells for the generation of HBV specific CIL targets in the following sections.

2. Expression of Transfected Cells with ELVIS Vectors

The pVGELVIS-HBe plasmid DNA is isolated and purified, and 2 ug of pVGELVIS-HBe DNA is complexed with 10 ul of LIPOFECTAMINE™ and transfected into $2\times10^5$ BHK cells contained in 35 mM petri plates. Two days post-transfection, supernatants and whole cell lysates were collected and an ELISA assay (see below) was used to determine the amount of expressed HBV-e antigen.

Cell lysates from cells infected by any of the sibling pVGELVIS-HBe vectors transfected, are made by washing $1.0\times10^6$ cultured cells with PBS, resuspending the cells to a total volume of 600 ul in PBS, and sonicating for two 5-second periods at a setting of 30 in a Branson sonicator, Model 350 (Fisher, Pittsburgh, Pa.) or by freeze thawing three times. Lysates are clarified by centrifugation at 10,000 rpm for 5 minutes.

Core antigen and precore antigen in cell lysates and secreted e antigen in culture supernatant are assayed using the Abbott HBe, rDNA EIA kit (Abbott Laboratories Diagnostic Division, Chicago, Ill.). Another sensitive EIA assay for precore antigen in cell lysates and secreted e antigen in culture supernatant is performed using the Incstar ETI-EB kit (Incstar Corporation, Stillwater, Minn.). A standard curve is generated from dilutions of recombinant hepatitis B core and e antigen obtained from Biogen (Geneva, Switzerland).

As shown in FIG. 19, using these procedures, approximately 2 ng/ml HBV e antigen is expressed in the cell lysates and also secreted from BHK cells transfected with different clones of the pVGELVISHBe plasmid.

Characterization of the precore/core and e antigens expressed by vector transfected cells is performed by immunoprecipitation followed by Western blot analysis. Specifically, 0.5-1.0 ml of cell lysate in PBS or culture supernatant is mixed with polyclonal rabbit anti-hepatitis B core antigen (DAKO Corporation, Carpinteria, Calif.) bound to protein G-Sepharose (Pharmacia LKB, Uppsala, Sweden) and incubated overnight at 4° C. Samples are washed twice in 20 mM Tris-Ha, pH 8.0, 100 mM NaCl, 10 mM EDTA and boiled in sample loading buffer with 0.5% 2-mercaptoethanol. Proteins are first resolved by SDS polyacrylamide gel electrophoresis, and then transferred to Immobilon (Millipore Corp., Bedford, Me.) and probed with the DAKO polyclonal rabbit anti-hepatitis core B antigen, followed by $^{125}$I-protein A.

3. Testing Immune Response (a) Administration Protocols

The mouse model system is also used to evaluate the induction of humoral and cell-mediated immune responses following direct administration of ELVIS vector expressing HBV core or e antigen. Briefly, six- to eight-week-old female Balb/c, C57B1/6, C3H/He mice (Charles River, Mass.) and HLA A2.1 transgenic mice (V. Engelhard, Charlottesville, Va.) are injected intramuscularly (i.m.) with, for example, 50 ug or greater, pVGELVIS-HBcore, pVGELVIS-HBVe or pVGELVIS-HBX vector DNA. Two injections are given one week apart. Seven or fourteen days after the second injection, the animals are sacrificed. Chromium release CTL assays are then performed essentially as described in Example 13E 1.a. Detection of humoral immune responses in mice is performed essentially as described in Example 13E 2 and detection of T cell proliferation in mice is performed essentially as described in Example 13E 3.

Example 14

Sindbis Vectors Expressing Viral Proteins for Induction of the Immune Response or for Blocking Virus Host Cell Interactions The following example describes procedures for constructing Sindbis vectors capable of generating an immune response by expressing an HIV viral antigen. Methods are also given to test expression and induction of an immune response.

Sindbis Vectors Used to Elicit an Immune Response

A. HIV IIIB Env Expression Vector

A 2.7 Kb Kpn I-Xho I DNA fragment was isolated from the HIV proviral clone BH10-R3 (for sequence, see Ratner et al., Nature 313:277, 1985) and a ~400 by Sal I-Kpn I DNA fragment from IIIexE7deltaenv (a Bal31 deletion to nt 5496) was ligated into the Sal I site in the plasmid SK$^+$. From this clone, a 3.1 kb env DNA fragment (Xho I-Not I) was purified and ligated into the previously described Sindbis vectors predigested with Xho I and NotI.

B. Creation of a Producer Cell Line which Expresses HIV Specific Antigens

To construct a vector producing cell line that expresses the HIV IIIB env derived from the vector described above, in vitro transcribed RNA transcripts are transfected in a Sindbis packaging cell line (Example 7). Specifically, the Sindbis RNA vector molecules are initially produced by using a SP6 in vitro transcribed RNA polymerase system used to transcribe from a cDNA Sindbis vector clone encoding the HIV specific sequences. The generated in vitro RNA vector products, are then transfected into a Sindbis packaging or hopping cell line which leads to the transient production of infectious vector particles within 24 hours. These vector particles are then collected from the supernatants of the cell line cultures and then filtered through a 0.45 micron filter to avoid cellular contamination. The filtered supernatants are then used to infect a fresh monolayer of Sindbis packaging cells. Within 24 hours of infection, Sindbis vector particles are produced containing positive stranded Sindbis recombinant RNA encoding Sindbis non-structural proteins and HIV specific sequences.

An alternative configuration of a Sindbis HIV IIIB env vector is a promoter driven cDNA Sindbis construct containing a selectable marker. In this configuration the above-described Xho Ito NotI fragment containing the specific HIV IIIB env sequence is placed in a similar cDNA Sindbis vector driven by a constitutive promoter in place of a bacteriophage polymerase recognition sequence. Using this configuration, the expression vector plasmids are transfected into the packaging cell line and selected for the drug resistance gene 24 to 48 hour post-transfection. Resistant colonies are then pooled 14 days later (dependent on the selection marker used) and dilutioned cloned. Several dilution clones are then propagated, and assayed for highest vector titer. The highest titer clones are then expanded and stored frozen. The stored clones are tested for HIV specific protein production and immune response induction.

C. Testing for HIV Specific Protein Production and an Immune Response

Cell lysates from the Sindbis HIV producer cell line are tested for HIV specific protein production by Western blot analysis. To test the ability of the vector to transfer expression in vitro, BHK-21 cells are infected with filtered supernatant containing viral vector and assayed by Western blot analysis 24 hours post infection. Once protein expression has been verified in vivo mouse and primate studies can be performed to demonstrate the ability of syngeneic cells expressing a foreign antigen after vector treatment to: (a) elicit a CTL response in mice by injecting either infected syngeneic cells or preparations of infectious vector, (b) elicit CTL responses in a human in vitro culture system; (c) to infect human, chimpanzee and macaque cells, including primary cells, so that these can be used to elicit CTL responses and can serve as targets in CTL assays; (d) map immune response epitopes; and (e) elicit and measure CTL responses to other non-HIV antigens such as mouse CMV(MCMV).

1. Immune Response to Sindbis Viral Vector-Encoded Antigens

To test the immune response elicited from a cell line transduced with a Sindbis HIV IIIB env vector, a murine tumor cell line (B/C10ME) (H-$2^d$) (Patek et al., *Cell. Immunol.* 72:113, 1982) is infected with a recombinant Sindbis virus carrying the HIV BIB vector. The HIV env expressing cell line (B/C10ME-IIIB) was then utilized to stimulate HIV env-specific CTL in syngeneic (i.e., MHC identical) Balb/c (H-$2^d$) mice. Mice are immunized by intraperitoneal injection with B/C10ME-IIIB cells ($1\times10^7$ cells) and boosted on day 7-14. (Boosting may not be required.) Responder spleen cell suspensions are prepared from these immunized mice and the cells cultured in vitro for 4 days in the presence of either B/C10ME-IIIB (BCenv) or B/C10ME (BC) mitomycin-C-treated cells at a stimulator:responder cell ratio of 1:50. The effector cells are harvested from these cultures, counted, and mixed with radiolabeled ($^{51}Cr$) target cells (i.e., B/C10MEenv-29 or B/C10ME) at various effector:target (E:T) cell ratios in a standard 4-5 hour $^{51}Cr$-release assay. Following incubation, the microtitre plates are centrifuged, 100 μl culture supernate is removed, and the amount of radiolabel released from lysed cells quantitated in a Beckman gamma spectrometer. Target cell lysis was calculated as: % Target Lysis=Exp CPM−SR CPM/MR CPM−SR CPM×100, where experimental counts per minute (Exp CPM) represents effectors plus targets; spontaneous release (SR) CPM represents targets alone; and maximum release (MR) CPM represents targets in the presence of 1M HCl.

2. Stimulation of an Immune Response in Mice by Direct Injection of Recombinant Sindbis Vector Experiments are performed to evaluate the ability of recombinant Sindbis viral vectors to induce expression of HIV envelope proteins following direct injection in mice. Approximately $10^4$ to $10^5$ (pfu) of recombinant Sindbis virus carrying the HIV IIIB env vector construct are injected twice (2×) at 3-week intervals either by the intraperitoneal (i.p.) or intramuscular (i.m.) route. This amount of Sindbis virus is determined to be less than the amount considered to stimulate an immune response. Spleen cells are prepared for CTL approximately 7 to 14 days after the second injection of vector.

D. Blocking Agents Derived from Viral Protein Analogues Expressed from Recombinant Sindbis Vectors Many infectious diseases, cancers, autoimmune diseases, and other diseases involve the interaction of viral particles with cells, cells with cells, or cells with factors. In viral infections, viruses commonly enter cells via receptors on the surface of susceptible cells. In cancers, cells may respond inappropriately or not at all to signals from other cells or factors. In autoimmune disease, there is inappropriate recognition of "self" markers. These interactions may be blocked by producing an analogue to either of the partners in an interaction, in vivo.

This blocking action may occur intracellularly, on the cell membrane, or extracellularly. The blocking action of a viral or, in particular, a Sindbis vector carrying a gene for a blocking agent, can be mediated either from inside a susceptible cell or by secreting a version of the blocking protein to locally block the pathogenic interaction.

In the case of HIV, the two agents of interaction are the gp120/gp 41 envelope protein and the CD4 receptor molecule. Thus, an appropriate blocker would be a vector construct expressing either an HIV env analogue that blocks HIV entry without causing pathogenic effects, or a CD4 receptor analogue. The CD4 analogue would be secreted and would function to protect neighboring cells, while the gp120/gp 41 is secreted or produced only intracellularly so as to protect only the vector-containing cell. It may be advantageous to add human immunoglobulin heavy chains or other components to CD4 in order to enhance stability or complement lysis. Delivery of a Sindbis vector encoding such a hybrid-soluble CD4 to a host results in a continuous supply of a stable hybrid molecule.

Vector particles leading to expression of HIV env analogues may also be constructed as described above. It will be evident to one skilled in the art which portions are capable of blocking virus adsorption without overt pathogenic side effects (Willey et al., *J. Virol.* 62:139, 1988; Fisher et al., *Science* 233:655, 1986).

Example 15

A. Construction of FIV Env/Rev/RRE Sindbis Vector for the Induction of an Immune Response Sequences encoding the FIV env/rev/RRE gene are amplified and isolated form plasmid pFIV-14-Petaluma (NIH Research and Reference Reagent Program, Maryland) using the following primers:
The sense primer sequence has two consecutive Xho I restriction sites that are placed at the 5' end at position 6020 of clone 34F10 (Talbott et al., *PNAS* 86:5743-5747, 1989): (SEQ. ID NO. 105)

```
                                     (SEQ ID NO: 105)
5'-3': CC CTC GAG CTC GAG GGG TCA CTG AGA AAC TAG

AAA AAG AAT TAG
```

The antisense primer sequence is complementary to a sequence at position 9387 of clone 34F10. The 5' end of the primer has a Not I site (SEQ. ID NO. 106)

```
                                     (SEQ ID NO: 106)
5'-3': CC GCG GCC GC GTA TCT GTG GGA GCC TCA AGG

GAG AAC
```

The PCR product is then placed in the pBluescript KSII+ plasmid (Stratagene, Calif.) and verified by DNA sequencing. This construct is designated pBluescript KSII+ FIV env/rev/RRE. The Xho I-Not I fragment is then excised and inserted into the Sindbis backbone.

Construction of a Sindbis vector expressing the FIV env/rev/RRE sequence is accomplished by digesting the SK+ FIV env/rev/RRE plasmid with Xho I and Not I restriction enzyme sites to release the cDNA fragment encoding FIV env/rev/RRE sequences. The fragment is then isolated by agarose gel electrophoresis, purified by GENECLEAN™ and inserted into the desired Sindbis vector backbone, prepared by digestion with Xho I and Not I. The Sindbis vectors described in Example 3, are suitable for the insertion of the FIV env/rev/RRE sequences. Such Sindbis vectors include pKSSINBV, pKSSINdlJRsjrc, pKSSINdlJRsjrPC, pKSSINdlJRsjrNP (7582-7601) and pKSSINdlJRsexjr.

The above Sindbis Fly env/rev/RRE expressing vectors may also be modified to coexpress a selectable drug resistance marker dependent on the requirements of the experiment or treatment of the vector infected cells. Any of the above Sindbis FIV env/rev/RRE expression vectors described may also be designed to coexpress for G418 resistance. This is accomplished by incorporating an internal ribosomal entry site (Example 5) followed by the bacterial neomycin phosphotransferase gene placed 3' of the FIV env/rev/RRE coding sequences and 5' of the terminal 3' end of the vector using the multiple cloning site of the vector. These G418 resistant vector constructs can be used for selecting vector infected cells for the generation of FIV env/rev/RRE specific CTL targets in the following sections.

B. Infection of Feline Cells with Sindbis Vector Expressing FIV Env/Rev/RRE

The feline kidney cell line (CRFK) is grown in DMEM containing 10% FBS. CRFK cells are infected with the Sindbis vector as described in Examples 3 and 7, and used to show vector expression in feline cells using Western blot analysis.

C. Expression of Infected Cells

Cell lysates from cells infected by any of the FIV env/rev/RRE expressing vectors are made by washing $1.0 \times 10^7$ cultured cells with PBS, resuspending the cells to a total volume of 600 ul in PBS, and sonicating for two 5-second periods at a setting of 30 in a Branson sonicator, Model 350 (Fisher, Pittsburgh, Pa.) or by freeze thawing three times. Lysates are clarified by centrifugation at 10,000 rpm for 5 minutes.

Proteins are separated according to their molecular weight (MW) by means of SDS polyacrylamide gel electrophoresis. Proteins are then transferred from the gel to a IPVH Immobilon-P membrane (Millipore Corp., Bedford, Mass.). The Hoefer HSI TTE transfer apparatus (Hoefer Scientific Instruments, CA) is used to transfer proteins from the gel to the membrane. The membrane is then probed with either CE4-13B1 or CE3-8, monoclonal antibodies directed against FIV env gp100. The bound antibody is detected using $^{125}$I-labeled protein A, which allows visualization of the transduced protein by autoradiography.

D. Testing Cellular Immune Response

1. Inbred Mice

Six- to eight-week-old female Balb/c (H-2d), C57B1/6 (H-2b) and C3H/He (H-2k) mice (Charles River, Mass.) are injected twice intraperitoneally (i.p.) at 1 week intervals with $1 \times 10^6$ pfu of Sindbis FIV env/rev/RRE vector. Animals are sacrificed 7 days later and the splenocytes ($3 \times 10^6$/ml) cultured in vitro with their respective irradited (10,000 rads) retroviral vector transduced syngeneic cells (WO 94/06921) ($6 \times 10^4$/ml) in T-25 flasks (Corning, Corning, N.Y.). These transduced cells include the murine fibroblast cell lines BC10ME (H-2d) (ATCC No. TIB85), B16 (H-2b) and L-M (TK−) (H-2k) (ATCC No. CCL 1.3). These cell lines are grown in DMEM containing 4500 mg/L glucose, 584 mg/L L-glutamine (Irvine Scientific, Santa Ana, Calif.) and 10% FBS (Gemini, Calabasas, Calif.). Culture medium consists of RPMI 1640, 5% heat-inactivated fetal bovine serum, 1 mM sodium pyruvate, 50 g/ml gentamycin and $10^{-5}$M 2-mercaptoethanol (Sigma, St. Louis, Mo.). Effector cells are harvested 4-7 days later and tested using various effector:target cell ratios in 96 well microtiter plates (Corning, Corning, N.Y.) in a standard chromium release assay. Targets are the retroviral vector transduced syngeneic cells (WO 94/06921) whereas the non-transduced syngeneic cell lines are used as negative controls. CTL targets may also be generated from infecting syngeneic cells with the Sindbis FIV env/rev/RRE vector coexpressing the G418 resistance marker. Infected cells are then selected using 800 ug/ml G418 for two weeks.

Specifically, Na$_2$$^{51}$CrO$_4$-labeled (Amersham, Arlington Heights, Ill.)(100 uCi, 1 hour at 37° C.) target cells (1×10$^4$ cells/well) are mixed with effector cells at various effector to target cell ratios in a final volume of 200 μl. Following incubation, 100 ml of culture medium is removed and analyzed in a Beckman gamma spectrometer (Beckman, Dallas, Tex.). Spontaneous release (SR) is determined as CPM from targets plus medium and maximum release (MR) is determined as CPM from targets plus 1M HCl. Percent target cell lysis is calculated as: [(Effector cell+target CPM)−(SR)/(MR)−(SR)]×100. Spontaneous release values of targets are typically 10%-20% of the MR.

For certain CTL assays, the effectors may be in vitro stimulated multiple times, for example, on day 8-12 after the primary in vitro stimulation. More specifically, 10$^7$ effector cells are mixed with 6×10$^5$ irradiated (10,000 rads) stimulator cells, and 2×10$^7$ irradiated (3,000 rads) "filler" cells (prepared as described below) in 10 ml of "complete" RPMI medium. (RPMI containing: 5% heat inactivated Fetal Bovine Serum. 2 mM L-glutamine, 1 mM sodium pyruvate, 1× non essential amino acids, and 5×10$^5$ M 2-mercaptoethanol). Stimulator cells for in vitro stimulation of effector cells are generated from irradiated retroviral vector transduced syngeneic cells. "Filler" cells are prepared from naive syngeneic mouse spleen cells resuspended in RPMI, irradiated with 3,000 rads at room temperature. Splenocytes are washed with RPMI, centrifuged at 3,000 rpm for 5 minutes at room temperature, and the pellet is resuspended in RPMI. The resuspended cells are treated with 1.0 ml tris-ammonium chloride (100 ml of 0.17 M tris base, pH 7.65, plus 900 ml of 0.155 M NH$_4$Cl; final solution is adjusted to a pH of 7.2) at 37° C. for 3-5 minutes. The secondary in vitro restimulation is then cultured for 5-7 days before testing in a CTL assay. Any subsequent restimulations are cultured as described above with the addition of 2-10 U of recombinant human IL-2 (200 U/ml, catalog #799068, Boehringer Mannheim, W. Germany).

2. Felines

Since the vectors are to be utilized for treating felines, an assay demonstrating immunological efficacy in felines is needed. The following is a description of the generation of the autologous T-cell lines needed for restimulator and target cells for the standard $^{51}$Cr release assay (Brown et al., *J. Vir.* 65:3359-3364, 1991). Briefly, peripheral blood mononuclear cells (PBMC) are obtained following venipuncture and Ficoll-sodium diatrizoate (Histopaque-1077; Sigma, St. Louis, Mo.) density gradient centrifugation. These PBMCs are stimulated by 5 ugm/ml concanavalin A (Con A, Sigma) for three days, and maintenance in medium containing 25 U/ml human recombinant interleukin-2 (IL-2) (Boehringer Mannheim Biochemicals, Indianapolis, Ind.) and 10% bovine T-cell growth factor (TCGF). Cells are seeded into round bottom 96-well microliter plates at an average of 1 or 0.3 cells per well with 5×10$^4$ irradiated (3,000 rads) autologous PBMC, 10% bovine TCGF, and 25 U/ml of IL-2 in a final volume of 200 ul of complete RPMI. Complete RPMI consist of RPMI 1640 medium containing 10% FBS, 2 mM L-glutamine, 5×10$^{-5}$ M 2-mercaptoethanol, and 50 ug of gentamycin per ml. Clones are expanded sequentially to 48-well and 24-well plates. After several weeks, cells are transduced with retroviral vectors expressing FIV env/rev genes (WO 94/06921), and selected with G418. Expression of these cell lines are monitored by Western blot analysis as in Example 15C. Cell lines expressing high levels of the desired protein function as stimulators and targets in a standard $^{51}$Cr release assay as in Example 15D 1. Effector cells are recovered for the CTL assay from the peripheral blood mononuclear cells (PBMC) obtained following venipuncture and Ficoll-sodium diatrizoate density gradient centrifugation.

E. Administration Protocols

Six- to eight-week-old female Balb/C, C57B16 or C3H/He mice are injected intramuscularly (i.m.) with 0.1 ml of reconstituted (with sterile deionized, distilled water) or intraperitoneally (i.p.) with 1.0 ml of lyophilized FIV env/rev/RRE expressing Sindbis vector. Two injections are given one week apart. Seven days after the second injection, the animals are sacrificed. Chromium release CTL assays are then performed essentially as described in Example 13D 1.

Felines are also injected intramuscularly (i.m.) with 0.5 ml of reconstituted (with sterile deionized, distilled water) or intraperitoneally (i.p.) with 2.0 ml of lyophilized FIV env/rev/RRE expressing Sindbis vector. Two injections are given one week apart. Seven days after the second injection, PBMCs are withdrawn for the CTL assay. Chromium release CTL assays are then performed essentially as described in Example 13D 2.

Example 16

Figure 5A:
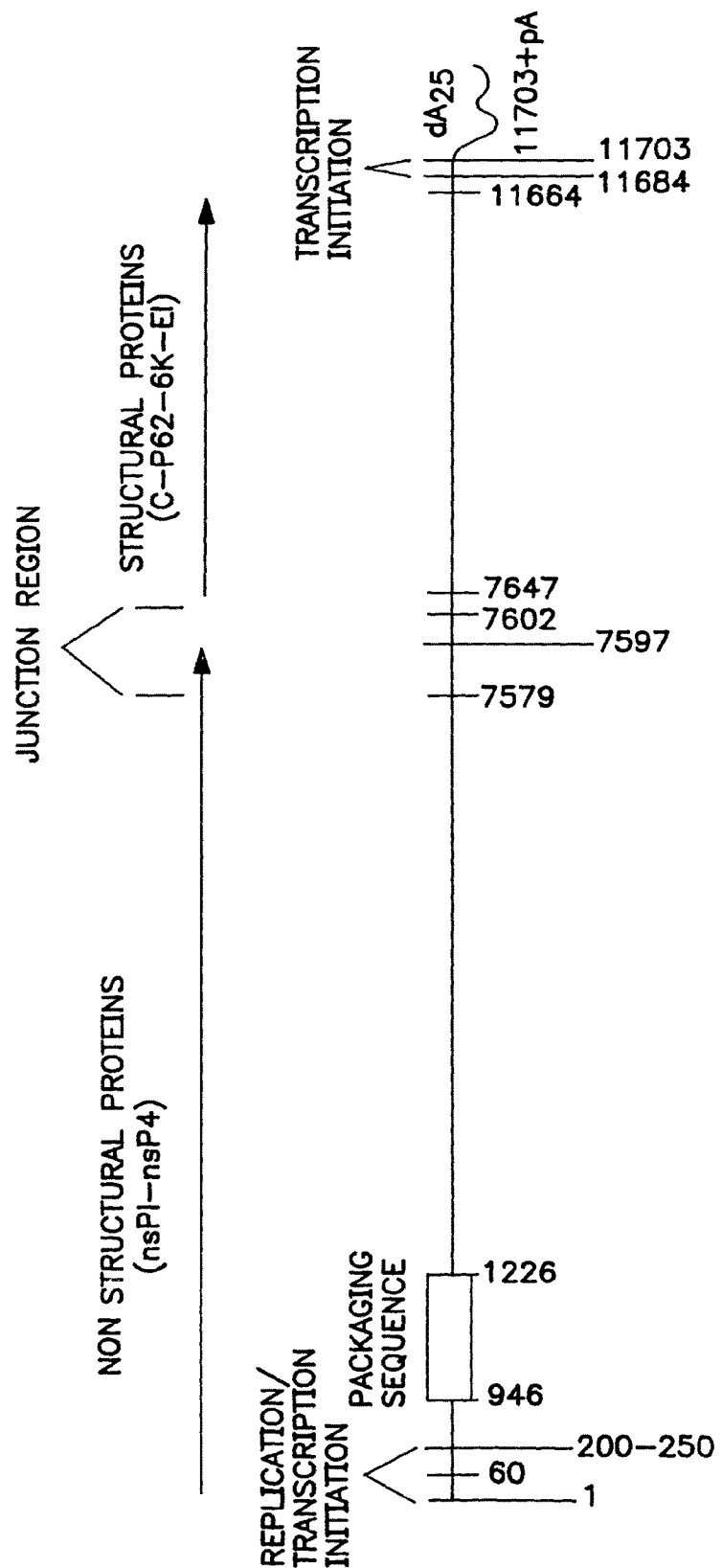
FIG. 5 is an illustration of Sindbis Helper Vector Construction.
Figure 5B:
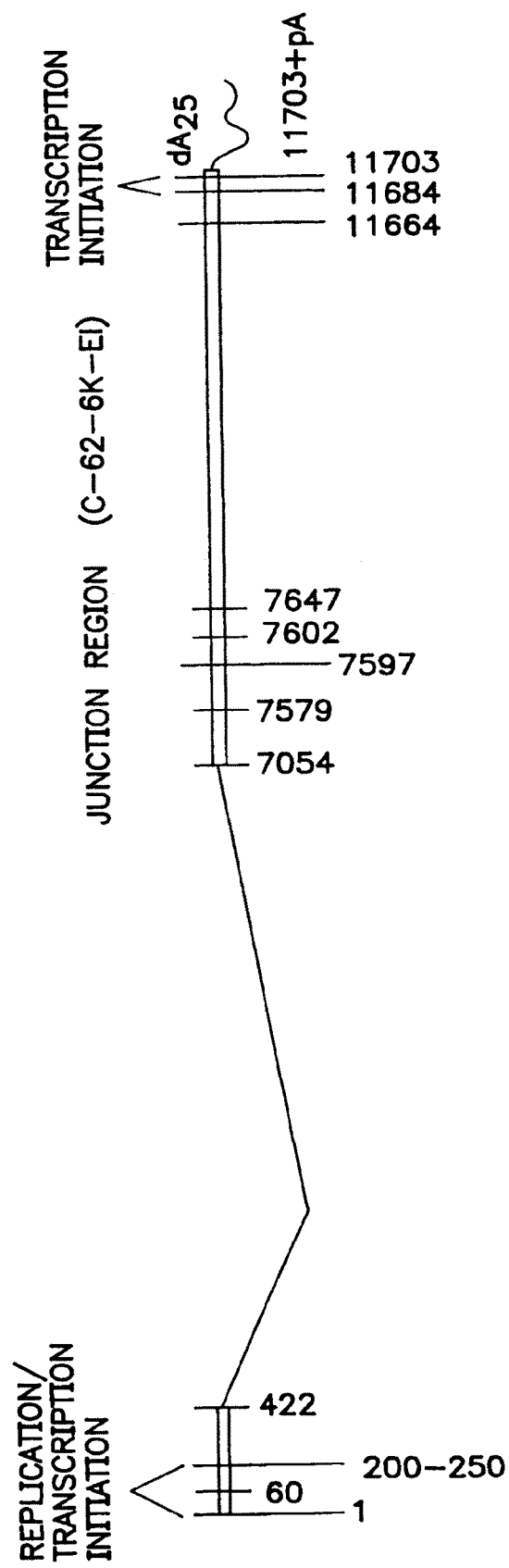

Tissue Specific Expression by Activation of Disabled Alphavirus Vectors Using Tissue Specific Cellular RNA: Construction of Alphavirus Tumor Specific Expression Vectors for the Treatment of Colorectal Cancer A. Construction of a Recombinant Sindbis Vector (SIN-CEA) Dependent on the Expression of The CEA Tumor Marker As described previously and shown diagrammatically in FIG. 20, the disabled junction loop out model is constructed with the junction region of the vector flanked by inverted repeat sequences which are homologous to the RNA of choice. In this example, sequences from the CEA tumor antigen cDNA (Beauchemin et al., *Molec. and Cell. Biol.* 7:3221, 1987) are used in the inverted repeats. To construct a CEA RNA responsive Sindbis vector, the junction region is preceded by two CEA anti-sense sequence domains (A$^1$ and B$^1$) separated by a six base pair hinge domain. A single twenty base pair CEA sense sequence (A2), which is complementary to A1, is placed at the 3' end of the junction region. In choosing the correct A1 and B1 antisense sequences, the only two requirements are that they be specific for the targeted RNA sequence and that the anti-sense sequences hybridize to two RNA sequence domains separated by three nucleotides. This three nucleotide gap will serve as a hinge domain for the polymerase to hop and switch reading strands bridging the non-structural protein domain of the vector to the junction region of the vector (FIG. 5). To construct such a configuration, two oligonucleotides are synthesized complementing each other to create a fragment insert containing convenient restriction enzyme sites at the extreme 5' and 3' ends. The oligonucleotide fragment insert is then ligated into the Sindbis vector between the disabled junction region and the multiple cloning sites of the Sindbis vector. The sense oligonucleotide strand, from 5' to 3', should contain an Apa I restriction site, followed by the A1 anti-sense domain, a six by hinge domain, a B1 anti-sense domain, a synthetic junction region domain, and the A2 sense domain, followed by a Xho I restriction enzyme site. The following oligonucleotide sequence is used to design a CEA RNA responsive Sindbis vector. The nucleotide number sequence is obtained from Beauchemin et al., *Molec. and Cell Biol.* 7:3221, 1987.

```
5'-3' CEA sense strand:
            CEA 618                       CEA 589
      Apa I   *--------------------------------*
CGC GC G GGC CCT GT G ACA T TG AAT AGA GT G AGG G TC CTG
TTG GG (SEQ. ID NO. 107)

CEA 651                       CEA 622
     *--------------------------------*    *   Synthetic
A AAG G TT TCA CAT TT G TAG C TT GCT GTG TC A TTG C GA TCT
CTA CG (SEQ. ID NO. 108)

CEA 599           CEA 618
 Junction Core   *   *--------------------*   Xho I
G TGG T CC TAA ATA GT T CAC T CT ATT CAA TG T CAC A CT CGA
GCC GG (SEQ. ID NO. 109)
```

The 5'-3' CEA anti-sense strand is complementary to the above oligonucleotide. After both oligonucleotides are synthesized, the oligonucleotides are mixed together in the presence of 10 mM Mg, heated to 100° C. for 5 minutes and cooled slowly to room temperature. The oligonucleotide pair is then digested with the Apa I and Xho I restriction enzymes, mixed and ligated at a 25:1 molar ratio of insert to plasmid, pCMV-SIN or pMET-SIN predigested with the same enzymes. These constructs are designated pCMV/SIN-CEA and pMET/SIN-CEA, respectively.

Construction of a SIN-CEA Vector and Producer Cell Line Expressing Gamma Interferon (SIN-CEA/IFN)

The human gamma interferon gene is subcloned from the retroviral vector plasmid pHu-IFN-γ (Howard et al., *Ann N.Y. Acad. Sci.* 716:167-187, 1994) by digesting with Xho I and Cla I. The resulting 500 by fragment containing the coding sequences of γ-IFN is isolated from a 1% agarose gel.

Alternatively, the human γ-IFN cDNA is derived from RNA isolated from PHA-stimulated Jurkat T cells by guanidinium thiocyanate extraction followed by ultracentrifugation through a CsCl gradient. The RNA (Sigma, St. Louis, Mo.) is then reverse-transcribed in vitro and a gene-specific oligonucleotide pair is used to amplify γ-IFN cDNA by polymerase chain reaction using Taq polymerase. The PCR DNA was repaired with T4 DNA polymerase and Klenow and cloned into the Hinc II site of SK+ plasmid (Stratagene, San Diego, Calif.) treated with CIAP. In the sense orientation, the 5' end of the cDNA is adjacent to the Xho I site of the SK+ polylinker and the 3' end adjacent to the NotI site. The 512 base pair fragment encoding the human γ-IFN molecule is placed into the Xho I/NoyI site of either the pCMV/SIN-CEA or pMET/SIN-CEA vectors. These new plasmids are designated pCMV/SIN-CEA/IFN-γ or pMET/SIN-CEA/IFN-γ, respectively.

B. Construction of a SIN-CEA Vector and Producer Cell Line Expressing Thymidine Kinase (SIN-CEA/TK)

A PCR amplified product containing the cDNA clone of the herpes simplex thymidine kinase ("HSVTK"), flanked with 5' Xho 1 and 3' NotI restriction enzyme sites is obtained using the pHS1TK3 KB (Mcknight et al., *Nuc. Acids Res.* 8:5949, 1980) clone as target DNA. The sequences for the primers used for the PCR amplification are obtained from published sequences (Wagner et al., *PNAS* 78:1442, 1981). The 1,260 base pair amplified product is then digested with Xho I and Nod ligated into the Xho I/NotI site of either the pCMV/SIN-CEA or pMET/SIN-CEA vectors. These new plasmids are designated pCMV/SIN-CEA/HSVTK or pMET/SIN-CEA/HSVTK, respectively.

C. Creation of CEA RNA Dependent Sindbis Vector Producer Cell Lines

Unlike the previous examples of creating producer cell lines (Example 7), it may be that only a single round of gene transfer into the packaging cell line is possible by vector transfection. Since these vectors will be disabled and prevented in the synthesis of full genomic vectors, re-infection of a fresh layer of Sindbis packaging cell lines will end in an aborted infection since these vectors are now dependent on the presence of the CEA RNA to become active. Higher titers may be achieved by dilution cloning transfected producer cell lines using the RT-PCR technique.

Example 17

Replacement Gene Therapy Using Recombinant Alphavirus Vectors

The following example describes the construction of alphavirus vectors capable of generating a therapeutic protein.

A. Construction of a Sindbis Factor VIII Vector

Hemophilia A disease is characterized by the absence of Factor VIII, a blood plasma coagulating factor. Approximately 1 in 20,000 males have hemophilia A in which the disease state is presented as a bleeding disorder, due to the inability of affected individuals to complete the blood clotting cascade.

The treatment of individuals with hemophilia A is replacement with the Factor VIII protein. The only source for human Factor VIII is human plasma. In order to process human plasma for Factor VIII purification, human donor samples are pooled in lots of over 1000 donors. Due to the instability of the Factor VIII protein, the resulting pharmaceutical products are highly impure, with an estimated purity by weight of approximately 0.04%. In addition, there is a serious threat of such infectious diseases as hepatitis B virus and the Human Immunodeficiency Virus, among others, which contaminate the blood supply and can thus be potentially co-purified with the Factor VIII protein.

The Factor VIII cDNA clone is approximately 8,000 bps. Insertion of the Factor VIII cDNA into pKSSINBV yields a vector/heterologous gene genomic size of approximately 15,830 bps. If the packaging of this large vector RNA into particles is inefficient, the size of the insert can be decreased further by eliminating the "B-domain" of the Factor VIII insert. It has been shown that the Factor VIII B-domain region can be removed from the cDNA without affecting the functionality of the subsequently expressed protein.

A Sindbis-Factor VIII vector is constructed as follows. Factor VIII cDNA is obtained from clone pSP64-VIII, an ATCC clone under the accession number 39812, containing a cDNA encoding the full-length human protein. pSP64-VIII is digested with Sal I, the termini are blunted with T4 DNA polymerase and 50 uM of each dNTP, and the ca. 7700 bp. fragment is electrophoresed in a 1% agarose/TBE gel and purified with GENECLEAN™. The Factor VIII cDNA containing blunt ends is then ligated into pKSII3'SIN (Example 3), prepared by digestion with Hinc II, treated with CIAP, and purified from a 1% agarose gel. This plasmid is known as pF83'SIN.

For insertion of Factor VIII into the various Sindbis vectors described in Example 3, plasmid pF83'SIN is digested with Xho I and a limited Sac I digest, and the resulting 7,850 by fragment is isolated from a 0.7% agarose/TBE gel. This Factor VIII-3'SIN fragment is then inserted into each of the vectors listed below. Prior to insertion of this fragment the plasmids are prepared by digestion with Xho I and Sac I, treated with CIAP, isolated by 1% agarose/TBE gel electrophoresis, and purified with GENECLEAN™:

| Vector | Functional Junction Region (+/−) |
|---|---|
| pKSSINBV | + |
| pKSSINd1JRsjrc | + |
| pKSSINd1JRsjrPC | + |
| pKSSINd1JRsjrNP(7,582-7,601) | + |
| pKSSINd1JRsexjr | + |

Following insertion of the Factor VIII cDNA, these vectors are designated:
pKSSINBVF8
pKSSINdlJRsjrcF8
pKSSINdlJRsjrPCF8
pKSSINdlJRsjrNP(7,582-7,601)F8
pKSSINdlJRsexjrF8
respectively.

Packaging of the Factor VIII cDNA containing vectors is accomplished by the transfection of packaging cell lines (described in Example 7) with in vitro transcribed vector/Factor VIII RNA. The efficiency of packaging is determined by measuring the level of Factor VIII expression in cells infected with the packaged vector and compared to similar experiments performed with the pKSSIN-luc vector described in Example 3.

B. Construction of a Glucocerebrosidase Sindbis Vector

Gaucher disease is a genetic disorder that is characterized by the deficiency of the enzyme glucocerebrosidase. This enzyme deficiency leads to the accumulation of glucocerebroside in the lysosomes of all cells in the body. However, the disease phenotype is manifested only in the macrophages, except in the very rare neuropathic forms of the disease. The disease usually leads to enlargement of the liver and spleen and lesions in the bones. (For a review, see Science 256:794, 1992, and The Metabolic Basis of Inherited Disease, 6th ed., Scriver et al., vol. 2, p. 1677.)

A glucocerebrosidase Sindbis vector is constructed as follows. Briefly, a glucocerebrosidase (GC) cDNA clone containing a Xho I restriction enzyme site 5' and 3' of the cDNA coding sequence is first generated. The clone is generated by digesting pMFG-GC (Ohashi et al., PNAS 89:11332, 1992) with Nco I, blunt-ending the termini with T4 DNA polymerase and dNTPs, ligating with Xho I linkers, and purifying the GC gene from a 1% agarose gel. The GC fragment is subsequently digested with Xho I and ligated with the desired Sindbis vector (for example, pKSSINBV) that has also been digested with Xho I. Packaging of the Sindbis-glucocerebrosidase vector is accomplished by introduction of vector RNA (for example, transfection of in vitro transcribed RNA) into any of the packaging cell lines described in Example 7.

Both the Sindbis Factor VIII and the Sindbis Glucocerebrosidase vectors are also readily convertible to plasmid DNA based-vectors which initiate vector replication and heterologous gene expression for use in direct delivery or the establishment of vector producer cell lines (see Examples 3 and 7).

Example 18

Inhibition of Human Papilloma Virus Pathogenicity by Sequence-Specific Antisense or Ribozyme Molecules Expressed from Sindbis Virus Vectors To date, more than sixty types of human papilloma viruses (HPV), which have a pronounced tropism for cells of epithelial origin, have been isolated and characterized. Among the HPV group are a substantial number of types which infect the human anogenital tract. This group of HPVs can be further subdivided into types which are associated with benign or with malignant proliferation of the anogenital tract.

There are between 13,000 and 20,000 cervical cancer deaths per year in the U.S. In developing countries, cervical cancer is the most frequent malignancy, and in developed countries cervical cancer ranks behind breast, lung, uterus, and ovarian cancers. One statistic which especially supports the notion that anogenital proliferation is a growing health problem is that medical consultations for genital warts increased from 169,000 in 1966 to greater than 2 million in 1988.

Several lines of evidence exist which link HPV to the pathogenesis of cervical proliferative disease. A distinct subset of types, so called 'low risk HPVs', are associated with benign proliferative states of the cervix (e.g., HPV 6, 11, 43, 44), while another subset of types, the 'high risk HPVs', are associated with lesions which may progress to the malignant state (e.g., HPV 16, 18, 31, 33, 35, etc.). Approximately 95% of cervical tumors contain HPV, with HPV type 16 or 18 DNA being found in about 70% of them.

The frequency of HPV in the young sexually active female population appears to be quite high. Indeed, in a recent study of 454 college women, 213, or 46% were HPV positive. Among the HPV positive group, 3% were HPV 6/11 positive, and 14% were HPV 16/18 positive. Of these 454 women, 33 (7.3%) had abnormal cervical proliferation, as determined by cytology.

With regard to the design of antisense and ribozyme therapeutic agents targeted to HPV, there are important parameters to consider relating to the HPV types to target (i.e., types associated with condyloma acuminatum or types associated with malignant cervical proliferation) and HPV expressed genes to target, including but not limited to, HPV genes E2, E6, or E7.

In general, the expression of HPV genes is defined temporally in two phases, early (E) genes expressed prior to viral DNA replication, and late (L) genes expressed after viral DNA replication. There are 7 early enzymatic HPV genes, and 2 late structural HPV genes.

Based on the discussion presented above, antisense/ribozyme therapeutics directed towards the HPV 6/11 groups may be constructed which target the viral E2 gene. It seems possible that the E2 gene target may be precarious with regard to the HPV 16/18 group, by a mechanism of driving integration of the virus through inhibition of E2 protein expression. Thus, it seems that the E6/E7 genes in HPV types 16/18 should be targeted directly.

Described below is the construction of antisense and ribozyme therapeutics into Sindbis virus vectors (described in Example 2) specific for HPV type 16 E6 and E7 RNA. Insertion of the HPV antisense and ribozyme moieties is between the Cla I and Xba I sites of the Sindbis vector.

A. Construction of an HPV 16 E6/E7 Antisense Therapeutic

The HPV 16 viral genomic clone, pHPV-16 (ATCC number 45113) is used as a template in a PCR reaction for the amplification of specific sequences from the viral E6/E7 genes. The HPV 16 antisense moiety is first inserted into the plasmid vector pKSII⁺; removal of the antisense therapeutic from the plasmid vector and insertion into the various Sindbis vector backbones is accomplished via the unique antisense moiety terminal Cla I and Xba I restriction endonuclease sites. Amplification of a portion of the HPV 16 E6/E7 genes is accomplished with the primer pair shown below:

```
Forward primer (buffer sequence/Xba I site/HPV 16
nucleotides 201-222):
                                        (SEQ. ID NO. 110)
TATATTCTAGAGCAAGCAACAGTTACTGCGACG Reverse primer (buffer sequence/Cla I site/HPV 16
nucleotides 759-738):
                                        (SEQ. ID NO. 111)
TATATATCGATCCGAAGCGTAGAGTCACACTTG
```

In addition to the HPV 16 E6/E7 complementary sequences, both primers contain a five nucleotide 'buffer sequences' at their 5' ends for efficient enzyme digestion of the PCR amplicon products. Generation of the HPV 16 amplicon with the primers shown above is accomplished with the PCR protocol described in Example 4. It has been shown previously that the E6/E7 mRNA in infected cervical epithelia is present in three forms, unspliced and two spliced alternatives (E6* and E6**), one in which nucleotides 226-525 of E6 are not present in the mature message (Smotkin et al., *J. Virol* 63:1441-1447, 1989). The region of complementary between the antisense moiety described here and the HPV 16 genome is viral nucleotides 201-759. Thus the antisense moiety will be able to bind to and inhibit the translation of the E6/E7 unspliced message and the spliced E6* and E6** spliced messages.

The HPV 16 E6/E7 580 by amplicon product is first purified with GENECLEAN™, digested with the restriction enzymes Cla I and Xba I, and electrophoresed on a 1% agarose/TBE gel. The 568 by band is then excised from the gel, the DNA purified with GENECLEAN™ and ligated into the pKSII$^+$ plasmid prepared by digestion with Cla I and Xba I, treatment with CIAP, and treatment with GENECLEAN™. This plasmid is known as pKSaHPV16E6/E7.

B. Construction of HPV 16 E6/E7 Hairpin Ribozyme Therapeutics

In order to efficiently inhibit the expression of HPV 16 E6 and E7 proteins, a hairpin ribozyme (HRBZ) with target specificities to E6 mRNA is constructed. The HPV 16 ribozyme moiety is first inserted into the plasmid vector pKSII$^+$; removal of the ribozyme therapeutic from the plasmid vector and insertion into the various Sindbis vector backbones is accomplished via the unique ribozyme moiety terminal Cla I and Xba I restriction endonuclease sites.

The HRBZ is homologous to the HPV 16 E6 RNA (nts 414-431) shown below:

```
TTAACTGTCAAAAGCCAC      (SEQ. ID NO. 112)
```

The HRBZ is designed to cleave after the T residue in the TCTC hairpin ribozyme loop 5 substrate motif, shown underlined above. Following cleavage, the HRBZ is recycled and able to hybridize to, and cleave, another unspliced E6/E7 mRNA or the E6* spliced mRNA molecule.

Double-stranded HRBZ as defined previously (Hampel et al., *Nucleic Acids Research* 18:299-304, 1990), containing a 4 base 'tetraloop' 3 and an extended helix 4, with specificity for the HPV 16 E6 RNA shown above, is chemically synthesized and includes both the 5' and 3' ends, respectively, Cla I and Xba I sites. The sequence of the chemically synthesized HPV 16 E6 HRBZ strands are shown below:

```
HPV 16 E6 HRBZ, sense strand (5'→3'):
                                        (SEQ. ID NO. 113)
5'-CGATGTGGCTTTTAGATGTTAAACCAGAGAAACACACGGACTTCGGT
CCGTGGTATATTAGCTGGTAT-3'

HPV 16 E6 HBRZ, antisense strand (5'→3'):
                                        (SEQ. ID NO. 114)
5'-CTAGATACCAGCTAATATACCACGGACCGAAGTCCGTGTGTTTCTCT
GGTTTAACATCTAAAAGCCACAT-3'
```

In order to form the double-stranded HPV 16 E6 specific HRBZ with Cla I and Xba I cohesive ends, equal amounts of the oligonucleotides are mixed together in 10 mM $Mg^{2+}$, heated at 95° C. for 5 minutes, then cooled slowly to room temperature to allow the strands to anneal.

The double-stranded HPV 16 E6 HRBZ with Cla I and Xba I cohesive ends is first ligated into the pKSII$^+$ plasmid vector, prepared by digestion with Cla I and Xba I, treatment with CIAP, and treatment with GENECLEAN™. This plasmid is known as pKSHPV16E6HRB Z.

The HPV 16 antisense and hairpin ribozyme moieties are liberated from their plasmid vectors, pKSaHPV16E6/E7 and pKSHPV16E6HRBZ, respectively, by digestion with Cla I and Xba I, purification by agarose electrophoresis and GENECLEAN™, and insertion into the desired vector backbone, prepared by digestion with Cla I and Xba I, and treatment with CIAP. Several possible Sindbis vectors some of which are shown below, and whose detailed construction is described in Example 2, are suitable for the insertion of the HPV 16 antisense and ribozyme therapeutic moieties:

| Vector | Functional Junction Region (+/−) |
|---|---|
| pKSSINBV | + |
| pKSSINBVdlJR | − |
| pKSSINdlJRsjrc | + |
| pKSSINdlJRsjrPC | + |
| pKSSINdlJRsjrNP(7582-7601) | + |
| pKSSINdlJRsexjr | + |

Since the antisense and ribozyme therapeutic operate at the level of RNA, it is not necessary that the vectors containing these moieties contain a functional junction region. That is, translation of the region corresponding to the Sindbis structural proteins occurs only from subgenomic RNA. However, because translation of the antisense and hairpin ribozyme therapeutic is not an issue, these moieties will exert their affect from the level of positive stranded Sindbis genomic vector RNA.

On the other hand, it may be desired to administer repeated doses to an individual; thus the antisense and hairpin palliative would be inserted downstream of the adenovirus E3 or human cytomegalovirus H301 genes, which down-regulate the expression of MHC class 1 molecules in infected cells. Insertion of the antisense and hairpin palliatives is accomplished in the vectors from Examples 3 and 4 shown below, between the Cla I and Xba I sites:

| Vector | Functional Junction Region (+/−) |
|---|---|
| pKSSINdlJRsjrcAdE3 | + |
| pKSSINdlJRsjrcH301 | + |

Subgenomic mRNA is synthesized in these vectors, which serves as a translational template for the Ad E3 and CMV H301 genes. Thus, in these constructions, functional HPV 16 antisense and hairpin ribozyme palliatives will be present on the levels of both subgenomic and positive stranded genomic Sindbis vector RNA.

Further, the HPV 16 antisense and hairpin ribozyme palliatives can be inserted downstream of a heterologous gene inserted into the described Sindbis vectors. For example, one could insert the HPV 16 antisense and hairpin ribozyme palliatives downstream of a heterologous gene coding for an immunogenic epitope of HPV 16 from, for example, the E6/E7 or L1 proteins. In these vectors, it would not be desired to include the immunoregulatory Ad E3 or CMV H301 genes.

Expression of the E6/E7 genes during infection with both the high- and low-risk HPV groups is required for proliferation of the cervical epithelium. The HPV E7 protein from all HPV types tested forms a complex with the retinoblastoma protein, and the E6 protein from HPV types 16 and 18 associates with and degrades the cellular p53 protein. The p53 and retinoblastoma cellular gene products are involved in the growth control of the cell, and altering the expression or function of these proteins can release the growth control in affected cells. Thus, an antisense or ribozyme therapeutic agent to both HPV groups should either directly or ultimately diminish the expression of one or both of these genes. Expression of the E6/E7 genes is trans-activated by the viral E2 protein. However, by utilizing an alternative splicing strategy, the E2 protein can also act as a trans-repressor. Integration of the oncogenic HPV types occurs in the viral E2 region and abrogates the expression of the E2 protein. Integration by the oncogenic HPV types appears to be a pivotal event in the frank induction and/or maintenance of cervical carcinoma. This event results in the constitutive expression of the E6/E7 genes. In the integrated state, expression of the E6/E7 genes is trans-activated by factors present in infected keratinocytes. The inactivation of the viral E2 control mechanism in response to the cellular keratinocyte factor activation of E6/E7 expression might be a critical event in viral integration.

Example 19

Inhibition of Human Interferon A Expression in Infected Cells by Sequence-Specific Ribozyme Molecules Expressed from Sindbis Virus Vectors Interferons (IFNs) comprise a family of small proteins which effect a wide range of biological activities in the mammalian cell, including the expression of MHC antigens, the expression of several genes which modulate cell growth control, and the resistance to viral infections (Pestka et al., *Ann. Rev. Biochem.* 56:727-777, 1987). Of the three classes of IFNs, α, β, and γ-IFN, α-IFN, or leukocyte interferon, has a key role in limiting viral replication in the infected cell.

The antiviral effects of IFN-α are associated with the induction of two cellular enzymes which inhibit the viral lifecycle in the infected cell. One enzyme is a double-stranded RNA dependent 68-kDa protein kinase that catalyzes the phosphorylation of the α subunit of the protein synthesis initiation factor eIF-2. The second enzyme induced by IFN-is 2',5'-oligoadenylate synthetase (2',5'-OAS), which in the presence of double-stranded RNA activates the latent endonuclease, RNase L, which is responsible for degradation of viral and cellular RNAs (Johnston and Torrence, *Interferons* 3:189-298, Friedman (ed.), Elsevier Science Publishers, B.V., Amsterdam, 1984).

Because their replication strategy includes a double-stranded RNA intermediate, the RNA viruses in particular are strong inducers of interferon. With regard to Sindbis virus, double-stranded RNA molecules are present during the replication of both positive- and negative-stranded genome length molecules, and during the transcription of subgenomic mRNA. It has been demonstrated that infection of cells with Sindbis virus results in the induction of interferon (Saito, *J. Interferon Res.* 9:23-24, 1989).

In applications where extended expression of the therapeutic palliative is desired, expression of IFN in the infected cell is inhibited by inclusion of a hairpin ribozyme with specificity for IFN-α mRNA in the Sindbis vector. Inhibition of IFN-expression thus mitigates induction of the cascade of cellular proteins, including the eIF-2 protein kinase and 2',5'-OAS, which inhibit the extent to which virus can replicate in the infected cell. Prolonged expression of the therapeutic palliative without induction of an immune response targeted towards the vector infected cell is desired in all applications other than antigen presentation and includes, for example, systemic protein production, antisense and ribozyme, and accessory molecules.

A. Construction of a Hairpin Ribozyme with Targeted Specificity for Interferon A mRNA In order to efficiently inhibit the expression of interferon α protein in cells infected with Sindbis vectors, a hairpin ribozyme (HRBZ) with target specificity for interferon α mRNA is constructed. The IFN-α ribozyme moiety is first inserted into the plasmid vector pKSII+ (Stratagene, La Jolla, Calif.); removal of the ribozyme therapeutic from the plasmid vector and insertion into the various Sindbis vector backbones is accomplished via the unique ribozyme moiety terminal Cla I and Xba I restriction endonuclease sites.

The HRBZ is homologous to nucleotides 1026-1041 of the human interferon alpha gene IFN-alpha 4b shown below, and to all IFN-α genes sequenced, including 5, 6, 7, 8, and 14, but not gene 16 (Henco et al., *J. Mol. Biol.* 185:227-260, 1985):

```
5'-TCT CTG TCC TCC ATG A   (SEQ. ID NO. 120)
```

The HRBZ is designed to cleave after the T residue in the TGTC hairpin ribozyme loop 5 substrate motif, shown underlined above. Following cleavage, the HRBZ is recycled and able to hybridize to, and cleave, another IFN-a mRNA molecule.

Double-stranded HRBZ as defined previously (Hampel et al., *Nucleic Acids Research* 18:299-304, 1990), containing a 4 base tetraloop 3 and an extended helix 4, with specificity for the IFN-a mRNA shown above, is chemically synthesized and includes at the 5' and 3' ends, respectively, Cla I and Xba I sites. The sequence of the chemically synthesized IFN-a HRBZ strands are shown below:

```
IFN-α HRBZ, sense strand (5' to 3'):
                                    (SEQ. ID NO. 121)
TCG AGT CAT GGA GAG AGG AGA ACC AGA GAA ACA CAC GGA
CTT CGG TCC GTG GTA TAT TAC CTG GAT IFN-α HBRZ, antisense strand (5' to 3'):
                                    (SEQ. ID NO. 122)
CGA TCC AGG TAA TAT ACC ACG GAC CGA AGT CCG TGT GTT
TCT CTG GTT CTC CTC TCT CCA TGA C
```

In order to form the double-stranded IFN-α specific HRBZ with Cla I and Xba I cohesive ends, equal amounts of the oligonucleotides are mixed together in 10 mM Mg2+, heated at 95° C. for 5 minutes, then cooled slowly to room temperature to allow the strands to anneal.

The double-stranded IFN-α HRBZ with Cla I and Xba I cohesive ends is first ligated into the pKSII+ plasmid vector, prepared by digestion with Cla I and Xba I, treatment with CIAP, and treatment with GENECLEAN™. This plasmid is known as pKSIFNαHRBZ.

The IFN-α hairpin ribozyme moiety is liberated from the pKSIFNaHRBZ plasmid by digestion with Cla I and Xba I, purification by 2% Nu-Sieve/1% agarose electrophoresis and GENECLEAN™, and insertion into the desired vector backbone, prepared by digestion with Cla I and Xba I, and treatment with CIAP. Several possible Sindbis vectors some of which are shown below, and whose detailed construction is described in Examples 2, 3, and 4 are suitable for the insertion of the IFN-α hairpin ribozyme moiety:

| Vector | Functional Junction Region (+/−) |
|---|---|
| pKSSINBV | + |
| pKSSINBVdlJR | − |
| pKSSINdlJRsjrc | + |
| pKSSINdlJRsjrPC | + |
| pKSSINdlJRsjrNP(7582-7601) | + |
| pKSSINdlJRsexjr | + |
| pKSSINdlJRsjrcAdE3 | + |
| pKSSINdlJRsjrcH301 | + |

Since the ribozyme activity operates at the level of RNA, it is not necessary that this region is expressed as a portion subgenomic mRNA. However, when placed downstream of a functional junction region, the level of ribozyme synthesized is much greater and perhaps more effective in cleaving the IFN-α RNA target.

Further, in some applications, for example systemic expression of protein, multiple dose administration to an individual is required. In these applications, prolonged expression of the therapeutic palliative without induction of an immune response targeted towards the vector infected cell is desired. In this configuration, the IFN-αHRBZ moiety could be inserted upstream of the adenovirus E3 or human cytomegalovirus H301 genes, which down-regulate the expression of MHC class 1 molecules in infected cells. Following the gene which modulates MHC class I expression is, consecutively, an IRES element selected from among the group described in Example 5, and the therapeutic palliative. Ordered insertion of the hairpin ribozyme, Ad E3 or CMV H301, IRES, and heterologous gene of interest components along the multiple cloning sequence located in the vector between the vector junction region and 3' end is accomplished by modification with the appropriate restriction enzyme recognition sites of the component 5' and 3' ends. In these constructions, functional INF-a hairpin ribozyme palliatives will be present at the level of both subgenomic and positive stranded genomic Sindbis vector RNA.

Example 20

Ex Vivo and In Vivo Treatment of Human Cancers by Administration of Recombinant Alphavirus Vector Particles or Alpha Virus Plasmid DNA Vectors which Express Cytokines, Cytokine Receptors, or Drug Potentiators A. Vector Constructions 1. Gamma Interferon Murine gamma interferon is subcloned from the retroviral vector plasmid pMu-γIFN (Howard et al., *Ann. N.Y. Acad. Sci.* 716:167-187, 1994) by digesting with Cla I and making the termini blunt by Klenow enzyme and dNTPs. After heat inactivation of the Klenow enzyme, the vector is digested with Xho I. The resulting 800 by fragment containing the coding sequences of gamma interferon is isolated from a 1% agarose gel. pKSSINBV (Example 3) is digested with Xho I and Stu I, and the vector is purified by GENECLEAN™ and ligated with the gamma interferon insert. The resulting vector construction is known as pKSSINγMu. The human gamma interferon gene (Howard et al., supra) is similarly inserted into pKSSINBV using the same strategy. The resulting vector construct is known as pKSSINγHu. The interferon expressing Sindbis vectors are then packaged into vector particles. This is accomplished by introducing RNA from these vectors into a packaging cell line as described in Example 7.

The mouse and human interferon genes are also cloned into pVGELVISSINBV-linker (see Example 3). Briefly, pVGELVISSINBV-linker is first digested with Asc I and the termini made blunt by the addition of Klenow enzyme and dNTPs. The Klenow is heat inactivated and the vector is subsequently digested with Xho I. This vector is purified by GENECLEAN™ and ligated to the gamma interferon inserts prepared as described above. The resulting vectors are described pVGELVIS-γMu and pVGELVIS-γHu, respectively.

2. Interleukin-2

The human IL-2 gene is cloned by PCR amplification into the KT-3 retroviral backbone (Howard et al., *Ann N.Y. Acad. Sci.* 716:167-187, 1994). The source for the IL-2 gene is a pBR322 based plasmid which contains the IL-2 cDNA (ATCC #61391). The cDNA is PCR amplified using a standard three-temperature protocol as described in Example 3. The 5' primer is the sense sequence of the h1L-2 gene complimentary to the 5' coding region beginning at the ATG start codon. Additionally, a Xho I site is built into the 5' end of the primer sequence.

```
5' hIL-2
                                    (SEQ ID NO: 23)
5'-GCCTCGAGACAATGTACAGGATGCAACTCCTGTCT
```

The 3' primer is an antisense sequence of the hIL-2 gene complementary to the 3' coding region ending at the TAA stop codon. Additionally, a Cla I site is built into the 5' end of the primer sequence.

3' hIL-2

(SEQ ID NO: 24)
5LGAATCGATTTATCAAGTCAGTGTMGAGATGATGCT

The PCR amplicon is purified in a 1% agarose gel. To place the IL-2 gene in the KT-3 retroviral backbone, pMu-IFN is digested with Xho I and Cla I to remove the interferon gene. After treatment with phosphatase, the vector is purified in a 1% agarose gel. The vector and IL-2 insert are ligated and transformed using standard procedures, and recombinant clones are screened by restriction enzyme analysis. The resulting vector is designated pKThIL-2.

Human IL-2 is subcloned from the retroviral vector pKThIL2, into the pKSSINBV vector, using the same strategy employed for murine gamma interferon. The resulting vector construction is known as pKSSIN-huIL-2. The human IL-2 gene is also cloned into pVGELVISSINBV-linker as described above for the gamma interferon genes. The resulting construct is designated pVGELVIS-IL-2.

3. HSV-TK

The coding region and transcriptional termination signals of HSV-1 thymidine kinase gene (HSV-TK) are isolated as a 1.8 kb Bgl II/Pvu II fragment from plasmid 322TK (McKnight et. al., *Nuc. Acids Res.* 8:5949, 1980) cloned into pBR 322 (ATCC No. 31344). The ends are made blunt by the addition of Klenow enzyme and dNTPs. The 1.8 kb fragment is isolated on a 1% agarose gel and ligated to pKS SINBV which had been previously digested with Stu I, phosphatased and gel purified. This construct is known as pKSSINBV-TK. For use is physical gene transfer experiments, the TK gene is similarly cloned into pVGELVIS-SINBV-linker. The vector is prepared by digestion with Pml I, phosphatase treatment and isolated on a 1% agarose gel. This vector construct is known as pVGELVISBV-TK.

B. Administration

Any of the above-described vector constructs may be utilized along with packaging cell lines described in Example 7, in order to produce recombinant alphavirus particles suitable for administration to humans or animals (either directly or indirectly), or for infecting target cells. Such vector constructs may also introduced directly into target cells as a "naked" DNA molecule, as a DNA complex with various liposome formulations, or as a DNA ligand complex including the alphavirus DNA vector molecule (e.g., along with a polycation compound such as polylysine, a receptor specific ligand, or a psoralen inactivated virus such as Sendai or Adenovirus).

This aspect of the invention relates to pharmaceutical compositions comprising alphavirus vector constructs, recombinant alphavirus particles, or eukaryotic layered vector initiation systems described above (individually and/or collectively referred to herein sometimes as "gene delivery vehicles"), in combination with a pharmaceutically acceptable carrier or diluent. Such gene delivery vehicles can be formulated in crude or, preferably, purified form. Pharmaceutical compositions comprising the gene delivery vehicles may be prepared either as a liquid solution or as a solid form (e.g., lyophilized) which is resuspended in a solution prior to administration. In addition, the composition may be prepared with suitable carriers or diluents for topical administration, injection, or nasal, oral, vaginal, sub-lingual, inhalant, intraocular, enteric, or rectal administration.

Pharmaceutically acceptable carriers or diluents are non-toxic to recipients at the dosages and concentrations employed. Representative examples of carriers or diluents for injectable solutions include water, isotonic saline solutions, preferably buffered at a physiological pH (such as phosphate-buffered saline or Tris-buffered saline), mannitol, dextrose, glycerol, and ethanol, as well as polypeptides or proteins such as human serum albumin (HSA).

Gene delivery vehicles according to the invention can be stored in liquid, or preferably, lyophilized form. Factors influencing stability include the formulation (liquid, freeze dried, constituents thereof, etc.) and storage conditions, including temperature, storage container, exposure to light, etc. Alternatively, pharmaceutical compositions according to the invention can be stored as liquids at low temperatures. In a preferred embodiment, the gene delivery vehicles of the invention are formulated to preserve infectivity in a lyophilized form at elevated temperatures, and for this form to be suitable for injection into patients following reconstitution.

In another aspect of the present invention, methods are provided for preventing or treating various diseases and genetic disorders. Such methods comprise administering a gene delivery vehicle as described above, such that a therapeutically efficacious amount of the desired, or "selected," gene product is produced. As used herein, a "therapeutically effective amount" is an amount that that is of clinical relevance, i.e., protective immunity is achieved, tumor progression is retarded, etc. A "therapeutically effective amount" of a gene delivery vehicle according to the invention refers to the amount that must be administered to produce a therapeutically effective amount of the desired gene product in a particular patient or application. For instance, in a patient suffering from hemophilia A, a therapeutically effective amount of a gene delivery vehicle is an amount that elicits production of sufficient factor VIII (the desired gene product expressed from the selected heterologous nucleotide sequence) to produce therapeutically beneficial clotting and will thus generally be determined by each patient's attending physician, although serum levels of about 0.2 ng/mL (about 0.1% of "normal" levels) or more will be therapeutically beneficial. Typical dosages will range from about $10^5$ to $10^{12}$ gene delivery vehicles.

In some cases, gene delivery vehicles according to the invention will be administered as an adjunct to other therapy, such as hormonal, radiation, and/or chemotherapeutic treatment.

In various embodiments of the invention, gene delivery vehicles may be administered by various routes in vivo, or ex vivo, as described in greater detail below. Alternatively, the gene delivery vehicles of the present invention may also be administered to a patient by a variety of other methods. Representative examples include transfection by various physical methods, such as lipofection (Felgner, et al., *Proc. Natl. Acad. Sci. USA*, 84:7413, 1989), direct DNA injection (Acsadi, et al., *Nature*, 352:815, 1991; microprojectile bombardment (Williams, et al., *Proc. Nat'l. Acad. Sci. USA*, 88:2726, 1991); liposomes of several types (see e.g., Wang, et al., *Proc. Nat'l. Acad. Sci. USA*, 84:7851, 1987); $CaPO_4$ (Dubensky, et al., *Proc. Nat'l. Acad. Sci. USA*, 81:7529, 1984); DNA ligand (Wu, et al., *J. Biol. Chem.*, 264:16985, 1989); or administration of nucleic acids alone (WO 90/11092). Other possible methods of administration can include injection of producer cell lines into the blood or, alternatively, into one or more particular tissues, grafting tissue comprising cells treated with gene delivery vehicles according to the invention, etc.

When pharmaceutical compositions according to the invention are administered in vivo, i.e., to the cells of patient without prior removal of the cells from the patient, administration can be by one or more routes. In this context, "administration" is equivalent to "delivery." Typical routes of administration include traditional parenteral routes, such as intramuscular (i.m.), subcutaneous (sub-q), intravenous (i.v.), and interperitoneal (i.p.) injection. Other suitable routes include nasal, pulmonary, and even direct administration into a particular tissue, such as the liver, bone marrow, etc. In addition, other routes may be employed, as described below.

Transdermal or topical application of a pharmaceutical composition comprising a gene delivery vehicle according to the invention may be used as an alternate route of administration because the skin is the most expansive and readily accessible organ of the human body. Transdermal delivery systems (TDS) are capable of delivering a gene delivery vehicle through intact skin so that it reaches the systemic circulation in sufficient quantity to be therapeutically effective. TDS provide a variety of advantages, including elimination of gastrointestinal absorption problems and hepatic first pass effect, reduction of dosage and dose intervals, and improved patient compliance. The major components of TDS are a controlled release device composed of polymers, a gene delivery vehicle according to the invention, excipients, and enhancers, and a fastening system to fix the device to the skin. A number of polymers have been described and include, but are not limited to, gelatin, gum arabic, paraffin waxes, and cellulose acetate phthalate (Sogibayasi, et al., *J. Controlled Release*, 29:177, 1994). These polymers can be dermatologically formulated into aqueous, powder, or oil phases. Various combinations can produce lotions, pastes, ointments, creams, and gels, alone or together with the aid of emulsifiers.

Additionally, iontophoresis may be used to cause increased penetration of ionized substances into or through the skin by the application of an electrical field. This method has the advantage of being able to deliver the drug in a pulsatile manner (Singh, et al, *Dermatology*, 187:235, 1993).

Topical administration may also be accomplished by encapsulating gene delivery vehicles according to the invention in liposomes. Hyaluronic acid has been used as a bioadhesive ligand for the formation of liposomes to enhance adherence and retention to the extracellular matrix in cases of burns and wound healing (Yerushalmi, et al., *Arch. Biochem. and Biophys*, 313:267, 1994). As those in the art will appreciate, methods of liposome preparation can be tailored to control size and morphology. Liposomes can also be made to include one or more targeting elements to target a specific cell type.

Ocular administration is an alternate route to achieve delivery of compositions described herein. Systemic absorption occurs through contact with the conjunctival and nasal mucosae, the latter occurring as the result of drainage through the nasolacrimal duct. Formulations such as those described above which further comprise inert ingredients such as buffers, chelating agents, antioxidants, and preservatives can be incorporated into ophthalmic dosage forms intended for multiple dose use. Formulations also may consist of aqueous suspensions, ointments, gels, inserts, bioadhesives, microparticles, and nanoparticles.

The nasal cavity also offers an alternative route of administration for compositions comprising a gene delivery vehicle as described herein. For instance, the human nasal cavities have a total surface area of approximately 150 $cm^2$ and are covered by a highly vascular mucosal layer. A respiratory epithelium, comprised of columnar cells, goblet cells, and ciliary cuboidal cells, lines most of the nasal cavity (Chien, et al, *Crit. Rev. in Therap. Drug Car. Sys.*, 4:67, 1987). The subepithelium contains a dense vascular network and the venous blood from the nose passes directly into the systemic circulation, avoiding first-pass metabolism in the liver. Thus, delivery to the upper region of the nasal cavity may result in slower clearance and increased bioavailability of gene delivery vehicles. The absence of cilia in this area is an important factor in the increased effectiveness of nasal sprays as compared to drops. The addition of viscosity-building agents, such as methycellulose, etc. can change the pattern of deposition and clearance of intranasal applications. Additionally, bioadhesives can be used as a means to prolong residence time in the nasal cavity. Various formulations comprising sprays, drops, and powders, with or without the addition of absorptive enhancers, have been described (see Wearley, L, supra).

Oral administration includes sublingual, buccal, and gastrointestinal delivery. Sublingual and buccal (cheek) delivery allow for rapid systemic absorption of gene delivery vehicles and avoid hepatic first-pass metabolism and degradation in the stomach and intestines. Unidirectional buccal delivery devices can be designed for oral mucosal absorption only. Additionally, these devices can prevent diffusion-limiting mucus buildup to allow for enhanced absorption. Delivery through the gastrointestinal tract allows for precise targeting for drug release. Depending on the formulation, gene delivery vehicles can be specifically delivered to areas in the stomach, duodenum, jejunum, ileum, cecum, colon, or rectum. Oral formulations include tablets, capsules, aqueous suspensions, and gels. These may contain bioadhesive polymers, hydrodynamically balanced systems, gastroinflatable delivery devices, intragastric retention shapes, enteric coatings, excipients, or intestinal absorption promoters (Ritschel, W. A., *Meth. Exp. Clin. Pharmacol.*, 13:313, 1991).

The human rectum has a surface area of between 200 to 400 $cm^2$ and is abundant in blood and lymphatic vessels. This offers an alternative route for administrating compositions according to the invention. Depending on the actual site of administration, it may be possible to bypass first-pass metabolism by the liver. Targeting of the systemic circulation can be achieved by delivering the vehicle to an area behind the internal rectal sphincter which allows absorption directly into the inferior vena cava, thereby bypassing the portal circulation and avoiding metabolism in the liver. The liver can be targeted by delivering the vehicle to the region of the ampulla recti, which allows absorption into the portal system (Ritschel, supra.).

Alternatively, pulmonary administration can be accomplished through aerosolization. As the lungs are highly vascularized, this type of administration allows systemic delivery. The three systems commonly used for aerosol production are: the nebulizer, the pressurized metered dose inhaler, and the dry powder inhaler, all of which are known in the art. Aerosol therapy is very common in obstructive bronchial diseases but can be used as well as for the treatment of systemic diseases. The surface area of the adult human lung is approximately 75 $m^2$ and requires only one puff of an aerosol to cover this entire area within seconds. Absorption occurs quickly because the walls of the alveoli in the deep lung are extremely thin. Absorption and clearance depends on a number of factors, including particle size and solubility (Wearley, L, supra). Particles are preferably smaller than 5 µm in diameter.

The vaginal mucosa consists of stratified squamous epithelium. Gene delivery vehicles can be administered through the vaginal orifice onto the mucosa. Formulations include ointments, creams, and suppositories. Additional information regarding these and other routes of administration may be found in U.S. Ser. No. 08/366,788, filed on Dec. 30, 1994.

As an alternative to in vivo administration of the gene delivery vehicles of the invention, ex vivo administration can be employed. Ex vivo treatment envisions withdrawl or removal of a population of cells from a patient. Exemplary cell populations include bone marrow cells, liver cells, and blood cells from the umbilical cord of a newborn. Such cells may be be processed to purify desired cells for transduction prior to such procedures, for instance to obtain subsets of such cell populations, e.g., CD34$^+$ bone marrow progenitor cells. Preferred methods of purification include various cell sorting techniques, such as antibody panning, FACS, and affinity chromatography using a matrix coupled to antibodies specifically reactive to the desired cell type(s). Isolated cells are then transduced, after which they may be immediately re-introduced to the patient from which they were withdrawn. Alternatively, the cells may be expanded in culture by various techniques known to those skilled in the art prior to re-introduction.

In another embodiment of the invention, gene delivery vehicles of the invention are administered to patients in conjunction with another therapeutic compound. As those in the art will appreciate, such compounds may include, but are not limited to, other gene delivery vehicles designed to deliver one or more other therapeutic genes to the patient, as is described in U.S. Ser. No. 08/368,210, (filed on Dec. 30, 1994).

In accordance with the non-parenteral administration the present invention, the gene delivery vehicles, particularly those comprised of unencapsidated nucleic acid, may be complexed with a polycationic molecule to provide polycation-assisted non-parenteral administration. Such a method of gene delivery facilitates delivery of a gene via mediation by a physical particle comprised of multiple components that augment the efficiency and specificity of the gene transfer. In particular, polycationic molecules, such as polylysine and histone, have been shown to neutralize the negative charges on a nucleic acid molecule and to condense the molecule into a compact form. This form of molecule is transferred with high efficiency in cells, apparently through the endocytic pathway. The uptake in expression of the nucleic acid molecule in the host cell results after a series of steps, as follows: (1) attachment to cell surface; (2) cell entry via endocytosis or other mechanisms; (3) cytoplasmic compartment entry following endosome release; (4) nuclear transport; and (5) expression of the nucleic acid molecule carried by the gene delivery vehicle. In a further preferred embodiment, multi-layer technologies are applied to the polycation-nucleic acid molecule complex to facilitate completion of one or more of these steps. For example, a ligand such as asialoglycoprotein, transferrin, and immunoglobulin may be added to the complex to facilitate binding of the cell complex to the cell surface, an endosomal disruption component (e.g., a viral protein, a fusogenic peptide such as the n-terminus of the influenza virus hemaglutinin or an inactivated virus) is added to facilitate the release of DNA from the endosome, or a nuclear protein (or a peptide containing a nuclear localization signal) is added to facilitate the transport of the DNA into the nucleus. In a further preferred embodiment, the composition comprising the complex includes inactivated adenovirus particles (Curiel, D. T., et al., *PNAS* 88: 8850-8854, 1991; Cristiano, R. J., *PNAS* 90: 2122-2126 1993; Cotten, M., et al., *PNAS* 89: 6094-6098 1992; Lozier, J. N., et al., *Human Gene Therapy* 5: 313-322, 1994; Curiel, D. T., et al., *Human Gene Therapy* 3: 147-154, 1992; Plank, C. et al., *Bioconjugate Chem.* 3: 533-539, 1992; Wagner, E. et al., *PNAS* 88: 4255-4259, 1991). The assorted components comprising the multi-layer complex may be varied as desired, so that the specificity of the complex for a given tissue, or the gene expressed from the gene delivery vehicle, may be varied to better suit a particular disease or condition.

As noted above, various methods may be utilized to administer gene delivery vehicles of the present invention, including nucleic acids which encode the immunogenic portion(s) discussed above, to warm-blooded animals such as humans, directly. Suitable methods include, for example, various physical methods such as direct DNA injection (Acsadi et al., *Nature* 352:815-818, 1991), and microprojectile bombardment (Williams et al., *PNAS* 88:2726-2730, 1991).

Within an in vivo context, the gene delivery vehicle can be injected into the interstitial space of tissues including muscle, brain, liver, skin, spleen or blood (see, WO 90/11092). Administration may also be accomplished by intravenous injection or direct catheter infusion into the cavities of the body (see, WO 93/00051), discussed in more detail below.

It is generally preferred that administration of the gene delivery vehicles at multiple sites be via at least two injections. In this regard, suitable modes of administration include intramuscular, intradermal and subcutaneous injections, with at least one of the injections preferably being intramuscular. In particularly preferred embodiments, two or more of the injections are intramuscular. However, although administration via injections is preferred, it will be evident that the gene delivery vehicles may be administered through multiple topical or separate ocular administrations. Further, a number of additional routes are suitable for use within the present invention when combined with one or more of the routes briefly noted above, including intraperitoneal, intracranial, oral, rectal, nasal, vaginal and sublingual administration. Methods of formulating and administering the gene delivery vehicles at multiple sites through such routes would be evident to those skilled in the art and are described in U.S. Ser. No. 08/366, 788, filed Dec. 30, 1994 and U.S. Ser. No. 08/367,071, filed Dec. 30, 1994, incorporated herein by reference in their entireties.

C. Liposome Formulation

Several methods may be used in the preparation of liposomes to incorporate gene delivery vehicles of the invention, particularly those that are DNA or RNA, see Gregoriadis et. al., (*Liposome Technology, CFC Press, New York* 1984), Ostro et. al., (*Liposomes, Marek Dekker,* 1987) and Lichtenberg et. al., (*Meth. Biochem. Anal.* 33:337, 1988). According to one embodiment of the invention, the gene delivery vehicles are complexed with cationic liposomes or lipid vesicles. Cationic liposome formulations may be prepared from a mixture of positively charged lipids, negatively charged lipids, neutral lipids and cholesterol or similar sterol. The positively charged lipids may be DMRIE (Felgner, et. al., *J. Biol. Chem.* 269:1, 1994), DOTMA, DOTAP or analogs thereof or a combination of two or more of these lipids. DMRIE is described in U.S. Ser. No. 07/686,746 which is hereby incorporated reference. The neutral and negatively charged lipids can be any natural or synthetic phospholipid or mono-, di- or triglycerols. The natural phospholipids may be derived from animal and plant sources. For example, natural phospholipids such as phosphotidylcholine, phosphotidylethanolamine, sphingomylin, phosphotidylserine, or phosphotidylinositol may be utilized. Synthetic phospholipids may be selected from those having fatty acid groups such as dimyristoylphophatidylcholine, distearoylphosphatidylcholine, dipalmitoylphosphatidylcholine, distearoylphophatidylcholine, and the corresponding phophatidylethanolamines and phosphatidylglycerols. The neutral lipids may be phosphatidylcholine, cardiolipin, phosphatidylethanolamine, mono-, di- or triacylglycerols, or analogs thereof such as dioleoylphosphatidylethanolamine (DOPE). The negatively charged lipids may be phosphatidylglycerol, phosphatidic acid or a similar phospholipid analog. Other additive known to those skilled in the art may also be used such as cholesterol, glycolipids, fatty acids, sphingolipids, prostaglandins, gangliosides, neobee, niomes, or any other natural or synthetic amphophiles.

Substitution of the cationic lipid component of liposomes may be used to alter the transfection efficiency of the liposome. For example, 1,2-dimyristyloxypropyl-3-dimethyl-hydroxyethyl ammonium bromide (DMRIE) is used in conjunction with DOPE which provides increased transfection efficiency and does not aggregate at high concentrations as other formulations such as DC-cholesterol/DOPE. These characteristics allows for higher absolute concentrations of DNA and liposomes to be introduced into patients in vivo without increased levels of toxicity. A preferred molar ratio of DMRIE to DOPE of 9:1 to 1:9 with a particularly preferred molar ratio of 5:5 (see WO 94/29469 incorporated herein by reference)

From the foregoing, it will be appreciated that, although specific embodiments of the invention have been described herein for purposes of illustration, various modifications may be made without deviating from the spirit and scope of the invention. Accordingly, the invention is not limited except as by the appended claims.

Additionally, the publications and other materials cited to illuminate the background of the invention, and in particular, to provide additional details concerning its practice as described in the detailed description and examples, are hereby incorporated by reference in their entirety.

A Sequence Listing has also been included herewith in accordance with the provisions of 37 C.F.R. §1.821 et seq. To the extent any discrepancy exists between the Specification Figures and the Sequence Listing, the specification or Figures should be considered to be the primary document.

We claim:

1. A method of inhibiting binding of a first ligand to a receptor, comprising introducing into a eukaryotic cell a eukaryotic layered vector initiation system which comprises a eukaryotic promoter 5' of alphaviral cDNA, wherein the eukaryotic promoter initiates within the eukaryotic cell 5' to 3' synthesis of alphaviral RNA from the alphaviral cDNA;

wherein the alphaviral RNA comprises a vector that autonomously amplifies in the eukaryotic cell;

wherein the vector comprises:

(1) a 5' sequence capable of initiating transcription of alphaviral RNA, (2) an RNA that encodes alphaviral nonstructural proteins, (3) an alphaviral RNA polymerase recognition sequence, and (4) a heterologous RNA which encodes a second ligand, whereby the second ligand binds to the receptor, thereby blocking binding of the first ligand.

2. The method of claim 1 wherein the second ligand is selected from the group consisting of a CD4 polypeptide, an Adenovirus gp19 polypeptide, and an HCMV H301 polypeptide.

3. The method of claim 1 wherein the receptor is a Class I MHC protein.

4. The method of claim 1 wherein the receptor is an HIV Env protein.

* * * * *